United States Patent
Lee et al.

(10) Patent No.: US 10,961,532 B2
(45) Date of Patent: Mar. 30, 2021

(54) METHODS FOR REACTIVATING GENES ON THE INACTIVE X CHROMOSOME

(71) Applicant: The General Hospital Corporation, Boston, MA (US)

(72) Inventors: Jeannie T. Lee, Boston, MA (US); Anand Minajigi, Boston, MA (US); Lieselot Carrette, Beernem (BE)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/565,060

(22) PCT Filed: Apr. 6, 2016

(86) PCT No.: PCT/US2016/026218
§ 371 (c)(1),
(2) Date: Oct. 6, 2017

(87) PCT Pub. No.: WO2016/164463
PCT Pub. Date: Oct. 13, 2016

(65) Prior Publication Data
US 2019/0048339 A1    Feb. 14, 2019

Related U.S. Application Data

(60) Provisional application No. 62/144,219, filed on Apr. 7, 2015, provisional application No. 62/168,528, filed on May 29, 2015, provisional application No. 62/181,083, filed on Jun. 17, 2015.

(51) Int. Cl.
| | |
|---|---|
| *C12N 15/113* | (2010.01) |
| *C12Q 1/6883* | (2018.01) |
| *C12N 9/10* | (2006.01) |
| *C12N 9/90* | (2006.01) |

(52) U.S. Cl.
CPC .......... *C12N 15/113* (2013.01); *C12N 9/1007* (2013.01); *C12N 9/90* (2013.01); *C12Q 1/6883* (2013.01); *C12Y 201/01037* (2013.01); *C12Y 599/01002* (2013.01); *C12N 2310/113* (2013.01); *C12N 2310/14* (2013.01); *C12N 2310/20* (2017.05); *C12N 2310/3231* (2013.01); *C12N 2310/531* (2013.01); *C12N 2320/34* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 9,328,346 B2 | 5/2016 | Lee et al. | |
| 9,567,581 B2 * | 2/2017 | Lee | .................. C07H 21/00 |
| 9,920,317 B2 | 3/2018 | Lee et al. | |
| 2009/0253203 A1 | 10/2009 | Eilertsen et al. | |
| 2010/0273863 A1 * | 10/2010 | Corey | .................. C12N 15/111 |
| | | | 514/44 R |
| 2013/0123123 A1 | 5/2013 | Chang et al. | |
| 2015/0118755 A1 * | 4/2015 | Jaenisch | ............ C07K 14/4702 |
| | | | 435/462 |
| 2018/0087110 A1 * | 3/2018 | Green | ................ G01N 33/5023 |

FOREIGN PATENT DOCUMENTS

| | | | | |
|---|---|---|---|---|
| WO | WO 2008/126932 | | 10/2008 | |
| WO | WO-2008124133 A1 * | 10/2008 | ......... C07K 14/4702 |
| WO | WO-2012065143 A1 * | 5/2012 | ........... C12N 15/113 |
| WO | 2014/025887 | | 2/2014 | |
| WO | WO 2014/180996 | | 11/2014 | |

OTHER PUBLICATIONS

Sarma et al. PNAS 107, 22196-22201 (Year: 2010).*
Cantone et al. Phil. Trans. R. Soc. 372: 1-8 (Year: 2017).*
Ohhata et al. Cell Mol Life Sci. 70: 2443-2461 (Year: 2013).*
International Search Report and Written Opinion dated Jul. 12, 2016 in international application No. PCT/US2016/026218, 16 pgs.
Bhatnagar et al., "Genetic and pharmacological reactivation of the mammalian inactive X chromosome," Proceedings of the National Academy of Sciences 111(35): 12591-12598 (Sep. 2014).
Hysolli et al. "The lesser known story of X-chromosome reactivation," Cell Cycle 11(2): 229-235 (Feb. 2012).
Berletch et al., "Genes that escape from X inactivation," Human Genetics, 2011, 130(2): 237-245.
Brown and Willard, "The human X-inactivation centre is not required for maintenance of X-chromosome inactivation," Nature, 1994, 368: 154-6.
Brown et al., "The human XIST gene: analysis of a 17 kb inactive X-specific RNA that contains conserved repeats and is highly localized within the nucleus," Cell, 1992, 71: 527-42.
Calabrese et al., "Site-specific silencing of regulatory elements as a mechanism of X inactivation," Cell, 2012, 151: 951-63.
Carrel and Willard, "X-inactivation profile reveals extensive variability in X-linked gene expression in females," Nature, 2005, 434: 400-4.
Csankovszki et al., "Synergism of Xist RNA, DNA methylation, and histone hypoacetylation in maintaining X chromosome inactivation," J Cell Biol, 2001, 153:773-784.
Disteche, "Dosage Compensation of the Sex Chromosomes," Annual Review of Genetics, 2012, 46:537-560.

(Continued)

*Primary Examiner* — Brian Whiteman
(74) *Attorney, Agent, or Firm* — Fish & Richardson P.C.

(57) ABSTRACT

Methods for reactivating genes on the inactive X chromosome that include administering one or both of a DNA methyltransferase (DNMT) Inhibitor and/or a topoisomerase inhibitor, e.g., etoposide and/or 5-azacytidine (aza), optionally in combination with an inhibitor of XIST RNA and/or an Xist-interacting protein, e.g., a chromatin-modifying protein, e.g., a small molecule or an inhibitory nucleic acid (such as a small inhibitory RNA (siRNAs) or antisense oligonucleotide (ASO)) that targets XIST RNA and/or a gene encoding an Xist-interacting protein, e.g., a chromatin-modifying protein.

18 Claims, 35 Drawing Sheets
Specification includes a Sequence Listing.

(56) References Cited

OTHER PUBLICATIONS

Dixon et al., "Topological Domains in Mammalian Genomes Identified by Analysis of Chromatin Interactions," Nature, May 2012, 485: 376-380.
Dowen et al., "Control of cell identity genes occurs in insulated neighborhoods in mammalian chromosomes," Cell, 2014, 159: 374-387.
Feig and Odom, "Cohesin's role as an active chromatin domain anchorage revealed," The EMBO Journal, 2013, 32(24): 3114-3115.
Hall et al., "AURKB-mediated effects on chromatin regulate binding versus release of XIST RNA to the inactive chromosome," J Cell Biol, 2009, 186: 491-507.
Hasegawa et al., "The matrix protein hnRNP U is required for chromosomal localization of Xist RNA," Dev Cell, 2010, 19: 469-76.
International Preliminary Report on Patentability in International Application No. PCT/US2016/026218, dated Oct. 19, 2017, 10 pages.
Jeon and Lee, "YY1 tethers Xist RNA to the inactive X nucleation center," Cell, 2011, 146(1): 119-133.
Kagey et al., "Mediator and cohesin connect gene expression and chromatin architecture," Nature, 2010, 467: 430-5.
Kohlmaier et al., "A Chromosomal Memory Triggered by Xist Regulates Histone Methylation in X Inactivation," PLoS Biol, 2004, 2: El 71.
Kung et al., "Locus-specific targeting to the X chromosome revealed by the RNA interactome of CTCF," Molecular Cell, 2015, 57: 361-75.
Li et al., "Functional roles of enhancer RNAs for oestrogen-dependent transcriptional activation," Nature, 2013, 498: 516-20.
Lin, et al., "Nonallelic Transcriptional Roles of CTCF and Cohesins at Imprinted Loci," Molecular and Cellular Biology, 2011, 31: 3094-3104.
Lyon, "X-chromosome inactivation and human genetic disease," Acta Paediatr Suppl, 2002, 91(439):107-12.
Mak et al., "Reactivation of the paternal X chromosome in early mouse embryos," Science, 2004, 303: 666-9.
Marahrens et al., "Xist-deficient mice are defective in dosage compensation but not spermatogenesis," Genes Dev, 1997 11: 156-66.
Merkenschlager and Odom, "CTCF and Cohesin: Linking Gene Regulatory Elements with Their Targets," Cell, 2013, 152: 1285-1297.
Nagano et al., "Single-cell Hi-C reveals cell-to-cell variability in chromosome structure," Nature, 2013, 502: 59-64.
Nora et al., "Spatial partitioning of the regulatory landscape of the X-inactivation centre," Nature, 2012, 485: 381-5.
Ong and Corces, "CTCF: an architectural protein bridging genome topology and function," Nat Rev Genet, 2014, 15: 234.
Pinter et al., "Spreading of X chromosome inactivation via a hierarchy of defined Polycomb stations," Genome Res, 2012, 22: 1864-76.
Plath et al., "Developmentally regulated alterations in Polycomb repressive complex 1 proteins on the inactive X chromosome," J Cell Biol, 2004, 167: 1025-35.
Plenge et al., "Skewed X-chromosome inactivation is a common feature of X-linked mental retardation disorders," Am. J. Hum. Genet, 2002, 71:168-173.
Rao et al., "A 3D map of the human genome at kilobase resolution reveals principles of chromatin looping," Cell, 2014, 159: 1665-80.
Sarma et al., "ATRX directs binding of PRC2 to Xist RNA and Polycomb targets," Cell, 2014, 159:869-83.
Schoeftner et al., "Recruitment of PRC1 function at the initiation of X inactivation independent of PRC2 and silencing," The EMBO Journal, 2006, 25: 3110-22.
Singh et al., "DNA methyltransferase-1 inhibitors as epigenetic therapy for cancer," Current Cancer Drug Targets, May 2013, 3: 379-99.
Splinter et al., "The inactive X chromosome adopts a unique three-dimensional conformation that is dependent on Xist RNA," Genes Dev, 2011 25: 1371.
Starmer and Magnuson, "A new model for random X chromosome inactivation," Development, Jan. 2009, 136: 1-10.
Sugimoto and Abe, "X chromosome reactivation initiates in nascent primordial germ cells in mice," PLoS Genet, 2007, 3: e116.
Van den Veyver, "Skewed X inactivation in X-linked disorders," Semin Reprod Med, 2001, 19(2):183-91.
Vietri Rudan et al., "Comparative Hi-C reveals that CTCF underlies evolution of chromosomal domain architecture," Cell Reports, 2015, 10: 1297.
Wang et al., "Imprinted X inactivation maintained by a mouse Polycomb group gene," Nat Genet, 2001, 28: 371-5.
Wutz and Agrelo, "Response: the diversity of proteins linking Xist to gene silencing," Dev Cell, Oct. 2012, 23: 680.
Yildirim et al., "Xist RNA is a potent suppressor of hematologic cancer in mice," Cell, 2013, 152:727-42.
Zhang et al., "Perinucleolar targeting of the inactive X during S phase: evidence for a role in the maintenance of silencing," Cell, 2007, 129: 693-706.
Zhao et al., "Genome-wide identification of polycomb-associated RNAs by RIP-seq," Molecular Cell, 2010, 40: 939.
Zhao et al., "Polycomb proteins targeted by a short repeat RNA to the mouse X chromosome," Science, 2008, 322: 750-6.
U.S. Appl. No. 62/010,342, Lee et al.
EP Partial Supplementary Search Report in EP Application No. 16777202.9, dated Mar. 4, 2019, 12 pages.
EP Partial Supplementary Search Report in EP Application No. 16777202.9, dated Nov. 30, 2018, 14 pages.
Franklin and Mansuy, "The involvement of epigenetic defects in mental retardation," Neurobiol Learn Mem. Apr. 2011, 96: 61-67.
Heerboth et al., "Use of Epigenetic Drugs in Disease: An Overview," Genetics & Epigenetics, Jan. 2014, 6: 9-19.
Kundakovic et al., "DNA Methyltransferase Inhibitors Coordinately Induce Expression of the Human Reelin and Glutamic Acid Decarboxylase 67 Genes," Molecular Pharmacology, Jan. 2007, 71: 644-653.
Moore et al., "DNA Methylation and Its Basic Function," Neuropsychopharmacology Reviews, Jul. 2012, 38: 23-38.
Weng et al., "DNA Modifications and Neurological Disorders," DNA Modifications and Neurological Disorders. Sep. 2013, 10: 556-567.
Yu et al., "Clonal Rett Syndrome cell lines to test compounds for activation of wild-type MeCP2 expression," Bioorganic & Medicinal Chemistry Letters, Jul. 2011, 21: 5202-5205.
Carrette et al., "Tsix—Mecp2 female mouse model for Rett syndrome reveals that low-level MECP2 expression extends life and improves neuromotor function," Proc. Natl. Acad. Sci., Aug. 2018, 115(32):8185-8190.
Chaumeil et al., "A novel role for Xist RNA in the formation of a repressive nuclear compartment into which genes are recruited when silenced," Genes & Development, Aug. 2006, 20(16):2223-2237.
EP Office Action in European Appln. No. 16777202.9, dated Feb. 27, 2020, 6 pages.
Kohlmaier et al., "A Chromosomal Memory Triggered by Xist Regulates Histone Methylation in X Inactivation," PLoS Biology, Jul. 2004, 2(7):0992-1003.
Minshawi et al., "The association between self-injurious behaviors and autism spectrum disorders," Psychology Research and Behavior Management, Apr. 2014, 7:125-136.
Obad et al., "Silencing of microRNA families by seed-targeting tiny LNAs," Nature Genetics, Apr. 2011, 43(4):371-378.
Trazzi et al., "CDKL5 protein substitution therapy rescues neurological phenotypes of a mouse model of CDKL5 disorder," Human Molecular Genetics, May 2018, 27(9):1572-1592.
Wutz & Jaensich, "A Shift from Reversible to Irreversible X Inactivation Is Triggered during ES Cell Differentiation," Molecular Cell, Apr. 2000, 5(4):695-705.

* cited by examiner

FIG. 3D

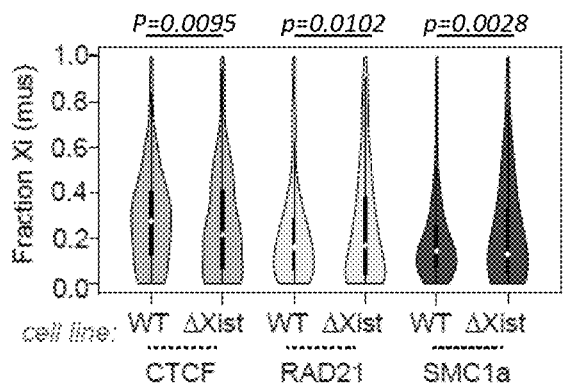
FIG. 4A
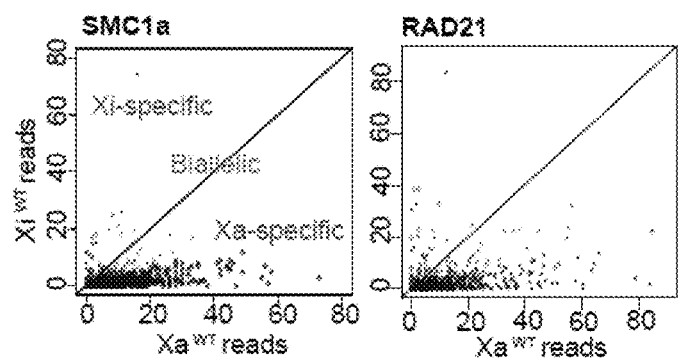
FIG. 4B
|  | SMC1a | | RAD21 | |
|---|---|---|---|---|
| cell line: | WT | ΔXist | WT | ΔXist |
| X-total | 1490 | 1490 | 871 | 871 |
| Allelic peaks | 736 | 896 | 491 | 507 |
| Xa-total | 717 | 873 | 476 | 468 |
| Xa-spec | 689 | 610 | 336 | 313 |
| Xi-total | 203 | 299 | 162 | 201 |
| Xi-spec | 20 | 23 | 18 | 39 |
| Xi-invariant | -- | 13 | -- | 13 |
| Restored on Xi^mut | -- | 106 | -- | 48 |
FIG. 4C

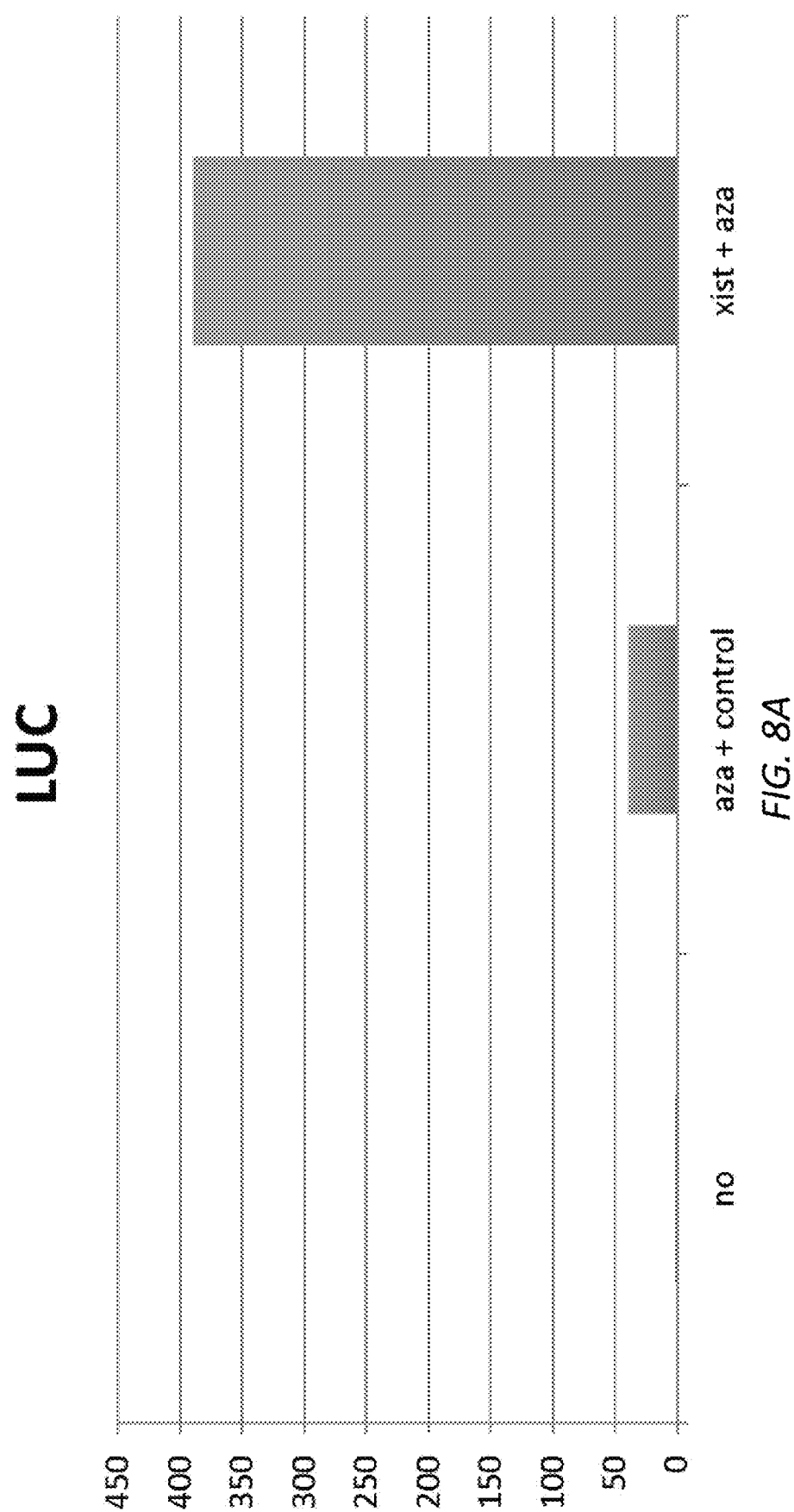

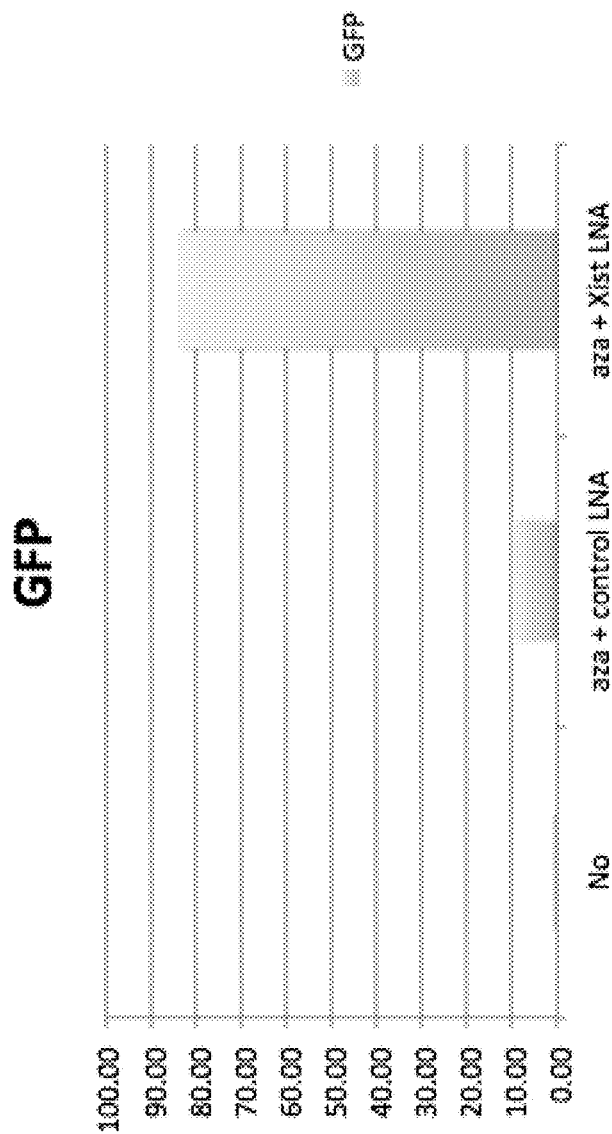

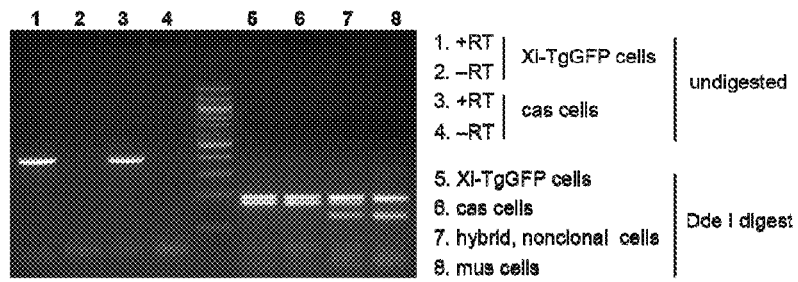
FIG. 10B
FIG. 11A
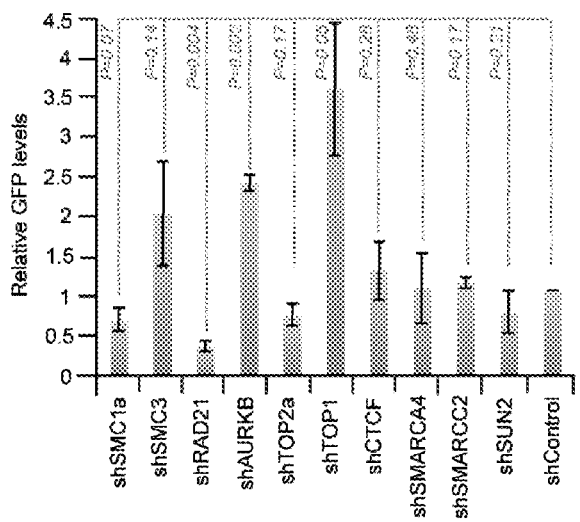
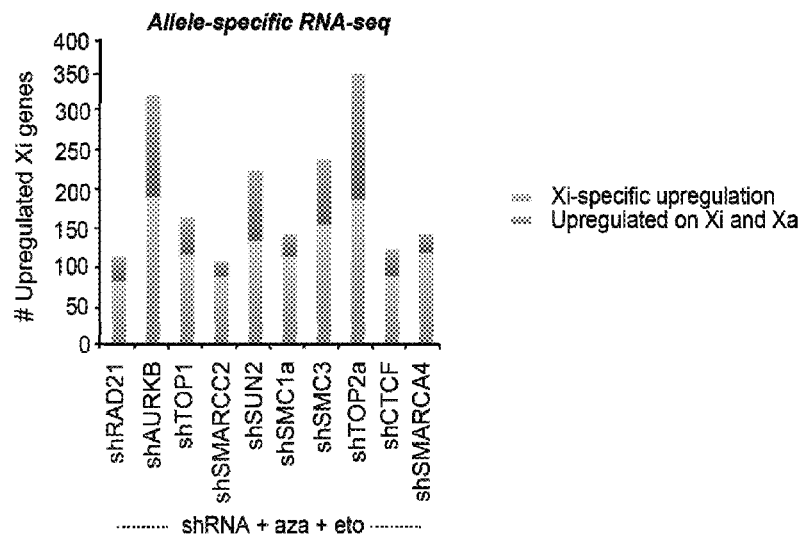
FIG. 11B

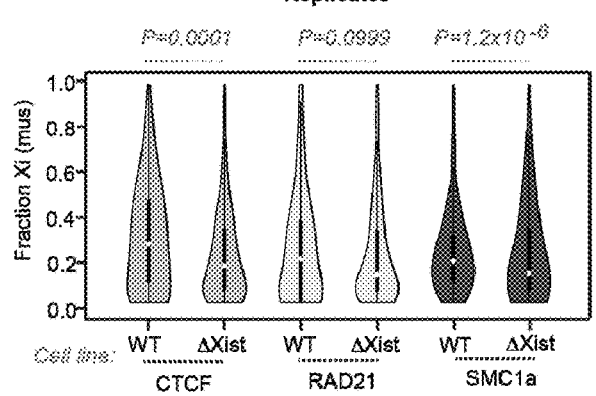
FIG. 16A
FIG. 16B
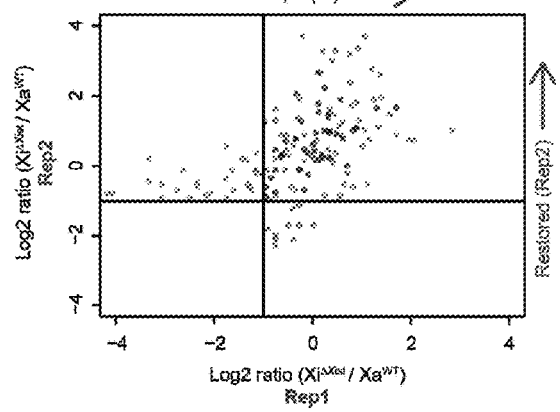
FIG. 16C
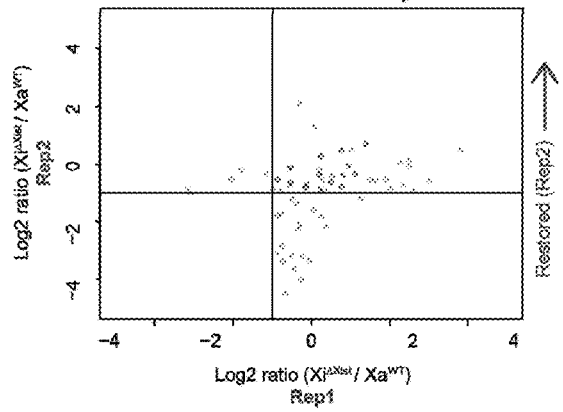
FIG. 16D

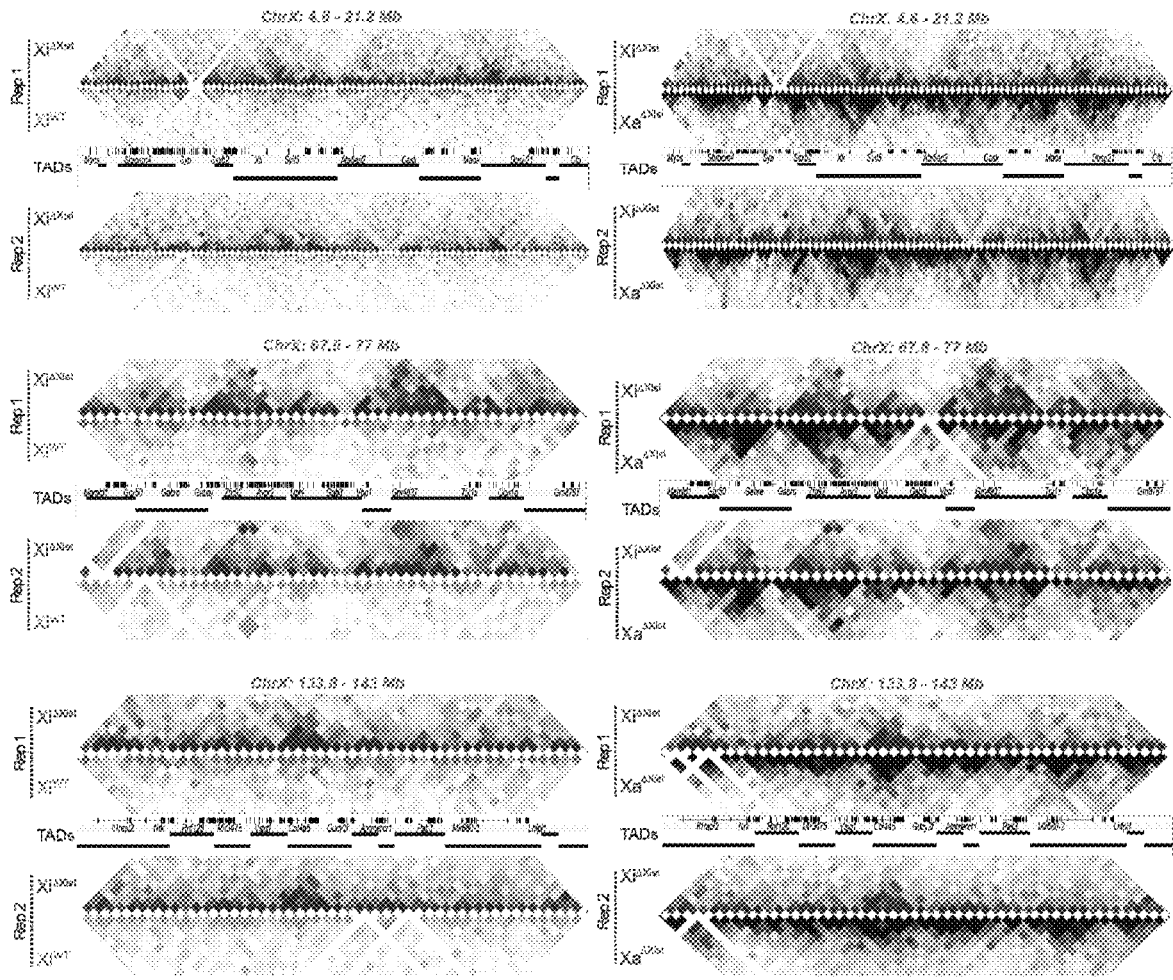
FIG. 22B
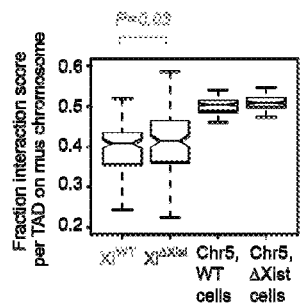 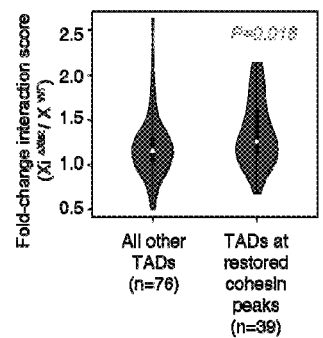
FIG. 23A
FIG. 23B

SEQUENCE LISTING

```
<160> NUMBER OF SEQ ID NOS: 66

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
cagtttaaga gcaaagtcgt ttttc                                         25
```

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 2
aatatgttta cattacaggt ggcaa                                  25

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 3
taaagaccaa gcaaagatac ttgtc                                  25

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
atgcttcata tattcagtgg ttcac                                  25

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
tgtattaagt gaaattccat gaccc                                  25

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 6
aacttagcaa ttaattctgg gactc                                  25

<210> SEQ ID NO 7
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 7
atgcatatct gtatgcatgc ttatt                                  25

<210> SEQ ID NO 8
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 8
catattactt ggggactaag gacta                                          25

<210> SEQ ID NO 9
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 9
atgggcactg cattttagca ata                                            23

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
ccagggcgag gcttatccat t                                              21

<210> SEQ ID NO 11
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 11
gcagtccccc actaccacaa at                                             22

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
gacgtaaacg gccacaagtt                                                20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
aagtcgtgct gcttcatgtg                                                20

<210> SEQ ID NO 14
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 14
ctcgcttcgg cagcaca                                                   17

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
aacgcttcac gaatttgcgt                                              20

<210> SEQ ID NO 16
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 16
tcggaccatt tcagaggttt acc                                          23

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 17
caggtgctcc atgtatcagg t                                            21

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 18
cgaagttacc gagaccaaac a                                            21

<210> SEQ ID NO 19
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 19
tcactgagaa caaactggat tgc                                          23

<210> SEQ ID NO 20
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 20
atgttctacg cacattttgt cct                                          23

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

```
<400> SEQUENCE: 21
tgcactcaaa tacatgggct tt                                              22

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
aggtgaaggg gattcccgta a                                               21

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
aaacacgcct tttatgagtg ga                                              22

<210> SEQ ID NO 24
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 24
ttgggaaact gatgaccata gc                                              22

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
acacaaacgt cagcctgctt                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
cagaaggaga acgcctaccc                                                 20

<210> SEQ ID NO 27
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 27
gagagcaagc gcagatgtc                                                  19

<210> SEQ ID NO 28
<211> LENGTH: 21
```

```
<212> TYPE: DNA
<213> ORGANISM: Artificial Sequence
<220> FEATURE:
<223> OTHER INFORMATION: synthetic oligonucleotide

<400> SEQUENCE: 28
ctgacctggg tgaacaatgc t                                              21

<210> SEQ ID NO 29
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 29
tggctccact gatccaatgt at                                             22

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
gagaggctac gactctgacc                                                20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
ctccaggtag ggggatgttg                                                20

<210> SEQ ID NO 32
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 32
aagatcgaga acaccggcat a                                              21

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
cttttcctcc ttcggtcttt cc                                             22

<210> SEQ ID NO 34
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 34
```
gatcctaccc ttctccagat gaa                                         23

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
gtaccgtcac aggaacaggt                                             20

<210> SEQ ID NO 36
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 36
caaagacaag catatcctag cca                                         23

<210> SEQ ID NO 37
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 37
cacgtagtgt gtgttaagga cc                                          22

<210> SEQ ID NO 38
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 38
gacaccgaga tggaggaagt a                                           21

<210> SEQ ID NO 39
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 39
cgaacagctc tgtctgcttt a                                           21

<210> SEQ ID NO 40
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 40
agctagattc ggtgcgagtc t                                           21

<210> SEQ ID NO 41
<211> LENGTH: 22
<212> TYPE: DNA
<213> ORGANISM: Artificial Sequence

```
<220> FEATURE:
<223> OTHER INFORMATION: synthetic oligonucleotide

<400> SEQUENCE: 41
ccaccagtcc agctagtgtt tt                                              22

<210> SEQ ID NO 42
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 42
gctgcctaca aattcaagag tga                                             23

<210> SEQ ID NO 43
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 43
aggaaaatgt taggtcgtga cag                                             23

<210> SEQ ID NO 44
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 44
tccgaggtgg gaaactacct g                                               21

<210> SEQ ID NO 45
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 45
cagagtgagg ggtatctctt gt                                              22

<210> SEQ ID NO 46
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 46
atccagacct tctatttcca ggc                                             23

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
cccggaagcg gtagatacac                                                 20
```

```
<210> SEQ ID NO 48
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 48
atggtagctg ggatgttagg g                                              21

<210> SEQ ID NO 49
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 49
gagcgaaaag cttttccctg g                                              21

<210> SEQ ID NO 50
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 50
tcttggttac taacag                                                    16

<210> SEQ ID NO 51
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 51
gaagaagcag agaaca                                                    16

<210> SEQ ID NO 52
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 52
agtagctcgg tggat                                                     15

<210> SEQ ID NO 53
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 53
tgagtcttga ggagaa                                                    16

<210> SEQ ID NO 54
<211> LENGTH: 22
<212> TYPE: DNA
<213> ORGANISM: Artificial Sequence
<220> FEATURE:
<223> OTHER INFORMATION: synthetic oligonucleotide
```

```
<400> SEQUENCE: 54
gctggttcgt ctatcttgtg gg                                          22

<210> SEQ ID NO 55
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 55
cagagtagcg aggacttgaa gag                                         23

<210> SEQ ID NO 56
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 56
atgaatacgg ctacagcaac agg                                         23

<210> SEQ ID NO 57
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 57
ctcttgctca gtgtccttgc tg                                          22

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
tctaaggaag tcggggaagc                                             20

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
ccctcgggtg taatcagaat                                             20

<210> SEQ ID NO 60
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 60
acggacaact gcgttgattt t                                           21

<210> SEQ ID NO 61
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
acttagctgg gaagcccaac                                          20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
accatcttct tcaaggacga                                          20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
ggctgttgta gttgtactcc                                          20

<210> SEQ ID NO 64
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 64
taggctcctc ttggacatt                                           19

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
gcaacccatc caagtagatt                                          20

<210> SEQ ID NO 66
<211> LENGTH: 33303
<212> TYPE: DNA
<213> ORGANISM: Homo sapiens

<400> SEQUENCE: 66
atcatggtgt gtgacctcgg gcacatgatg taacctctat aggactctat tttaatgtat    60
aaaacaggaa taatcccttta ttattatcta tgcaatacat attccattat ctattacatg  120
ggataatgga atgggaagtc ccttgaagat ggtactaacc tcaatgtatt actccttttct  180 agcttctttg gttcaaaagt ttggtggagg agttacaaat tctggttttga atgatatatt  240 tggatacttt atcaacacat caaagctcta cctatccctt cccccattct caaaaccaag  300
ctgaattaac atctttacat ttattatgca gtttatggag gattttagca ttaattattg  360
cttgatttac tcaatgtccc catgttatag atgagaactg gaaaacccat tgaagttgtg  420
```

```
actcctggtc tagaaatgaa gtctacttcc agttaatgtt ctttctggta tgtctttgct    480
ttcttgaaat ttcccttttt tgtccttact gggtaaattt tgaaccaacc aaatcacaaa    540
gatgtccggc tttcaatctt ctaggccacg cctcttatgc tctctccgcc ctcagcccc    600
ccttcagttc ttaaagcgct gcaattcgct gctgcagcca tatttcttac tctctcgggg    660
ctggaagctt cctgactgaa gatctctctg cacttggggt tctttctaga acattttcta    720
gtcccccaac acccttatg gcgtatttct ttaaaaaaat cacctaaatt ccataaaata    780
ttttttttaaa ttctatactt tctcctagtg tcttcttgac acgtcctcca tatttttta    840
aagaaagtat ttggaatatt ttgaggcaat tttaatatt taaggaattt ttctttggaa    900
tcattttttgg ttgacatctc tgttttttgt ggatcagttt tttactcttc cactctcttt    960
tctatattt gcccatcggg gctgcggata cctggtttta tattttttc tttgcccaac   1020
ggggccgtgg atacctgcct tttaattctt ttttattcgc ccatcggggc cgcggatacc   1080
tgcttttat tttttttcc ttagcccatc gggtatcgg atacctgctg attcccttcc   1140
cctctgaacc cccaacactc tggcccatcg gggtgacgga tatctgcttt ttaaaaattt   1200
tcttttttttg gcccatcggg gcttcggata cctgcttttt ttttttttat ttttccttgc   1260
ccatcgggc ctcggatacc tgctttaatt tttgttttc tggcccatcg gggccgcgga   1320
tacctgcttt gattttttt tttcatcgcc catcggtgct ttttatggat gaaaaatgt   1380
tggttttgtg ggttgttgca ctctctggaa tatctacact ttttttgct gctgatcatt   1440
tggtggtgtg tgagtgtacc taccgctttg gcagagaatg actctgcagt taagctaagg   1500
gcgtgttcag attgtggagg aaaagtggcc gccattttag acttgccgca taactcggct   1560
tagggctagt cgtttgtgct aagttaaact agggaggcaa gatggatgat agcaggtcag   1620
gcagaggaag tcatgtgcat tgcatgagct aaacctatct gaatgaattg atttgggct   1680
tgttaggagc tttgcgtgat tgttgtatcg ggaggcagta agaatcatct tttatcagta   1740
caagggacta gttaaaaatg gaaggttagg aaagactaag gtgcagggct taaaatggcg   1800
attttgacat tgcggcattg ctcagcatgg cgggctgtgc tttgttaggt tgtccaaaat   1860
ggcggatcca gttctgtcgc agtgttcaag tggcgggaag gccacatcat gatgggcgag   1920
gctttgttaa gtggttagca tggtggtgga catgtgcggt cacacaggaa aagatggcgg   1980
ctgaaggtct tgccgcagtg taaaacatgg cgggcctctt tgtctttgct gtgtgctttt   2040
cgtgttgggt tttgccgcag ggacaatatg gcaggcgttg tcatatgtat atcatggctt   2100
ttgtcacgtg gacatcatgg cgggcttgcc gcattgttaa agatggcggg ttttgccgcc   2160
tagtgccacg cagagcggga gaaaaggtgg gatggacagt gctggattgc tgcataaccc   2220
aaccaattag aaatgggggt ggaattgatc acagccaatt agagcagaag atggaattag   2280
actgatgaca cactgtccag ctactcagcg aagacctggg tgaattagca tggcacttcg   2340
cagctgtctt tagccagtca ggagaaagaa gtggaggggc cacgtgtatg tctcccagtg   2400
ggcggtacac caggtgtttt caaggtcttt tcaaggacat ttagcctttc cacctctgtc   2460
ccctcttatt tgtcccctcc tgtccagtgc tgcctcttgc agtgctggat atctggctgt   2520
gtggtctgaa cctccctcca ttcctctgta ttggtgcctc acctaaggct aagtatacct   2580
ccccccccac ccccaaccc cccaactcc cccaccccac ccccaccccc ccacctcccc   2640
accccctac ccccctaccc ccctaccccc ctctggtctg ccctgcactg cactgttgcc   2700
atgggcagtg ctccaggcct gcttggtgtg gacatggtgg tgagccgtgg caaggaccag   2760
```

```
aatggatcac agatgatcgt tggccaacag gtggcagaag aggaattcct gccttcctca    2820 agaggaaacac ctaccccttg gctaatgctg gggtcggatt ttgatttata tttatctttt    2880
ggatgtcagt catacagtct gattttgtgg tttgctagtg tttgaattta agtcttaagt    2940
gactattata gaaatgtatt aagaggcttt atttgtagaa ttcactttaa ttacatttaa    3000 tgagttttg ttttgagttc cttaaaattc cttaaagttt ttagcttctc attacaaatt    3060
ccttaacctt tttttggcag tagatagtca aagtcaaatc atttctaatg ttttaaaaat    3120
gtgctggtca ttttctttga aattgactta actattttcc tttgaagagt ctgtagcaca    3180
gaaacagtaa aaaatttaac ttcatgacct aatgtaaaaa agagtgtttg aaggtttaca    3240
caggtccagg ccttgctttg ttcccatcct tgatgctgca ctaattgact aatcacctac    3300
ttatcagaca ggaaacttga attgctgtgg tctggtgtcc tctattcaga cttattatat    3360
tggagtattt caattttttcg ttgtatcctg cctgcctagc atccagttcc tccccagccc    3420
tgctcccagc aaacccctag tctagcccca gccctactcc caccccgccc cagccctgcc    3480 ccagcccag tcccctaacc ccccagccct agccccagtc ccagtcctag ttcctcagtc    3540
ccgcccagct tctctcgaaa gtcactctaa ttttcattga ttcagtgctc aaaataagtt    3600
gtccattgct tatcctatta tactgggata ttccgtttac ccttggcatt gctgatcttc    3660
agtactgact ccttgaccat tttcagttaa tgcatacaat cccatttgtc tgtgatctca    3720
ggacaaagaa tttccttact cggtacgttg aagttaggga atgtcaattg agagcttttct    3780 atcagagcat tattgcccac aatttgagtt acttatcatt ttctcgatcc cctgcccta    3840 aaggagaaac catttctctg tcattgcttc tgtagtcaca gtcccaattt tgagtagtga    3900
tcttttcttg tgtactgtgt tggccaccta aaactctttg cattgagtaa aattctaatt    3960
gccaataatc ctacccattg gattagacag cactctgaac cccatttgca ttcagcaggg    4020
ggtcgcagac aacccgtctt ttgttggaca gttaaaatgc tcagtcccaa ttgtcatagc    4080
tttgcctatt aaacaaaggc accctactgc gcttttttgct gtgcttctgg agaatcctgc    4140
tgttcttgga caattaaaga acaaagtagt aattgctaat tgtctcaccc attaatcatg    4200
aagactacca gtcgcccttg catttgcctt gaggcagcgc tgactacctg agatttaaga    4260 gttcttaaa ttattgagta aaatcccaat tatccatagt tctgttagtt acactatggc    4320
ctttgcaaac atctttgcat aacagcagtg ggactgactc attcttagag ccccttccct    4380
tggaatatta atggatacaa tagtaattat tcatggttct gcgtaacaga gaagacccac    4440
ttatgtgtat gcctttatca ttgctcctag atagtgtgaa ctacctacca ccttgcatta    4500
atatgtaaaa cactaattgc ccatagtccc actcattagt ctaggatgtc ctctttgcca    4560
ttgctgctga gttctgacta cccaagtttc cttctcttaa acagttgata tgcataattg    4620
catatattca tggttctgtg caataaaaat ggattctcac cccatcccac cttctgtggg    4680
atgttgctaa cgagtgcaga ttattcaata acagctcttg aacagttaat ttgcacagtt    4740
gcaattgtcc agagtcctgt ccattagaaa gggactctgt atcctatttg cacgctacaa    4800
tgtgggctga tcacccaagg actcttcttg tgcattgatg ttcataattg tatttgtcca    4860
cgatcttgtg cactaaccct tccactccct ttgtattcca gcaggggacc cttactactc    4920
aagacctctg tactaggaca gtttatgtgc acaatcctaa ttgattagaa ctgagtcttt    4980
tatatcaagg tccctgcatc atctttgctt tacatcaaga gggtgctggt tacctaatgc    5040
ccctcctcca gaaattattg atgtgcaaaa tgcaatttcc ctatctgctg ttagtctggg    5100
gtctcatccc ctcatattcc ttttgtctta cagcaggggg tacttgggac tgttaatgcg    5160
```

| | |
|---|---|
| cataattgca attatggtct tttccattaa attaagatcc caactgctca caccctctta | 5220 |
| gcattacagt agagggtgct aatcacaagg acatttcttt tgtactgtta atgtgctact | 5280 |
| tgcatttgtc cctcttcctg tgcactaaag accccactca cttccctagt gttcagcagt | 5340 |
| ggatgacctc tagtcaagac cttttgcacta ggatagttaa tgtgaaccat ggcaactgat | 5400 |
| cacaacaatg tctttcagat cagatccatt ttatcctcct tgttttacag caagggatat | 5460 |
| taattaccta tgttaccttt ccctgggact atgaatgtgc aaaattccaa tgttcatggt | 5520 |
| ctctcccttt aaacctatat tctaccccct ttacattata gaaagggatg ctggaaaccc | 5580 |
| agagtccttc tcttgggact cttaatgtgt atttctaatt atccatgact cttaatgtgc | 5640 |
| atattttcaa ttgcctaatt gatttcaatt gtctaagaca tttcaaatgt ctaattgatt | 5700 |
| agaactgagt cttttatatc aagctaatat ctagctttta tcaagcta atatcttgac | 5760 |
| ttctcagcat catagaaggg ggtactgatt cctaaagtc tttcttgaat ttctattatg | 5820 |
| caaaattgcc ctgaggccgg gtgtggtggc tcacacctgt aatcccagca ctttgggagg | 5880 |
| ctgaggtggg aagatccctt actgccagga gtttgagacc agcctggcca acattaaaaa | 5940 |
| aaaaaaaaag taagacaatt gccctggaat cccatccccc tcacacctcc ttggcaaagc | 6000 |
| agcaggagtg ctaactagct agtgcttctt ctcttatact gcttaaatgc gcataattag | 6060 |
| cagtagttga tgtgcccta tgttagagta gaatcccgct tccttgctcc atttgcatta | 6120 |
| ctgcaggagc ttctaactag cctgaattca ctctcttgga ctgttaatgt gcatacttat | 6180 |
| atttgctgct gtactttttt accatgtaag gaccccaccc actgtattta catcccagct | 6240 |
| ggaagtacct actacttaag acccttagac tagtaaagtt agcgtgcata atcttaggtg | 6300 |
| ttatatacac attttcagtt gcatacagtt gtgccttta tcaggactcc tgtacttatc | 6360 |
| aaagcagaga gtgctaatca atattaagcc cttctcttcg aactgtagat ggcatgtaat | 6420 |
| tgcagttgtc aatggtcctt caattagact tgggtttctg acctatcaca ccctctttgc | 6480 |
| tttattgcat ggggtactat tcacttaagg ccccttctc aaactgttaa tgtgcctaat | 6540 |
| gacaattaca tcagtatcct tccttttgaa ggacagcatg gttggtgaca cctaaggccc | 6600 |
| catttcttgg cctcccaata tgtgtgattg tatttgtcga ggttgctatg cactagagaa | 6660 |
| ggaaagtgct cccctcatcc ccacttttcc cttccagcag gaagtgccca ccccataaga | 6720 |
| cccttttatt tggagagtct aggtgcacaa ttgtaagtga ccacaagcat gcatcttgga | 6780 |
| catttatgtg cgtaatcgca cactgctcat tccatgtgaa taaggtccta ctctccgacc | 6840 |
| ccttttgcaa tacagaaggg ttgctgataa cgcagtcccc ttttcttggc atgttgtgtg | 6900 |
| tgattataat cgtctgggat cctatgcact agaaaggag gtcctctcc acatacctca | 6960 |
| gtctcacctt tccttccag caggagtgc ccactccata agactctcac atttggacag | 7020 |
| tcaaggtgcg taattgttaa gtgaacacaa ccatgcacct tagacatgga tttgcataac | 7080 |
| tacacacagc tcaacctatc tgaataaaat cctactctca gacccctttt gcagtacagc | 7140 |
| aggggtgctg atcaccaagg cccttttttcc tggcctggta tgcgtgtgat tatgtttgtc | 7200 |
| ccggttcctg tgtattagac atggaagcct cccctgccac actccacccc caatcttcct | 7260 |
| ttcccttccg gcagggagtg ccctctccat aagacgctta cgtttggaca atcaaggtgc | 7320 |
| acagttgtaa gtgaccacag gcatacacct tggacattaa tgtgcataac cactttgccc | 7380 |
| attccatctg aataaggtcc tactctcaga ccccttttgc agtacagcag gggtgctgat | 7440 |
| caccaaggcc ccttttcttg gcctgttatg tgcgtgatta tatttgtctg ggttcctgtg | 7500 |

| | |
|---|---|
| tattagacaa ggaagccttc cccccgcccc cacccccact cccagtcttc ctttcccttc | 7560 |
| cagcagggag tgccccctcc ataagatcat tacatttgga caatcaaggt gcacaattat | 7620 |
| aagtgaccac agccatgcac cttggacatt attggacatt aatgtgcgta actgcacatg | 7680 |
| gcccatccca tctgaataag gtcctactct cagatgccct ttgcagtaca gcaggggtac | 7740 |
| tgaatcacca aggcccttt tcttggcctg ttatgtgtgt gattatattt atcccagttt | 7800 |
| ctgtgtaata gacatgaaag cctcccctgc cacaccccac ctccaatctt cctttccctt | 7860 |
| ccaccaggga gtgtccactc catataccct tacatttgga caatcaaggt gcacaattgt | 7920 |
| aagtgagcat aggcactcac cttggacatg aatgtgcata actgcacatg gcccatccca | 7980 |
| tctgaataag gtcctactct cagaccccttt ttgcagtaca gcaggggtgc tgatcaccaa | 8040 |
| ggccccttt cctggcctgt tatgtgtgtg attatatttg ttccagttcc tgtgtaatag | 8100 |
| acatggaagc ctcccctgcc acactccacc cccaatcttc ctttcccttc tggcaggaag | 8160 |
| tacccgctcc ataagaccct tacatttgga cagtcaaggt gcacaattgt atgtgaccac | 8220 |
| aaccatgcac cttggacata aatgtgtgta actgcacatg gcccatccca tctgaataag | 8280 |
| gtcctactct cagaccccttt ttgcagtaca gtaggtgtgc tgataaccaa ggcccctctt | 8340 |
| cctggcctgt taacgtatgt gattatattt gtctgggttc cagtgtataa gacatggaag | 8400 |
| cctcccctgc cccaccccac cctcaatctt cctttccctt ctggcaggga gtgccagctc | 8460 |
| cataagaacc ttacatttgg acagtcaagg tgcacaattc taagtgaccg cagccatgca | 8520 |
| ccttggtcaa taatgtgtgt aactgcacac ggcctatctc atctgaataa ggccttactc | 8580 |
| tcagacccct tttgcagtac agcaggggtg ctgataacca aggcccattt tcctggcctg | 8640 |
| ttatgtgtgt gattatattt gtccaggttt ctgtgtacta gacaaggaag cctcctctgc | 8700 |
| cccatcccat ctacgcataa tctttctttt cctcccagca gggagtgctc actccataag | 8760 |
| accccttacat ttggacaatc aaggtgcaca attgtaagtg accacaacca tgcatcttgg | 8820 |
| aaatttatgt gcataactgc acatggctta tcctatttga ataaagtcct actctcagac | 8880 |
| ccccttttgca gtatagctgg ggtgctgatc actgaggcct ctttgcttgg cttgtctata | 8940 |
| ttcttgtgta ctagataagg gcaccttctc atggactccc tttgcttttc aacaaggagt | 9000 |
| acccactact ttttaagatt cttatatttg tccaaagtac atggttttaa ttgaccacaa | 9060 |
| caatgtccct tggacattaa tgtatgtaat caccacatgg ttcatcctaa ttaaacaaag | 9120 |
| ttctaccttc tcaccctcca tttgcagtat accagggttg ctgaccccct aagtccccttt | 9180 |
| ttcttggctt gttgacatgc ataattgcat ttatgttggt tcttgtgccc tagacaagga | 9240 |
| tgccccacct cttttcaata gtgggtgccc actccttatg atctttacat ttgaacagtt | 9300 |
| aatgtgaata attgcagttg tccacaaccc tatcacttct aggaccatta tacctctttt | 9360 |
| gcattactgt ggggtatact gtttccctcc aaggcccctt ctggtggact atcaacatat | 9420 |
| aattgaaatt ttcttttgtc tttgtcagta gattaaggtc ataccccatc acctttcctt | 9480 |
| tgtagtacaa cagggtgtcc tgatcaacca aagtcctgtt gttttggact gttaatatgt | 9540 |
| gcaattacat ttgctcctga tctgtgcact agataaggat cctacctact ttcttagtgt | 9600 |
| ttttagcagg tagtgcccac tactcaagac tgtcacttgg aatgttcatg tgcacaaact | 9660 |
| caattctcta agcatgttcc tgtaccacct ttgctttaga gcaggggat gatattcact | 9720 |
| aagtgcccct tcttttggac ttaatatgca ttaatgcaat tgtccacctc ttcttttaga | 9780 |
| ctaagagttg atctccacat attccccttg catcaggggc atgttaatta tgaatgaacc | 9840 |
| cttttctttt aatattaatg tcataattgt atttgtggac ctgtgtagga gaaaaagacc | 9900 |

```
ctatgttcct cccattaccc tttggattgc tgctgagaag tgttaactac tcataatctc    9960
agctcttgga caattaatag cattaataac aattatcaag ggcactgatc attagataag   10020
actcctgctt cctcgttgct tacatcgggg gtactgaccc actaaggccc cttgtactgt   10080
taatgtgaat atttgcaatt atatatgtct ccttctggta gagtgggata ttatgcccta   10140
gtatcccctt tgcattactg cagggctgc tgactactca aaacttctcc tgggactgtt    10200
aataggcaca atggcagtta tcaatggttt tctccctccc tgaccttgtt aagcaagcgc   10260
cccaccccac ccttagtttc ccatggcata ataaagtata agcattggag tattccatgc   10320
acttgtctat caaacagtgg tccatactcc caacccttt gcattgcgcc agtgtgtaaa    10380
atcacaggta gccatggtgt catgctttat atacgaagtc ttccctctct ctgcccttg    10440 tgtgcccttg gcccctttt acagactatt gctcacaatc tcaggtgtcc atatttgcag    10500
ctattaggta agattgtgct gtctccctct tcccttccct ctgccctgcc cttttgcct    10560 ctttgctggg taatgttgac cagacaaggc cctttctctt ggacttaaac aattctcagt   10620
tgcactttcc ttggtcccac ccattataca tgaacccctc tacttccttt cgcattgctt   10680
ctgagtatgc tgactaccca aagccccttc tgtgttatta ataaacacag tactgattgt   10740 cccattttc agcccatcag tccaagatct ccctaccact ttggtgtgtt ggtgcagtgt    10800
tgactatgaa aagcaggcct gaactaggtg gataagcctt cactcatttt ctttcattta   10860
ttaatgatcc tagtttcaat tattgtcaga ttctggggac aagaaccatt cttgcccacc   10920
tgtgttactg ctttactgtg caaaatactg aaggcaagtc agacccaggg agctggattg   10980
ccatccttta ttttgtgttt ccagtgtaca ctataaaatt gtctccccag gaaggaaggt   11040
tggcactttc tctgcattct tctttccaga gcagattgcc tggttaagaa tctcttgttg   11100 tccccttgt atattgttat tgtaaagtgc caaatgccag gatacagcca gaaaaattgc    11160
ttattattat taaaaaaatt ttttaagaa agacatctgg attgtagggt ggactcgata    11220
acctggtcat tattttttg aagccaaaat atccatttat actatgtacc tggtgaccag    11280
tgtctctcat tttaactgag ggtggtgggt ctgtggatag aacactgact cttgctattt   11340
taatatcaaa gatattctag agtggaactc ttaagaccag tatctttgtg tgggctttac   11400
cagcattcac ttttagaaaa actacctaaa tttataatc ctttaatttc ttcatctgga    11460
gcacctgccc ctacttattt caagaagatt gcagtaaaac gattaaatga gggaacatat   11520
gcagaggtgc ttttaaaaag catatgccac cttttttatt aattattata taaaatgaag   11580
catttaatta tagtaataat ttgaagtagt ttgaagtacc acactgaggt gaggacttaa   11640
aaatgataag acgagttccc tattttataa gaaaaataag ccaaaattaa atattctttt   11700
ggatataaat ttcaacagtg agatagctgc ctagtggaaa tgaataatat cccagccact   11760
agtgtacagg gtgttttgtg gcacaggatt atgtaatatg gaactgctca agcaaataac   11820
tagtcatcac aacagcagtt cttttgtaata actgaaaaag aatattgttt ctcggagaag   11880
gatgtcaaaa gatcggccca gctcagggag cagtttgccc tactagctcc tcggacagct   11940
gtaaagaaga gtctctggct ctttagaata ctgtaagtac tacttcgtag ctattaagta   12000 atcttttcc tattctattt tctttctctt agatgccacc tatagaaaag tcagagggtc    12060
cagtaagttt cttccttct tcccacctca tctgcaatat atatatatag agagagaaat    12120
agatacatac atacatgcat aaatacacat atgtgagtta accagcagaa ctgtagaatt   12180
aatattgtgg acccagctct atgctaggtt acactgataa cctgggtagg aatgatatca   12240
```

```
tcctatataa tttcattcct gagatgattt tatcgttgag gagctaatgt gagcacattt    12300
gaaataactt tagaaaataa taagtgctgt tttgtgtgaa tcataagtag tagttttagg    12360
aagggaaccc acaaggattt gaagttgata gaataaactt aaggaagtgg gtttgctttt    12420
tctctttaag ccaagatagg attaatattg cagccatctg gatagtccag ttggtttatt    12480
ttaatttcat ttgttttta cctcttttgg agccatggaa agagatgaaa gggatagagc    12540
atagccattg tgtttggcta tttgcgaagg ttggcaaatt agtgattgct aaatctcata    12600
agcttgagta ttttaaagtt cagagattga gggcataaat ctaatacttc ggctccttcc    12660
acaattttac tacatttctg cccaagaaca gatgaccatg gataatgcat atcgtagata    12720 cttttaagt ttggaacctt tttgccaaga gggtagtgga gaagtgaagt caaaaccttg    12780 accttcctg cctactttat gctgtagttt atataccttc tttcctccca cctttcgtaa    12840
agctaaaaga agcttagcct ccttaatgtt ttccagctga caaaatattg tttaacataa    12900
cattcgaaac ttttttctg gtgcacattc atgcatcaca gcaggagcaa caagaaccat    12960
ataagtgaac tggcttcact tatagcccgt tttaattcat atccatattt cctcagggct    13020
tgtttccatg cctcccagcc ccactccata tgcttaacaa cattgtctgg ctgactgagg    13080
gttatataca tcatggtctt gaaccttctt ggaaacatgg tctgtgccat tgtttctcaa    13140
acccaagtaa tgcttcatga tgaaacacct tctaaaggaa caaaattttc tgagatccta    13200
aaaaaatgtg ttttgaggaa cactgactta acaaagatat ttgaaatgta aatatgtttt    13260
ccaatttcac gttgtctttg tcaaagatgt gttttatata acttatgtag aacttgggga    13320
tccattagaa tatattcaca aatccccagg gttatcaccc caatttgaga aaccctggtc    13380
tatgcttatg aaatcttcta ttggtaatta aattgtcatt cattgtcaac atacaattat    13440
aattattatt ggaatttgtt ttaaatgaat gaatttggag gtgattctgt accttaagtc    13500
aagaggaagg atggcttgat tttaggtgga ttgattatac tagatagcat ccaaaggtga    13560
atcttgaagc tgtatttaaa ttcattgctt gaaataattt ccacccttaa gaaaaatctc    13620
tagcaattgt aaaaagggat gctctggaaa tgtgggcatc ttcaaaatag agataattct    13680
tgtgttagtt caacaaatat tattgtacca ggtgctggaa taaatagcaa aaccaaagac    13740
aggatttata tcaaggaatt tgctttctta tggaggatgc agaaggaaat cattatggtt    13800
ttgggcagaa atgcttagac tttagtcctg gctctgagtt tggttcagat caccatcaat    13860
ctgaccatct cgagactgct agtgaaataa gatagggct tatatcaaat acctaaatcc    13920
ctgaaaatga cattttgtga tttggaaaat tttcaaaagt ctaatgaagg aaactttttt    13980
ggcatttctt taaatgatta ttgtcatttc ttttctgact tttcccttta taaaaccta    14040 acatgtagga ttggaggaag ttttctgacc attttctcat atcctctttc agctttatct    14100
ttctgtaact tccatttctc tagccacctc cctaaattac agaagactgt gagacccagg    14160
gctgctgtga ttaggcattc ataatttctt ttcagggtgt ttgtgccctg attatcaaat    14220
gtacagcttg aagggagttc atgtcttaaa gtaatgaatt aagagttgac cttttgttgac   14280 tgctaaaata ttcttatatg tgaaagcatc ctggaaaaat acgttaccag cttaaagaga    14340
aagaaactaa tgattatatc tgaactgagc taatgcctct tctcttcccc caaacccttat   14400 cagtttggat ggcaaagagt aatgatgtgt cagttaaaca gagctaatgc cttcctctgc    14460
cttgtcttaa agactggatt gggagaaaat tgatattctc actaccatat tttgggctgt    14520
aggcaagtag cattttacac aggtttcctt caaaaatcca actcaagttg gagctcatgt    14580
atttaagaca tagctggcct gctgaattta acaagttaaa cttcagtggc catgtacagt    14640
```

```
tatatatcac tatatatatg tgtattaggc tgtcgagttg gtcatgtttt tgttggtgac    14700
ttaggcttta cttgatagct cttccttgac ctttccaaat tgagtactga tacatggagc    14760
ttgggcttct tctgcatctt atacaaatga gtttggtaaa gaagcctctc ctttactgtt    14820
ttgatgttta tattagaaat aacttttgat tattttttt catgttagga tgagaaactg    14880
aaacaaaatg taaatttgac cggtgctaga cttcttaaat tatgggtaga cttaaagtat    14940
tattttcctt aaccaattag aatgctagtc ttctagtgtt cccggaaaca tgagaggtta    15000
tgcagtagac ccaagcaata ccctcttatt acataatcaa gtgcgtataa gaatttaaaa    15060
atagggatat gactggaaca tcactgtact ttaccaggtc ccattataaa attatctatg    15120
ttactttacc catagctttg aaaactagtg gcatagtata ttttatagta tgctgttagt    15180
gtgattggca ttgaacagtg atgggatata atcactctac aatctatatg ttattaaagt    15240
tttccagcct tatagatctc ccttgactga aaattagcta ctaacttacg acttattttt    15300
tacagcagat tgactaggtc tttccaggaa atctgttgat gtacaaaaac aaagtttaat    15360
tgctaatgtt ttttttaaaaa ataacttttt gatattacgg atacctggtt atttgggcct    15420
tgtatatttt aacatcaaaa ttacctatta taaatccata taaacagaaa agaaagagag    15480 taagtctttta gatcagatct gcaaacaatg atggtacgta ctgtagaaaa atctggaaca    15540
tagacttacc agttcttagg ttccatttg cttgcttttt aaaaactgtg tcttataagt    15600
cttcagcaac tggttgggag attttagaa aaaataacct tttaatgtta gaacagtgta    15660
gagatttaca gaatgattct gaagatagag tttctgtgta cttcacaccc agtttttccc    15720
agtgttaaca tttttacatta gtttggtaca tttgtcacaa caaaccaata ttgatacatt    15780
attattaact agagtccata ttttattcag atttccttag ttttccttta atgttctttt    15840
tgtgttccag gatcccattg aagataccac gctgcatgtg tccttagtag tcatgtctcc    15900
ttaggctcct cttggtaatg acagtttctc agactctttg ttttgatga acttcacagt    15960 tttgaggact aatggtccag tattctatag aatgtctctc tattggaatt tgtctgatgt    16020
tcttctcatg actagattgg gtttatgagt gtttaggagg aagaccacaa aggtagagtg    16080
ccattcttat cacttatcaa gagtacatac tatcaacatg acttatcact gtttatgtta    16140
tccttaatca cctgtctgag gtactatttg tcaggtttct ccagcgtaaa attagtcttt    16200
atttctccat ttccctacta tactgttcac ataggaagtc actatgtgca gccagcactt    16260
aaggaatggg aaattacctt ccacctcatt gagggcagag tatttacata aattatttgg    16320
aattcttttg cacaggatgt cttttctcca caatgtattg tgtttattca gtcatttata    16380
tcagtatgat ctcagggata ttttatactc tgggttataa tacagtatta ctttattctg    16440
ttgttcaaat tgttccagct ttggccattg ggaggtcttt catttggctt tgatataacc    16500
ccatgaatgt gggttttttg tttgagcact ttcttatttt tggaactaca acatgcttca    16560
gactcatttg catatctcct gcctggacct aaaatgatgt atttctgcaa ggagccttga    16620 tacttttttat tggagagtaa tattagaaat caagaagtga atgctaggtg cgctcattac    16680
tactggagtg tcattccttc aagaccttt cagttgacaa gagcaaggag atatatattt    16740
gcattctaac gtgtgtatat gcacatagct ataaatatat ataaccatct gtatctatat    16800
taaactaaat gtgtttatac ctacgtctcc aactctaatc attgccacat ggatcattat    16860
agtctcacct ccttgcttat ctgttacctc ccatttctac agtgagaaac ctggcttggt    16920
tgggaaattt ttctgttaat attacggtag tgagtgtttg acatttgctt ctatggttaa    16980
```

```
gtttagggag agtttagctg tagggtattc ttgaaactag aaatgaccct tctgccctaa    17040
atgtttctgc cagttttgaa acgtaaaata ggttgcagaa acaaacttta tcttaagaac    17100
cagaatttac ttcaatccac attttgacat tgattttcag attaaattat tctgatatcg    17160
ccaggtaagc tgttccttgg gtatgcattt cttctttccg ttttttttcta agagctaaag    17220 gaccctgaga acactggagg tgggaaagga agggaaaggc atgttcacac gtgggatagg    17280
aaaggttcat ttactgacct ccagctagcc ttccaaagtg cctatttaag acccaaggag    17340
tagatgtctt ccttggcaat tgtaacccaa atataatttt taacctttca attttagtca    17400
agaaagttgg tgtgctgtta caaaaagtgc cctgattaac agcattgtca tgtgcattgc    17460
atattaatca gcaatttaaa ataacatgaa attatgttga gtataatttt aatattttat    17520
attagatatt agtttgagac agtgtttctc aagtctgtat aataagtttg atagtaggga    17580
ggttttctct caagaaaaga attattcagt gtgcacctac ataatcactg cttagattct    17640
acaattaata ttttgctata tttgattaaa cgttttctgt aaaagaaaaa tattattatg    17700
tactatttag gtttatggga ataattgtta agttaaagtg tatgaacaaa cctggaatga    17760
aatctgtttg cctacatcta taatacaact ataaaacata gcagatgtac aaattagtag    17820
ttaatagata actaaaatgc aaatatggca ctactattat agtattatag tttcttttga    17880
gtggcgtgtc tgtaatatca catgctgtgt tgatgcactt caccaaactg ctgttttcaa    17940
actgctttaa atcctgccat tatagcacat agcaatgcta tttcactttc atttggcaca    18000
aaacacattt atatattgtt tgcttctctt cttttctgta atccccaggc aacaaaacta    18060
gaacatttgc cactaatctg gcaacgtggt cctatattat gaagtagtca tatagctgat    18120
ctaaactatc cttacagtga aatgagagta ttgtgaaagt tttgtagaaa gctccccata    18180
tgtcctgaga atctatgcac agaccccaca gttaaaagac ctttgaattg tgggaagaca    18240
tgggtttaag tatcacttgg ttaccttcta tttgtgtaac attgaggtag tttcatcttc    18300
tgggttccca gttccttag agaatgaaaa tgttgaatta tgtgattttt tttttttttt    18360
gagacggagt tttgctcttt cgcccaggct ggagtgaagt agcacgatct cgactcactg    18420
caacctcctt cccccatgat caagcaattc tcctgcctca gcctcccaag tagctgggat    18480
tacaggcacc cgccccccac ccccgcccc cagctaatgt ttgtattttt agtacagatg    18540
gagttttgcc gtgttggcca ggctggtctc gaacttctga cctcaggtga tccactcgcc    18600
ttggcctccc aaagtgctag gattacaggc atgagccact gcgcctggcc tatgtgatta    18660
ttaatatcac gtctagctgt gacaattctg tctgatgctg gagtatttga accagatggc    18720
tggctgtgcc actcagttat tctctccata agactttgat attttgttgg tctgcaagat    18780
gacggattct caaaattctt gtcagtgaat attgaaccct agtgaaatgt atggttctgt    18840
atcagttcca aaatgtaacc actttctcta gccttagatt cccagttcca aaatgtaacc    18900
attttctcta gccttagatt cccgttaagg gaaagggaat gctctttgag tatgtcatca    18960
ccatagtaac aggcaaaact agagggcttt gatgctaaag caagatactc cataaatatg    19020
cttaagaaga cttggggaga ctggaatagt tgttcccttt tagatgccag tgtataaatg    19080
aatttgagct aggatccgtt tatttaaaat ttctttaggt gtatttgctt gcatatggag    19140 tgcacatttta ctctcattaa tggagtttta ggaagcagta gagtaaatgc ataaacatgt    19200
atgaaccgcc atgtttaact ggaagcctgc atttggaagt caagtatcta atcttagatt    19260
aaattaggat ggggaaggat gttggcaaga gattttgaag cttgttctgc ttatattgag    19320
aacatcatag aacagtttgg ccttttttaaa gctagagaat agtgttgaat aagtgatgtt    19380
```

```
ccatatattc ctgtttgaca ttgacataaa ggtttcctca tgatacagta atccctgatc   19440
agggatctgg aagcctgtat tcatttaagg tactcaggtt taacatactg ggtgcttttc   19500
acaccatact atacagtacc atgcaaagtg cttttcaagac tgcaaatttg cttagatcc   19560 cctttagtga gctcctatgc tatagtaaag gtagatagcc aattattaaa aacagtcaag   19620
acaattgcac ctctaagcag tagtagcagt tgccacacca ccttgaatct tgaagtattt   19680
tcagcaacag gatgaccatt agccacaaat ttagtgtcag cccttaaggt cggtattggt   19740
ttgacccata ttttcatgta gttcttttc ttcacttgtc taatcttccc gtgtactgcc   19800
agggcttgtc attagaggac tttagggaga ccaagcaggc tagaaagtag agacaggaga   19860
tacctatgtc taatgcttca gtttatactt cctaggtttt tttcattggg gttttttgtaa   19920 ctcttttggt atcctaccgg tgctttggta gcctactgaa ccctgtcttt cttcttaagg   19980
acattctgag catgtgagac ctgaggactg caaacagcta aagaggctc caaattaatc    20040 atatctttcc ctttgagaat ctggccaagc tccagctaat ctacttggat gggttgccag   20100
ctatctggag aaaaaggtag tttggggaat ttattgttgt agtgcttctg tctttggatt   20160
gaacttccca caactctcct ttttaaagca gaacacagct gggcatggtg gctcctgctt   20220
gtaattccag ggctttggga ggttgaggtg gggggatcac ttgaggccag gagttgaaga   20280
cccatgtctc tacaataaaa taaaattagt tgggcatggt ggtacgtgcc tgtagtccta   20340
cctactctgg aggctgaggc agcaggattg cttgagccca ggagttcaag gctgcagtga   20400
gccatcatta gccactgcac tccagcctag gtggcagagc gggacccagt ctcttaaaaa   20460
gaaagaaaag cagaacgtga gccagttttc atcaattcct atacttttc ttttgcatgt    20520 acacatacat tttaacttta cataatgagt tcggcctgtt tcatttatcc ctcagagctg   20580
ggctccagtg aggtctgtaa gggcaagcat acttgatccc caatgaagaa tgagagatgc   20640
aaagcactaa attatttctt ttctcaccac acagcaagat agatttaatg aacttaacac   20700
cttttgatta gtggcctttt aaattattcc cactttcctt tggcagatgg gtattaagtt   20760
ctcaggattt gtttacaaat aagactaact tcatctgtat tagctcagtt ttggtaggcc   20820
taattccatt atcactgcca tttccttgtt ttaagaaatc aaaatttctt agcttgaaaa   20880
acaattgaaa ttgttaaaaa gtggaatagg agagccccgg gggcctgtat aaggaattta   20940
ctgaatccct ggttttctgt accttgtttt tccttctgca tagatttgct taactgtttt   21000
tgtggcgtgt atttttttt tttcgcagtt tcgctcttgt tgcccaggct ggagtgcaat    21060
ggcgcaatct cagctcactg caacctctgt ctcctgggtt caagttattc tcctgcctca   21120
gcctctcgag tagctgagat tacaggcatg cgcgaccacg ccaggctaat tttgtatttt   21180
tagtagagac ggggtttctc catgttggtc aggctggtct caaactcctg acctcaggtg   21240
attcacccgc ctcgacctcc caaactgctg ggattacagg cgtgagccac cacgcctggc   21300
cagctgttgt tataactgga gttctatgtg cttgtgacca ttcttggttt ctccgaatat   21360
cctagaactt tggtggcgcc ctattataca ggttgttgaa gaaatgttac catgtggatt   21420
gagtaggaaa caattctctt tatcttggca atattatggc atggcactac ttaaagtaca   21480
aattaaaaga gggggatgct acagaactag ctgacaggca ctttgataga ggtggatttc   21540
tcagttctta aaatagctct ttataaagga agccagaggc attgtggagg agaattctta   21600
cataactcat agggttagac cacatccgac cttttctgtg tggcttcatg gctctcttgg   21660
ttgagaaagc attagtttct ccttccatta gtttcaacct cttgatttct tgacccccct   21720
```

```
actatatttt gtgctgagaa cacaagggta ttaacaaccc acattgtaga ggatcgctca   21780
gtaataaaga ctggagaata aaatgcagca tgggaatatt ggcaattact cagttctaaa   21840
tttctcttgg aaatgaggga agcatacag aatagagctg gaatgaatag gataattttt   21900
tttttttttg ctaagttggt agccagaata taacagctcc gcacaactgt aaatgtccac   21960
tcttcaatcc acatgaagaa aagggtaaaa atatggttga actcaaccac tagttgccca   22020
ttagaacaga ctttcccagt gtactgcatt tcaatacttt ttcttttatc tcttttcaga   22080
tcttcctcag aagaataggc ttgttgtttt acagtgttag tgatccattc cctttgacga   22140
tccctaggtg gagatggggc atgaggatcc tccaggggaa aagctcacta ccactgggca   22200
acaaccctag gtcaggaggt tctgtcaaga tactttcctg gtcccagata ggaagataaa   22260
gtctcaaaaa caaccaccac acgtcaaggt gcgtaagctg tccctaaaag cataataagt   22320
agtcttaatt ttgattttgt tttccagtat acattgcact tagtgtttca ctgaggtcgt   22380
attcatcatt attctgcata tgatttggta aaaacagctt cctaactaac ctgggaagca   22440
actgggtgtg agattaactg gttaaagtga tgatgtaaag agggtagcgg gttgcatgtg   22500
ttcgggtgtt tggagtggga ctatagcacg tggcagaggc ttacagctaa gttgttcttt   22560
taggagaaca tggacaactg tcacatcagt gacattgatc acatgggcaa atcattctgt   22620
tccatgtggt ccccaaagtc tctcttaaag ccttacagaa gaactttgcc aatcatttac   22680
atacttcagg atggcttggg atgccatggt gtataataca acaagtgaga ggtgtgtctt   22740
tttatgctat ggttgctgat tgatggaagc cgcataaata caaatggaaa cctgactaaa   22800
aatggcacaa agttatctgt catcaggcag gagctaaaga accaggaccc tacattctct   22860
aggtcagtgt tgggagaggc tgattagcga gtgagaattg gcagataaag gtgaccattc   22920
ggtgcaataa atcctgaacg tataggcttt gcccagcatt cttcgtaaat agtgggtagc   22980
tataaatttc atgaaatatt ttcatgggta agaactcttg aaatgttata attgactaga   23040
aatctctgta gatttagaaa tagagagtta ctaacaaatt gttagaaagt ctaggaacta   23100
gaaagctaag ttgagagtta tctaggaaga tctatctatt gtactcataa tctttagata   23160
aattctccta gggccagtag tctatgtgaa ttttcttttt cttcttcttc ttcttctttt   23220
tttttgtatt ttagctgcaa tgttaaacaa cctatgtgaa ttttcttatt gtgagaatat   23280
ttgccttcca gagtgactca cctttatctc aaagagcaat attgtgagtt ttgaaaatgc   23340
tgctctaagg ctgtgttttg ttagtcctga gccaggagac ttaaagcaaa cttgaggggt   23400
cttaaaacat cgaagtgagc cttaaacatt gggaagacct tatgttttc cctctctcatat   23460 ctattatttt tgtgatctca gttattaatc atttaaaggg actctttcct agctgattgg   23520
cacttaaaac aggatggaag tctttttttt tttttttttt tttgagatgg agttttgctc   23580
ttgttgccca ggctggagtg caatggtgca atctcagctc actgcaacct ctgcctcccg   23640
ggttcaagcg attctcctgc ctcagcctcc caagtagctg ggattacagt catgcaccac   23700
cacgcccggc taatttttgta ttttttaatag agacggtgtt tctccatgtt ggtcaggctg   23760
gtctcaaact cctgacctca ggtgatccgc ccacctcaac ctcccaaagt gctgggatta   23820
tgggcgtgag ccaccgcgcc cggcagttct ggtctttaac taaggtataa ggctatgact   23880
ggtagtggtg tctctagtga ctcatcaagt gatatttggc aagacatttt cccatttatg   23940
ccagtttcct attctgttga atgaggaaat tttctctcta aagacctaaa agttttgact   24000
ttataggttt caaagttctg tggaaacatt ttcattgct tattaatttg aatcttatgt   24060
aactctagca cagtactcaa tatttatggc atttacatgg tttatctcat gttttttttat  24120
```

```
agctcttcat tgttcctatc tgccaaatca ttatacttcc tacaagcagt gcagagagct   24180
gagtcttcag caggtccaag aaatttgaac acactgaagg aagtcagcct tcccacctga   24240
agatcaacat gcctggcact ctagcacttg aggatagctg aatgaagtaa gttgttgatg   24300
ttgcagtcct gtgaggatca cttcagaact gttataacag ctgttttttg ggagctggtg   24360
ttggatgggg tgtgttggtc taatgtgaag tggggctaaa tgtgagatgg aaagatgacc   24420
agtcttccat attactgact gggttcactg aagcaactca aagacattat ggtcttctta   24480
ccagttgtat cacagaagaa tttagccttt gcttgtgtgt tctatgtctt cactgtatag   24540
gccctctgtc attcttagag ccttaaacgt tgagaagctt aaaacaccat ttctgctttc   24600
tgctgaaagg gtaaccctt ctcatctccg tttgtgagag actctgtcgt cagttaagat   24660
tagtgtaaaa agaaaactaa actctgaagt agccattata aaagtgtgag aatgaagtca   24720
gttttctaaa gagttgggga aaggtgatgc taaaggaggg gattgagcaa gtcctatcaa   24780
agagcctttt atgaaaatac ttagtcatct gtgacatccc atttggctct tccagaaaatc   24840 ctagtaaata gttgtaacag gatgttaaga ggcatacatt gtgtgtttta aatcctctgc   24900
tactcattag gtatatgacc tttgacaact taaagtctct agacttctct gtttgtgagg   24960
gttaaatgaa atcatgtatg taaagtgctc acctattgca gtgcctggca catgtcaagt   25020
aaaaggtaac ccaagaagac tcataagttc atttcccaca atataagtga ccactagcac   25080
tatcaggtag caggcagagt tggcatgctt tggttctatg taagaaatcc ctaaggtaaa   25140
agtttataaa tagaagagca tctgtgttgg tattggtggt tgttattatt gtagtactat   25200
aagtagtatt cgtagtaaca atagtttatt ataattacta atgacactt ttgattttt   25260 ttatctttct gtgatgcttt tcatgcctct tgtgccctc actgtatctt gcctcttcta   25320
ctacttactt cctctgaatg tctgccttg cttatctctt gcactcaagt gtgtatttct   25380
ttgtctcttt ctttcttgtc tttgctcttt gttctctatc taaagtgtgt cttacccatt   25440
tccatgtttc tcttgctaat ttctttcgtg tgtgcctttg cctcattttc tcttttttgtt   25500 cacaagagtg gtctgtgtct tgtcttagac atatctctca tttttcattt tgttgctatt   25560
tctctttgct ctcctagatg tggctcttct ttcacgcttt atttcatgtc tccttttttgg   25620 gtcacatgct gtgtgctttt tgtccttttc ttgttctgtc tacctctcct ttctctgcct   25680
acctctcttt tctctttgtg aactgtgatt atttgttacc ccttccctt ctcgttcgtt   25740 ttaaatttca ccttttttct gagtctggcc tcctttctgc tgtttctact ttttatctca   25800
catttctcat ttctgcattt cctttctgcc tctcttgggc tattctctct ctcctcccct   25860
gcgtgcctca gcatctcttg ctgtttgtga ttttctattt cagtattaat ctctgttggc   25920
ttgtatttgt tctctgcttc ttcccttct actcacctt tgagtatttca gcctcttcat   25980 gaatctatct ccctctcttt gatttcatgt aatctctcct taaatatttc tttgcatatg   26040
tgggcaagtg tacgtgtgtg tgtgtcatgt gtggcagagg ggcttcctaa cccctgcctg   26100
ataggtgcag aacgtcggct atcagagcaa gcattgtgga gcggttcctt atgccaggct   26160
gccatgtgag atgatccaag accaaaacaa ggccctagac tgcagtaaaa cccagaactc   26220
aagtagggca gaaggtggaa ggctcatatg gatagaaggc ccaaagtata agacagatgg   26280
tttgagactt gagacccgag gactaagatg gaaagcccat gttccaagat agatagaagc   26340
ctcaggcctg aaaccaacaa aagcctcaag agccaagaaa acagagggtg gcctgaattg   26400
gaccgaaggc ctgagttgga tggaagtctc aaggcttgag ttagaagtct taagacctgg   26460
```

```
gacaggacac atggaaggcc taagaactga gacttgtgac acaaggccaa cgacctaaga    26520
ttagcccagg gttgtagctg gaagacctac aacccaagga tggaaggccc ctgtcacaaa    26580
gcctacctag atggatagag gacccaagcg aaaaaggtat ctcaagacta acggccggaa    26640
tctggaggcc catgacccag aacccaggaa ggatagaagc ttgaagacct ggggaaatcc    26700
caagatgaga accctaaacc ctacctcttt tctattgttt acacttctta ctcttagata    26760
tttccagttc tcctgtttat ctttaagcct gattcttttg agatgtactt tttgatgttg    26820
ccggttacct ttagattgac agtattatgc ctgggccagt cttgagccag ctttaaatca    26880
cagcttttac ctatttgtta ggctatagtg ttttgtaaac ttctgtttct attcacatct    26940
tctccacttg agagagacac caaaatccag tcagtatcta atctggcttt tgttaacttc    27000
cctcaggagc agacattcat ataggtgata ctgtatttca gtcctttctt ttgaccccag    27060
aagccctaga ctgagaagat aaaatggtca ggttgttggg gaaaaaaaag tgccaggctc    27120
tctagagaaa aatgtgaaga gatgctccag gccaatgaga agaattagac aagaaataca    27180
cagatgtgcc agacttctga gaagcacctg ccagcaacag cttccttctt tgagcttagg    27240
tgagcaggat tctggggttt gggatttcta gtgatggtta tggaaagggt gactgtgcct    27300
gggacaaagc gaggtcccaa ggggacagcc tgaactccct gctcatagta gtggccaaat    27360
aatttggtgg actgtgccaa cgctactcct gggtttaata cccatctcta ggcttaaaga    27420
tgagagaacc tgggactgtt gagcatgttt aatactttcc ttgatttttt tcttcctgtt    27480
tatgtgggaa gttgatttaa atgactgata atgtgtatga aagcactgta aaacataaga    27540
gaaaaaccaa ttagtgtatt ggcaatcatg cagttaacat ttgaaagtgc agtgtaaatt    27600
gtgaagcatt atgtaaatca ggggtccaca gttttctgt aaggggtcaa atcataaata    27660
ctttagactg tgggccatat ggtttctgtt acatatttgt ttttaaaca acgttttttat    27720
aaggtcaaaa tcattcttag ttttttgagcc aattggattt ggcctgctgt tcatagctta    27780
ccaccccctg atgtattatt tgttattcag agaaaatttc tgaatactac tagttttcctt    27840
ttctgtgcct gtccctgtgc taggcactaa aaatgcaatg attattgata tctaggtgac    27900
ctgaaaaaaa atagtgaatg tgcttttgtaa actgtaaagc acttgtattc tactgtgata    27960
agcgttgtgg atacaaagaa aggagcaagc ataaaaagt gctcttttcaa aaggatatag    28020
tactatgcag acacaaggaa ttgtttgata atgaataaa ttatatgtat atttgaggcc    28080
aatttgtgtt tgctgctctg gtaattttga gtaaaaatgc agtattccag gtatcagaaa    28140
cgaaaacaca tggaaactgc tttaaacctt aaaatatac tgaaaacata agggactaag    28200
cttgttgtgg tcacctataa tgtgccagat accatgctgg gtgctagagc taccaaaggg    28260
ggaaaagtat tctcatagaa caaaaaattt cagaaaggtg catattaaag tgctttgtaa    28320
actaaagcat gatacaaatg tcaatgggct acatatttat gaatgaatga atggatgaat    28380
gaatattaag tgcctcttac ataccagcta tttttgggtac tgtaaaatac aagattaatt    28440
ctcctatgta ataagaggaa agtttatcct ctatactatt cagatgtaag gaatgatata    28500
ttgcttaatt ttaaacaatc aagactttac tggtgaggtt aagttaaatt attactgata    28560
catttttcca ggtaaccagg aaagagctag tatgaggaaa tgaagtaata gatgtgagat    28620
ccagaccgaa agtcacttaa ttcagcttgc gaatgtgctt tctaaattat aaagcacttg    28680
taaatgaaaa atttgatgct ttctgtatga ataaaacttt ctgtaagcta ggtattgtct    28740
ctacaaaatt ctcattgtat agttaaacca cagtgagaag ggttctataa gtagttatac    28800
aaaccaaggg tttaaatacc tgttaaatag atcaatttttg attgcctact atgtgaactc    28860
```

```
actgttaaag gcactgaaaa tttatcatat ttcatttagc cacagccaaa aataaggcaa    28920
tacctatgtt agcattttgt gaactctaag gcaccatata aatgtaactg ttgattttct    28980
cacttggtgc tgggtactag gtttataaaa ttgtatgata gttattatat tgtgcaaata    29040
aagtaggaaa atttgaataa caatgattat cttttgaata cgcatacgca agggattggt    29100
tgtctgaaga atgccactat agtagttatc tattgtgtgc caatctcatt gctaggcatt    29160
ggggatgcaa agataaacca tctttattgt gtcttgggta gcagaagaaa atatgtgtaa    29220
aatcaattta aatttgtaa actgccaccc atatataagc tatatctgct gaatgatcat    29280
tgattactct tatccttaga gataacaact gggggcacaa acatttatta tcattattga    29340
acctacaaca gagatctatg tgtagattta caaagcctac agttctatac agataggaat    29400
gaactattgg cttactgaat ggtgattact ttctgtgggg ctcggaacta catgccctag    29460
gatataaaaa tgatgttatc attatagagt gctcacagaa ggaaatgaag taatataggt    29520
gtgagatcca gaccaaaagt catttaacaa gtttattcag tgatgaaaac atgggacaaa    29580
tggactaata taaggcagtg tactaagctg agtagagaga taaagtcctg tccagaagat    29640
acatgcttcc tggcctgatt gaggagatgg aaaattttttg caaaaaacaa ggtgttgtgg    29700
tcttccatcc agtttcttaa gtgctgatga taaaagtgaa ttagacccac cttgacctgg    29760
cctacagaag taaaggagta aaaataaatg cctcaggcgt gctttttgat tcatttgata    29820
aacaaagcat cttttatgtg gaatatacca ttctgggtcc tgaggataag agagatgagg    29880
gcattagatc actgacagct gaagatagaa gaacatcttt ggtttgattg tttaaataat    29940
atttcaatgc ctattctctg caaggtacta tgtttcgtaa attaaatagg tctggcccag    30000
aagacccact caattgcctt tgagattaaa aaaaaaaaaa aaagaaaga aaatgcaag     30060 tttcttcaa aataaagaga cattttttcct agtttcagga atccccaaa tcacttcctc    30120 attggcttag tttaaagcca ggagactgat aaaagggctc agggtttgtt ctttaattca    30180
ttaactaaac attctgcttt tattacagtt aaatggttca agatgtaaca actagttta    30240 aaggtatttg ctcattggtc tggcttagag acaggaagac atatgagcaa taaaaaaaag    30300
attcttttgc atttaccaat ttagtaaaaa tttattaaaa ctgaataaag tgctgttctt    30360
aagtgcttga aagacgtaaa ccaaagtgca ctttatctca tttatcttat ggtggaaaca    30420
caggaacaaa ttctctaaga gactgtgttt ctttagttga gaagaaactt cattgagtag    30480
ctgtgatatg ttcgatacta aggaaaaact aaacagatca cctttgacat gcgttgtaga    30540
gtgggaataa gagagggctt tttattttttt cgttcatacg agtattgatg aagatgatac    30600
taaatgctaa atgaaatata tctgctccaa aaggcattta ttctgacttg gagatgcaac    30660
aaaaacacaa aaatggaatg aagtgatact cttcatcaaa cagaagtgac tgttatctca    30720
accattttgt taaatcctaa acagaaaaca aaaaaaatca tgacgaaaag acacttgctt    30780
attaattggc ttggaaagta gaatatagga gaaaggttac tgtttatttt ttttcatgta    30840
ttcattcatt ctacaaatat attcgggtgc caataggtac ttggtataag gttttggcc    30900 ccagagacat gggaaaaaaa tgcatgcctt cccagagaat gcctaatact ttccttttgg    30960
cttgttttct tgttaggggc atggcttagt ccctaaataa cattgtgtgg tttaattcct    31020
actccgtatc tcttctacca ctctggccac tacgataagc aggtagctgg gttttgtagt    31080
gagcttgctc cttaagttac aggaactctc cttataatag acacttcatt ttcctagtcc    31140
atccctcatg aaaaatgact gaccactgct gggcagcagg agggatgatg accaactaat    31200
```

```
tcccaaaccc cagtctcatt ggtaccagcc ttggggaacc acctacactt gagccacaat    31260
tggttttgaa gtgcatttac aaggtttgtc tattttcagt tctttacttt ttacatgctg    31320
acacatacat acactgccta aatagatctc tttcagaaac aatcctcaga taacgcatag    31380
caaaatggag atggagacat gatttctcat gcaacagctt ctctaattat accttagaaa    31440
tgttctcctt tttatcatca aatctgctca agaagggct tttatagtag aataatatca     31500
gtggatgaaa acagcttaac attttaccat gcttaagttt taagaataaa ataaaaattg    31560
gaaataattg gccaaaattg aaaggaaaaa ttttttaaa atttctctaa atgtaggcct     31620
ggctgggctt tgacctttc cgttttaaa tcactcacag agggtgggac aggaggaaga      31680
gtgaaggaaa aggtcaaacc tgttttaagg gcaacctgcc tttgttctga attggtctta    31740
agaacattac cagctccagg tttaaattgt tcagtttcat gcagttccaa tagctgatca    31800
ttgttgagat gaggacaaaa tcctttgtcc tcactagttt gctttacatt tttgaaaagt    31860 attattttg tccaagtgct tatcaactaa accttgtgtt aggtaagaat ggaatttatt     31920
aagtgaatca gtgtgaccct tcttgtcata agattatctt aaagctgaag ccaaaatatg    31980
cttcaaaaga agaggacttt attgttcatt gtagttcata cattcaaagc atctgaactg    32040
tagtttctat agcaagccaa ttacatccat aagtggagaa ggaaatagat aaatgtcaaa    32100
gtatgattgg tggagggagc aaggttgaag ataatctggg gttgaaattt tctagttttc    32160
attctgtaca tttttagtta gacatcagat ttgaaatatt aatgtttacc tttcaatgtg    32220
tggtatcagc tggactcagt aacacccctt tcttcagctg gggatgggga atggattatt    32280
ggaaaatgga agaagaaag taactaaaag ccttcctttc acagtttctg gcatcactac      32340
cactactgat taaacaagaa taagagaaca ttttatcatc atctgcttta ttcacataaa    32400
tgaagttgtg atgaataaat ctgcttttat gcagacacaa ggaattaagt ggcttcgtca    32460
ttgtccttct acctcaaaga taatttattc caaaagctaa gataaatgga agactcttga    32520
acttgtgaac tgatgtgaaa tgcagaatct cttttgagtc tttgctgttt ggaagattga    32580
aaaatattgt tcagcatggg tgaccaccag aaagtaatct taagccatct agatgtcaca    32640
attgaaacaa actggggagt tggttgctat tgtaaaataa aatatactgt tttgaaaact    32700
ttgtattttg atgtgacaat ttctaactca ctgtccctaa ccacactaat taccgtaagt    32760
tcttcatttc ttttttcttt ttcttttta attaataaat taatttattt tttggagatg    32820
gagtctcgct tgttgccca ggctggagtg cagtggtgcc atcttggctc actgtaacct      32880
ctgcctcctg ggttcaagcg attctcctgc ctcagcctca ccagtagctg ggattacagt    32940
catgagccac catgcctggc taatggttgt attttagta gagacggggt tttgccatgt      33000
tggccaggct ggtcacgaac tcctgactta aagtgaaaca cctgcctcgg cctcccaaag    33060
ttctgggatt acaggcggga gccaccgtgc ctggcctcat ttctttttt aaactacctt     33120 aatcacccag tgtgggtaaa tggtttgaag tctcatttct tacagcatca gttgctttgg    33180
tcaaggatac tgagaagcac aaacccagta aaaaatgtga gaagcaaaaa acttgaggat    33240
caaaagtggg agaggagaag ggtataaact gtaaggctgt gggaattaag cattcatgaa    33300
aga                                                                   33303
```

METHODS FOR REACTIVATING GENES ON THE INACTIVE X CHROMOSOME

CLAIM OF PRIORITY

This application is a U.S. National Phase Application under 35 U.S.C. § 371 of International Patent Application No. PCT/US2016/026218, filed on Apr. 6, 2016, which claims the benefit of U.S. Patent Application Ser. Nos. 62/144,219, filed on Apr. 7, 2015; 62/168,528, filed on May 29, 2015; and 62/181,083, filed on Jun. 17, 2015. The entire contents of the foregoing are hereby incorporated by reference.

FEDERALLY SPONSORED RESEARCH OR DEVELOPMENT

This invention was made with Government support under Grant Nos. R01-DA-38695 and R03-MH97478 awarded by the National Institutes of Health. The Government has certain rights in the invention.

TECHNICAL FIELD

Described herein are methods for reactivating genes on the inactive X chromosome that include administering one or both of a DNA methyltransferase (DNMT) Inhibitor and/or a topoisomerase inhibitor, e.g., etoposide and/or 5'-azacytidine (aza), optionally in combination with an inhibitor of Xist RNA and/or an Xist-interacting protein, e.g., a chromatin-modifying protein, e.g., a small molecule or a nucleic acid such as a small inhibitory RNA (siRNAs), e.g., an antisense oligonucleotide (ASO), e.g., locked nucleic acid (LNA), that targets Xist RNA and/or a gene encoding an Xist-interacting protein, e.g., a chromatin-modifying protein.

BACKGROUND

X chromosome inactivation (XCI) achieves dosage balance in mammals by repressing one of two X chromosomes in females. X-linked diseases occur in both males and females. In males, X-linked mutations result in disease because males carry only one X-chromosome. In females, disease occurs when a defective gene is present on the active X chromosome (Xa). In some cases, a normal, wild type copy of the gene is present on the inactive X chromosome (Xi), and the severity of the disease may depend on the prevalence (skewing) of inactivation of the X chromosome carrying the wild type gene. The invention described herein may be utilized to treat both male and female X-linked disease. In both females and males, upregulation of a hypomorphic or epigenetically silenced allele may alleviate disease phenotype, such as in Fragile X Syndrome. In females, reactivating a non-disease silent allele on the Xi would be therapeutic in many cases of X-linked disease, such as Rett Syndrome.

SUMMARY

Provided herein are methods and compositions for reactivating genes on the inactive or active X chromosome.

Provided herein are compositions comprising a DNMT Inhibitor and/or topoisomerase inhibitor, and optionally an inhibitor of Xist RNA and/or an Xist-interacting protein.

Also provided herein are methods for activating an inactive X-linked allele in a cell, preferably a cell of a female heterozygous subject or a male hemizygous subject. The methods include administering to the cell (i) one or both of a DNA methyltransferase (DNMT) Inhibitor and/or a topoisomerase inhibitor; and optionally (ii) an inhibitor of Xist RNA and/or an Xist-interacting protein. As used herein, "an inhibitor of an Xist-interacting protein" can include one or more inhibitors, e.g., one or more small molecules or inhibitory nucleic acids. As used herein, "an inhibitor of Xist RNA" can include one or more inhibitors, e.g., one or more small molecules or inhibitory nucleic acids, e.g., an antisense oligonucleotide (ASO), e.g., locked nucleic acid (LNA), that target XIST RNA or a gene encoding XIST RNA.

In addition, provided herein are methods for activating an epigenetically silenced or hypomorphic allele on the active X-chromosome, e.g., FMRI, in a cell, e.g., in a cell of a male or female heterozygous subject. The methods include administering to the cell (i) one or both of a DNA methyltransferase (DNMT) Inhibitor and/or a topoisomerase inhibitor; and optionally (ii) an inhibitor of Xist RNA and/or an Xist-interacting protein.

Also provided here are a DNMT Inhibitor and/or topoisomerase inhibitor, and optionally an inhibitor of Xist and/or an Xist-interacting protein, for use in activating an inactive X-linked allele in a cell, preferably a cell of a female heterozygous subject, preferably wherein the inactive X-linked allele is associated with an X-linked disorder.

Also provided here are a DNMT Inhibitor and/or topoisomerase inhibitor, and optionally an inhibitor of Xist RNA and/or an Xist-interacting protein, for use in activating an epigenetically silenced or hypomorphic allele on the active X chromosome in a cell, either in a female heterozygous or male hemizygous subject, preferably wherein the active X-linked allele is associated with an X-linked disorder.

Also provided here are a DNMT Inhibitor and/or topoisomerase inhibitor, and optionally an inhibitor of Xist RNA and/or an Xist-interacting protein, for use in treating an X-linked disorder in a female heterozygous or male hemizygous subject.

In some embodiments of the methods or compositions described herein, the inhibitor of Xist RNA is an inhibitory nucleic acid that targets the Xist lncRNA, e.g., e.g., an antisense oligonucleotide (ASO), e.g., locked nucleic acid (LNA), or that targets a gene encoding XIST.

In some embodiments of the methods or compositions described herein, the inhibitor of an Xist-interacting protein inhibits a protein described herein, e.g., shown in Tables 5 or 6 or 7, e.g., SMC1a; SMC3; WAPL, RAD21; KIF4; PDS5a/b; CTCF; TOP1; TOP2a; TOP2b; SMARCA4 (BRG1); SMARCA5; SMARCC1; SMARCC2; SMARCB1; RING1a/b (PRC1); PRC2 (EZH2, SUZ12, RBBP7, RBBP4, EED); AURKB; SPEN/MINT/SHARP; DNMT1; SmcHD1; CTCF; MYEF2; ELAV1; SUN2; Lamin-B Receptor (LBR); LAP; hnRPU/SAF-A; hnRPK; hnRPC; PTBP2; RALY; MATRIN3; MacroH2A; and ATRX.

In some embodiments of the methods or compositions described herein, the inhibitor of an Xist-interacting protein is a small molecule inhibitor or an inhibitory nucleic acid that targets a gene encoding the Xist-interacting protein. In some embodiments, the inhibitor of an Xist-interacting protein is a small molecule inhibitor of cohesin or a cohesin subunit, e.g., a small molecule inhibitor of ECO-I or HDAC6, e.g., PCI34051, tubacin, apicidin, MS275, TSA, or saha.

In some embodiments of the methods or compositions described herein, the inactive X-linked allele is associated with an X-linked disorder, and the DNMT Inhibitor and/or topoisomerase inhibitor, and the optional inhibitor of Xist RNA and/or Xist-interacting protein, are administered in a therapeutically effective amount.

In some embodiments of the methods or compositions described herein, the active X-linked allele is associated with an X-linked disorder, and the DNMT Inhibitor and/or topoisomerase inhibitor, and the optional inhibitor of Xist RNA and/or Xist-interacting protein, are administered in a therapeutically effective amount.

In some embodiments of the methods described herein, the cell is in a living subject.

In some embodiments, the methods described herein optionally include administering (iii) one or more of an inhibitory nucleic acid targeting a strong or moderate RNA-binding protein binding site on the X chromosome, i.e., complementary or identical to a region within a strong or moderate RNA-binding protein site, and/or an inhibitory nucleic acid targeting (i.e., complementary to) a suppressive RNA (supRNA) associated with the X-linked allele.

In some embodiments, the compositions described herein optionally include (iii) one or more of: an inhibitory nucleic acid targeting a strong or moderate RNA-binding protein binding site on the X chromosome, i.e., complementary or identical to a region within a strong or moderate RNA-binding protein site, and/or an inhibitory nucleic acid targeting (i.e., complementary to) a suppressive RNA (supRNA) associated with the X-linked allele.

In some embodiments of the methods or compositions described herein, the inhibitory nucleic acid is identical or complementary to at least 8 consecutive nucleotides of a strong or moderate binding site nucleotide sequence as set forth in Tables A, IVA-C, or XIII-XV of WO 2014/025887 or Table 1 of U.S. Ser. No. 62/010,342, or complementary to at least 8 consecutive nucleotides of a supRNAs as set forth in Tables VI-IX or XVI-XVIII of WO 2014/025887.

In some embodiments of the methods or compositions described herein, the inhibitory nucleic acid does not comprise three or more consecutive guanosine nucleotides or does not comprise four or more consecutive guanosine nucleotides.

In some embodiments of the methods or compositions described herein, the inhibitory nucleic acid is 8 to 30 nucleotides in length.

In some embodiments of the methods or compositions described herein, at least one nucleotide of the inhibitory nucleic acid is a nucleotide analogue.

In some embodiments of the methods or compositions described herein, at least one nucleotide of the inhibitory nucleic acid comprises a 2' O-methyl, e.g., wherein each nucleotide of the inhibitory nucleic acid comprises a 2' O-methyl.

In some embodiments of the methods or compositions described herein, the inhibitory nucleic acid comprises at least one ribonucleotide, at least one deoxyribonucleotide, or at least one bridged nucleotide.

In some embodiments of the methods or compositions described herein, the bridged nucleotide is a LNA nucleotide, a cEt nucleotide or a ENA modified nucleotide.

In some embodiments of the methods or compositions described herein, each nucleotide of the inhibitory nucleic acid is a LNA nucleotide.

In some embodiments of the methods or compositions described herein, one or more of the nucleotides of the inhibitory nucleic acid comprise 2'-fluoro-deoxyribonucleotides and/or 2'-O-methyl nucleotides.

In some embodiments of the methods or compositions described herein, one or more of the nucleotides of the inhibitory nucleic acid comprise one of both of ENA nucleotide analogues or LNA nucleotides.

In some embodiments of the methods or compositions described herein, the nucleotides of the inhibitory nucleic acid comprise comprising phosphorothioate internucleotide linkages between at least two nucleotides, or between all nucleotides.

In some embodiments of the methods or compositions described herein, the inhibitory nucleic acid is a gapmer or a mixmer.

Also provided herein are methods for identifying proteins that interact with a selected nucleic acid, e.g., an RNA such as an supRNA. The methods include providing a sample comprising a living cell expressing the selected nucleic acid; exposing the living cell to ultraviolet radiation sufficient to crosslink proteins to DNA, to provide protein-DNA complexes; optionally isolating a nucleus from the cell; treating the isolated nucleus with DNase, e.g., DNase I; solubilizing chromatin in the nucleus; contacting the DNA-protein complexes with capture probes specific for the selected nucleic acid, treating the DNA-protein complexes with DNase, e.g., DNase I, and isolating the DNA-protein complexes from the sample using the capture probes.

In some embodiments, the capture probes comprise a sequence that hybridizes specifically to the selected nucleic acid, and an isolation moiety. In some embodiments, the isolation moiety is biotin, and isolating the DNA-protein complexes comprises contacting the sample with streptavidin or avidin, e.g., bound to a surface, e.g., bound to a bead (e.g., a magnetic bead). In some embodiments, the methods include washing the sample comprising DNA-protein complexes to eliminate protein factors covalently linked by UV to the selected nucleic acid.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-E: De-repression of Xi genes by targeting Xist interactors.
(A) Relative GFP levels determined by RT-qPCR analysis in female fibroblasts stably knocked down for indicated Xist interactors, with or without 0.3 µM 5'-azacytidine (aza) and/or etoposide (eto). Xa-GFP, control X-linked GFP expression from male fibroblasts. Mean±SE of two independent experiments shown. P, determined by Student t-test.
(B) Allele-specific RNA-seq analysis: Number of unregulated Xi genes (range: 2×-250×)(Log 2 fold-change 2-8) for each indicated triple-drug treatment (aza+eto+shRNA). Blue, genes specifically reactivated on Xi (fold-change, FC>2); red, genes also unregulated on Xa (FC>1.3).
(C) RNA-seq heat map indicating that a large number of genes on the Xi were reactivated. X-linked genes reactivated in at least one of the triple-drug treatment (aza+eto+shRNA) were shown in the heat map. Color key, Log 2 fold-change (FC). Cluster analysis performed based on similarity of KD profiles (across) and on the sensitivity and selectivity of various genes to reactivation (down).
(D) Chromosomal locations of Xi reactivated genes for each triple-drug treatment (aza+eto+indicated shRNA). Positions of representative Refseq genes shown at the top. Reactivated genes shown as ticks in each track.
(E) Read coverage of 4 representative reactivated Xi genes after various triple-drug treatments. Xi, mus reads (scale: 0-2). Comp, total reads (scale: 0-6). Reactivation can be appreciated when comparing shControl to various shRNA KDs (Red tags appear only in exons with SNPs).

FIGS. 4A-H: Ablating Xist in cis restores cohesin binding on the Xi.
(A) Allele-specific ChIP-seq results: Violin plots of allelic skew for CTCF, RAD21, SMC1a in wild-type (WT) and $Xi^{\Delta Xist}/Xa^{WT}$ (ΔXist) fibroblasts. Fraction of mus reads [mus/(mus+cas)] is plotted for every peak with ≥10 allelic reads. P values determined by the (KS) test.
(B) Differences between SMC1a or RAD21 peaks on the $Xi^{WT}$ versus $Xa^{WT}$. Black diagonal, 1:1 ratio. Plotted are read counts for all SMC1a or RAD21 peaks. Allele-specific skewing is defined as ≥3-fold skew towards either Xa (cas, blue dots) or Xi (mus, red dots). Biallelic peaks, grey dots.
(C) Table of total, Xa-specific, and Xi-specific cohesin binding sites in WT versus ΔXist ($Xi^{\Delta Xist}/Xa^{WT}$) cells. Significant SMC1a and RAD21 allelic peaks with ≥5 reads were analyzed. Allele-specific skewing is defined as ≥3-fold skew towards Xa or Xi. Sites were considered "restored" if $Xi^{\Delta Xist}$'s read counts were ≥50% of Xa's. X-total, all X-linked binding sites. Allelic peaks, sites with allelic information. Xa-total, all Xa sites. Xi-total, all sites. Xa-spec, Xa-specific. Xi-spec, Xi-specific. Xi-invariant, Xi-specific in both WT and $Xi^{\Delta Xist}/Xa^{WT}$ cells. Note: There is a net gain of 96 sites on the Xi in the mutant, a number different from the number of restored sites (106). This difference is due to defining restored peaks separately from calling ChIP peaks (macs2). Allele-specific skewing is defined as ≥3-fold skew towards either Xa or Xi.
(D) Partial restoration of SMC1a or RAD21 peaks on the $Xi^{\Delta Xist}$ to an Xa-like pattern. Plotted are peaks with read counts with ≥3-fold skew to $Xa^{WT}$ ("Xa-specific"). x-axis, normalized $Xa^{WT}$ read counts. y-axis, normalized $Xi^{\Delta Xist}$ read counts. Black diagonal, 1:1 $Xi^{\Delta Xist}/Xa^{WT}$ ratio; red diagonal, 1:2 ratio.
(E) Xi-specific SMC1a or RAD21 peaks remained on $Xi^{\Delta Xist}$. Black diagonal, 1:1 ratio. Plotted are read counts for SMC1a or RAD21 peaks with ≥3-fold skew to $Xi^{WT}$ ("Xi-specific peaks").
(F) Comparison of fold-changes for CTCF, RAD21, and SMC1 binding in $X^{\Delta Xist}$ cells relative to WT cells. Shown are fold-changes for Xi versus Xa. The Xi showed significant gains in RAD21 and SMC1a binding, but not in CTCF binding. Method: $X^{WT}$ and $X^{\Delta Xist}$ ChIP samples were normalized by scaling to equal read counts. Fold-changes for Xi were computed by dividing the normalized mus read count in $X^{\Delta Xist}$ by the mus read count $X^{WT}$; fold-changes for Xa were computed by dividing the normalized cas read count in $Xi^{\Delta Xist}$ by the cas read count $X^{WT}$. To eliminate noise, peaks with <10 allelic reads were eliminated from analysis. P values determined by a paired Wilcoxon signed rank test.
(G) The representative examples of cohesion restoration on $Xi^{\Delta Xist}$. ChIP-seq peaks were called by MACS2 software with default settings. Arrowheads, restored peaks.
(H) Allelic-specific cohesin binding profiles of Xa, $Xi^{WT}$, and $Xi^{\Delta Xist}$. Shown below restored sites are regions of Xi-reactivation following shSMC1a and shRAD21 combination-drug treatments, as defined in FIG. 3.

(B) Allele-specific HiC-seq analysis: Contact maps for three different ChrX regions at 100-kb resolution comparing $Xi^{\Delta Xist}$ (red) to the Xi of WT cells ($Xi^{WT}$; orange), and $Xi^{\Delta Xist}$ (red) versus the Xa (blue) of the mutant cell line. Our Xa TAD calls are shown with RefSeq genes.

(C) Fraction of interaction frequency per TAD on the Xi (mus) chromosome. The positions of TAD borders were rounded to the nearest 100 kb and submatrices were generated from all pixels between the two endpoints of the TAD border for each TAD. We calculated the average interaction score for each TAD by summing the interaction scores for all pixels in the submatrix defined by a TAD and dividing by the total number of pixels in the TAD. We then averaged the normalized interaction scores across all bins in a TAD in the Xi (mus) and Xa (cas) contact maps, and computed the fraction of averaged interaction scores from mus chromosomes. ChrX and a representative autosome, Chr5, are shown for the WT cell line and the $Xi^{\Delta Xist}/+$ cell line. P value determined by paired Wilcoxon signed rank test.

(D) Violin plots showing that TADs overlapping restored peaks have larger increases in interaction scores relative to all other TADs. We calculated the fold-change in average interaction scores on the Xi for all X-linked TADs and intersected the TADs with SMC1a sites ($Xi^{\Delta Xist}/Xi^{WT}$). 32 TADs occurred at restored cohesin sites; 80 TADs did not overlap restored cohesin sites. Violin plot shows distributions of fold-change average interaction scores between $Xi^{WT}$ and $Xi^{\Delta Xist}$. p-value determined by Wilcoxon ranked sum test.

(E) Restored TADs overlap regions with restored cohesins on across $Xi^{\Delta Xist}$. Several datasets were used to call restored TADs, each producing similar results. Restored TADs were called in two separate replicates (Rep1, Rep2) where the average interaction score was significantly higher on $Xi^{\Delta Xist}$ than on $Xi^{WT}$. We also called restored TADs based on merged Rep1+Rep2 datasets. Finally, a consensus between Rep1 and Rep2 was derived. Method: We calculated the fold-change in mus or cas for all TADs on ChrX and on a control, Chr5; then defined a threshold for significant changes based on either the autosomes or the Xa. We treated Chr5 as a null distribution (few changes expected on autosomes) and found the fraction of TADs that crossed the threshold for several thresholds. These fractions corresponded to a false discovery rate (FDR) for each given threshold. An FDR of 0.05 was used.

Figure 6:
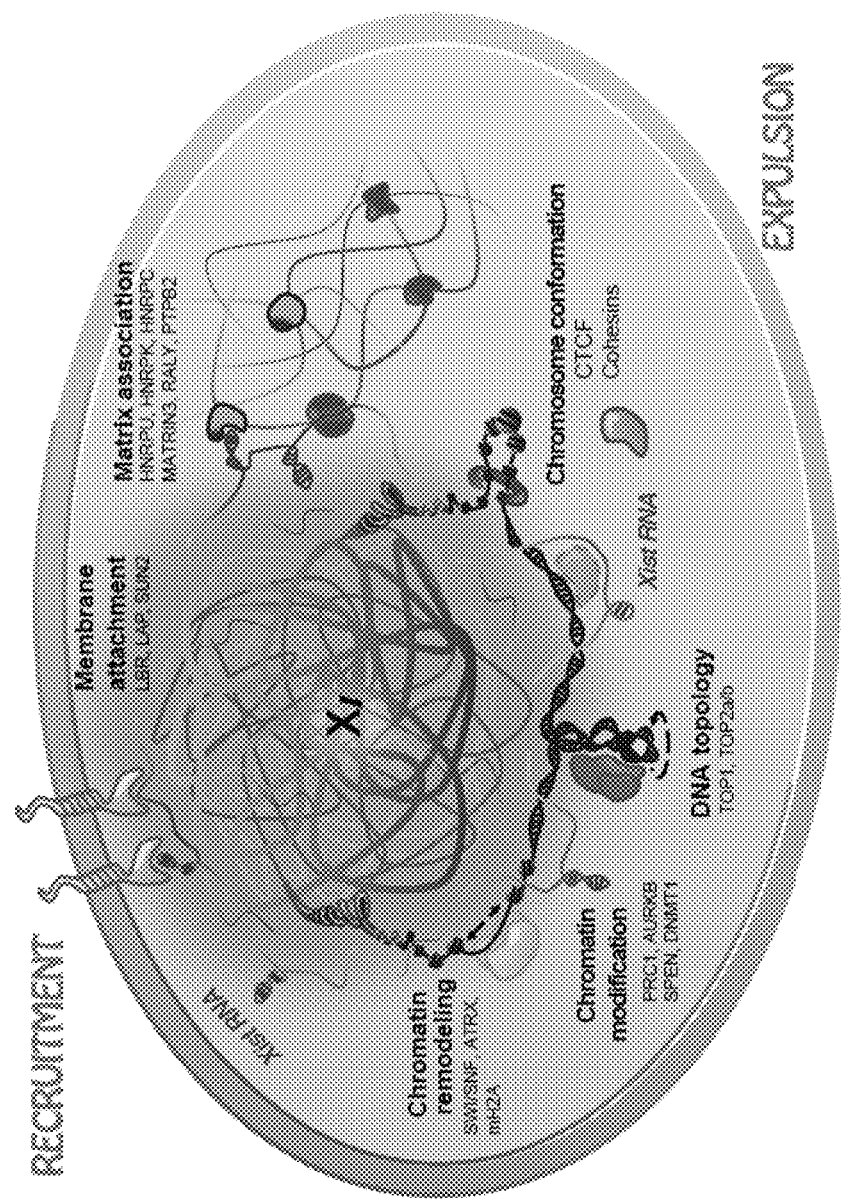

FIG. 6: The Xi is suppressed by multiple synergistic mechanisms.

Xist RNA (red) suppresses the Xi by either recruiting repressive factors (e.g., Polycomb complexes PRC1, PRC2) or expelling architectural factors (e.g., cohesins).

Figure 7:
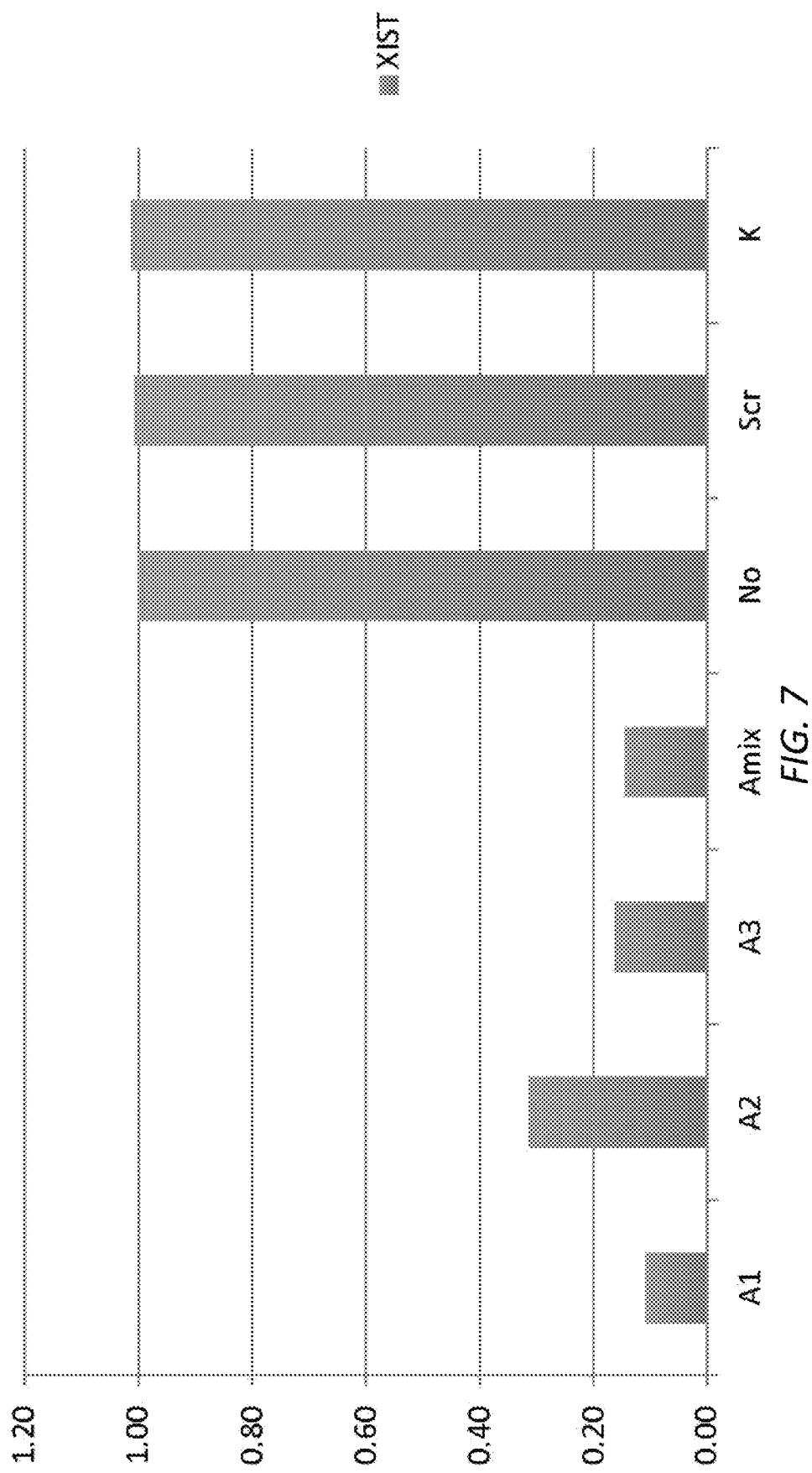

FIG. 7. Xist knockdown with LNA. Knockdown of XIST was achieved using one of three gapmers, or a combination of all three. No=no LNA control, Scr=Scramble, K=mixmer, A1-A3=3 gapmers, Amix=3 gapmers combined, all at 20 nM FIGS. 8A-B. Luciferase and GFP Controls. Bar graphs showing reactivation of Mecp2 on the Xi, measured by luciferase or GFP reporter levels, after treatment with Aza plus a control LNA or Aza plus a LNA targeting XIST. The MEF cells carried either an Mecp2:luciferase fusion or an Mecp2:GFP fusion.

Figure 9:
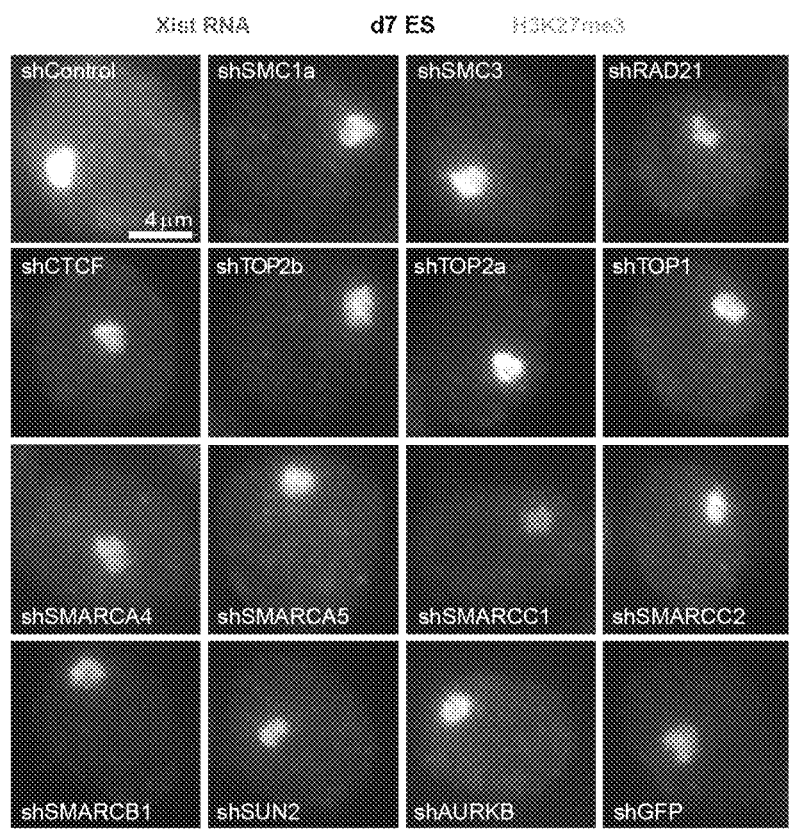

FIG. 9. The microscopic images of knock down day 7 ESCs.

The stable knock down embryonic stem cells (ESCs) were differentiated after the withdrawal of LIF for seven days. On day 4, the cells were plated on the gelatin coated coverslips until day 7 of differentiation. The coverslips were prepared for immunoFISH, as described in methods, followed by imaging for Xi markers, Xist (Red) and H3K27me3 (Green).

Figure 10A:
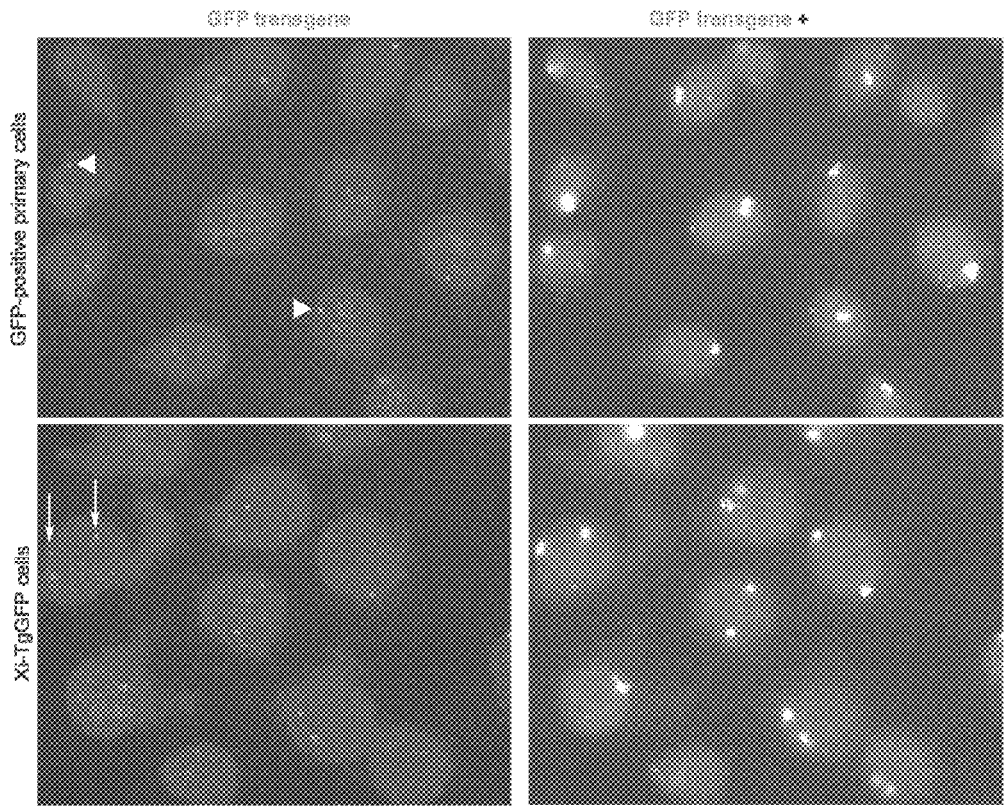

FIGS. 10A-B. Confirmation that the GFP transgene of Xi-TgGFP cells is on the inactive X.

(A) Fluorescent In Situ Hybridization (FISH) indicates the location of the GFP transgene (DNA FISH, red) relative to the inactive X (characterized by a cloud of Xist RNA, identified by RNA FISH in green). In primary fibroblasts selected for high GFP expression (top panels), the transgene is on the active X and does not colocalize with the inactive X (examples indicated by white arrowheads). However, in Xi-TgGFP cells the GPF transgene does colocalize with the inactive X (bottom panels, arrowheads indicate one cell as an example. Xi-TgGFP cells are tetraploid; thus two inactive X chromosomes are seen per cell).

(B) Allele-specific expression of the X-linked gene Mecp2 shown by RT-PCR. Hybrid Xi-TgGFP cells have one *M. musculus* (mus) X chromosome with the GFP transgene, and one *M. castaneus* (cas) X. A mus-cas single nucleotide polymorphism is detected by Dde I digest, yielding a 179-bp band for expression from the cas allele, or a 140-bp band for expression from the mus allele. A 200-bp band is common to both alleles. Only the expected cas allele of Mecp2 is expressed in Xi-TgGFP cells (lanes 1, 2, 5), as for purely cas cells (lanes 3, 4, 6), and in contrast to cells of a pure mus background (lane 8), or from a non-clonal hybrid cell population with expression from both alleles (lane 7).

FIGS. 11A-B. Xi reactivation by inhibiting single versus multiple Xist interactors.

(A) Quantitative RT-PCR demonstrated that shRNA knockdown of single Xist interactors resulted in a maximum of 4-fold GFP upregulation.

(B) Biological replicates for allele-specific RNA-seq analysis: Number of upregulated Xi genes for triple-drug treated cells (aza+eto+shRNA). Blue, genes specifically reactivated on Xi; red, genes also upregulated on Xa. There was a net increase in expression level (ΔFPKM) from the Xi in the triple-drug treated samples relative to the shControl+aza+eto, whereas the Xa and autosomes showed no obvious net increase, thereby suggesting direct effects on the Xi as a result of disrupting the Xist interactome. X-reactivation can be observed in various cell types, including proliferating fibroblasts and post-mitotic neurons.

Figure 12:
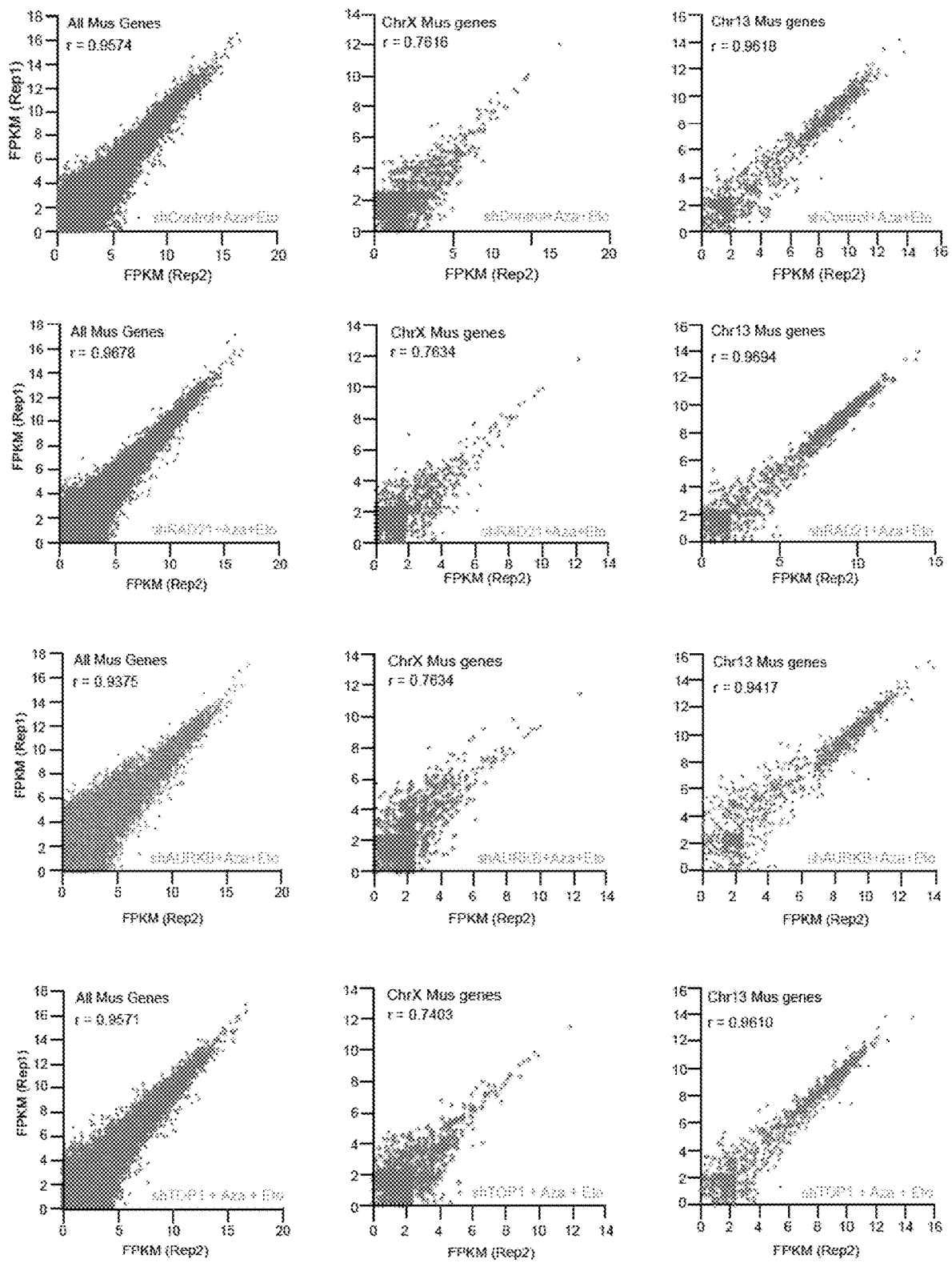

FIG. 12. Correlations between biological replicates for allelic-specific RNA-seq analysis.

Shown are allelic (mus) FPKM values for replicate 1 (Rep1) and replicate 2 (Rep2) for indicated triple-drug treatment (orange text) for all genes, Xi genes, and Chr13 genes.

Figure 13:
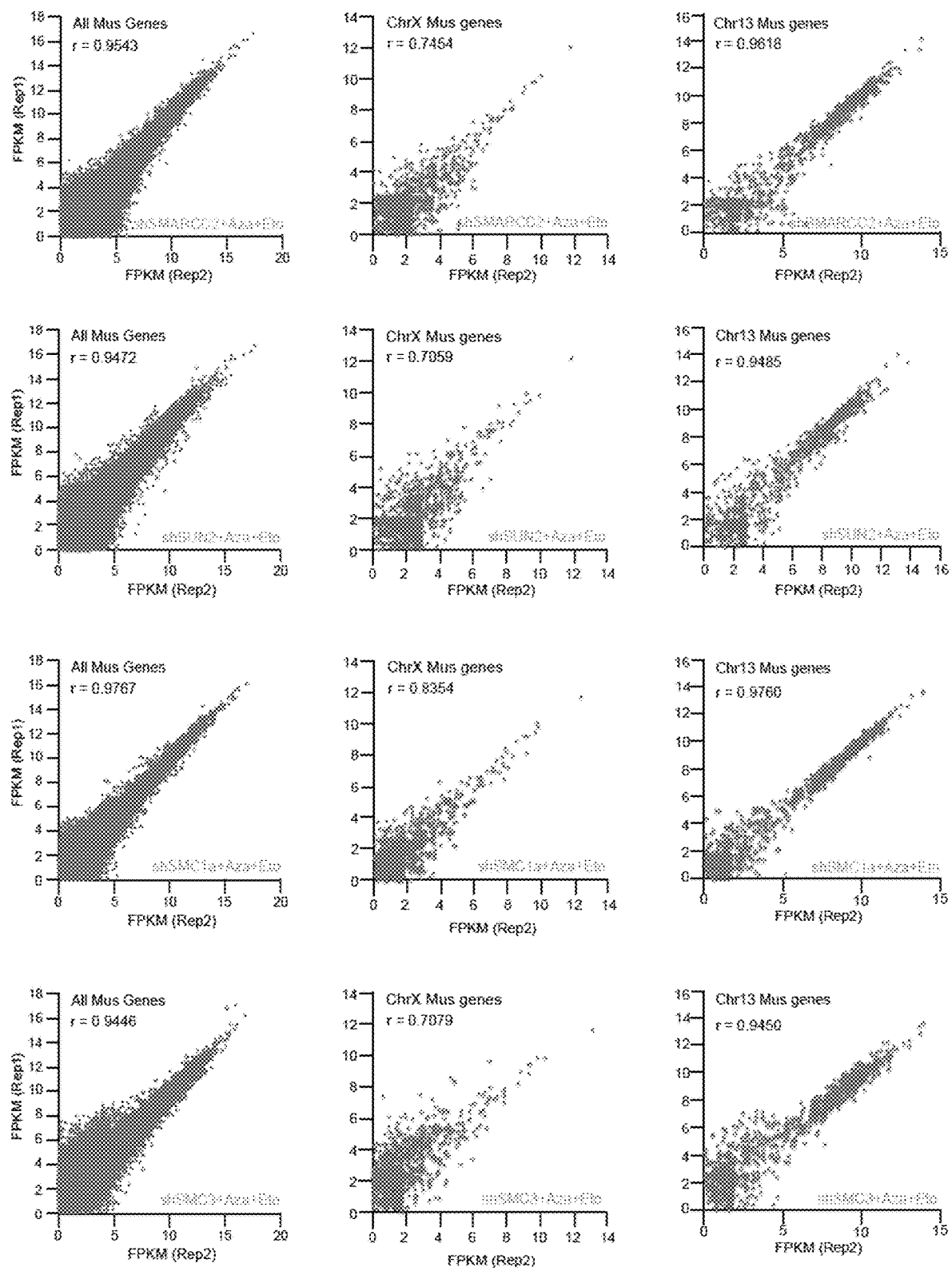

FIG. 13. Correlations between biological replicates for allelic-specific RNA-seq analysis.

Shown are allelic (mus) FPKM values for replicate 1 (Rep1) and replicate 2 (Rep2) for indicated triple-drug treatment (orange text) for all genes, Xi genes, and Chr13 genes.

Figure 14:
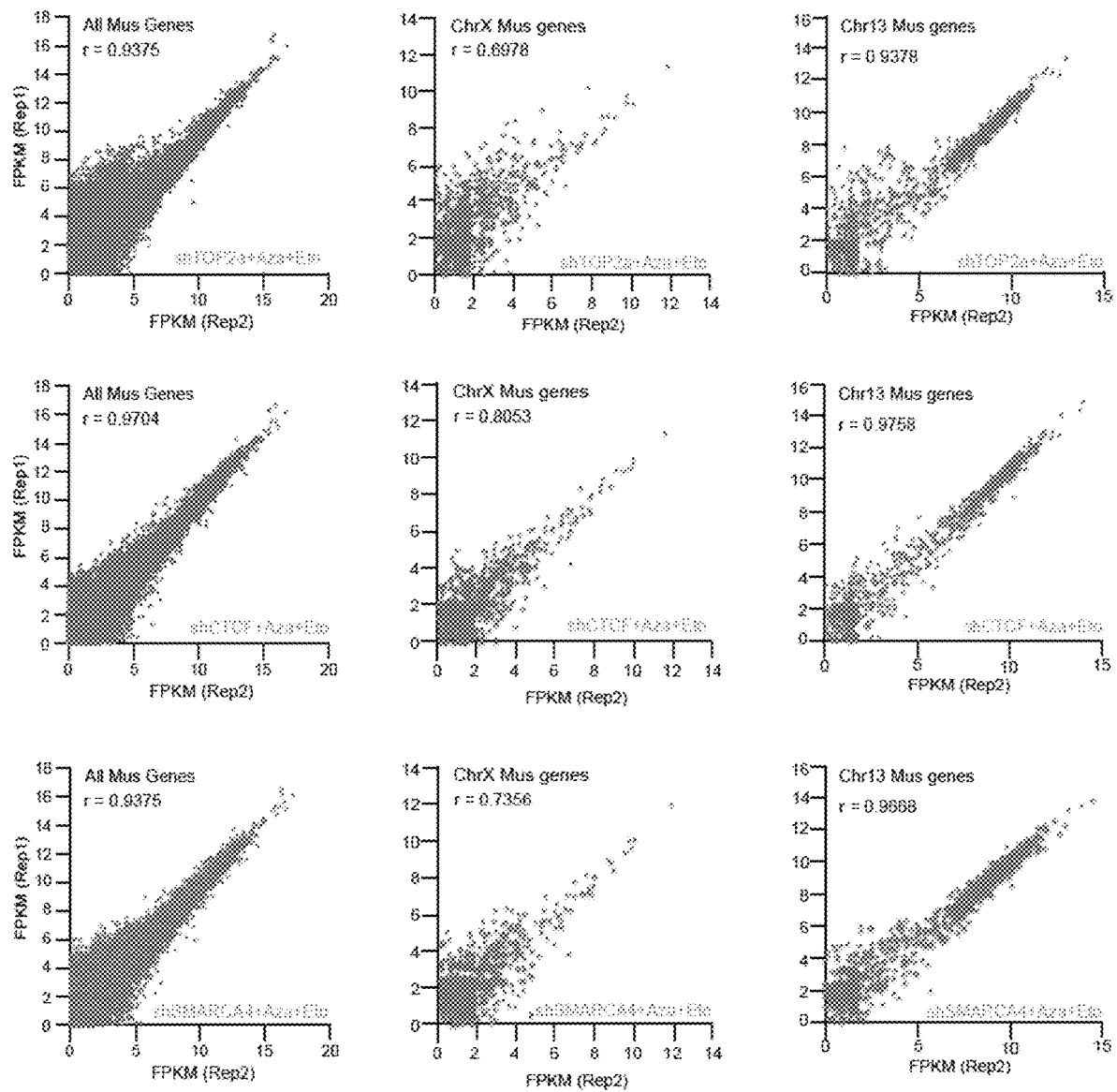

FIG. 14. Correlations between biological replicates for allelic-specific RNA-seq analysis.

Shown are allelic (mus) FPKM values for replicate 1 (Rep1) and replicate 2 (Rep2) for indicated triple-drug treatment (orange text) for all genes, Xi genes, and Chr13 genes.

Figure 15A:
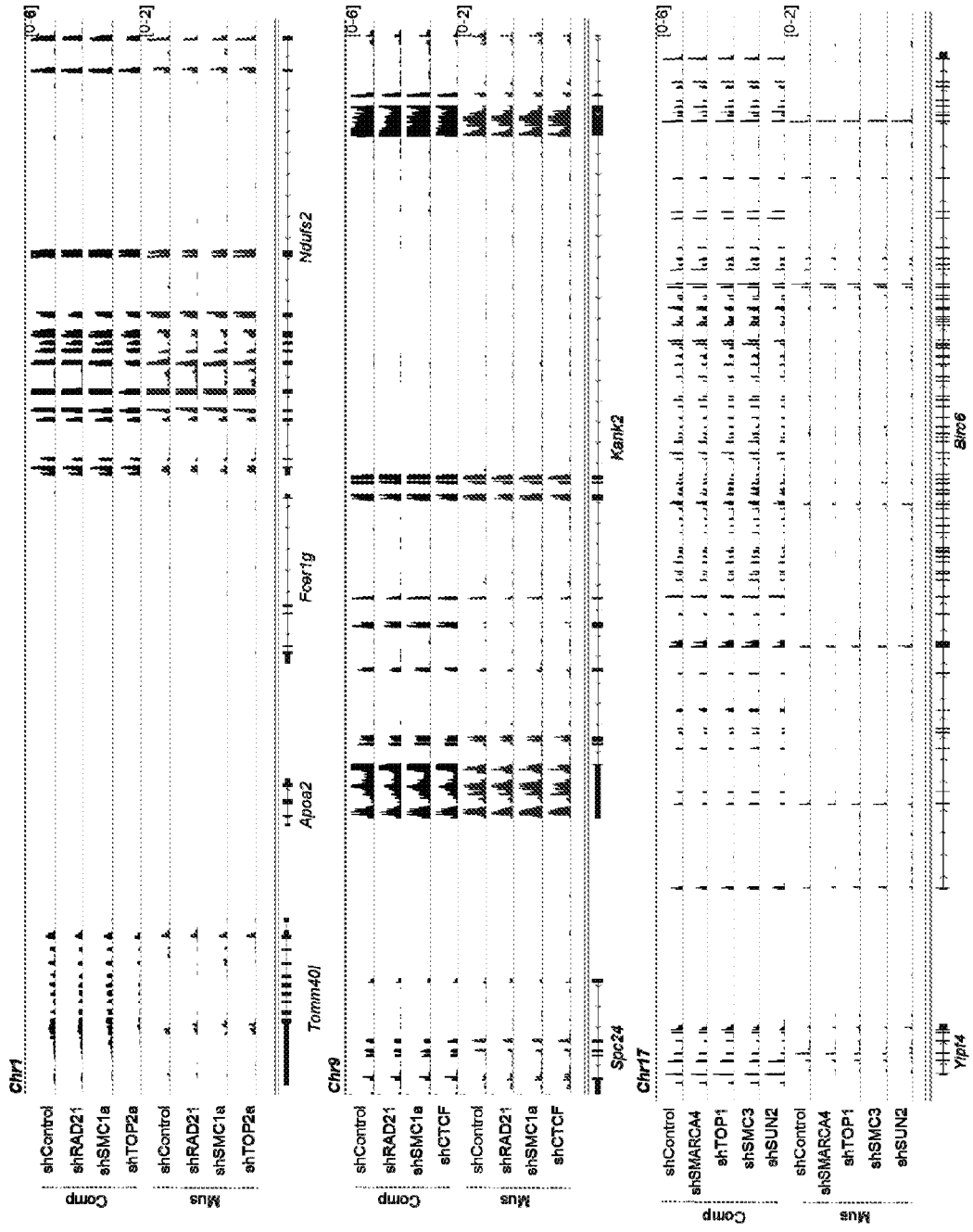
Figure 15B:
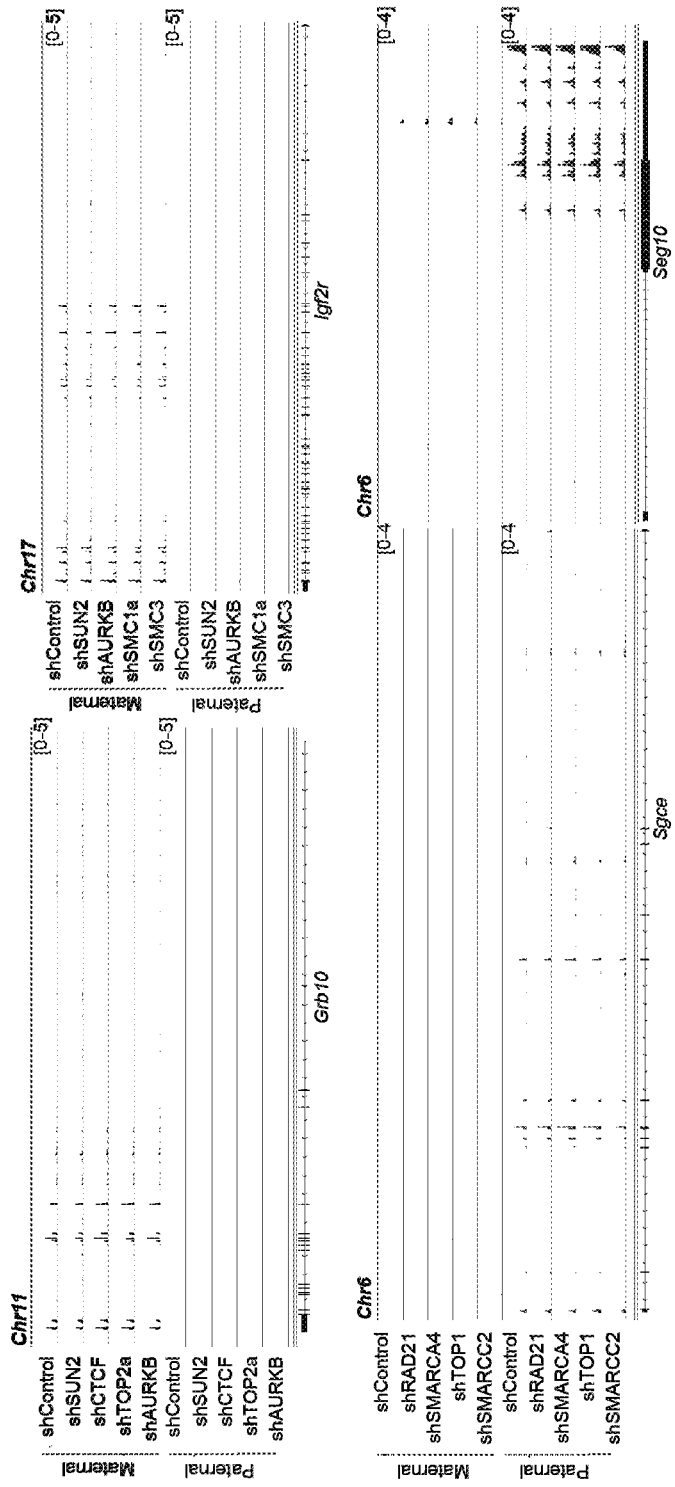

FIGS. 15A-B. Allelic expression of autosomal genes, including imprinted genes, is not affected by the triple-drug treatments.

Read coverages of three representative autosomal genes (A) and four representative imprinted genes (B) after triple-drug treatment. Mus, *Mus musculus* allele. Comp, total reads. Tracks are shown at the same scale within each grouping. Red tags appear only in exons with SNPs.

FIGS. 16A-D. Analysis of CTCF and cohesin ChIP-seq replicates demonstrates similar allelic trends on ChrX.

(A) Allele-specific ChIP-seq results of biological replicates: Violin plots of allelic skew for CTCF, RAD21, SMC1a in wild-type (WT) and $Xi^{\Delta Xist}/Xa^{WT}$ ($\Delta Xist$) fibroblasts. Fraction of mus reads [mus/(mus+cas)] is plotted for every peak with ≥10 allelic reads. P values determined by the Kolmogorov-Smirnov (KS) test.

(B) Table of total, Xa-specific, and Xi-specific cohesin binding sites in WT versus $\Delta Xist$ ($Xi^{\Delta Xist}/Xa^{WT}$) cells. Significant SMC1a and RAD21 allelic peaks with ≥5 reads were analyzed. Allele-specific skewing is defined as ≥3-fold skew towards Xa or Xi. Sites were considered "restored" if $Xi^{\Delta Xist}$'s read counts were ≥50% of Xa's. X-total, all X-linked binding sites. Allelic peaks, sites with allelic information. Xa-total, all Xa sites. Xi-total, all sites. Xa-spec, Xa-specific. Xi-spec, Xi-specific. Xi-invariant, Xi-specific in both WT and $Xi^{\Delta Xist}/Xa^{WT}$ cells. Note: The net gain of sites on the Xi in the mutant does not equal the number of restored sites. This difference is due to defining restored peaks separately from calling ChIP peaks (macs2). Allele-specific skewing is defined as ≥3-fold skew towards either Xa or Xi.

(C) Correlation analysis showing Log 2 $Xi^{\Delta Xist}$ to $Xa^{WT}$ ratios of SMC1a coverage in replicates 1 and 2 (Rep1, Rep2). Rep1, blue dots. Rep2, red dots. Both, purple dots. Consensus, upper right quadrant.

(D) Correlation analysis showing Log 2 $Xi^{\Delta Xist}$ to $Xa^{WT}$ ratios of RAD21 coverage in replicates 1 and 2 (Rep1, Rep2). Rep1, blue dots. Rep2, red dots. Both, purple dots. Consensus, upper right quadrant.

Figure 17:
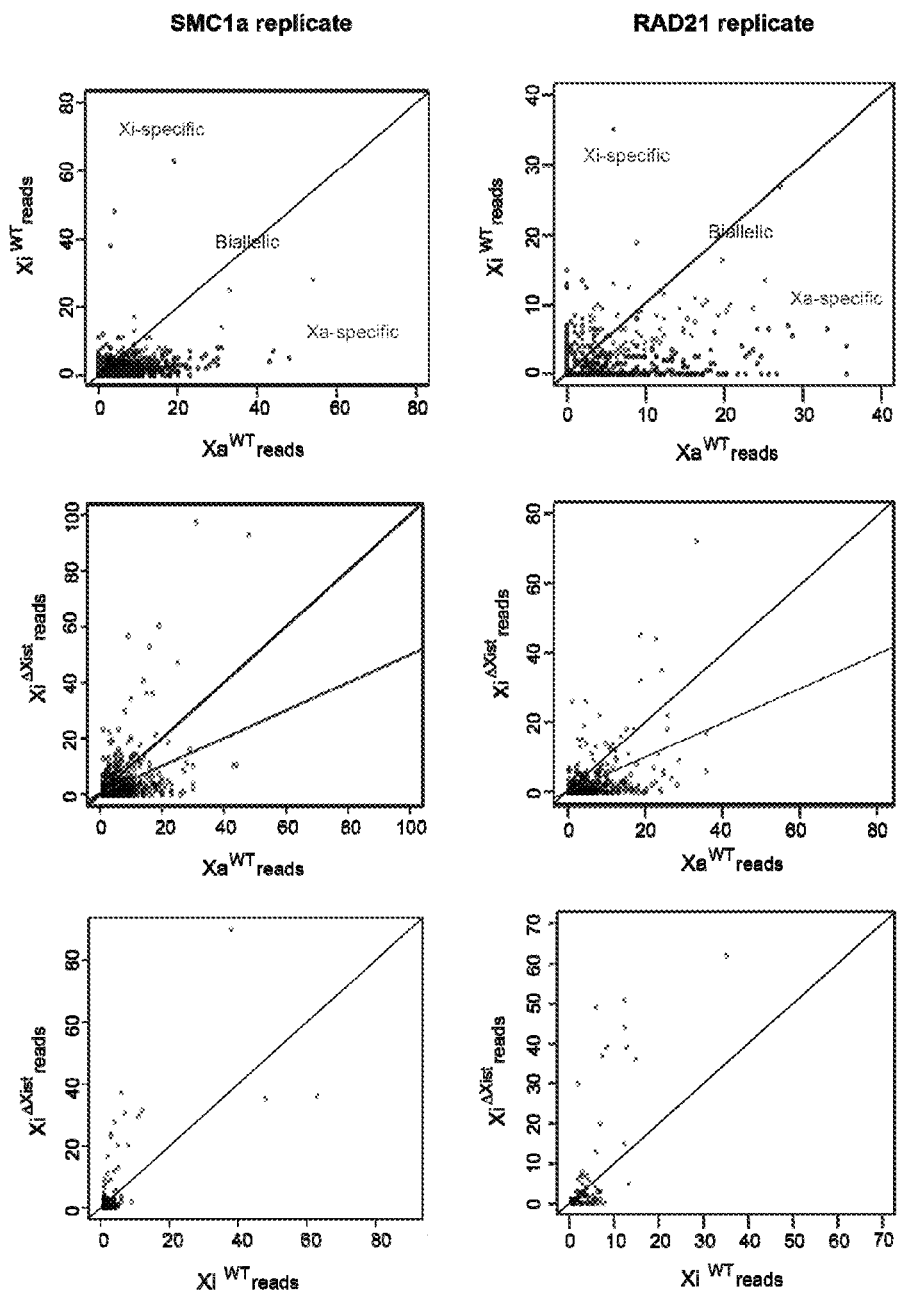

FIG. 17. Analysis of biological replicates for cohesin ChIP-seq confirms cohesin restoration in cis when Xist is ablated.

Allele-specific ChIP-seq analysis of SMC1a and RAD21 biological replicates. Top panels: Differences between SMC1a or RAD21 peaks on the $Xi^{WT}$ versus $Xa^{WT}$. Black diagonal, 1:1 ratio. Plotted are read counts for all SMC1a or RAD21 peaks. Allele-specific skewing is defined as ≥3-fold skew towards either Xa (cas, blue dots) or Xi (mus, red dots). Biallelic peaks, grey dots. Middle panels: Partial restoration of SMC1a or RAD21 peaks on the $Xi^{\Delta Xist}$ to an Xa pattern. Plotted are peaks with read counts with ≥3-fold skew to $Xa^{WT}$ ("Xa-specific"). x-axis, normalized $Xa^{WT}$ read counts. y-axis, normalized $Xi^{\Delta Xist}$ read counts. Black diagonal, 1:1 $Xi^{\Delta Xist}/Xa^{WT}$ ratio; red diagonal, 1:2 ratio. Bottom panels: Xi-specific SMC1a or RAD21 peaks remained on $Xi^{\Delta Xist}$. Plotted are read counts for SMC1a or RAD21 peaks with ≥3-fold skew to $Xi^{WT}$ ("Xi-specific").

Figure 18:
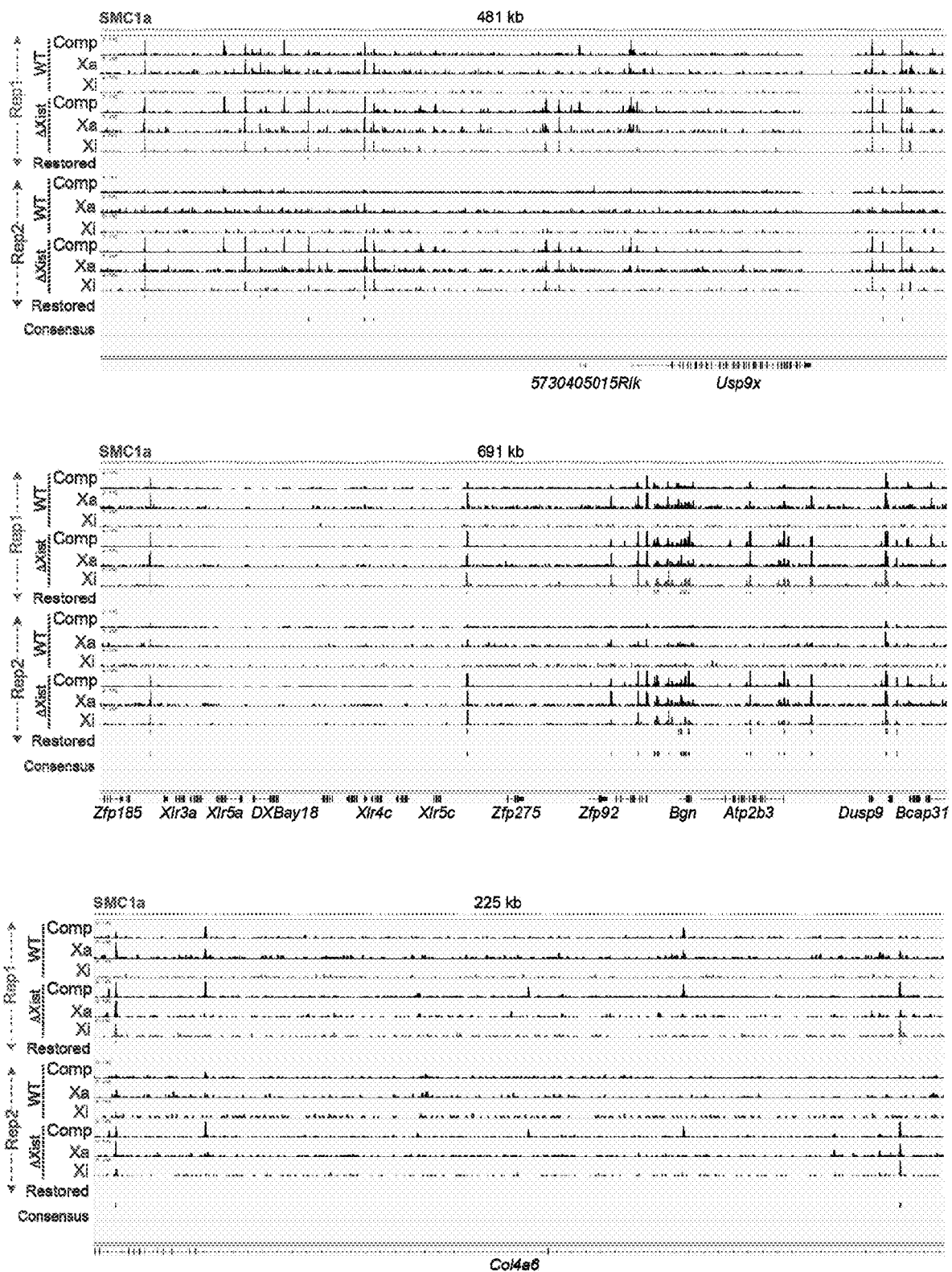

FIG. 18. Restored SMC1a peaks are reproducible in biological replicates and occur throughout $Xi^{\Delta Xist}$ (Example set 1).

The representative examples of SMC1a restoration on $Xi^{\Delta Xist}$. "Restored" peaks shown as ticks under each biological replicate (Rep1, Rep2). The "consensus" restored peaks are shown in the last track of each grouping.

Figure 19:
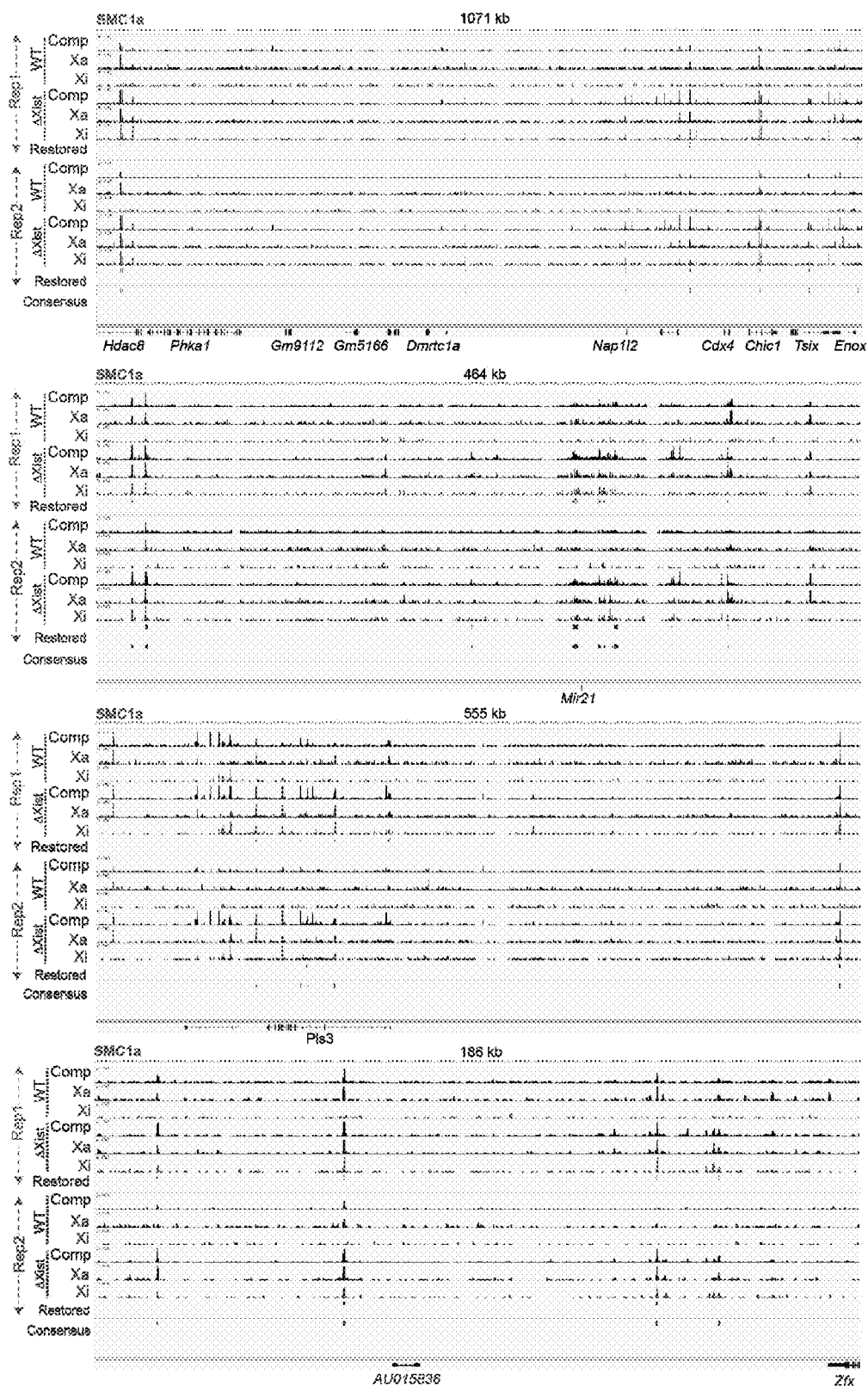

FIG. 19. Restored SMC1a peaks are reproducible in biological replicates and occur throughout $Xi^{\Delta Xist}$ (Example set 2).

The representative examples of SMC1a restoration on $Xi^{\Delta Xist}$. "Restored" peaks shown as ticks under each biological replicate (Rep1, Rep2). The "consensus" restored peaks are shown in the last track of each grouping.

Figure 20:
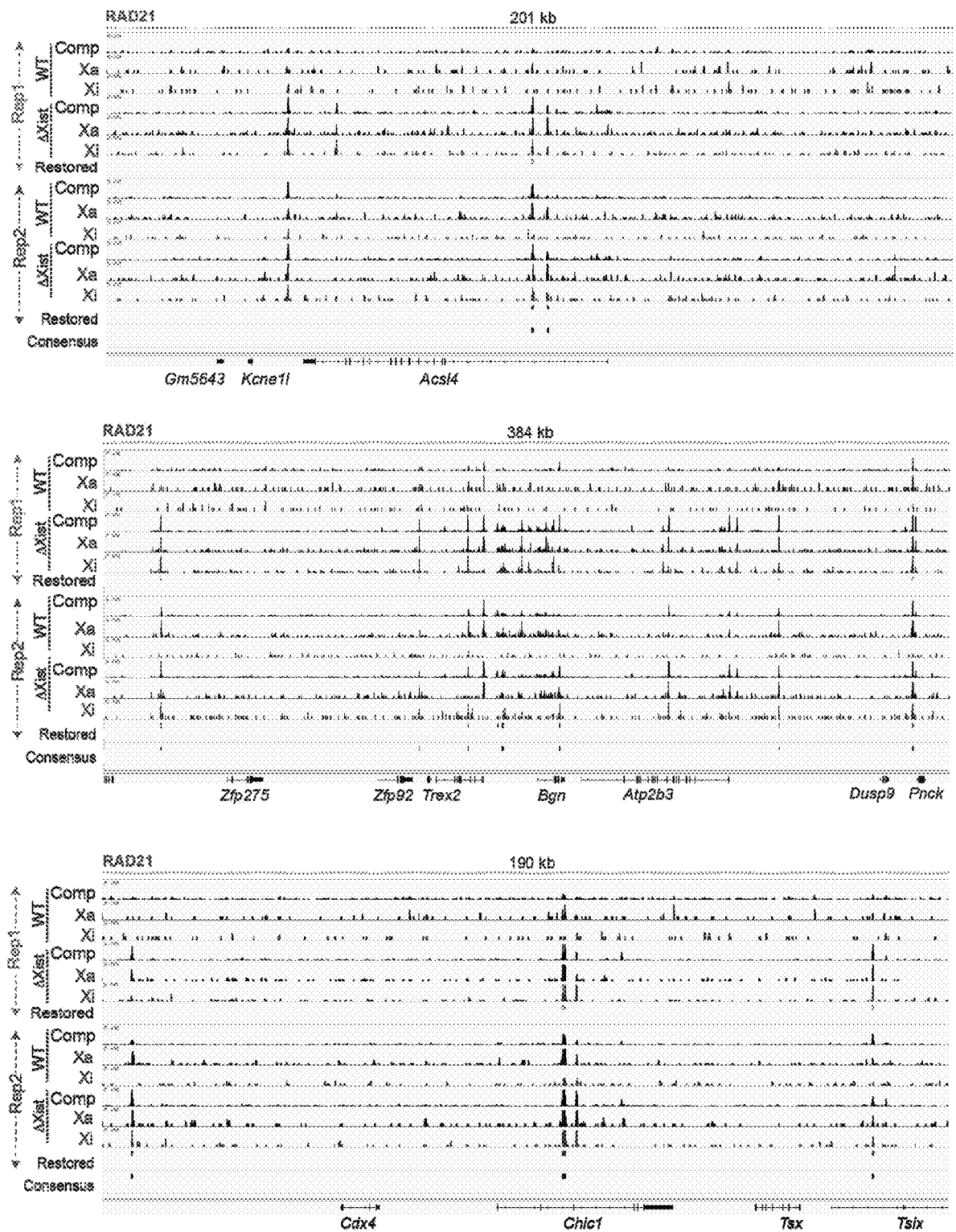

FIG. 20. Restored RAD21 peaks are reproducible in biological replicates and occur throughout $Xi^{\Delta Xist}$.

The representative examples of RAD21 restoration on $Xi^{\Delta Xist}$. "Restored" peaks shown as ticks under each biological replicate (Rep1, Rep2). The "consensus" restored peaks are shown in the last track of each grouping.

Figure 21:
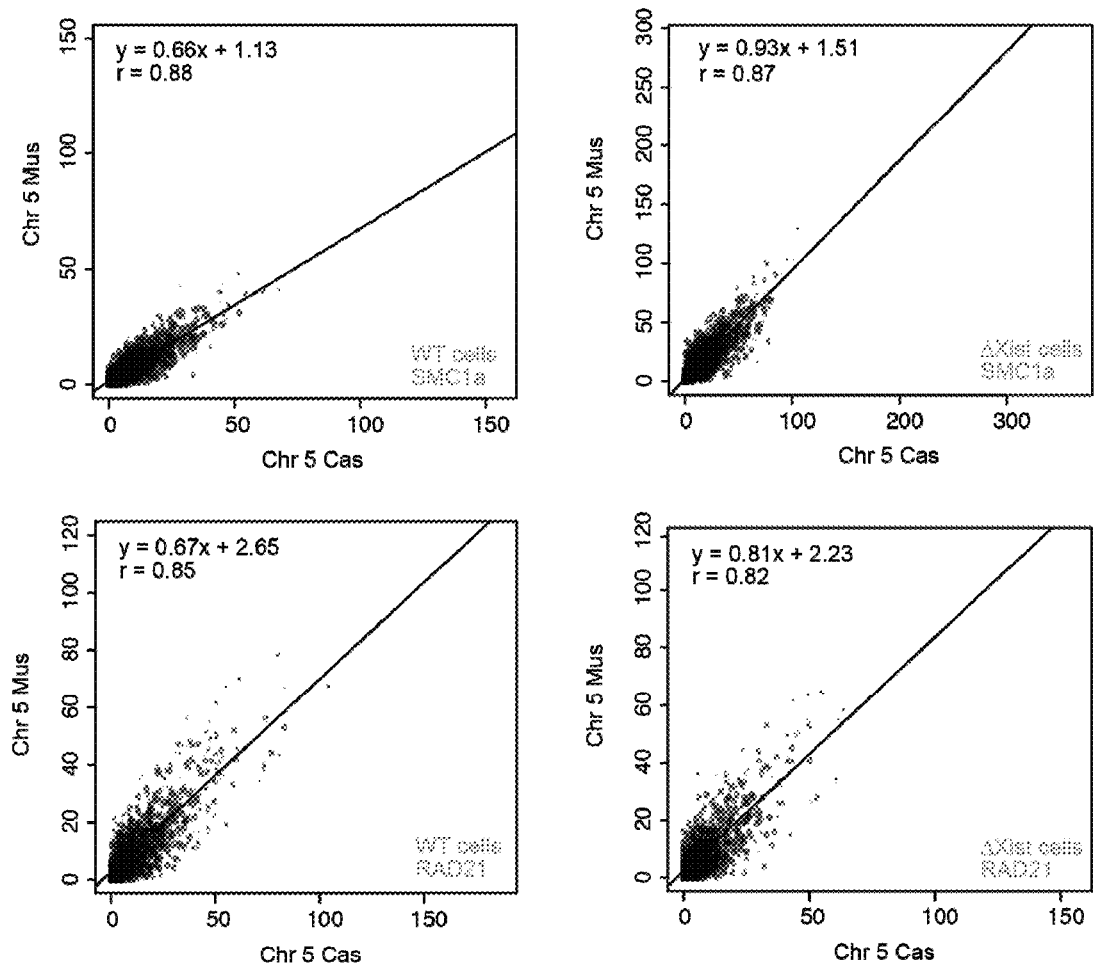

FIG. 21. Cohesin restored in $Xi^{\Delta Xist}/Xa^{WT}$ fibroblasts was Xi-specific and did not occur on autosomes.

Correlation plots comparing SMC1a or RAD21 coverages on the mus versus cas alleles in wildtype fibroblasts (WT) versus $Xi^{\Delta Xist}/Xa^{WT}$ fibroblasts ($\Delta Xist$). Representative autosome, Chr5, is shown. Equation shows the slope and y-intercepts for the black diagonals as a measure of correlation. Pearson's r also shown.

Figure 22A:
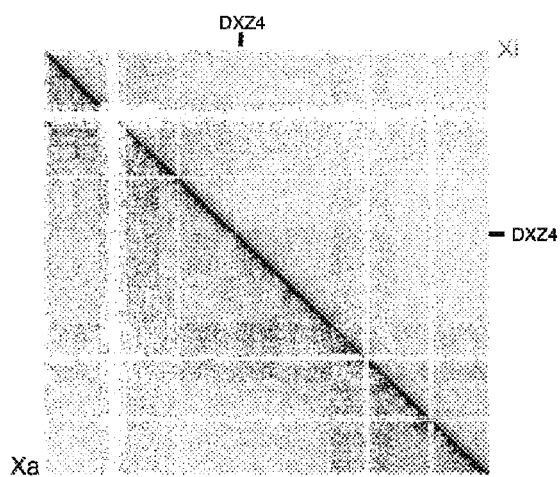

FIGS. 22A-B. Biological replicates of HiC-seq analysis yield similar findings.

(A) Allele-specific contact map for the X-chromosome in wild-type fibroblasts at 100 kb resolution. Orange, Xi. Blue, Xa. DXZ4 location is indicated. The Xi appears to be partitioned into megadomains at DXZ4.

(B) Contact maps for various ChrX regions at 40-kb resolution comparing $Xi^{\Delta Xist}$ (red) to $Xi^{WT}$ (orange), and $Xi^{\Delta Xist}$ (red) versus Xa (blue) of the mutant cell line. Our TAD calls are shown with RefSeq genes. Rep1 contact maps are shown above Rep2 contact maps.

Figure 23C:
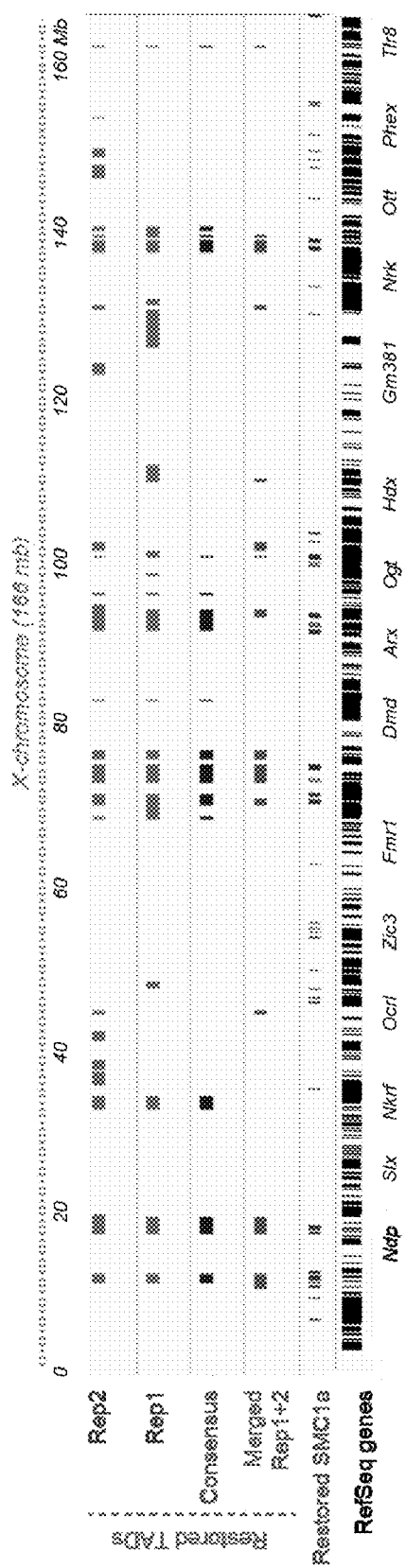

FIG. 23A-C. Restored TADs identified in $Xi^{\Delta Xist}$ using Xa TADs of Dixon et al. (28) as reference.

Figure 5A:
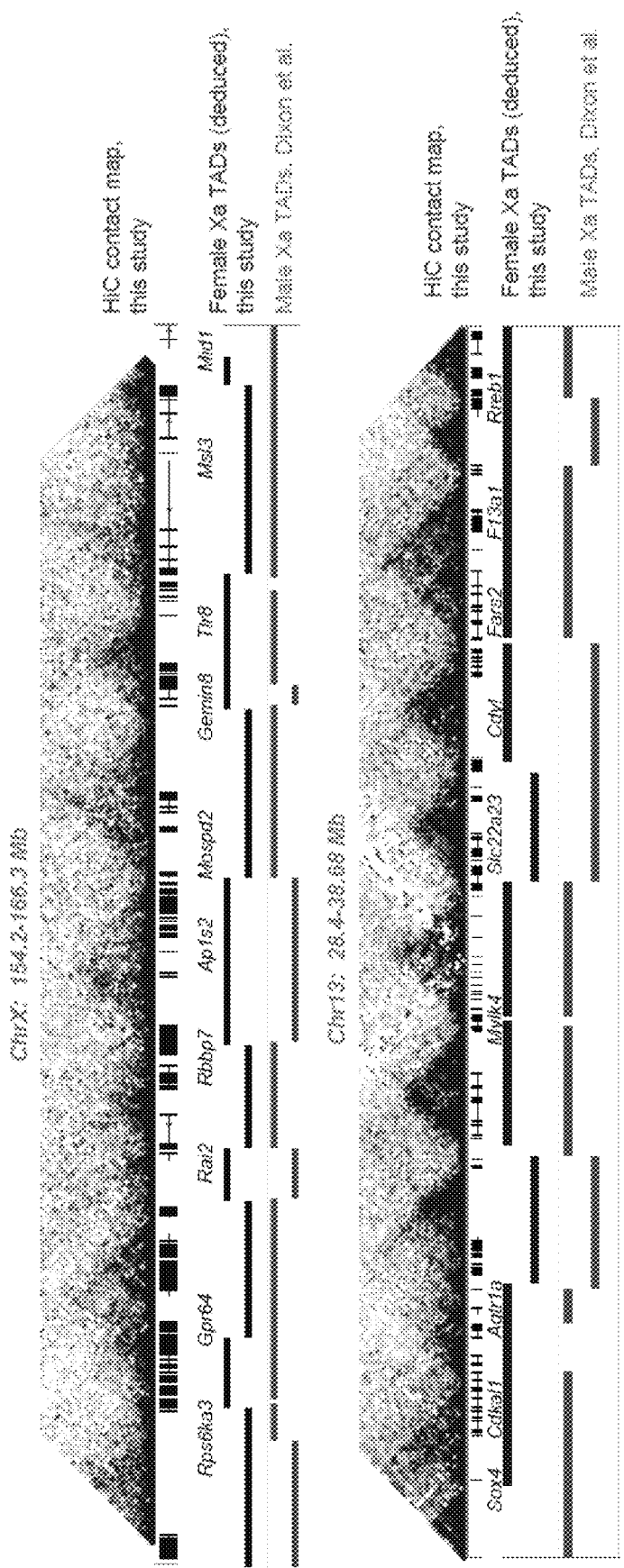
FIGS. 5A-E: Ablating XIST results in Xi reversion to an Xa-like chromosome conformation.
(A) Chr13 and ChrX contact maps showing triangular domains representative of TADs. Purple shades correspond to varying interaction frequencies (dark, greater interactions). TADs called from our composite (non-allelic) HiC data at 40-kb resolution (blue bars) are highly similar to those (gray bars) called previously by Dixon et al. (27). Representative regions from ChrX and Chr13 are shown.

(A) Using TADs called by Dixon et al. (Dixon et al., Nature 485, 376 (May 17, 2012)) (rather than our own called TADs, as shown in FIG. 5C) as a basis for identifying restored TADs, we calculated the fraction of interaction frequency per TAD on the Xi (mus) chromosome. Highly similar results were obtained. The positions of our Xa TAD borders were rounded to the nearest 100 kb and submatrices were generated from all pixels between the two endpoints of the TAD border for each TAD. We calculated the average interaction score for each TAD by summing the interaction scores for all pixels in the submatrix defined by a TAD and dividing by the total number of pixels in the TAD. We then averaged the normalized interaction scores across all bins in a TAD in the Xi (mus) and Xa (cas) contact maps, and computed the fraction of averaged interaction scores from mus chromosomes. ChrX and a representative autosome, Chr5, are shown for the WT cell line and the Xist$^{\Delta Xist}$/+ cell line. P value determined by KS test. P-value determined by paired Wilcoxon signed rank test.

(B) Using TADs called by Dixon et al. (28) (rather than our own called TADs, as shown in FIG. 5C) as a basis for identifying restored TADs, violin plots also showed that TADs overlapping restored peaks have larger increases in interaction scores relative to all other TADs. We calculated the fold-change in average interaction scores on the Xi for all X-linked TADs and intersected the TADs with SMC1a sites (Xi$^{\Delta Xist}$/Xi$^{WT}$) 32 TADs occurred at restored cohesin sites; 80 TADs did not overlap restored cohesin sites. Violin plot shows distributions of fold-change average interaction scores between Xi$^{WT}$ and Xi$^{\Delta Xist}$, P-value determined by Wilcoxon ranked sum test.

(C) Using TADs called by Dixon et al. (28) (rather than our own called TADs, as shown in FIG. 5C) as a basis for identifying restored TADs, we also found that restored TADs overlapped regions with restored cohesins on across Xi$^{\Delta Xist}$. Note highly similar results obtained here relative to FIG. 5E. Several datasets were used to identify restored TADs, each producing similar results. Restored TADs were called in two separate replicates (Rep1, Rep2) where the average interaction score was significantly higher on Xi$^{\Delta Xist}$ than on Xi$^{WT}$. We also called restored TADs based on merged Rep1+Rep2 datasets. Finally, a consensus between Rep1 and Rep2 was derived. Method: We calculated the fold-change in mus or cas for all TADs on ChrX and on a control, Chr5; then defined a threshold for significant changes based on either the autosomes or the Xa. We treated Chr5 as a null distribution (few changes expected on autosomes) and found the fraction of TADs that crossed the threshold for several thresholds. These fractions corresponded to a false discovery rate (FDR) for each given threshold. An FDR of 0.05 was used.

DETAILED DESCRIPTION

The mammalian X chromosome is unique in its ability to undergo whole-chromosome silencing. In the early female embryo, X-chromosome inactivation (XCI) enables mammals to achieve gene dosage equivalence between the XX female and the XY male (1-3). XCI depends on Xist RNA, a 17-kb long noncoding RNA (lncRNA) expressed only from the inactive X-chromosome (Xi)(4) and that implements whole-chromosome silencing by recruiting repressive complexes (5-8). While XCI initiates only once during development, the female mammal stably maintains the Xi through her lifetime. In mice, a germline deletion of Xist results in peri-implantation lethality due to a failure of Xi establishment (9), whereas a lineage-specific deletion of Xist causes a lethal blood cancer due to a failure of Xi maintenance (10). Thus, both the de novo establishment and proper maintenance of the Xi are crucial for viability and homeostasis. There are therefore two critical phases to XCI: (i) A one-time initiation/establishment phase that occurs in pen-implantation embryonic development that is recapitulated by differentiating embryonic stem (ES) cells in culture, and (ii) a life-long maintenance phase that persists in all somatic lineages.

Once established, the Xi is extremely stable and difficult to disrupt genetically and pharmacologically (11-13). In mice, X-reactivation is programmed to occur only twice— once in the blastocyst to erase the imprinted XCI pattern and a second time in the germline prior to meiosis (14, 15).

Although the Xi's epigenetic stability is a homeostatic asset, an ability to unlock this epigenetic state is of great current interest. The X-chromosome is home to nearly 1000 genes, at least 50 of which have been implicated in X-linked diseases, such as Rett syndrome and Fragile X syndrome. The Xi is therefore a reservoir of functional genes that could be tapped to replace expression of a disease allele on the active X (Xa). A better understanding of repression would inform both basic biological mechanisms and treatment of X-linked diseases.

It is believed that Xist RNA silences the Xi through conjugate protein partners. A major gap in current understanding is the lack of a comprehensive Xist interactome. In spite of multiple attempts to define the complete interactome, only four directly interacting partners have been identified over the past two decades, including PRC2, ATRX, YY1, and HNRPU: Polycomb repressive complex 2 (PRC2) is targeted by Xist RNA to the Xi; the ATRX RNA helicase is required for the specific association between Xist and PRC2 (16, 17); YY1 tethers the Xist-PRC2 complex to the Xi nucleation center (18); and the nuclear matrix factor, HNRPU/SAF-A, enables stable association of Xist with the chromosomal territory (19). Many additional interacting partners are expected, given the large size of Xist RNA and its numerous conserved modular domains. Here, we develop a new RNA-based proteomic method and implement an unbiased screen for Xist's comprehensive interactome. We identify a large number of high-confidence candidates, demonstrate that it is possible to destabilize Xi repression by inhibiting multiple interacting components, and then delve into a focused set of interactors with the cohesins.

Using iDRiP, we have identified a comprehensive Xist interactome and revealed multiple synergistic pathways to Xi repression (FIG. 6). With Xist physically contacting 80-250 proteins at any given time, the Xist ribonucleoprotein particle may be as large as the ribosome. Our study supports a model in which Xist RNA simultaneously acts as (i) scaffold for the recruitment of repressive complexes (such as PRC1, PRC2, ATRX, mH2A, and SmcHD1) to establish and maintain the inactive state; and as (ii) a repulsion mechanism to extrude architectural factors such as cohesins in order to avoid acquisition of a transcription-favorable chromatin conformation. Without Xist, cohesins return to their default Xa binding state. Repulsion could be based on eviction, with Xist releasing cohesins as it extrudes them, or on sequestration, with Xist sheltering cohesins to prevent Xi binding. Our study shows that the Xi harbors three types of cohesin sites: (i) Xi-specific sites that do not depend on Xist; (ii) biallelic sites that are also Xist-independent; and (iii) Xa-specific sites, many of which cannot be established on the Xi because of active repulsion by Xist. The type i and type iii sites likely explain the paradoxical observations that, on the one hand, depleting cohesins leads to Xi reactivation but, on the other, loss of Xist-mediated cohesin recruitment leads to an Xa-like chromosome conformation that is permissive for transcription. In essence, modulating the Type i and Type iii sites both have the effect of destabilizing the Xi, rendering the Xi more accessible to transcription. Disrupting Type i sites by cohesin knockdown would change the repressive Xi structure, while ablating Xist would restore the Type iii sites that promote an Xa-like conformation. Our study has focused on cohesins, but RNA-mediated repulsion may be an outcome for other Xist interactors and may be as prevalent an epigenetic mechanism as RNA-mediated recruitment (47).

The robustness of Xi silencing is demonstrated by the observation that we destabilized the Xi only after pharmacologically targeting two or three distinct pathways. The fact that the triple-drug treatments varied with respect to reactivated loci and depth of de-repression creates the possibility of treating X-linked disease in a locus-specific manner by administering unique drug combinations. Given the existence of many other disease-associated lncRNAs, the iDRiP technique could be applied systematically towards identifying new drug targets for other diseases and generally for elucidating mechanisms of epigenetic regulation by lncRNA.

Based on the perturbation experiments, it is proposed that Xist interacting factors act synergistically to repress the Xi, possibly explaining why it has been difficult historically to achieve X reactivation by disrupting single genes (11-13). The present data show that drug combinations that hit three distinct pathways are required to achieve reactivation levels that approximate half to full levels of the Xa (FIG. 3). The combinations vary with respect to affected loci and depth of de-repression, thereby creating possibilities with respect to therapies for specific X-linked diseases. In conclusion, the Xist interactome unveiled by iDRiP contains a wealth of new factors to advance understanding of XCI and general lncRNA mechanisms, and to implement new strategies of tackling X-linked disease.

Methods of Reactivating Genes on the Inactive X Chromosome (Xi)

The present disclosure provides methods for reactivating genes on Xi by combining inhibitors for two or three Xist-interacting factors (listed in Tables 5 and 6). The methods include co-administering a DNA methyltransferase (DNMT) Inhibitor and/or a topoisomerase inhibitor, optionally with an inhibitor of another Xist-interacting factor (listed in Tables 5-6), e.g., a small molecule or a nucleic acid such as a small inhibitory RNA (siRNAs) that targets Xist RNA and/or a gene encoding Xist or an Xist-interacting protein, e.g., a chromatin-modifying protein or a small molecule. These methods can be used, e.g., to reactivate genes in single cells, e.g., isolated cells in culture, or in tissues, organs, or whole animals. In some embodiments, the methods are used to reactivate genes on Xi in a cell or subject that has an X-linked disease. X-reactivation can be achieved in various cell types, including proliferating fibroblasts and post-mitotic neurons.

The methods described herein can be also be used to specifically re-activate one or more genes on Xi, by co-administering an inhibitory nucleic acid targeting a suppressive RNA or genomic DNA at strong and/or moderate binding sites as described in WO 2012/065143, WO 2012/087983, and WO 2014/025887 or in U.S. Ser. No. 62/010, 342 (which are incorporated herein in their entirety), to disrupt RNA-mediated silencing in cis on the inactive X-chromosome. The suppressive RNAs can be noncoding (long noncoding RNA, lncRNA) or occasionally part of a coding mRNA; for simplicity, we will refer to them together as suppressive RNAs (supRNAs) henceforth. supRNAs that mediate silencing of genes on the X chromosome are known in the art; see, e.g., WO 2012/065143, WO 2012/087983, WO 2014/025887 and U.S. Ser. No. 62/010,342, and inhibitory nucleic acids and small molecules targeting (e.g., complementary to) the sRNAs, or complementary or identical to a region within a strong or moderate binding site in the genome, e.g., as described in WO 2014/025887, can be used to modulate gene expression in a cell, e.g., a cancer cell, a stem cell, or other normal cell types for gene or epigenetic therapy. The nucleic acids targeting supRNAs that are used in the methods described herein are termed "inhibitory" (though they increase gene expression) because they inhibit the supRNAs-mediated repression of a specified gene, either by binding to the supRNAs itself (e.g., an antisense oligo that is complementary to the supRNAs) or by binding to a strong or moderate binding site for an RNA-binding protein (e.g., PRC2—also termed an EZH2 or SUZ12 binding site- or CTCF) in the genome, and (without wishing to be bound by theory) preventing binding of the RNA-binding protein complex and thus disrupting silencing in the region of the strong or moderate binding site. The inhibitory nucleic acids that bind to a strong or moderate RNA-binding protein binding site can bind to either strand of the DNA, but preferably bind to the same strand to which the supRNAs binds. See, e.g., WO 2012/065143, WO 2012/087983, WO 2014/025887 and U.S. Ser. No. 62/010,342.

The cells can be in vitro, including ex vivo, or in vivo (e.g., in a subject who has cancer, e.g., a tumor).

In some embodiments, the methods include introducing into the cell (or administering to a subject) a DNA methyltransferase (DNMT) Inhibitor and/or a topoisomerase inhibitor, optionally with an inhibitor of XIST RNA or an Xist-interacting protein, e.g., a chromatin-modifying protein, e.g., a small molecule inhibitor of Xist or an Xist-interacting protein.

In some embodiments, the methods include introducing into the cell (or administering to a subject) a DNA methyltransferase (DNMT) Inhibitor and/or a topoisomerase inhibitor, optionally with an inhibitory nucleic acid (e.g., targeting Xist RNA or a gene encoding Xist or an Xist-interacting protein, e.g., a chromatin-modifying protein as described herein) that is modified in some way, e.g., an inhibitory nucleic acid that differs from the endogenous nucleic acids at least by including one or more modifications to the backbone or bases as described herein for inhibitory nucleic acids. Such modified nucleic acids are also within the scope of the present invention.

In some embodiments, the methods include introducing into the cell (or administering to a subject) a DNA methyltransferase (DNMT) Inhibitor and/or a topoisomerase inhibitor, optionally with an inhibitor of Xist RNA or an Xist-interacting protein, e.g., a chromatin-modifying protein, e.g., a small molecule inhibitor or an inhibitory nucleic acid such as a small inhibitory RNA (siRNA) or LNA that targets XIST or a gene encoding XIST or an Xist-interacting protein, e.g., a chromatin-modifying protein, and optionally an inhibitory nucleic acid that specifically binds, or is complementary, to a strong or moderate binding site or a supRNA described in WO 2012/065143, WO 2012/087983, WO 2014/025887 and U.S. Ser. No. 62/010,342. A nucleic acid that binds "specifically" binds primarily to the target, i.e., to the target DNA, mRNA, or supRNA to inhibit regulatory function or binding of the DNA, mRNA, or supRNA, but does not substantially inhibit function of other non-target nucleic acids. The specificity of the nucleic acid interaction thus refers to its function (e.g., inhibiting gene expression) rather than its hybridization capacity. Inhibitory nucleic acids may exhibit nonspecific binding to other sites in the genome or other RNAs without interfering with binding of other regulatory proteins and without causing degradation of the non-specifically-bound RNA. Thus this nonspecific binding does not significantly affect function of other non-target RNAs and results in no significant adverse effects. These methods can be used to treat an X-linked condition in a subject by administering to the subject a composition or compositions (e.g., as described herein) comprising a DNA methyltransferase (DNMT) Inhibitor and/or a topoisomerase inhibitor, optionally with an inhibitor of Xist RNA or an Xist-interacting protein, e.g., a chromatin-modifying protein, e.g., a small molecule inhibitor or an inhibitory nucleic acid such as a small inhibitory RNA (siRNA) or LNA that targets a gene encoding Xist or an Xist-interacting protein, e.g., a chromatin-modifying protein, and optionally an inhibitory nucleic acid that specifically binds, or is complementary, to a strong or moderate binding site or a supRNA (e.g., as described in WO 2012/065143, WO 2012/087983, WO 2014/025887 and U.S. Ser. No. 62/010,342) that is associated with an X-linked disease gene. Examples of genes involved in X-linked diseases are shown in Table 8.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a DNA methyltransferase (DNMT) Inhibitor and/or a topoisomerase inhibitor, and optionally a composition, e.g., a sterile composition, comprising an inhibitory nucleic acid that is complementary to Xist or a gene encoding Xist RNA or an Xist-interacting protein, e.g., a chromatin-modifying protein, and optionally an inhibitory nucleic acid that is complementary to a supRNA as known in the art, e.g., as described in WO 2012/065143, WO 2012/087983, and/or WO 2014/025887. Inhibitory nucleic acids for use in practicing the methods described herein can be an antisense or small interfering RNA, including but not limited to an shRNA or siRNA. In some embodiments, the inhibitory nucleic acid is a modified nucleic acid polymer (e.g., a locked nucleic acid (LNA) molecule).

Inhibitory nucleic acids have been employed as therapeutic moieties in the treatment of disease states in animals, including humans. Inhibitory nucleic acids can be useful therapeutic modalities that can be configured to be useful in treatment regimens for the treatment of cells, tissues and animals, especially humans.

For therapeutics, an animal, preferably a human, who has an X-linked disorder is treated by administering a DNA methyltransferase (DNMT) Inhibitor and/or a topoisomerase inhibitor, an optionally inhibitor of XIST RNA and/or an Xist-interacting protein, e.g., a chromatin-modifying protein, e.g., a small molecule inhibitor or an inhibitory nucleic acid such as a small inhibitory RNA (siRNA) or LNA that targets a gene encoding Xist RNA and/or an Xist-interacting protein, e.g., a chromatin-modifying protein, and optionally an inhibitory nucleic acid that is complementary to a supRNA. For example, in some embodiments, the methods comprise the step of administering to the animal in need of treatment, a therapeutically effective amount of a DNA methyltransferase (DNMT) Inhibitor and/or a topoisomerase inhibitor and optionally an inhibitory nucleic acid that is complementary to XIST RNA or a gene encoding XIST and/or an Xist-interacting protein, e.g., a chromatin-modifying protein as described herein.

DNA Methyltransferase (DNMT) Inhibitors

A number of DNMT inhibitors (against DNMT1, DNMT2, DNMT3a/b, as several examples) are known in the art, including 5-azacytidine (azacytidine, Azacitidine, 4-amino-1-beta-D-ribofuranosyl-s-triazin-2(1H)-one, Vidaza), decitabine (5-aza-2'-deoxycytidine, Dacogen), Zebularine (pyrimidin-2-one beta-ribofuranoside), procainamide, procaine, hydralazine, NSC14778, Olsalazine, Nanaomycin, SID 49645275, $\Delta^2$-isoxazoline, epigallocatechin-3-gallate (EGCG), MG98, SGI-110 (2'-deoxy-5-aza-cytidylyl-(3→5')-2'-deoxyguanosine), RG108 (N-phthalyl-L-tryptophan), SGI-1027, SW155246, SW15524601, SW155246-2, and DZNep (SGI-1036, 3-deazaneplanocin A). See also Medina-Franco et al., Int. J. Mol. Sci. 2014, 15(2), 3253-3261; Yoo et al., Computations Molecular Bioscience, 1(1):7-16 (2011)

Topoisomerase Inhibitors

A number of topoisomerase inhibitors (against TOP1, TOP2a/b, as examples) are known in the art; in some embodiments, the topoisomerase inhibitor is an inhibitor of topoisomerase II. Exemplary inhibitors of topoisomerase I include camptothecin and its derivatives such as topotecan, irinotecan, lurtotecan, exatecan, diflometecan, S39625, CPT 11, SN38, gimatecan and belotecan; stibogluconate; indenoisoquinolines (e.g., 2,3-dimethoxy-12h-[1,3]dioxolo[5,6] indeno[1,2-c]isoquinolin-6-ium and 4-(5,11-dioxo-5h-indeno[1,2-c]isoquinolin-6(11h)-yl)butanoate) and indolocarbazoles. See, e.g., Pommier, Chem Rev. 2009 July; 109(7): 2894-2902; Pommier, Nat Rev Cancer. 2006 October; 6(10):789-802; Sheng et al., Curr Med Chem. 2011; 18(28):4389-409. Exemplary inhibitors of topoisomerase II include etoposide, teniposide, mitoxantrone, amsacrine, saintopin, ICRF-193, genistein, CP-115,953, ellipticine, banoxantrone, Celastrol, NU 2058, Dexrazoxane, and anthracyclines (e.g., doxorubicin, daunorubicin, epirubicin, and idarubicin). See, e.g., Froelich-Ammon and Osheroff, Journal of Biological Chemistry, 270:21429-21432 (1995); Hande, Update on Cancer Therapeutics 3:13-26 (2008).

Inhibitor of XIST RNA

The methods can optionally include administering an inhibitor of an XIST RNA itself, e.g., an inhibitory nucleic acid targeting XIST RNA. (Although in typical usage XIST refers to the human sequence and Xist to the mouse sequence, in the present application the terms are used interchangeably). The human XIST sequence is available in the ensemble database at ENSG00000229807; it is present on Chromosome X at 73,820,651-73,852,753 reverse strand (Human GRCh38.p 2). The full sequence is shown in SEQ ID NO:66; XIST exons correspond to 601-11972 (exon 1); 15851-15914 (exon 2); 19593-20116 (exon 3); 21957-21984 (exon 4); 22080-22288 (exon 5); and 23887-33304 (exon 6). Alternatively, see NCBI Reference Sequence: NR 001564.2, *Homo sapiens* X inactive specific transcript (non-protein coding) (XIST), long non-coding RNA, wherein the exons correspond to 1-11372, 11373-11436, 11437-11573, 11574-11782, 11783-11946, and 11947-19280. The inhibitory nucleic acid targeting XIST RNA can be any inhibitory nucleic acid as described herein, and can include modifications described herein or known in the art. In some embodiments, the inhibitory nucleic acid is an antisense oligonucleotide (ASO) that targets a sequence in XIST RNA, e.g., a sequence within an XIST exon as shown in SEQ ID NO:66 or within the RNA sequence as set forth in NR 001564.2. In some embodiments, the inhibitory nucleic includes at least one locked nucleotide, e.g., is a locked nucleic acid (LNA).

Xist-Interacting Proteins

The methods can optionally include administering an inhibitor of an Xist-interacting protein. Tables 5 and 6 list Xist-interacting proteins, e.g., chromatin-modifying proteins that can be targeted in the methods described herein.

Small molecule inhibitors of many of these Xist interactors are known in the art; see, e.g., Table 7, for strong examples. In addition, small molecule inhibitors of PRc1 or PRC2 components can be used; for example, inhibitors of EZH2 include UNC1999, E7438, N-[(4,6-dimethyl-2-oxo-1,2-dihydro-3-pyridinyl)methyl]-3-methyl-1-[(1S)-1-methylpropyl]-6-[6-(1-piperazinyl)-3-pyridinyl]-1H-indole-4- carboxamide, EPZ-6438 (N-((4,6-dimethyl-2-oxo-1,2-dihydropyridin-3-yl)methyl)-5-(ethyl(tetrahyd-ro-2H-pyran-4-yl)amino)-4-methyl-4'-(morpholinomethyl)-[1,1'-biphenyl]-3-c-arboxamide), GSK-126 ((S)-1-(sec-butyl)-N-(4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-((6-methyl-2-oxo-4-propyl-1,2-dihydropyridin-3-yl)-methyl)-6-(2-(4-methylpiperazin-1-yl)pyridine-4-yl)-1H-indazole-4-carboxam-ide), E11, 3-deazaneplanocin A (DNNep, 5R-(4-amino-1H-imidazo[4,5-c]pyridin-1-yl)-3-(hydroxymethyl)-3-cyclopente-ne-1S,2R-diol), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, US20140378470, US20140275081, US20140357688, and 2013/0195843; see also PCT/US2011/035336, PCT/US2011/035340, PCT/US2011/035344.

Cohesin is a multisubunit chromosome-associated protein complex that is highly conserved in eukaryotes; subunits include SMC1, SMC1b, SMC3, Scc1/RAD21, Rec8, SA-1/STAG-1, SA-2/STAG-2, SA-3/STAG-3, Pds5A, Pds5B, Wap1, and Sororin. See, e.g., Peters et al., Genes & Dev. 22:3089-3114 (2008); Lyons and Morgan, Mol Cell. 2011 May 6; 42(3):378-89; Jahnke et al., Nucleic Acids Res. 2008 November; 36(20): 6450-6458. In some embodiments, inhibitors of a cohesin are used, e.g., small molecule inhibitors of ECO-I and HDAC6, which in are a part of a cycle of acetylation-deacetylation that regulates the cohesins; inhibitors include, e.g., PCI34051, tubacin, apicidin, MS275, TSA, or saha. In some embodiments, of the methods described herein, an inhibitor of cohesin is used alone, e.g., without the DNA methyltransferase (DNMT) Inhibitor and/or a topoisomerase inhibitor, or in combination with one or both of them.

Tables 5 and 6, at the end of the Examples, provide the full list of possible Xist-interacting targets.

TABLE 7

Exemplary Xist-Interacting Proteins and Chromatin-Modifying Proteins

| Xist-Interacting Protein | Small molecule inhibitor |
|---|---|
| WAPL | — |
| SNC1a | See above |
| SMC3 | See above |
| RAD21 | See above |
| KIF4 | — |
| PDS5a/b | See above |
| CTCF | 3-aminobenzamide |
| TOP1 | See above |
| TOP2a | See above |
| TOP2b | See above |
| SMARCA4 (BRG1) | PFI3 ((E)-1-(2-Hydroxyphenyl)-3-((1R,4R)-5-(pyridin-2-yl)-2,5-diazabicyclo[2.2.1]heptan-2-yl)prop-2-en-1-one); JQ1(+); AGN-PC-0DAUWN |
| SMARCA5 | — |
| SMARCC1 | — |
| SMARCC2 | — |
| SMARCB1 | — |
| CBX2 | — |
| CBX4 | — |
| CBX5 | — |
| CBX6 | — |
| CBX7 | MS37452 |
| CBX8 | — |
| RINB1a | PRT4165 (2-pyridine-3-yl-methylene-indan-1,3-dione) |
| RING1b | — |
| AURKB | ZM447439, Hesperadin, VX-680/MK-0457 (4,6-diaminopyrimidine), AT9283, AZD1152, AKI-001, PHA-680632, VE-465, JNJ-7706621, CCT129202, MLN8237, ENMD-2076, MK-5108, PHA-739358, CYC116, SNS-314, R763, PF-03814375, GSK1070916, AMG-900 (see Kollareddy et al., Invest New Drugs. 2012 Dec; 30(6): 2411-2432) |
| SPEN/MINT/SHARP | MG132 |
| DNMT1 | See above |
| SmcHD1 | — |
| CTCF | — |
| MYEF2 | — |
| ELAVL1 | — |
| SUN2 | mevinolin |
| Lamin-B Receptor (LBR) | — |
| LAP | bestatin |
| hnRPU/SAF-A | -DPQ |
| hnPRK | — |
| hnRPC | — |
| PTBP2 | — |
| RALY | — |
| MATRIN3 | plumbagin |
| MacroH2A | |

TABLE 7-continued

Exemplary Xist-Interacting Proteins and Chromatin-Modifying Proteins

| Xist-Interacting Protein | Small molecule inhibitor |
|---|---|
| ATRX | Berberine, Inhibitors of histone deacteylases (HDAC) such as trichostatin A (TSA), depsipeptide, vorinostat, |
| RYBP | — |
| YY1 | — |
| EZH2 | See above |
| SUZ12 | — |
| EED | Astemizole (inhibits EZH2-EED interaction) |
| RBBP7 | — |
| RBBP4 | — |
| JARID2 | — |

Inhibitory Nucleic Acids

The methods and compositions described herein can include nucleic acids such as a small inhibitory RNA (siRNA) or LNA that targets (specifically binds, or is complementary to) XIST RNA or to a gene encoding XIST or an XIST-interacting protein, e.g., a chromatin-modifying protein, and optionally an inhibitory nucleic acid that targets a strong or moderate binding site or a supRNA described in WO 2012/065143, WO 2012/087983, WO 2014/025887 and U.S. Ser. No. 62/010,342. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., U.S. Ser. No. 62/010,342, WO 2012/065143, WO 2012/087983, and WO 2014/025887. However, in some embodiments the inhibitory nucleic acid is not an miRNA, an stRNA, an shRNA, an siRNA, an RNAi, or a dsRNA.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids), as well as WO 2012/065143, WO 2012/087983, and WO 2014/025887 (inhibitory nucleic acids targeting non-coding RNAs/supRNAss), all of which are incorporated herein by reference in their entirety.

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the inhibitory nucleic acid into which they are incorporated more resistant to nuclease digestion than the native oligodeoxynucleotide; these modified oligos survive intact for a longer time than unmodified inhibitory nucleic acids. Specific examples of modified inhibitory nucleic acids include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are inhibitory nucleic acids with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the inhibitory nucleic acid is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid inhibitory nucleic acid mimetics are described in Wang et al., J. Am. Chem. Soc., 2000, 122, 8595-8602.

Modified inhibitory nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an inhibitory nucleic acid; or a group for improving the pharmacodynamic properties of an inhibitory nucleic acid and other substituents having similar properties. A preferred modification includes 2'-methoxyethoxy [2'-0-$CH_2CH_2OCH_3$, also known as 2'-O-(2-methoxyethyl)](Martin et al, Helv. Chim. Acta, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the inhibitory nucleic acid, particularly the 3' position of the sugar on the 3' terminal nucleotide and the 5' position of 5' terminal nucleotide. Inhibitory nucleic acids may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given inhibitory nucleic acid to be uniformly modified, and in fact more than one of the aforementioned modifications may be incorporated in a single inhibitory nucleic acid or even at within a single nucleoside within an inhibitory nucleic acid.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an inhibitory nucleic acid mimetic that has been shown to have excellent hybridization properties, is referred to as a peptide nucleic acid (PNA). In PNA compounds, the sugar-backbone of an inhibitory nucleic acid is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the inhibitory nucleic acid. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463;

5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., inhibitory nucleic acids containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of inhibitory nucleic acids of 10-30 nucleotides spanning the length of a target RNA can be prepared, followed by testing for activity. Optionally, gaps, e.g., of 5-10 nucleotides or more, can be left between the LNAs to reduce the number of inhibitory nucleic acids synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) inhibitory nucleic acids). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising a DNMT inhibitor and/or topoisomerase inhibitor, and optionally an inhibitor of XIST RNA and/or an Xist-interacting protein, e.g., a chromatin-modifying protein, e.g., a small molecule inhibitor or an inhibitory nucleic acid such as a small inhibitory RNA (siRNA) or LNA that targets XIST RNA and/or a gene encoding Xist or an Xist-interacting protein, e.g., a chromatin-modifying protein, and optionally an inhibitory nucleic acid that specifically binds, or is complementary, to a strong or moderate binding site or a supRNA described in WO 2012/065143, WO 2012/087983, WO 2014/025887 and U.S. Ser. No. 62/010,342. The methods can include administration of a single composition comprising a DNMT inhibitor and/or topoisomerase inhibitor, and an optional inhibitor of Xist or an Xist-interacting protein, e.g., a chromatin-modifying protein, or multiple compositions, e.g., each comprising one, two, or all three of a DNMT inhibitor, a topoisomerase inhibitor, and an optional inhibitor of Xist or an Xist-interacting protein, e.g., a chromatin-modifying protein.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages.

Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Disorders Associated with X-Inactivation

The present disclosure provides methods for treating X-linked diseases formulated by administering a DNA methyltransferase (DNMT) Inhibitor and/or a topoisomerase inhibitor, optionally with an inhibitor of an Xist interacting protein, e.g., a small molecule inhibitor or an inhibitory nucleic acid such as a small inhibitory RNA (siRNA) or LNA that targets XIST or a gene encoding XIST or an Xist-interacting protein, e.g., a chromatin-modifying protein, and optionally an inhibitory nucleic acid that specifically binds, or is complementary, to a strong or moderate binding site or a supRNA described in WO 2012/065143, WO 2012/087983, WO 2014/025887 and U.S. Ser. No. 62/010,342, to disrupt silencing of genes controlled by the PRC2 sites (e.g., all of the genes within a cluster), or to disrupt silencing of one specific gene. This methodology is useful in X-linked disorders, e.g., in heterozygous women who retain a wildtype copy of a gene on the Xi (See, e.g., Lyon, Acta Paediatr Sunni. 2002; 91(439):107-12; Carrell and Willard, Nature. 434(7031):400-4 (2005); den Veyver, Semin Reprod Med. 19(2):183-91 (2001)). In females, reactivating a non-disease silent allele on the Xi would be therapeutic in many cases of X-linked disease, such as Rett Syndrome (caused by MECP2 mutations), Fabry's Disease (caused by GLA mutations), or X-linked hypophosphatemia (caused by mutation of PHEX). The methodology may also be utilized to treat male X-linked disease. In both females and males, upregulation of a hypomorphic or epigenetically silenced allele may alleviate disease phenotype, such as in Fragile X Syndrome, where the mechanism of epigenetic silencing of FMK/may be similar to epigenetic silencing of a whole Xi in having many different types of heterochromatic marks.

As a result of X-inactivation, heterozygous females are mosaic for X-linked gene expression; some cells express genes from the maternal X and other cells express genes from the paternal X. The relative ratio of these two cell populations in a given female is frequently referred to as the "X-inactivation pattern." One cell population may be at a selective growth disadvantage, resulting in clonal outgrowth of cells with one or the other parental X chromosome active; this can cause significant deviation or skewing from an expected mean X-inactivation pattern (i.e., 50:50). See, e.g., Plenge et al., Am. J. Hum. Genet. 71:168-173 (2002) and references cited therein.

The present methods can be used to treat disorders associated with X-inactivation, which includes those listed in Table 8. The methods include administering a DNA methyltransferase (DNMT) Inhibitor and/or a topoisomerase inhibitor, optionally with an inhibitor of XIST RNA an Xist-interacting protein, e.g., a chromatin-modifying protein, e.g., a small molecule inhibitor or an inhibitory nucleic acid such as a small inhibitory RNA (siRNA) or LNA that targets Xist or a gene encoding Xist or an Xist-interacting protein, e.g., a chromatin-modifying protein, and optionally an inhibitory nucleic acid that specifically binds, or is complementary, to a strong or moderate binding site or a supRNA described in WO 2012/065143, WO 2012/087983, WO 2014/025887 and U.S. Ser. No. 62/010,342, i.e., a supRNA associated with the gene that causes the disorder, as shown in Table 8 and WO 2012/065143, WO 2012/087983, and WO 2014/025887.

TABLE 8

X Linked Disorders and Associated Genes

| Disorder | OMIM # | Locus | Gene |
|---|---|---|---|
| Dent's disease 1 | 300009 | Xp11.22 | CLCN5 |
| Testicular feminization syndrome | 300068 | Xq11-q12 | AR |
| Addison's disease with cerebral sclerosis | 300100 | Xq28 | ABCD1 |
| Adrenal hypoplasia | 300200 | XP21.3-p21.2 | DAX1 |
| siderius X-linked mental retardation syndrome | 300263 | Xp11.22 | PHF8 |
| Agammaglobulinaemia, Bruton type | 300300 | Xq21.3-q22 | BTK |
| Choroidoretinal degeneration | 300389 | Xp21.1 | RPGR |
| Choroidoaemia | 300390 | Xq21.2 | CHM |
| Albinism, ocular | 300500 | Xp22.3 | OA1 |
| Dent's disease 2 | 300555 | Xq25-q26 | OCRL |
| fragile X syndrome | 300624 | Xq27.3 | FMR1 |
| Rett/Epileptic encephalopathy, early infantile, 2 | 300672 | Xp22.13 | CDKL5 |
| Albinism-deafness syndrome | 300700 | Xq26.3-q27.1 | ADFN |
| paroxysmal nocturnal hemoglobinuria | 300818 | Xp22.2 | PIGA |
| Aldrich syndrome | 301000 | Xp11.23-p11.22 | WAS |
| Alport syndrome | 301050 | Xq22.3 | COL4A5 |
| Anaemia, hereditary hypochromic | 301300 | Xp11.21 | ALAS2 |
| Anemia, sideroblastic, with ataxia | 301310 | Xq13.3 | ABCB7 |
| Fabry disease | 301500 | Xq22 | GLA |
| Spinal muscular atrophy 2 | 301830 | Xp11.23 | UBA1 |
| Cataract, congenital | 302200 | Xp | CCT |
| Charcot-Marie-Tooth, peroneal | 302800 | Xq13.1 | GJB1 |
| Spastic paraplegia | 303350 | Xq28 | L1CAM |
| Colour blindness | 303800 | Xq28 | OPN1MW |
| Diabetes insipidus, nephrogenic | 304800 | Xq28 | AVPR2 |
| Dyskeratosis congenita | 305000 | Xq28 | DKC1 |
| Ectodermal dysplasia, anhidrotic | 305100 | Xq12-q13.1 | ED1 |
| Faciagenital dysplasia (Aarskog syndrome) | 305400 | Xp11.21 | FGD1 |
| Glucose-6-phosphate dehydrogenase deficiency | 305900 | Xq28 | G6PD |
| Glycogen storage disease type VIII | 306000 | Xp22.2-p22.1 | PHKA2 |
| Gonadal dysgenesis (XY female type) | 306100 | Xp22.11-p21.2 | GDXY |
| Granulomatous disease (chronic) | 306400 | Xp21.1 | CYBB |
| Haemophilia A | 306700 | Xq28 | F8 |
| Haemophilia B | 306900 | Xq27.1-q27.2 | F9 |
| Hydrocephalus (aqueduct stenosis) | 307000 | Xq28 | L1CAM |
| Hydrophrophataemic rickets | 307800 | Xp22.2-p22.1 | PHEX |
| Lesch-Nyhan syndrome (hypoxanthine-guanine-phosphoribosyl transferase deficiency) | 308000 | Xq26-q27.2 | HPRT1 |
| Incontinentia pigmenti | 308300 | Xq28 | IBKBG |
| Kallmann syndrome | 308700 | Xp22.3 | KAL1 |
| Keratosis follicularis spinulosa | 308800 | Xp22.1 | SAT |
| Lowe (oculocerebronal) syndrome | 309000 | Xq26.1 | OCRL |
| Menkes syndrome | 309400 | Xq12-q13 | ATP7A |
| Renpenning syndrome | 309500 | Xp11.23 | PQBP1 |
| Mental retardation, with or without fragile site (numerous specific types) | 309530 | Xp11.3-q21.1 | MRX1 |
| Coffin-Lowry syndrome | 309580 | Xq13 | ATRX |
| Microphthalmia with multiple anomalies (Lenz syndrome) | 309800 | Xq27-q28 | MAA |
| Muscular dystrophy (Becker, Duchenne and Emery-Dreifuss types) | 310300 | Xq28 | EMD |
| Myotubular myopathy | 310400 | Xq28 | MTM1 |
| Night blindness, cogenital stationary | 310500 | Xp11.4 | CSNB1 |
| Norrie's disease (pseudoglioma) | 310600 | Xp11.4 | NDP |
| Nystagmus, oculomotor or 'jerky' | 310700 | Xq26-q27 | NYS1 |

TABLE 8-continued

X Linked Disorders and Associated Genes

| Disorder | OMIM # | Locus | Gene |
| --- | --- | --- | --- |
| Orofaciodigital syndrome (type I) | 311200 | Xp22.2-p22.2 | OFD1 |
| Ornithine transcarbamylase deficiency (type I hyperammonaemia) | 311250 | Xp21.1 | OTC |
| Phosphoglycerate kinase deficiency | 311800 | Xq13 | PGK1 |
| Phosphoribosylpyrophosphate synthetase deficiency | 311850 | Xq22-q24 | PRPS1 |
| Retinitis pigmentosa | 312610 | Xp21.1 | RPGR |
| Retinoschisis | 312700 | Xp22.2-p22.1 | RS1 |
| Rett syndrome | 312750 | Xq28, Xp22 | MECP2 |
| Muscular atrophy/ Dihydrotestosterone receptor deficiency | 313200 | Xq11-q12 | AR |
| Spinal muscular atrophy | 313200 | Xq11-q12 | AR |
| Spondyloepiphyseal dysplasia tarda | 313400 | Xp22.2-p22.1 | SEDL |
| Thrombocytopenia, hereditary | 313900 | Xp11.23-p11.22 | WAS |
| Throxine-binding globulin, absence | 314200 | Xq22.2 | TBG |
| McLeod syndrome | 314850 | Xp21.1 | XK |

Table 8 was adapted in part from Germain, "Chapter 7: General aspects of X-linked diseases" in Fabry Disease: Perspectives from 5 Years of FOS. Mehta A, Beck M, Sunder-Plassmann G, editors. (OXford: Oxford PharmaGenesis; 2006).

Identification of Direct Rna Interacting Proteins (iDRIP)

Also described herein is a method for identifying proteins that interact with a selected nucleic acid, e.g., an RNA such as an supRNA. The methods include in vivo UV crosslinking the proteins to the DNA in a living cell, preparing the nuclei, solubilizing the chromatin (e.g., by DNase I digestion), creating protein-RNA complexes through hybridization to capture probes specific for the selected RNA, treating the protein-RNA complexes with DNase, isolating the protein-RNA complexes using the capture probes (e.g., capture probes bound to beads) and washing, preferably under denaturing conditions to eliminate protein factors that were not covalently linked by UV to the selected RNA. To minimize background due to DNA-bound proteins, a critical DNase I treatment can be performed prior to elution. These methods can be used to identify proteins bound to any nucleic acid, e.g., RNA, e.g., any non-coding or coding RNA.

EXAMPLES

The invention is further described in the following examples, which do not limit the scope of the invention described in the claims.

Materials and Methods

The following materials and methods were used in the Examples, below.

Identification of Direct RNA interacting Proteins (iDRiP)

Mouse Embryonic Fibroblasts (MEFs) were irradiated with UV light at 200 mJ energy (Stratagene 2400) after rinsing with PBS. The pellets were resuspended in CSKT-0.5% (10 mM PIPES, pH 6.8, 100 mM NaCl, 3 mM $MgCl_2$, 0.3 M sucrose, 0.5% Triton X-100, 1 mM PMSF) for 10 min at 4° C. followed by a spin. The pellets were again resuspended in Nuclear Isolation Buffer (10 mM Tris pH 7.5, 10 mM KCl, 0.5% Nonidet-P 40, 1× protease inhibitors, 1 mM PMSF), and rotated at 4° C. for 10 min. The pellets were collected after a spin, weighed, flash frozen in liquid nitrogen, and stored at −80° C. until use.

Approximately, equal amounts of female and male UV cross linked pellets were thawed and resuspended for treatment with Turbo DNase I in the DNase I digestion buffer (50 mM Tris pH 7.5, 0.5% Nonidet-P 40, 0.1% sodium lauroyl sarcosine, 1× protease inhibitors, SuperaseIn). The tubes were rotated at 37° C. for 45 min. The nuclear lysates were further solubilized by adding 1% sodium lauroyl sarcosine, 0.3 M lithium chloride, 25 mM EDTA and 25 mM EGTA to final concentrations and continued incubation at 37° C. for 15 min. The lysates were mixed with biotinylated DNA probes (Table 1A) prebound to the streptavidin magnetic beads (MyOne streptavidin C1 Dyna beads, Invitrogen) and incubated at 55° C. for 1 hr before overnight incubation at 37° C. in the hybridization chamber. The beads were washed three times in Wash Buffer (10 mM Tris, pH 7.5, 0.3 M LiCl, 1% LDS, 0.5% Nonidet-P 40, 1× protease inhibitor) at room temperature followed by treatment with Turbo DNase I in DNase I digestion buffer with the addition of 0.3 M LiCl, protease inhibitors, and superaseIn at 37° C. for 20 min. Then, beads were washed two more times in the Wash Buffer. For MS analysis, elution was done in Elution Buffer (10 mM Tris, pH 7.5, 1 mM EDTA) at 70° C. for 4 min followed by brief sonication in Covaris. For the quantification of pulldown efficiency, MEFs, without crosslinking, were used and elution was done at 95° C. The elute was used for RNA isolation and RT-qPCR. When crosslinked MEFs were used, elute was subjected for proteinase-K treatment (50 mM Tris pH 7.5, 100 mM NaCl, 0.5% SDS, 10 µg proteiase K) for 1 hr at 55° C. RNA were isolated by Trizol and quantified with SYBR green qPCR. Input samples were used to make standard curve by 10 fold dilutions, to which the RNA pulldown efficiencies were compared and calculated. The efficiency of Xist pulldown was relatively lower after UV crosslinking, similar to (48, 49).

TABLE 1A

Biotinylated Oligos used in Xist interactome capture

| | Sequence | SEQ ID NO: |
| --- | --- | --- |
| X1 | CAGTTTAAGAGCAAAGTCGTTTTTC | 1 |
| X2 | AATATGTTTACATTACAGGTGGCAA | 2 |
| X3 | TAAAGACCAAGCAAAGATACTTGTC | 3 |
| X4 | ATGCTTCATATATTCAGTGGTTCAC | 4 |
| X5 | TGTATTAAGTGAAATTCCATGACCC | 5 |
| X6 | AACTTAGCAATTAATTCTGGGACTC | 6 |
| X7 | ATGCATATCTGTATGCATGCTTATT | 7 |
| X8 | CATATTACTTGGGGACTAAGGACTA | 8 |
| X9 | ATGGGCACTGCATTTTAGCAATA | 9 |

TABLE 1B

Primers used in qPCR

| | Sequence | SEQ ID NO: |
| --- | --- | --- |
| U1 snRNA-F | CCAGGGCGAGGCTTATCCATT | 10 |
| U1 snRNA-R | GCAGTCCCCCACTACCACAAAT | 11 |
| eGFP-F | GAC GTA AAC GGC CAC AAG TT | 12 |

TABLE 1B-continued

Primers used in qPCR

| | Sequence | SEQ ID NO: |
|---|---|---|
| eGFP-R | AAG TCG TG CTG CTT CAT GTG | 13 |
| U6 snRNA-F | CTC GCT TCG GCA GCA CA | 14 |
| U6 snRNA-R | AAC GCT TCA CGA ATT TGC GT | 15 |
| Smc1a-F | TCG GAC CAT TTC AGA GGT TTA CC | 16 |
| Smc1a-R | CAG GTG CTC CAT GTA TCA GGT | 17 |
| Smc3-F | CGA AGT TAC CGA GAC CAA ACA | 18 |
| Smc3-R | TCA CTG AGA ACA AAC TGG ATT GC | 19 |
| Rad21-F | ATG TTC TAC GCA CAT TTT GTC CT | 20 |
| Rad21-R | TGC ACT CAA ATA CAT GGG CTT T | 21 |
| Kif4-F | AGG TGA AGG GGA TTC CCG TAA | 22 |
| Kif4-R | AAA CAC GCC TTT TAT GAG TGG A | 23 |
| Pds5a-F | TTG GGA AAC TGA TGA CCA TAG C | 24 |
| Pds5a-R | ACA CAA ACG TCA GCC TGC TT | 25 |
| Aurkb-F | CAG AAG GAG AAC GCC TAC CC | 26 |
| Aurkb-R | GAG AGC AAG CGC AGA TGT C | 27 |
| Top2b-F | CTG ACC TGG GTG AAC AAT GCT | 28 |
| Top2b-R | TGG CTC CAC TGA TCC AAT GTA T | 29 |
| Top2a-F | GAG AGG CTA CGA CTC TGA CC | 30 |
| Top2a-R | CTC CAG GTA GGG GGA TGT TG | 31 |
| Top1-F | AAG ATC GAG AAC ACC GGC ATA | 32 |
| Top1-R | CTT TTC CTC CTT CGG TCT TTC C | 33 |
| Ctcf-F | GAT CCT ACC CTT CTC CAG ATG AA | 34 |
| Ctcf-R | GTA CCG TCA CAG GAA CAG GT | 35 |
| Smarca4-F | CAA AGA CAA GCA TAT CCT AGC CA | 36 |
| Smarca4-R | CAC GTA GTG TGT GTT AAG GAC C | 37 |
| Smarca5-F | GAC ACC GAG ATG GAG GAA GTA | 38 |
| Smarca5-R | CGA ACA GCT CTG TCT GCT TTA | 39 |
| Smarcc1-F | AGC TAG ATT CGG TGC GAG TCT | 40 |
| Smarcc1-R | CCA CCA GTC CAG CTA GTG TTT T | 41 |
| Smarcc2-F | GCT GCC TAC AAA TTC AAG AGT GA | 42 |
| Smarcc2-R | AGG AAA ATG TTA GGT CGT GAC AG | 43 |
| Smarcb1-F | TCC GAG GTG GGA AAC TAC CTG | 44 |
| Smarcb1-R | CAG AGT GAG GGG TAT CTC TTG T | 45 |
| Sun2-F | ATC CAG ACC TTC TAT TTC CAG GC | 46 |
| Sun2-R | CCC GGA AGC GGT AGA TAC AC | 47 |

Quantitative Proteomics

Proteins co-enriched with Xist from female or male cells were quantitatively analyzed either using a label-free approach based on spectral-counting (21) or by multiplexed quantitative proteomics using tandem-mass tag (TMT) reagents (50, 51) on an Orbitrap Fusion mass spectrometer (Thermo Scientific). Disulfide bonds were reduced with ditheiothreitol (DTT) and free thiols alkylated with iodoacetamide as described previously (22). Proteins were then precipitated with tricholoracetic acid, resuspended in 50 mM HEPES (pH 8.5) and 1 M urea and digested first with endoproteinase Lys-C(Wako) for 17 hours at room temperature and then with sequencing-grade trypsin (Promega) for 6 hours at 37° C. Peptides were desalted over Sep-Pak $C_{18}$ solid-phase extraction (SPE) cartridges (Waters), the peptide concentration was determined using a BCA assay (Thermo Scientific). For the label-free analysis peptides were then dried and re-suspended in 5% formic acid (FA) and 5% acetonitrile (ACN) and 5 µg of peptides were analyzed by mass spectrometry as described below. For the multiplexed quantitative analysis a maximum of 50 µg of peptides were labeled with one out of the available TMT-10plex reagents (Thermo Scientific) (51). To achieve this, peptides were dried and resuspended in 50 µl of 200 mM HEPES (pH 8.5) and 30% (ACN) and 10 µg of the TMT in reagent in 5 µl of anhydrous ACN was added to the solution, which was incubated at room temperature (RT) for one hour. The reaction was then quenched by adding 6 µl of 5% (w/v) hydroxylamine in 200 mM HEPES (pH 8.5) and incubation for 15 min at RT. The labeled peptide mixture was then subjected to a fractionation using basic pH reversed phase liquid chromatography (bRPLC) on an Agilent 1260 Infinity HPLC system equipped with an Agilent Extend-C18 column (4.6×250 mm; particle size, 5 µm) basically as described previously (52). Peptides were fractionated using a gradient from 22-35 ACN in 10 mM ammonium bicarbonate over 58 min at a flowrate of 0.5 ml/min. Fractions of 0.3 ml were collected into a 96-well plate to then be pooled into a total twelve fractions (A1-A12, B1-B12, etc.) that were dried and re-suspended in 8 µl of 5% FA and 5% ACN, 3 of which were analyzed by microcapillary liquid chromatography tandem mass spectrometry on an Orbitrap Fusion mass spectrometer and using a recently introduced multistage (MS3) method to provide highly accurate quantification (53).

The mass spectrometer was equipped with an EASY-nLC 1000 integrated autosampler and HPLC pump system. Peptides were separated over a 100 µm inner diameter microcapillary column in-house packed with first 0.5 cm of Magic C4 resin (5 µm, 100 Å, Michrom Bioresources), then with 0.5 cm of Maccel $C_{18}$ resin (3 µm, 200 Å, Nest Group) and 29 cm of GP-C18 resin (1.8 µm, 120 Å, Sepax Technologies). Peptides were eluted applying a gradient of 8-27% ACN in 0.125% formic acid over 60 min (label-free) and 165 min (TMT) at a flow rate of 300 nl/min. For label-free analyses we applied a tandem-MS method where a full-MS spectrum (MS1; m/z 375-1500; resolution 6×$10^4$; AGC target, 5×$10^5$; maximum injection time, 100 ms) was acquired using the Orbitrap after which the most abundant peptide ions where selected for linear ion trap CID-MS2 in an automated fashion. MS2 scans were done in the linear ion trap using the following settings: quadrupole isolation at an isolation width of 0.5 Th; fragmentation method, CID; AGC target, 1×$10^4$; maximum injection time, 35 ms; normalized collision energy, 30%). The number of acquired MS2 spectra was defined by setting the maximum time of one experimental cycle of MS1 and MS2 spectra to 3 sec (Top Speed). To identify and quantify the TMT-labeled peptides we applied a synchronous precursor selection MS3 method (22, 53, 54) in a data dependent mode. The scan sequence was started with the acquisition of a full MS or MS1 one spectrum acquired in the Orbitrap (m/z range, 500-1200; other parameters were set as described above), and the most intense peptide ions from detected in the full MS spectrum were then subjected to MS2 and MS3 analysis, while the acquisition time was optimized in an automated fashion (Top Speed, 5 sec). MS2 scans were performed as described above. Using synchronous precursor selection the 10 most abundant fragment ions were selected for the MS3 experiment following each MS2 scan. The fragment ions were further fragmented using the HCD fragmentation (normalized collision energy, 50%) and the MS3 spectrum was acquired in the Orbitrap (resolution, 60,000; AGC target, $5 \times 10^4$; maximum injection time, 250 ms).

Data analysis was performed on an on an in-house generated SEQUEST-based (55) software platform. RAW files were converted into the mzXML format using a modified version of ReAdW.exe. MS2 spectra were searched against a protein sequence database containing all protein sequences in the mouse UniProt database (downloaded Feb. 4, 2014) as well as that of known contaminants such as porcine trypsin. This target component of the database was followed by a decoy component containing the same protein sequences but in flipped (or reversed) order (56). MS2 spectra were matched against peptide sequences with both termini consistent with trypsin specificity and allowing two missed trypsin cleavages. The precursor ion m/z tolerance was set to 50 ppm, TMT tags on the N-terminus and on lysine residues (229.162932 Da, only for TMT analyses) as well as carbamidomethylation (57.021464 Da) on cysteine residues were set as static modification, and oxidation (15.994915 Da) of methionines as variable modification. Using the target-decoy database search strategy (56) a spectra assignment false discovery rate of less than 1% was achieved through using linear discriminant analysis with a single discriminant score calculated from the following SEQUEST search score and peptide sequence properties: mass deviation, XCorr, dCn, number of missed trypsin cleavages, and peptide length (57). The probability of a peptide assignment to be correct was calculated using a posterior error histogram and the probabilities for all peptides assigned to a protein were combined to filter the data set for a protein FDR of less than 1%. Peptides with sequences that were contained in more than one protein sequence from the UniProt database were assigned to the protein with most matching peptides (57).

For a quantitative estimation of protein concentration using spectral-counts we simply counted the number of MS2 spectra assigned to a given protein (Tables 5-6). TMT reporter ion intensities were extracted as that of the most intense ion within a 0.03 Th window around the predicted reporter ion intensities in the collected MS3 spectra. Only MS3 with an average signal-to-noise value of larger than 28 per reporter ion as well as with an isolation specificity (22) of larger than 0.75 were considered for quantification. Reporter ions from all peptides assigned to a protein were summed to define the protein intensity. A two-step normalization of the protein TMT-intensities was performed by first normalizing the protein intensities over all acquired TMT channels for each protein based to the median average protein intensity calculated for all proteins. To correct for slight mixing errors of the peptide mixture from each sample a median of the normalized intensities was calculated from all protein intensities in each TMT channel and the protein intensities were normalized to the median value of these median intensities.

UV RIP

The protocol followed is similar to the one described in (18). Briefly, MEFs were crosslinked with UV light at 200 mJ and collected by scraping in PBS. Cell pellets were resuspended in CSKT-0.5% for 10 min at 4° C. followed by a spin. The nuclei were resuspended in the UV RIP buffer (PBS buffer containing 300 mM NaCl (total), 0.5% Nonidet-P 40, 0.5% sodium deoxycholate, and 1× protease inhibitors) with Turbo DNase I 30 U/IP for 30 min at 37° C. Supernatants were collected after a spin and incubated with 5 µg specific antibodies prebound to 40 µl protein-G magnetic beads (Invitrogen) at 4° C. overnight. Beads were washed three times with cold UV RIP buffer. The beads were resuspended in 200 µl Turbo DNase I buffer with 20 U Turbo DNase, SuperaseIN, 1× protease inhibitors) for 30 min at 37° C. The beads were resuspended and washed three more times in the UV RIP washing buffer containing 10 mM EDTA. The final 3 washes were given after three fold dilution of UV RIP washing buffer. The beads were resuspended in 200 µl proteinase-K buffer with 10 µg proteinase-K and incubated at 55° C. for 1 hr. RNA was isolated by Trizol and pulldown efficiencies were calculated by SYBR qPCR using input for the standard curve.

Generation of Xi-TgGFP Clonal Fibroblasts

Xi-TgGFP (68-5-11) tail-tip fibroblasts (TTF) were initially derived from a single female pup, a daughter of a cross between a *M. castaneus* male and a *M. musculus* female, homozygous for an X-linked GFP transgene driven by a strong, ubiquitous promoter (58). The fibroblasts were immortalized by SV40 transformation, and clonal lines were derived from individual GFP-negative cells selected by fluorescence-activated cell sorting. In our experience, occasional clones with undetectable GFP expression nevertheless have the transgene located on the active X chromosome. Thus, we confirmed the GFP transgene location on the inactive X for the particular clone used here, 68-5-11 (see FIG. 10).

Generation of Stable KD of Xi-TgGFP TTF and 16.7 ES Cells

A cocktail of 3 shRNA viruses were used for infections (Table 2) followed with puromycin selection using standard methodology. In all the experiments, polyclonal knock down cells were used.

TABLE 2

Lentiviral shRNA constructs used for stable knockdowns of candidate Xist interactors.

| RefSeq_shRNA viruses | Xist interacting candidates |
|---|---|
| TRCN0000011883 | Top1 |
| TRCN0000321370 | Ctcf |
| TRCN0000071385 | Smarca4 |
| TRCN0000295773 | Smarca5 |
| TRCN0000321371 | Ctcf |
| TRCN0000109008 | SMc3 |
| TRCN0000276847 | Rad21 |
| TRCN0000174832 | Rad21 |
| TRCN0000321718 | Aurkb |
| TRCN0000317702 | Smarcb1 |
| TRCN0000071383 | SMarca4 |
| TRCN0000325493 | Top2a |
| TRCN0000295713 | Smarca5 |
| TRCN0000309135 | Kif4 |
| TRCN0000321651 | Aurkb |
| TRCN0000109007 | Smc3 |
| TRCN0000090909 | Kif4 |
| TRCN0000321444 | Ctcf |
| TRCN0000071388 | Smarcc1 |
| TRCN0000288446 | Smarca5 |

TABLE 2-continued

Lentiviral shRNA constructs used for stable knockdowns of candidate Xist interactors.

| RefSeq_shRNA viruses | Xist interacting candidates |
|---|---|
| TRCN0000072181 | GFP |
| TRCN0000071389 | Smarcc1 |
| TRCN0000070988 | Top2b |
| TRCN0000011884 | Top1 |
| TRCN0000070990 | Top2b |
| TRCN0000229486 | Pds5a |
| TRCN0000011886 | Top1 |
| TRCN0000085541 | Smarcc2 |
| TRCN0000317622 | Smarcb1 |
| TRCN0000324673 | Smc1a |
| TRCN0000229484 | Pds5a |
| TRCN0000085540 | Smarcc2 |
| TRCN0000070987 | Top2a |
| TRCN0000071386 | Smarca4 |
| TRCN0000109009 | Smc3 |
| TRCN0000246806 | Sun2 |
| TRCN0000276903 | Rad21 |
| TRCN0000071391 | Smarcc1 |
| TRCN0000070992 | Top2b |
| TRCN0000317701 | Smarcb1 |
| TRCN0000085542 | Smarcc2 |
| TRCN0000321719 | Aurkb |
| TRCN0000246805 | Sun2 |
| TRCN0000246804 | Sun2 |
| TRCN0000217996 | Pds5a |
| TRCN0000090908 | Kif4 |
| TRCN0000324674 | Smc1a |
| TRCN0000324672 | Smc1a |
| TRCN0000353984 | Top2a |
| TRCN0000231782_pLKO_TRC021 | control |
| TRCN0000231782_pLKO_TRC021 | control |

Assay for the Reactivation of Xi-TgGFP

Approximately, 125,000-150,000 Xi-TgGFP (68-5-11) cells were plated along with control (shNegative control, i.e., shNC) cells treated with DMSO or stable KD cells treated with 0.3 µM azacytidine and 0.3 µM Etoposide for 3 days in 6 well plates. RNA was isolated by Trizol twice, with an intermittent TurboDNase treatment after the first isolation for 30 min at 37° C. One µg RNA was used for each of the RT+ and RT− reactions (Superscript III, Invitrogen) followed by the SYBR green qPCR using the primers listed in Table 3, with annealing temperature of 60° C. for 45 cycles. The relative efficiency of Xi-TgGFP reactivations was calculated by comparing to U1 snRNA as the internal control.

TABLE 3

Primers used in PCR for generation of Xi-TgGFP cell line

| | Sequence | SEQ ID NO: |
|---|---|---|
| MeCP2-F | ATGGTAGCTGGGATGTTAGGG | 48 |
| MeCP2-R | GAGCGAAAAGCTTTTCCCTGG | 49 |

ImmunoFISH

Cells were grown on coverslips, rinsed in PBS, pre-extracted in 0.5% CSKT on ice, washed once in CSK, followed by fixation with 4% paraformaldehyde in PBS at room temperature. After blocking in 1% BSA in PBS for 20 min supplemented to with 10 mM VRC (New England Biolabs) and RNase inhibitor (Roche), incubation was carried out with primary antibodies (Table 4) at room temperature for 1 hr. Cells were washed three times in PBST-0.02% Tween-20. After incubating with secondary antibody at room temperature for 30 min, cells were washed three times by PBS/0.02% Tween-20. Cells were fixed again in 4% paraformaldehyde and dehydrated in ethanol series. RNA FISH was performed using a pool of Cy3B or Alexa 568 labeled Xist oligonucleotides for 4-6 hours at 42° C. in a humid chamber. Cells were washed three times in 2×SSC and nuclei were counter-stained by Hoechst 33342. Cells were observed under Nikon 90i microscope equipped with 60×/1.4 N.A. objective lens, Orca ER CCD camera (Hamamatsu), and Volocity software (Perkin Elmer). Xist RNA FISH probes, a set of total 37 oligonucleotides with 5' amine modification (IDT), were labeled with NHS-Cy3B (GE Healthcare) overnight at room temperature followed by ethanol precipitation. In the case of confirmation of Xi-TgGFP cells, probes were made by nick-translation of a GFP PCR product with Cy3-dUTP and of a plasmid containing the first exon of the mouse Xist gene, with FITC-dUTP.

TABLE 4

Antibodies

| Brand | Antibodies and Catalog # |
|---|---|
| NOVUS BIOLOGICALS INC | SMC3 antibody (NB100-207) |
| NOVUS BIOLOGICALS INC | SMC1 Antibody (A300-055A) |
| BETHYL LABORATORIES INC | TOP1 Antibody (A302-589A) |
| SIGMA-ALDRICH INC | ANTI-SUN2 antibody (HPA001209-100UL) |
| ABCAM INC | Anti-BRG1 antibody [EPNCIR111A] (ab110641) |
| PROTEINTECH GROUP INC | TOP2A-Specific Antibody (20233-1-AP) |
| ABCAM INC | Anti-Aurora B Kinase antibody (ab2254) |
| ABCAM INC | Anti-Rad21 antibody - ChIP Grade (ab992) |
| ACTIVE MOTIF | Histone H3K27me3 antibody (pAb) (39155) |
| PROTEINTECH GROUP INC | TOP2B Polyclonal Antibody (20549-1-AP) |
| CELL SIGNALING TECHNOLOGY | SMARCC2/BAF170 (D8O9V) Rabbit mAb (12760) |
| E M D MILLIPORE | Anti-CTCF Antibody (07-729) |

Allelic ChIP-Seq

Allele-specific ChIP-seq was performed according to the method of Kung et al (25), in two biological replicates. To increase available read depth, we pooled together two technical replicates for $Xi^{\Delta xist}/Xa^{WT}$ Rad21 replicate 1 sequenced on a 2×50 bp HiSeq2500 rapid run and we also pooled two technical replicates of wild-type Rad21 replicate 1, one sequenced on a HiSeq 2×50 bp run and one on a MiSeq 2×50 bp run. All other libraries were sequenced on using 2×50 bp HiSeq2500 rapid runs. To visualize ChIP binding signal, we generated fpm-normalized bigWig files from the raw ChIP read counts for all reads (comp), mus-specific (mus) and cas-specific reads separately. For Smc1a, CTCF and Rad21, peaks were called using macs2 with default settings. To generate consensus peak sets for all three epitopes, peaks for the two wild-type and Xi$^{\Delta xist}$/Xa$^{WT}$ replicates were pooled and peaks present in at least two experiments were used as the common peak set. To make comparisons between allelic read counts between different experiments, we defined a scaling factor as the ratio of the total read numbers for the two experiments and multiplied the allelic reads for each peak in the larger sample by the scaling factor. We plotted the number of reads on Xi vs Xa in wild-type for all peaks on the X-chromosome to determine if there is a general bias towards binding to the Xa or the Xi. To evaluate allelic skew on an autosome, we generated plots of mus read counts vs cas read counts for all peaks on chromosome 5 from 1-140,000,000. We used this particular region of chromosome 5 because Xi$^{\Delta xist}$/Xa$^{WT}$ is not fully hybrid, and this is a large region of an autosome that is fully hybrid based on even numbers of read counts from input and from our Hi-Cs over this region in Xi$^{\Delta xist}$/Xa$^{WT}$ (data not shown). To identify peaks that are highly Xa-skewed in wild-type but bind substantially to the Xi in Xi$^{\Delta xist}$/Xa$^{WT}$ (restored peaks), for Xa-skewed peaks in wild-type, we plotted normalized read counts on Xi in Xi$^{\Delta xist}$/Xa$_{WT}$ versus read counts on Xa in wild-type. We defined restored peaks as peaks that are 1.) more than 3×Xa-skewed in wild-type 2.) have at least 5 allelic reads in wild-type 3.) exhibit normalized read counts on Xi in Xi$^{\Delta xist}$/Xa$^{WT}$ that are at least half the level of Xa in wild-type. This threshold ensures that all restored peaks have at least a 2× increase in binding to the Xi in Xi$^{\Delta xist}$/Xa$^{WT}$ relative to wild-type. We identified restored peaks using these criteria in both replicates of Smc1a and Rad21 ChIP separately, and to merge these calls into a consensus set for each epitope, we took all peaks that met criteria for restoration in at least one replicate and had at least 50% wild-type Xa read counts on Xi in Xi$^{\Delta xist}$/Xa$^{WT}$ in both replicates.

Allele Specific RNA-Seq

Xi-TgGFP TTFs (68-5-11) with the stable knock down of candidates were treated with 5'-azacytidine and etoposide at 0.3 µM each for 3 days. Strand-specific RNA-seq, the library preparation, deep sequencing, and data analysis was followed as described in (25). Two biological replicates of each drug treatment were produced. All libraries were sequenced with Illumina Hiseq 2000 or 2500 using 50 cycles to obtain paired end reads. To determine the allelic origin of each sequencing read from the hybrid cells, reads were first depleted of adaptors dimers and PCR duplicates, followed by the alignment to custom mus/129 and cas genomes to separate mus and cas reads. After removal of PCR duplicates, ~90% of reads were mappable. Discordant pairs and multi-mapped reads were discarded. Reads were then mapped back to reference mm9 genome using Tophat v2.0.10 (-g 1—no-coverage-search—read-edit-dist 3—read-mismatches 3—read-gap-length 3—b2-very-sensitive—mate-inner-dist 50—mate-std-dev 50—library-type fr-first-strand), as previously described (59, 32, 25). Following alignment, gene expression levels within each library were quantified using Homer v4.7 (rna mm9-count genes-strand+-noadj-condenseGenes) (59) and the normalized differential expression analyses across samples were performed by using EdgeR (60).

HiC Library Preparation and Analysis

Hi-C libraries were generated according to the protocol in Lieberman-Aiden et al., 2009 (61). Two biological replicate libraries were prepared for wild-type and Xi$^{\Delta xist}$/Xa$^{WT}$ fibroblasts each. We obtained 150-220 million 2×50 bp paired-end reads per library. The individual ends of the read-pairs were aligned to the mus and cas reference genomes separately using novoalign with default parameters for single-end alignments, and the quality score of the alignment was used to determine whether each end could be assigned to either the mus or the cas haplotype (62). The single-end alignments were merged into a Hi-C summary file using custom scripts. Reads were filtered for self-ligation events and short fragments (less than 1.5× the estimated insert length) likely to be random shears using Homer (59, 63). Hi-C contact maps were generated using Homer. "Comp" maps were made from all reads. "Xi" and "Xa" reads were from reads where at least one read-end could be assigned to either the mus or cas haplotype, respectively. A small fraction of reads (~5% of all allelic reads) aligned such that one end aligned to mus, the other to cas. These "discordant" reads were excluded from further analysis, as they are likely to be noise arising due to random ligation events and/or improper SNP annotation (64, 46). All contact maps were normalized using the matrix balancing algorithm of Knight and Ruiz (65), similar to iterative correction (66, 46), using the MATLAB script provided at the end of their paper. We were able to generate robust contact maps using the comp reads in one replicate at 40 kb resolution, but due to the fact that only ~44% of reads align allele-specifically, we were only able to generate contact maps for the cas and mus haplotypes at 200 kb. To increase our resolution, we pooled together both biological replicates and analyzed the comp contact map at 40 kb resolution and the mus and cas contact maps at 100 kb. We called TADs at 40 kb on chrX, chr5 and chr13 using the method of Dixon et al. (27). specifically, we processed the normalized comp 40 kb contact maps separately into a vector of directionality indices using DI_from_matrix.pl with a bin size of 40000 and a window size of 200000. We used this vector of directionality indices as input for the HMM_calls.m script and following HMM_generation, we processed the HMM and generated TAD calls by passing the HMM output to file_ends_cleaner.pl, converter_7col.pl, hmm_probablity_correcter.pl, hmm-state_caller.pl and finally hmm-state_domains.pl. We used parameters of min=2, prob=0.99, binsize=40000 as input to the HMM probability correction script.

To create a general metric describing interaction frequencies within TADs at resolution available in the allele-specific interaction maps, for each TAD, on chrX and chr5 we averaged the normalized interaction scores for all bins within each TAD, excluding the main diagonal. To make comparisons between interaction frequency over TADs between the cas (Xa) and mus (Xi) haplotypes at the resolution available with our current sequencing depth, we defend the "fraction mus" as the average interaction score for a TAD in the mus contact map divided by the sum of the average interaction scores in the mus and cas contact maps.

To discover TADs that show significantly increased interaction frequency in Xi$^{\Delta xist}$/Xa$^{WT}$, we generated a null distribution of changes in average normalized interaction scores for all TADs on chromosome 5, 1-140 Mb using the cas and mus contact maps. We reasoned that there would be few changes in interaction frequency on an autosome between the mus or cas contact maps for wild-type and Xi$^{\Delta xist}$/Xa$^{WT}$, thus the distribution of fold changes in interaction score on an autosome constitutes a null distribution. Using this distribution of fold changes allowed us to calculate a threshold fold change for an empirical FDR of 0.05, and all TADs that had a greater increase in average normalized interaction score on Xi between wild-type and Xi$^{\Delta xist}$/Xa$^{WT}$ were considered restored TADs. We preformed this analysis of restored TADs separately in each biological replicate using the 200 kb contact maps to generate interaction scores over TADs, and using the combined data at 100 kb resolution.

REFERENCES FOR MATERIALS AND
METHODS SECTION ONLY

1. A. Castello et al., Insights into RNA biology from an atlas of mammalian mRNA-binding proteins. Cell 149, 1393-1406 (2012).
2. S. C. Kwon et al., The RNA-binding protein repertoire of embryonic stem cells. Nature structural & molecular biology 20, 1122-1130 (2013).
3. D. H. Lundgren, S. I. Hwang, L. Wu, D. K. Han, Role of spectral counting in quantitative proteomics. Expert review of proteomics 7, 39-53 (2010).
4. G. C. McAlister et al., Increasing the multiplexing capacity of TMTs using reporter ion isotopologues with isobaric masses. Analytical chemistry 84, 7469-7478 (2012).
5. A. Thompson et al., Tandem mass tags: a novel quantification strategy for comparative analysis of complex protein mixtures by MS/MS. Analytical chemistry 75, 1895-1904 (2003).
6. L. Ting, R. Rad, S. P. Gygi, W. Haas, MS3 eliminates ratio distortion in isobaric multiplexed quantitative proteomics. Nature methods 8, 937-940 (2011).
7. A. C. Tolonen, W. Haas, Quantitative proteomics using reductive dimethylation for stable isotope labeling. Journal of visualized experiments: JoVE, (2014).
8. G. C. McAlister et al., MultiNotch MS3 enables accurate, sensitive, and multiplexed detection of differential expression across cancer cell line proteomes. Analytical chemistry 86, 7150-7158 (2014).
9. M. P. Weekes et al., Quantitative temporal viromics: an approach to investigate host-pathogen interaction. Cell 157, 1460-1472 (2014).
10. J. K. Eng, A. L. McCormack, J. R. Yates, An approach to correlate tandem mass spectral data of peptides with amino acid sequences in a protein database. Journal of the American Society for Mass Spectrometry 5, 976-989 (1994).
11. J. E. Elias, S. P. Gygi, Target-decoy search strategy for increased confidence in large-scale protein identifications by mass spectrometry. Nature methods 4, 207-214 (2007).
12. E. L. Huttlin et al., A tissue-specific atlas of mouse protein phosphorylation and expression. Cell 143, 1174-1189 (2010).
13. Y. Jeon, J. T. Lee, YY1 tethers Xist RNA to the inactive X nucleation center. Cell 146, 119-133 (2011).
14. A. K. Hadjantonakis, L. L. Cox, P. P. Tam, A. Nagy, An X-linked GFP transgene reveals unexpected paternal X-chromosome activity in trophoblastic giant cells of the mouse placenta. Genesis 29, 133-140 (2001).
15. J. T. Kung et al., Locus-Specific Targeting to the X Chromosome Revealed by the RNA Interactome of CTCF. Molecular cell 57, 361-375 (2015).
16. J. T. Kung et al., Locus-specific targeting to the X chromosome revealed by the RNA interactome of CTCF. Molecular cell 57, 361-375 (2015).
17. S. F. Pinter et al., Spreading of X chromosome inactivation via a hierarchy of defined Polycomb stations. Genome research 22, 1864-1876 (2012).
18. S. Heinz et al., Simple combinations of lineage-determining transcription factors prime cis-regulatory elements required for macrophage and B cell identities. Molecular cell 38, 576-589 (2010).
19. M. D. Robinson, D. J. McCarthy, G. K. Smyth, edgeR: a Bioconductor package for differential expression analysis of digital gene expression data. Bioinformatics 26, 139-140 (2010).
20. E. Lieberman-Aiden et al., Comprehensive mapping of long-range interactions reveals folding principles of the human genome. Science (New York, N.Y.) 326, 289-293 (2009).
21. E. Yildirim, R. Sadreyev, S. Pinter, J. Lee, X-chromosome hyperactivation in mammals via nonlinear relationships between chromatin states and transcription. Nature structural & molecular biology 19, 56-61 (2012).
22. C. L. Yin et al., Global changes in the nuclear positioning of genes and intra- and interdomain genomic interactions that orchestrate B cell fate. Nature Immunology 13, 1196-1204 (2012).
23. H. Sven et al., Simple Combinations of Lineage-Determining Transcription Factors Prime cis-Regulatory Elements Required for Macrophage and B Cell Identities. Molecular Cell 38, (2010).
24. S. Selvaraj, J. R Dixon, V. Bansal, B. Ren, Whole-genome haplotype reconstruction using proximity-ligation and shotgun sequencing. Nature biotechnology, (2013).
25. S. S. Rao et al., A 3D map of the human genome at kilobase resolution reveals principles of chromatin looping. Cell 159, 1665-1680 (2014).
26. P. A. Knight, D. Ruiz, A fast algorithm for matrix balancing. IMA Journal of Numerical Analysis, (2012).
27. I. Maxim et al., Iterative correction of Hi-C data reveals hallmarks of chromosome organization. Nature Methods 9, 999-1003 (2012).
28. J. Dixon et al., Topological domains in mammalian genomes identified by analysis of chromatin interactions. Nature 485, 376-380 (2012).

Example 1. iDRiP Identifies Multiple Classes of Xist-Interacting Proteins

Figure 1A:
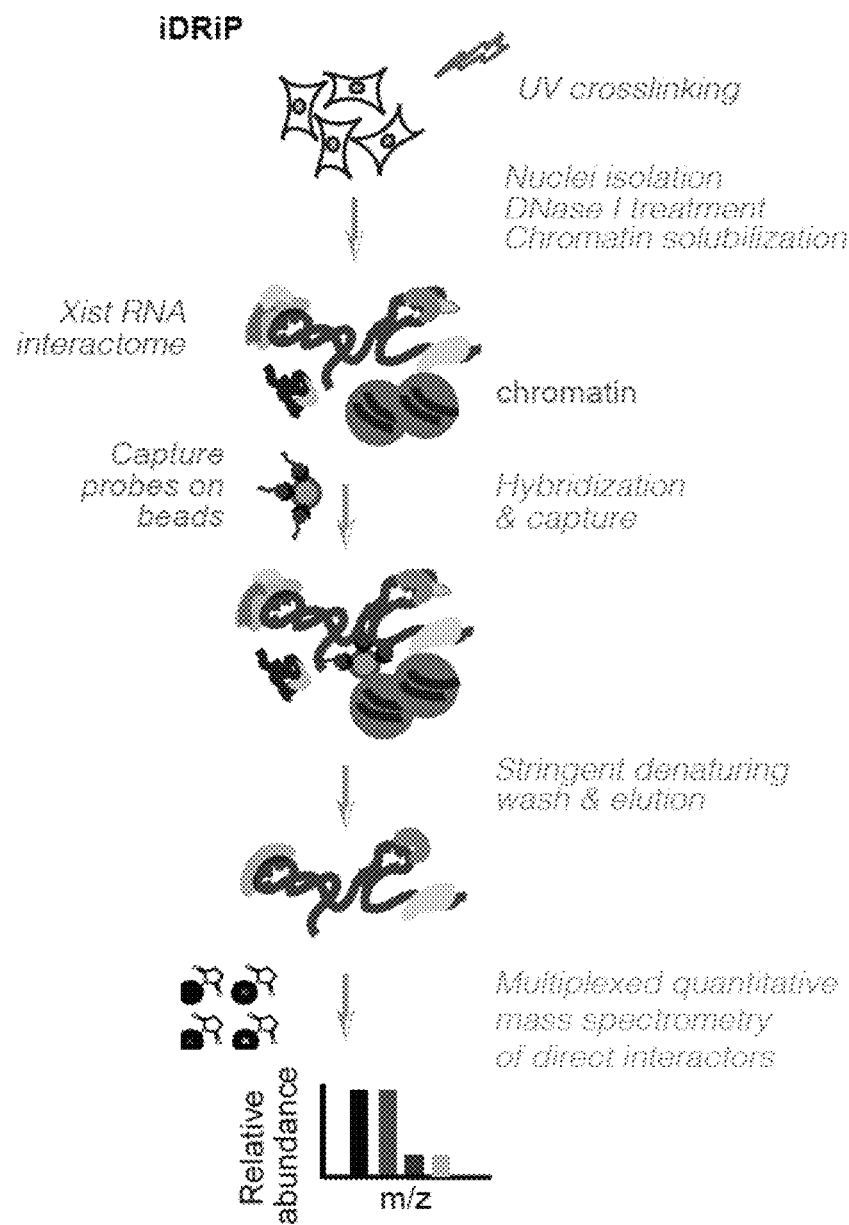
FIGS. 1A-E: iDRiP-MS reveals a large Xist interactome.
(A) Exemplary iDRiP schematic. UV-irradiated MEF cells (male, female) were subjected to in vivo capture of Xist RNA-bound proteins. Washes were performed under stringent denaturing conditions to eliminate non-covalently linked proteins. Quantitative mass spectrometry revealed the identity of bound proteins.
(B) RT-qPCR demonstrated the specificity of Xist pulldown by iDRiP. Xist and control luciferase probes were used for pulldown from UV-crosslinked female and control male fibroblasts. Efficiency of Xist pulldown was calculated by comparing to a standard curve generated using 10-fold dilutions of input. Data are shown as Mean±standard error (SE) of two three independent experiments shown. P values determined by the Student t-test.
(C) Select high-confidence candidates from three biological replicates grouped into multiple functional classes. Additional candidates are shown in Tables 5-6.
(D) UV-RIP-qPCR validation of candidate interactors. The enrichment is calculated as % input for corresponding transcripts, as in (1B). P values determined by the Student t-test.
(E) RNA immunoFISH to examine localization of candidate interactors (green) in relation to Xist RNA (red). Immortalized MEF cells are tetraploid and harbor two Xi.
Figures 1B, 1C:
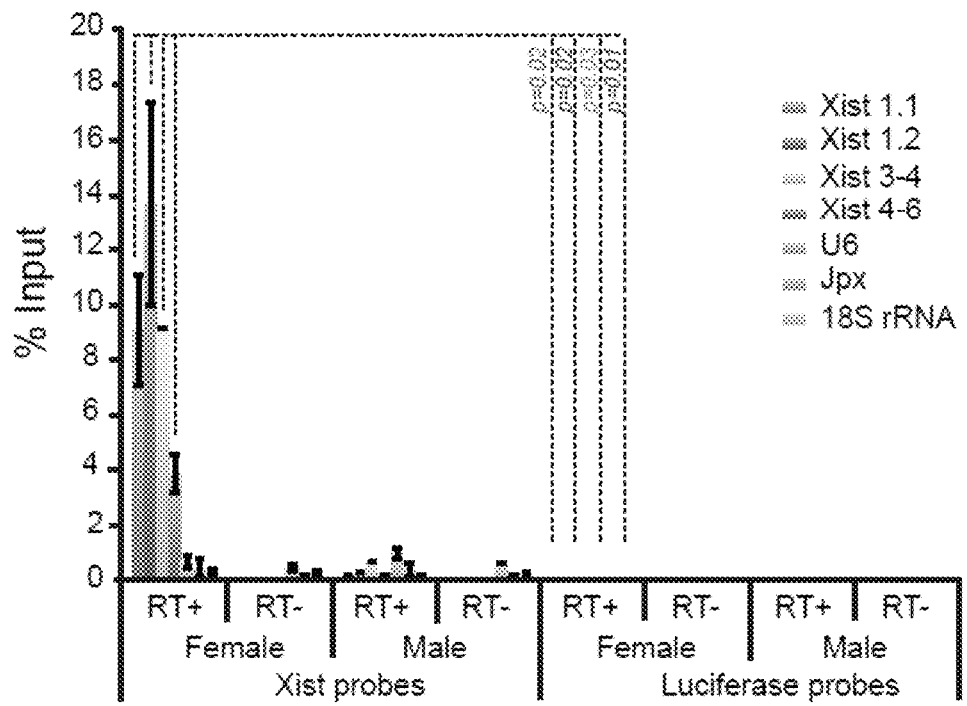

A systematic identification of interacting factors has been challenging because of Xist's large size, the expected complexity of the interactome, and the persistent problem of high background with existing biochemical approaches (20). A high background could be particularly problematic for chemical crosslinkers that create extensive covalent networks of proteins, which could in turn mask specific and direct interactions. We developed iDRiP (identification of direct RNA interacting proteins) using the zero-length crosslinker, UV light, to implement an unbiased screen of directly interacting proteins in female mouse fibroblasts expressing physiological levels of Xist RNA (FIG. 1A). We performed in vivo UV crosslinking, prepared nuclei, and solubilized chromatin by DNase I digestion. Xist-specific complexes were captured using 9 complementary oligonucleotide probes spaced across the 17-kb RNA, with a 25-nt probe length designed to maximize RNA capture while reducing non-specific hybridization. The complexes were washed under denaturing conditions to eliminate factors not covalently linked by UV to Xist RNA. To minimize background due to DNA-bound proteins, a key step was inclusion of DNase I treatment before elution of complexes. We observed significant enrichment of Xist RNA over highly abundant cytoplasmic and nuclear RNAs (U6, Jpx, 18S rRNA) in eluates of female fibroblasts (FIG. 1B). Enrichment was not observed in male eluates or with luciferase capture probes. Eluted proteins were subjected to quantitative mass spectrometry (MS), with spectral counting (21) and multiplexed quantitative proteomics (22) yielding similar enrichment sets (Tables 5-6).

Figure 1D:
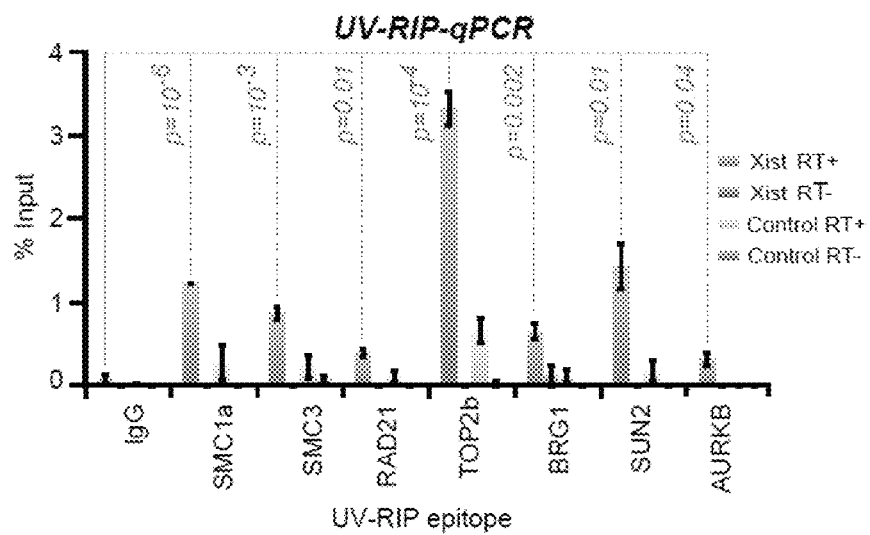

From three independent replicates, iDRiP-MS revealed a large Xist protein interactome (FIG. 1C; Tables 5 and 6). Recovery of known Xist interactors PRC2 (RBBP4, RBBP7), ATRX, and HNRPU provided a first validation of the iDRiP technique. Also recovered were PRC1 (RING1), macrohistone H2A (mH2A) and the condensin component, SmcHD1, all of which proteins are known to be enriched on the Xi (23, 24, 19), but not previously shown to interact directly with Xist. More than 80 proteins were found to be ≥3-fold enriched over background; >200 proteins were ≥2-fold enriched (Tables 5-6). In many cases, multiple subunits of the epigenetic complex were identified, boosting our confidence in them as interactors. We verified select interactions by performing a test of reciprocity: By baiting with candidate proteins in an antibody capture, RIP-qPCR of UV-crosslinked cells reciprocally identified Xist RNA in the pulldowns (FIG. 1D). Called on the basis of high enrichment values, presence of multiple subunits within a candidate epigenetic complex, and tests of reciprocity, novel high-confidence interactors fell into several functional categories: (i) Cohesin complex proteins, SMC1a, SMC3, RAD21, WAPL, PDS5a/b, as well as CTCF (25), which are collectively implicated in chromosome looping and transcriptional regulation (26-28); (ii) histone modifiers such as aurora kinase B (AURKB), a serine/threonine kinase that phosphorylates histone H3 (29); RING1, the catalytic subunit of Polycomb repressive complex 1 (PRC1) for H2A-K119 ubiquitylation (23); and SPEN and RBM15, which associate with HDACs; (iii) SWI/SNF chromatin remodeling factors; (iv) topoisomerases, TOP2a, TOP2b, and TOP1, that relieve torsional stress during transcription and DNA replication; (v) miscellaneous transcriptional regulators, MYEF2 and ELAV1; (vi) nucleoskeletal proteins that anchor chromosomes to the nuclear envelope, SUN2, Lamin-B receptor (LBR), and LAP2; (vii) nuclear matrix proteins, hnRPU/SAF-A, hnRPK, and MATRIN3; and (viii) the DNA methyltransferase, DNMT1, known as a maintenance methylase for CpG dinucleotides (30).

Figure 1E:
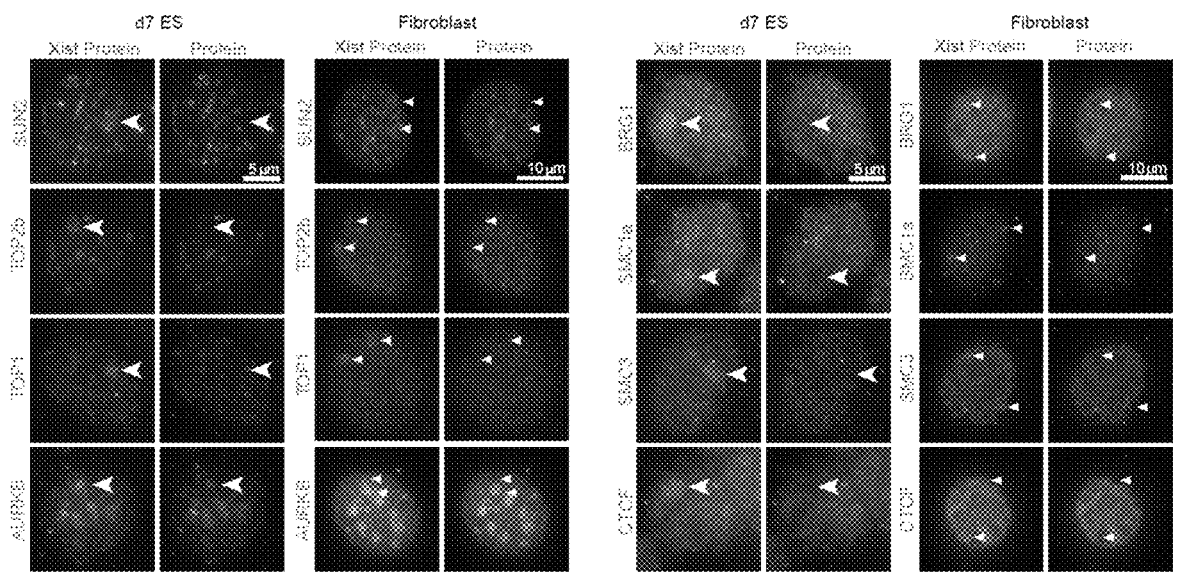

To study their function, we first performed RNA immunoFISH of female cells and observed several patterns of Xi coverage relative to the surrounding nucleoplasm (FIG. 1E). Like PRC2, RING1 (PRC1) has been shown to be enriched on the Xi (23) and is therefore not pursued further. TOP1 and TOP2a/b appeared neither enriched nor depleted on the Xi (100%, n>50 nuclei). AURKB showed two patterns of localization—peri-centric enrichment (20%, n>50) and a more diffuse localization pattern (80%, data now shown), consistent with its cell-cycle dependent chromosomal localization (29). On the other hand, while SUN2 was depleted on the Xi (100%, n=52), it often appeared as pinpoints around the Xi in both day 7 differentiating female ES cells (establishment phase; 44%, n=307) and in fibroblasts (maintenance phase; 38.5%, n=52), consistent with SUN2's function in tethering telomeres to the nuclear envelope. Finally, the cohesins and SWI/SNF remodelers unexpectedly showed a depletion relative to the surrounding nucleoplasm (100%, n=50-100). These patterns suggest that the Xist interactors operate in different XCI pathways.

Figure 2A:
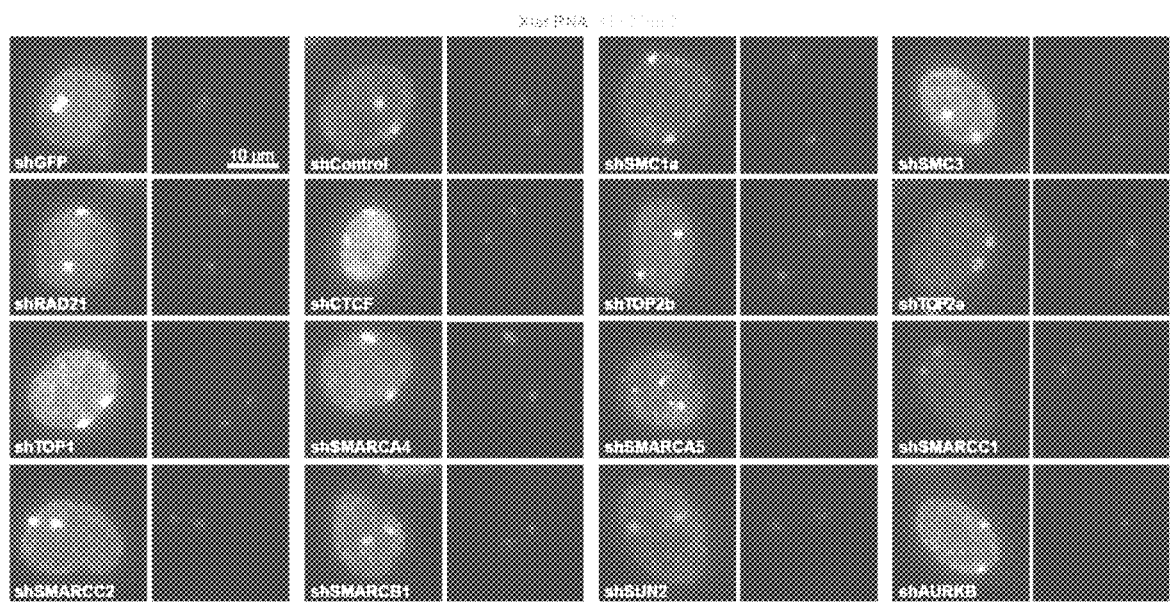
FIGS. 2A-C: Impact of depleting Xist interactors on H3K27 trimethylation.
(A) RNA immunoFISH of Xist (red) and H3K27me3 (green) after shRNA KD of interactors in fibroblasts (tetraploid; 2 Xist clouds). KD efficiencies (fraction remaining): SMC1a-0.48, SMC3-0.39, RAD21-0.15, AURKB-0.27, TOP2b-0.20, TOP2a-0.42, TOP1-0.34, CTCF-0.62, SMARCA4-0.52, SMARCA5-0.18, SMARCC1-0.25, SMARCC2-0.32, SMARCB1-0.52 and SUN2-0.72. Some factors are essential; therefore, high percentage KD may be inviable. All images presented at the same photographic exposure and contrast.
(B) Quantitation of RNA immunoFISH results from Panel A. n, sample size. % aberrant, percentage of nuclei with aberrant Xist/H3K27me3 associations.
(C) RT-qPCR of Xist RNA levels in fibroblasts after indicated KD. Data are normalized to shControl cells. Mean±SD of two independent experiments shown.
Figure 2B:
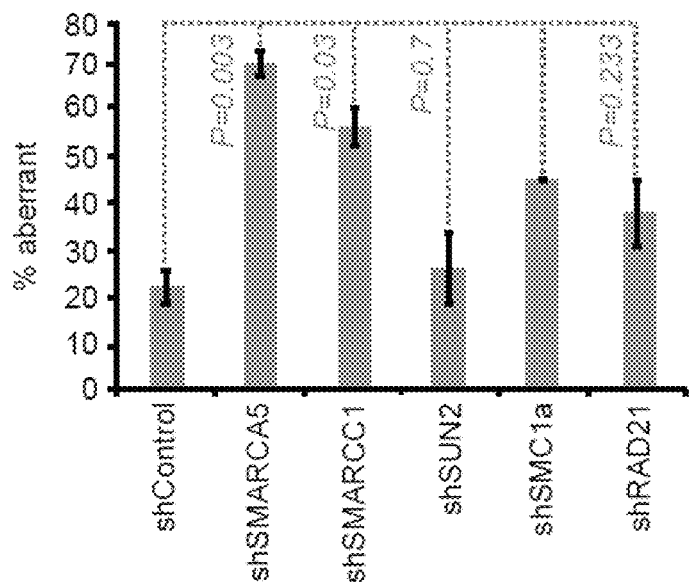
Figure 2C:
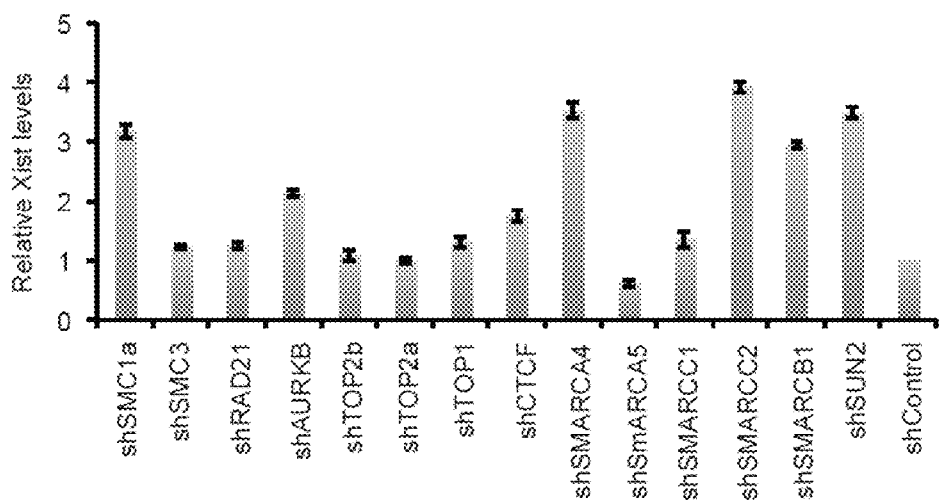

To ask if the factors intersect the PRC2 pathway, we stably knocked down (KD) top candidates using shRNAs (Table 2) and performed RNA immunoFISH to examine trimethylation of histone H3-lysine 27 (H3K27me3; FIGS. 2A,B). No major changes to Xist localization or H3K27me3 were evident in d7 ES cells (FIG. 9). There were, however, long-term effects in fibroblasts: The decreased in H3K27me3 enrichment in shSMARCC1 and shSMARCA5 cells (FIG. 2A,B) indicated that SWI/SNF interaction with Xist is required for proper maintenance of PRC2 function on the Xi. Steady state Xist levels did not change by more than 2-fold (FIG. 2C) and were therefore unlikely to be the cause of the Polycomb defect. Knockdowns of other factors (cohesins, topoisomerases, SUN2, AURKB) had no obvious effects on Xist localization and H3K27me3. Thus, whereas the SWI/SNF factors intersect the PRC2 pathway, other interactors do not overtly impact PRC2.

Example 2. Xi-Reactivation Via Targeted Inhibition of Synergistic Interactors

Figure 3A:
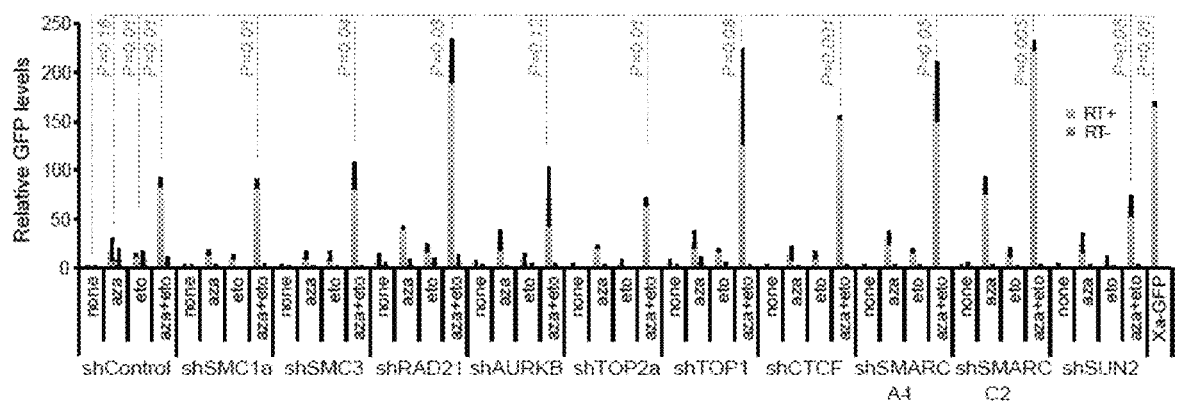
Figure 3B:
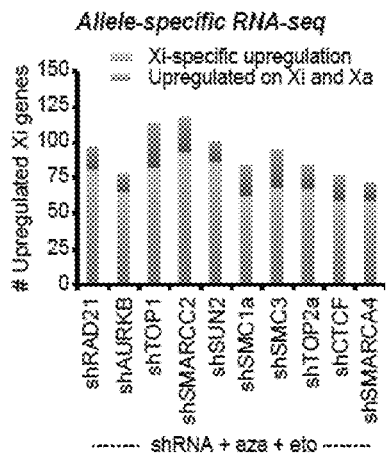

Given the large number of interactors, we created a screen to analyze effects on Xi gene expression. We derived clonal fibroblast lines harboring a transgenic GFP reporter on the Xi (FIG. 10) and shRNAs against Xist interactors. Knockdown of any one interactor did not reactivate GFP by more than 4-fold (FIG. 3A, shControl+none; FIG. 11A). Suspecting synergistic repression, we targeted multiple pathways using a combination drugs. To target DNMT1, we employed the small molecule, 5'-azacytidine (aza)(30) at a nontoxic concentration of 0.3 μM (≤$IC_{50}$) which minimally reactivated GFP (FIG. 3A, shControl+aza). To target TOP2a/b (31), we employed etoposide (eto) at 0.3 μM (≤$IC_{50}$), which also minimally reactivated GFP (FIG. 3A, shControl+eto). Combining 0.3 μM aza+eto led to an 80- to 90-fold reactivation—a level that was almost half of GFP levels on the Xa (Xa-GFP, FIG. 3A), suggesting strong synergy between DNMT1 and TOP2 inhibitors. Using aza+eto as priming agents, we designed triple-drug combinations inclusive of shRNAs for proteins that have no specific small molecule inhibitors. In various shRNA+aza+eto combinations, we achieved up to 230-fold GFP reactivation—levels that equaled or exceeded Xa-GFP levels (FIG. 3A). Greatest effects were observed for combinations using shSMARCC2 (227×), shSMARCA4 (180×), and shRAD21 (211×). shTOP1 and shCTCF were also effective (175×, 154×). Combinations involving remaining interactors yielded 63× to 94× reactivation.

Figure 3C:
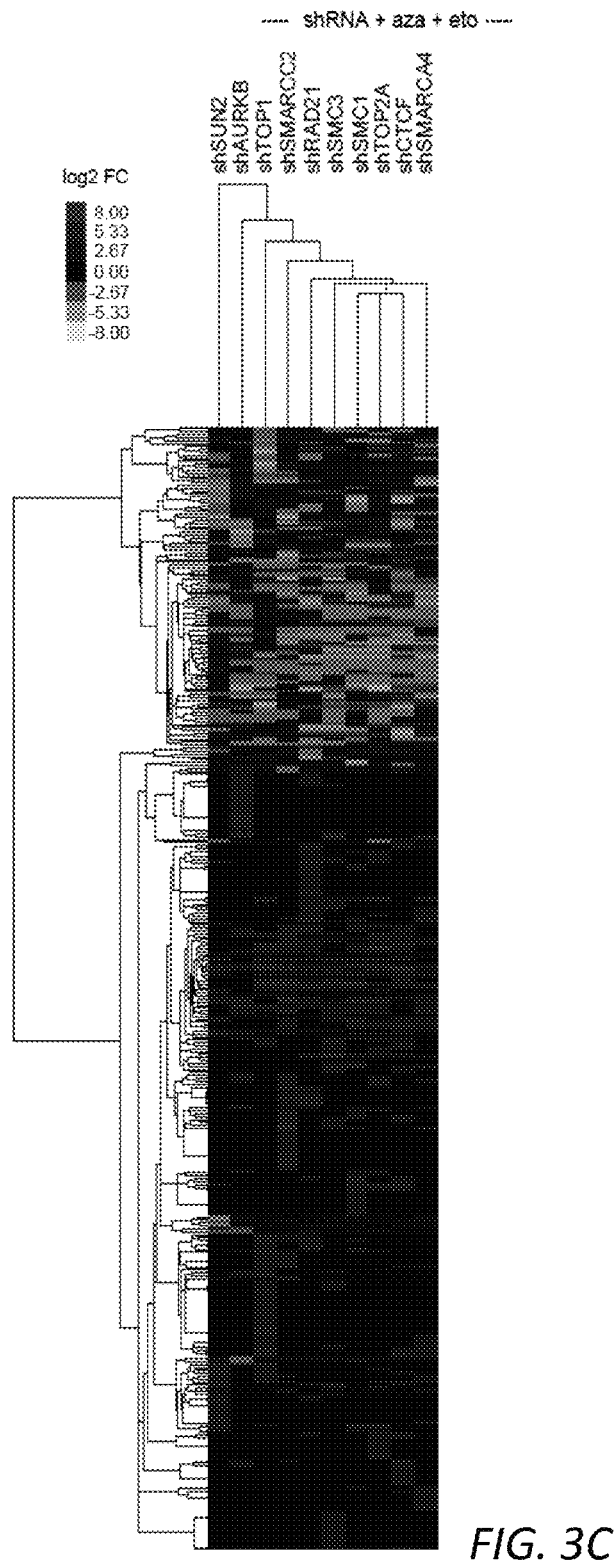
Figure 3D:
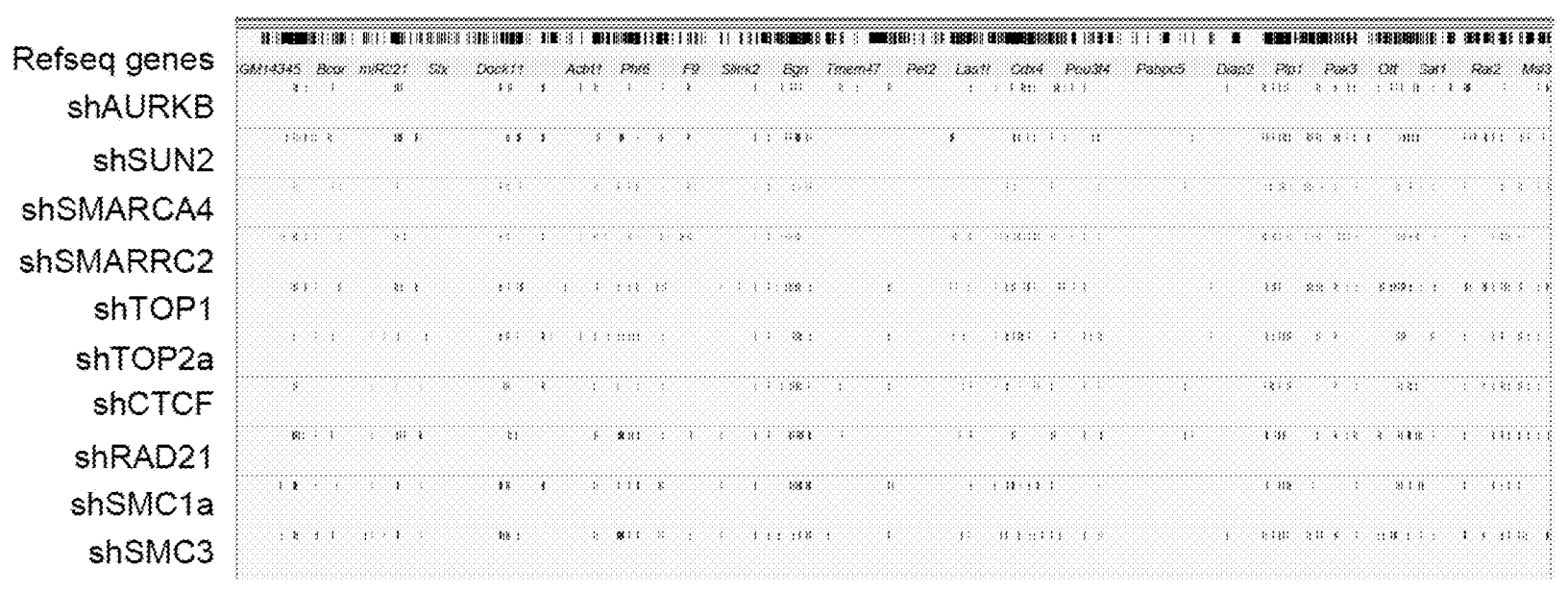

We then performed allele-specific RNA-seq to investigate native Xi genes. In an F1 hybrid fibroblast line in which the Xi is of *Mus musculus* (mus) origin and the Xa of *Mus casteneus* (cas) origin, >600,000 X-linked sequence polymorphisms enabled allele-specific calls (32). Two biological replicates of each of the most promising triple-drug treatments showed good correlation (FIG. 12-14). RNA-seq analysis showed reactivation of 75-100 Xi-specific genes in one replicate (FIG. 3B) and up to 200 in a second replicate (FIG. 11B), representing a large fraction of expressed X-linked genes, considering that only ~210 X-linked genes have an FPKM≥1.0 in this hybrid fibroblast line. Heatmap analysis demonstrated that, for individual Xi genes, reactivation levels ranged from 2×-80× for various combinatorial treatments (FIG. 3C). There was a net increase in expression level (ΔFPKM) from the Xi in the triple-drug treated samples relative to the shControl+aza+eto, whereas the Xa and autosomes showed no obvious net increase, thereby suggesting preferential effects on the Xi due to targeting synergistic components of the Xist interactome. Reactivation was not specific to any one Xi region (FIG. 3D). Most effective were shRAD21, shSMC3, shSMC1a, shSMARCA4, shTOP2a, and shAURKB drug combinations.

Figure 3E:
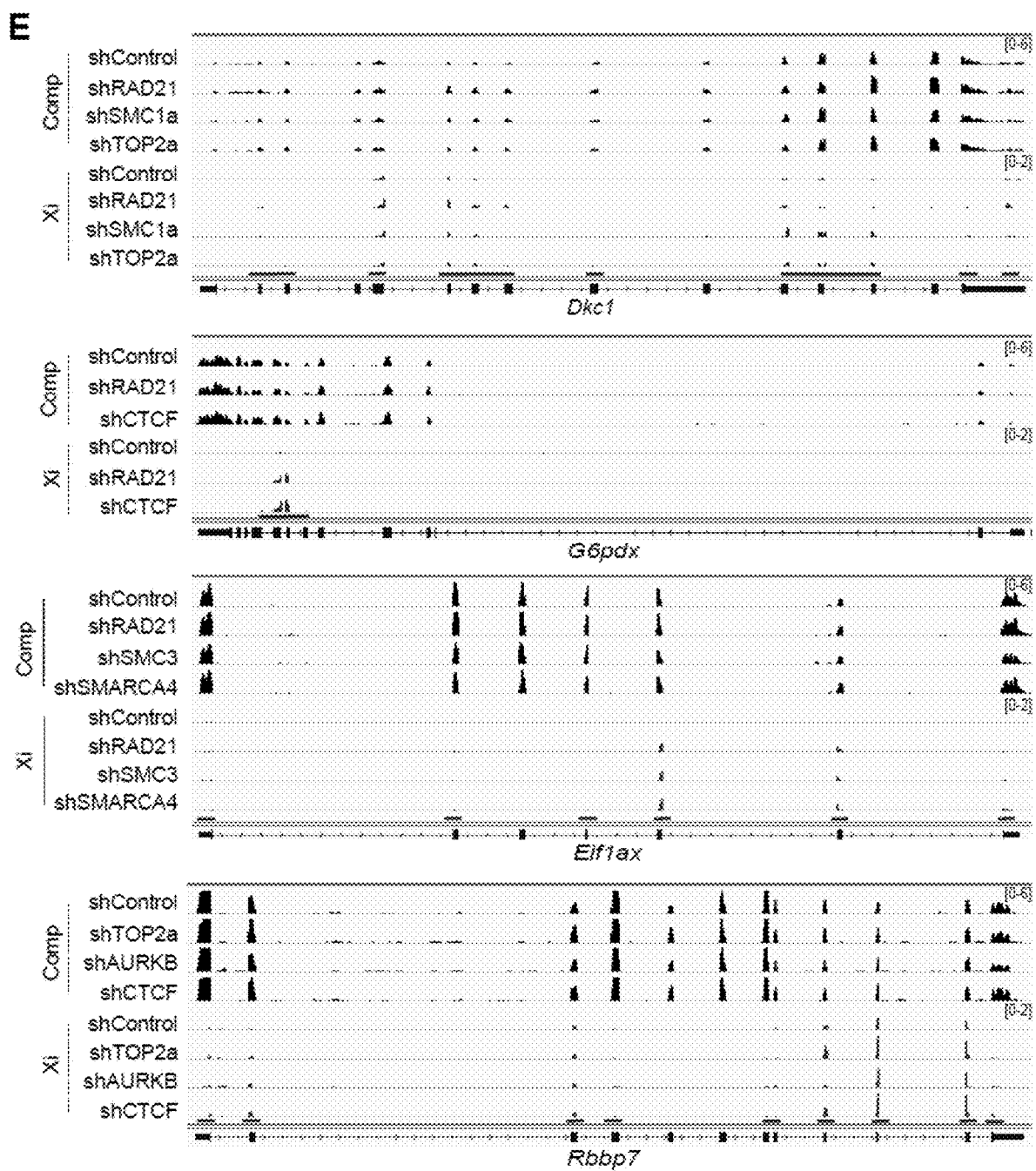

Genic examination confirmed increased representation of mus-specific tags (red) relative to the shControl (FIG. 3E). Such allelic effects were not observed at imprinted loci and other autosomal genes (FIG. 14), further suggesting Xi-specific allelic effects. The set of reactivated genes varied among drug treatments, though some genes (Rbbp7, G6pdx, Fmr1, etc.) appeared more prone to reactivation. Thus, the Xi is maintained by multiple synergistic pathways and Xi genes can be reactivated preferentially by targeting two or more synergistic Xist interactors.

Example 3. Xist Interaction Leads to Cohesin Repulsion

Figure 4D:
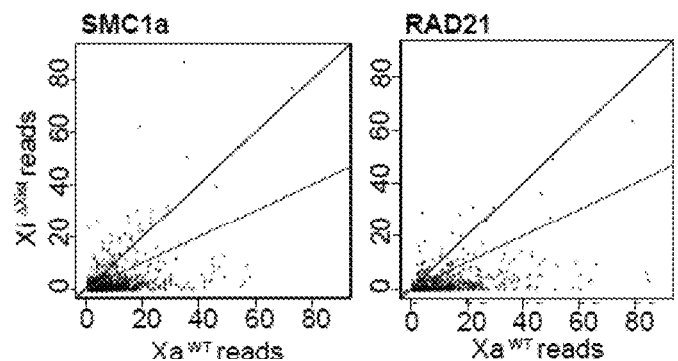
Figure 4E:
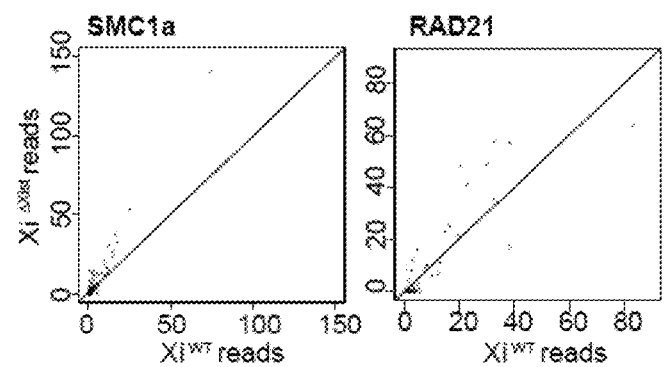

To investigate mechanism, we focused on one group of interactors—the cohesins—because they were among the highest-confidence hits and their knockdowns consistently destabilized Xi repression. To obtain Xa and Xi binding patterns, we performed allele-specific ChIP-seq for two cohesin subunits, SMC1a and RAD21, and for CTCF, which works together with cohesins (33, 34, 28, 35). In wildtype cells, CTCF binding was enriched on Xa (cas), but also showed a number of Xi (mus)-specific sites (FIG. 4A)(36, 25). Allelic ratios ranged from equal to nearly complete Xa or Xi skewing (FIG. 4A). For the cohesins, 1490 SMC1a and 871 RAD21 binding sites were mapped onto ChrX in total, of which allelic calls could be made on ~50% of sites (FIG. 4B,C). While the Xa and Xi each showed significant cohesin binding, Xa-specific greatly outnumbered Xi-specific sites. For SMC1a, 717 sites were called on Xa, of which 589 were Xa-specific; 203 sites were called on Xi, of which 20 were Xi-specific. For RAD21, 476 sites were called on Xa, of which 336 were Xa-specific; 162 sites were called on Xi, of which 18 were Xi-specific. Biological replicates showed similar trends (FIGS. 16A,B).

Figure 4F:
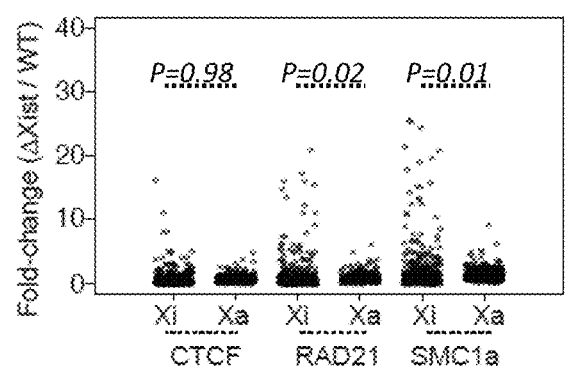
Figure 4G:
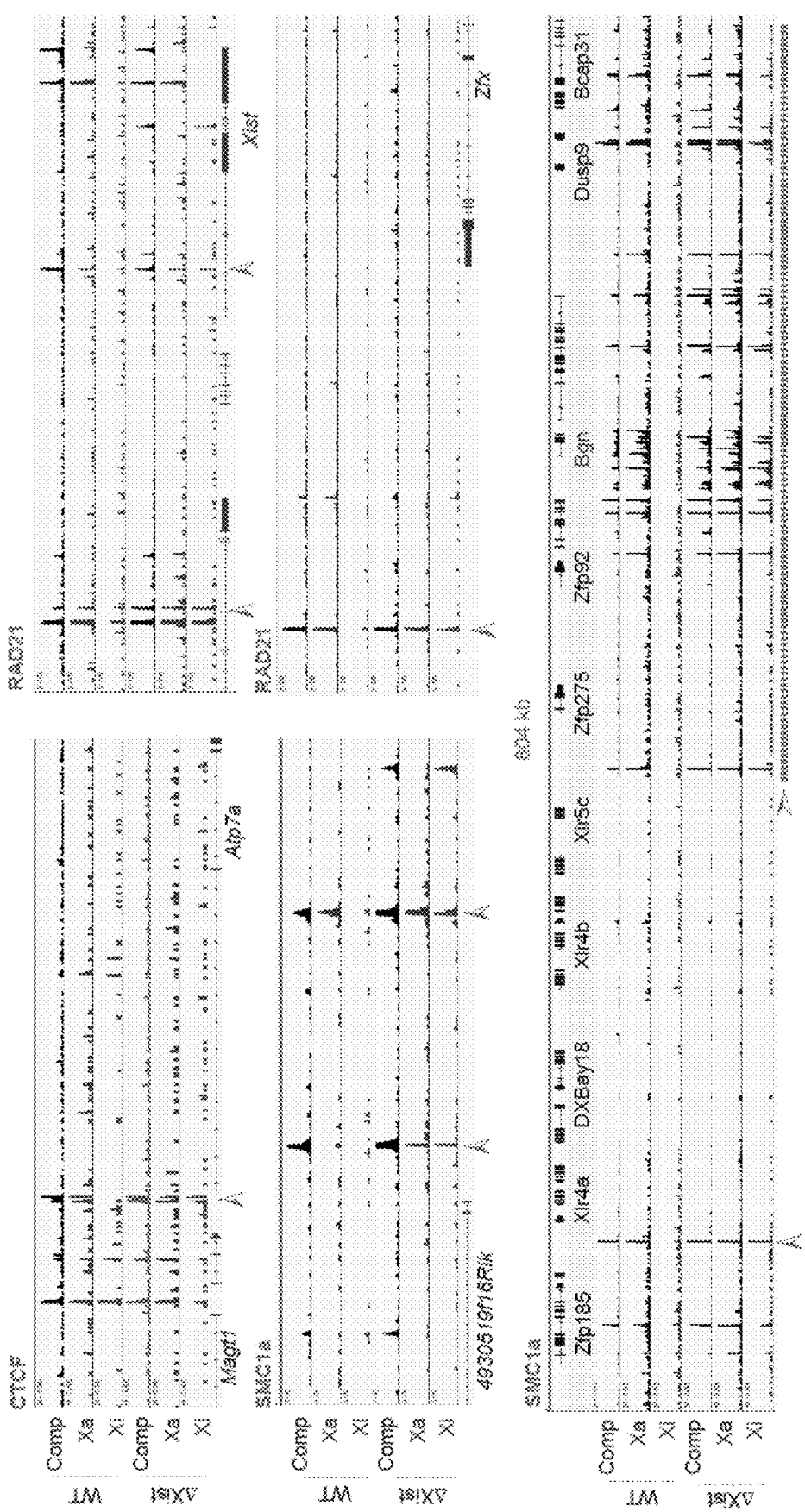
Figure 4H:
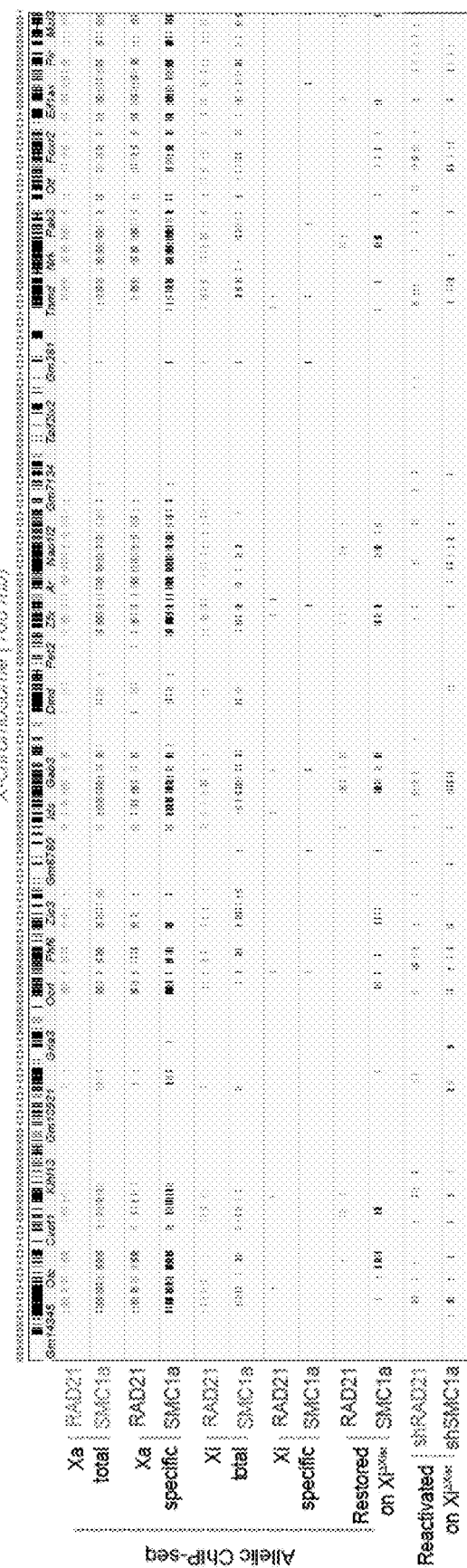

Cohesin's Xa preference was unexpected in light of Xist's physical interaction with cohesins—an interaction suggesting that Xist might recruit cohesins to the Xi. We therefore conditionally ablated Xist from the Xi ($Xi^{\Delta\Delta Xist}$) and repeated ChIP-seq analysis in the $Xi^{\Delta\Delta Xist}/Xa^{WT}$ fibroblasts (37). Surprisingly, $Xi^{\Delta\Delta Xist}$ acquired 106 SMC1a and 48 RAD21 sites in cis, at positions that were previously Xa-specific (FIG. 4C,D). Biological replicates trended similarly (FIG. 16-17). In nearly all cases, acquired sites represented a restoration of Xa sites, rather than binding to random positions. By contrast, sites that were previously Xi-specific remained intact (FIGS. 4C,E, 16B), suggesting that they do not require Xist for their maintenance. The changes in cohesin peak densities were Xi-specific and significant (FIG. 4F). Cohesin restoration occurred throughout $Xi^{\Delta\Delta Xist}$, resulting in domains of biallelic binding (FIGS. 4G, 18-20), and often favored regions that harbor genes that escape XCI (e.g., Bgn)(38, 39). There were also shifts in CTCF binding, more noticeable at a locus-specific level than at a chromosomal level (FIG. 4A,G), suggesting that CTCF and cohesins do not necessarily track together on the Xi. The observed dynamics were ChrX-specific and were not observed on autosomes (FIG. 21). To determine whether there were restoration hotspots, we plotted restored SMC1a and RAD21 sites (FIG. 4H; purple) on $Xi^{\Delta\Delta Xist}$ and observed clustering within gene-rich regions. We conclude that Xist does not recruit cohesins to the Xi-specific sites. Instead, Xist actively repels cohesins in cis to prevent establishment of the Xa pattern.

Example 4. Xist RNA Directs an Xi-Specific Chromosome Conformation

Cohesins and CTCF have been shown to facilitate formation of large chromosomal domains called TADs (topologically associated domains)(27, 40, 34, 28, 35, 41, 42). The function of TADs is currently not understood, as TADs are largely invariant across development. However, X-linked domains are exceptions to this rule and are therefore compelling models to study function of topological structures (43-46). By carrying out allele-specific Hi-C, we asked whether cohesin restoration altered the chromosomal architecture of $Xi^{\Delta\Delta Xist}$. First, we observed that, in wildtype cells, our TADs called on autosomal contact maps at 40-kb resolution resembled published composite (non-allelic) maps (27)(FIG. 5A, bottom). Our ChrX contact maps were also consistent, with TADs being less distinct due to a summation of Xa and Xi reads in the composite profiles (FIG. 5A, top). Using the 44% of reads with allelic information, our allelic analysis yielded high-quality contact maps at 100-kb resolution by combining replicates (FIG. 5B, 22A) or at 200-kb resolution with a single replicate. In wildtype cells, we deduced 112 TADs at 40-kb resolution on ChrX using the method of Dixon et al. (27). We attempted TAD calling for the Xi on the 100 kb contact map, but were unable to obtain obvious TADs, suggesting the 112 TADs are present only on the Xa. The Xi instead appeared to be partitioned into two megadomains at the DXZ4 region (FIG. 22A) (46). Thus, while the Xa is topologically organized into structured domains, the Xi is devoid of TADs across its full length.

Figure 5B:
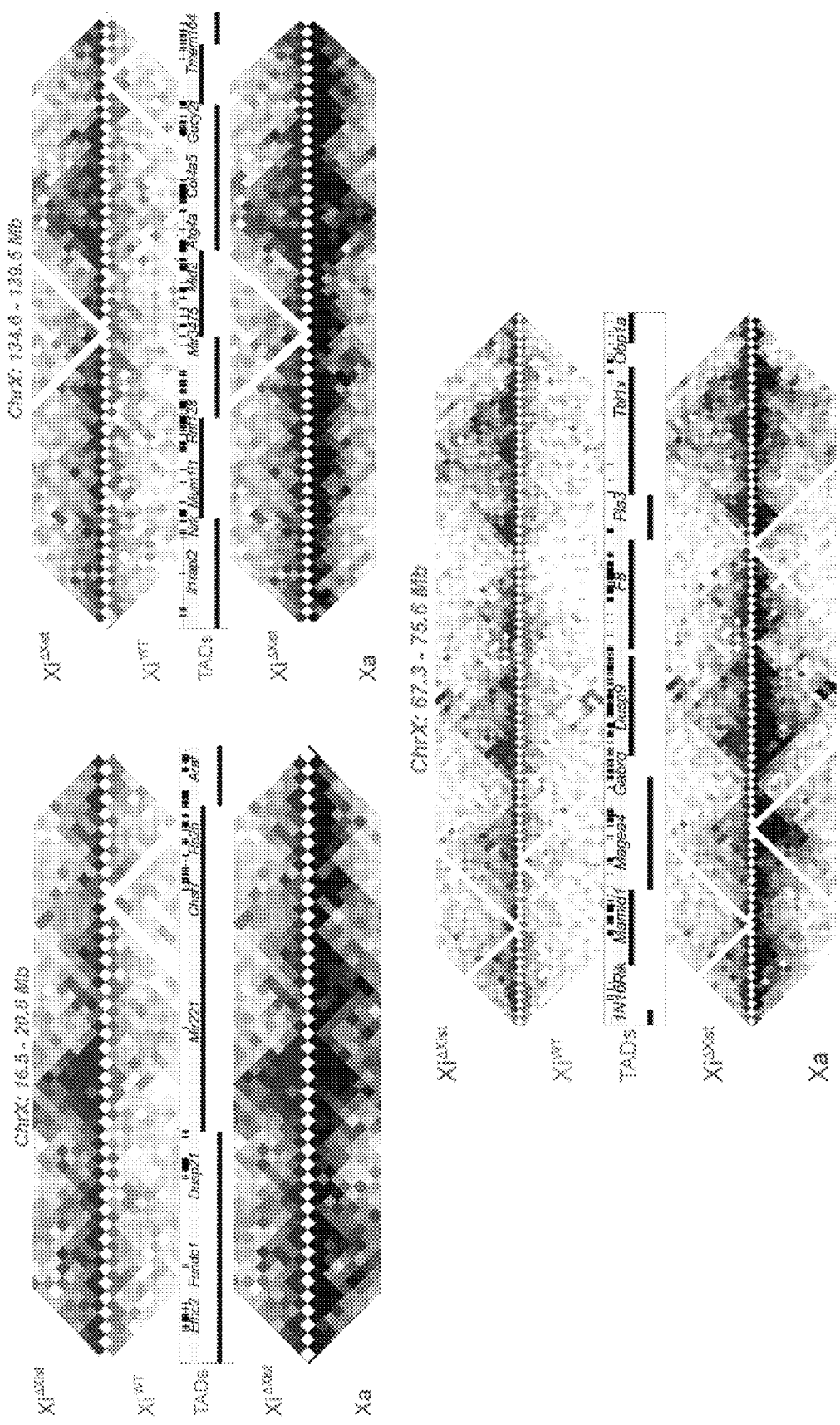
Figure 5D:
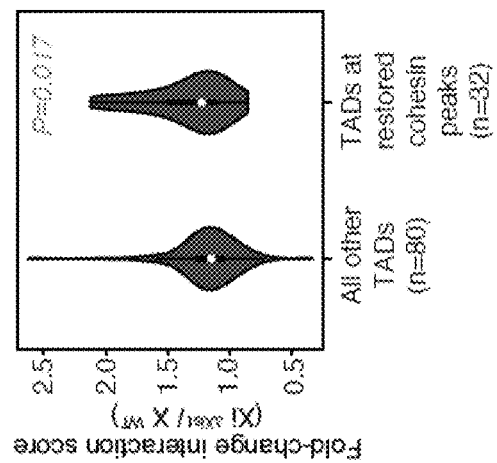
Figure 5C:
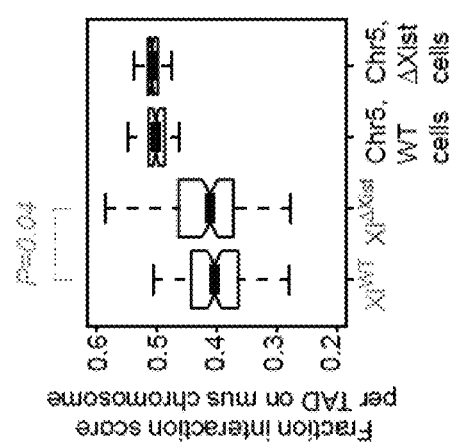
Figure 5E:
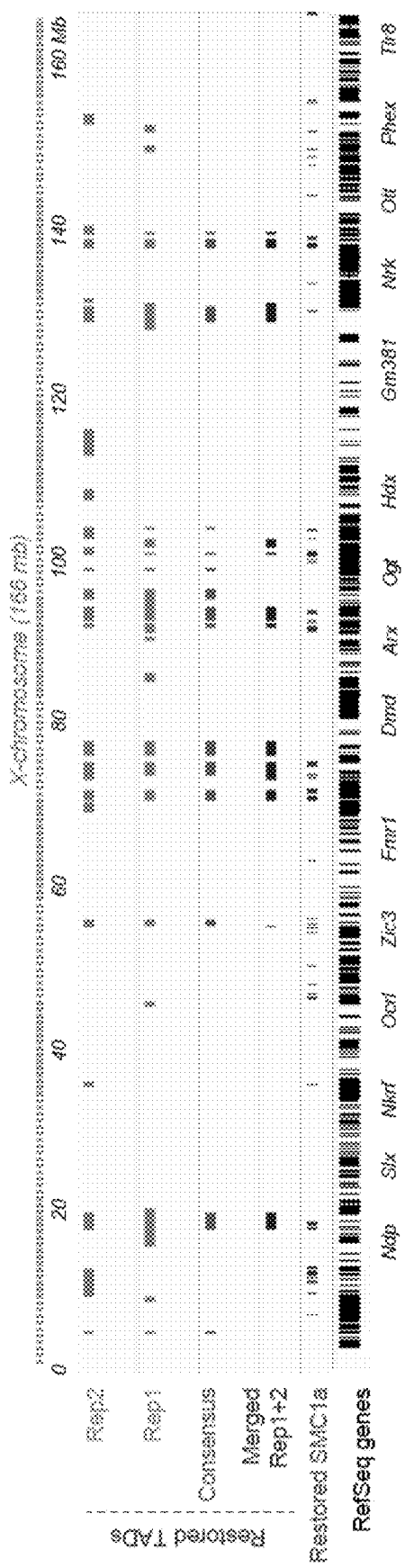

When Xist was ablated, however, TADs were restored in cis and the Xi reverted to an Xa-like conformation (FIG. 5B, 22B). In mutant cells, ~30 TADs were gained on $Xi^{\Delta\Delta Xist}$ in each biological replicate. Where TADs were restored, $Xi^{\Delta\Delta Xist}$ patterns (red) became nearly identical to those of the Xa (blue), with similar interaction frequencies. These $Xi^{\Delta\Delta Xist}$ regions now bore little resemblance to the Xi of wildtype cells ($Xi^{WT}$, orange). Overall, the difference in the average interaction scores between $Xi^{WT}$ and $Xi^{\Delta\Delta Xist}$ was highly significant (FIG. 5C, 23A). Intersecting TADs with SMC1a sites on $Xi^{\Delta\Delta Xist}$ revealed that 61 restored cohesin sites overlapped restored TADs (61 did not overlap). In general, restored cohesin sites occurred both within TADs and at TAD borders. TADs overlapping restored peaks had larger increases in interaction scores relative to all other TADs (FIG. 5D, 23B) and we observed an excellent correlation between the restored cohesin sites and the restored TADs (FIG. 5E, 23C), consistent with a role of cohesins in re-establishing TADs following Xist deletion. Taken together, these data uncover a role for RNA in establishing topological domains of mammalian chromosomes and demonstrate that Xist must actively and continually repulse cohesins from the Xi, even during the maintenance phase, to prevent formation of an Xa chromosomal architecture.

Example 5. Xist Knockdown with an LNA Results in Increased Reactivation

To determine whether an LNA targeting XIST could also be used in addition to or as an alternative to an agent described herein, experiments were performed in the following cells: immortalized monoclonal MEFs with the reporter GFP (Bird) or LUC (Bedalov) fused to Mecp2, on the Xi or Xa, immortalized human fibroblasts from a 3 year old female with Rett syndrome (Coriell) and primary mouse cortical neurons.

The LNAs were designed with the Exiqon web tool. Xist LNA for mouse (TCTTGGTTACTAACAG; SEQ ID NO:50) targets exon 1 between rep C and rep D. The human Xist LNAs target the following sequences: A1: GAAGAAGCAGAGAACA; SEQ ID NO:51; A2:

AGTAGCTCGGTGGAT; SEQ ID NO:52; A3: TGAGTCTTGAGGAGAA; SEQ ID NO:53. The LNAs were delivered into the cells (0.5 105/ml) with Lipofectamine LTX with Plus (Life Technologies), and incubated for 3 days. 5-azadeoxycitidine (in DMSO) was added to a final concentration of 0.5 uM (except in the titration experiment 0.1-2.5 uM). Synergistic reactivation could be observed with AzadC or EED knockdown.

qPCR was performed with Sybr chemistry (SybrGreen supermix Bio-Rad), with the primers shown in Table 9. RNA for these experiments was extracted with Triazol (Ambion), DNAse treated (Turbo DNAse kit from Ambion) and reverse transcribed with Superscript III.

TABLE 9

| Target | Sequence | SEQ ID NO: |
| --- | --- | --- |
| Xist F | GCTGGTTCGTCTATCTTGTGGG | 54 |
| Xist R | CAGAGTAGCGAGGACTTGAAGAG | 55 |
| GapdH F | ATGAATACGGCTACAGCAACAGG | 56 |
| GapdH R | CTCTTGCTCAGTGTCCTTGCTG | 57 |

TABLE 9-continued

| Target | Sequence | SEQ ID NO: |
| --- | --- | --- |
| Luc F | TCTAAGGAAGTCGGGGAAGC | 58 |
| Luc R | CCCTCGGGTGTAATCAGAAT | 59 |
| TBP F | ACGGACAACTGCGTTGATTTT | 60 |
| TBP R | ACTTAGCTGGGAAGCCCAAC | 61 |
| GFP F | ACCATCTTCTTCAAGGACGA | 62 |
| GFP R | GGCTGTTGTAGTTGTACTCC | 63 |
| hXist F | TAGGCTCCTCTTGGACATT | 64 |
| hXist R | GCAACCCATCCAAGTAGATT | 65 |

FIG. 7 shows the results of experiments in the Mecp2-GFP fusion Xi cell line, after treatment for 3 days with 20 nM Xist LNA administered with lipofectamine LTX with Plus reagent. qPCR analysis of XIST expression using the primers above showed that the LNAs produced a significant reduction in XIST levels.

Luciferase experiments were performed on a Microbeta2 LumiJet with a luciferase assay system (Promega). Mecp2-Luc fusion Xi and Xa cell lines (0.5 $10^5$ cells/ml) were contacted with 20 nM Xist LNA administered with Lipofectamine LTX with Plus reagent, with or without 5-aza-deoxycitidine 0.5 uM, for three days. Afterwards, the cells were trypsinized, washed, and lysed using cell culture lysis reagent. Normalized measurements were performed in 96 well plates, during 10 seconds after a 2 second incubation period. Table 11 shows the results of the luciferase screen, demonstrating a significant level of reactivation with an XIST LNA plus Aza.

TABLE 11

| | 20 uM LNA, 0.5 uM aza 3 days, New 1 $10^{\wedge}5$ cells/ml 24-well trial 1 | | 20 uM LNA, 0.5 uM aza 3 days, NEW 0.5 $10^{\wedge}5$ cells/ml 6-well trial 3 | | 20 uM LNA, 0.5 uM aza 3 days, new 0.5 $10^{\wedge}5$ cells/ml 6-well trial 6 | |
| --- | --- | --- | --- | --- | --- | --- |
| | LCPS | raw CPS | LCPS | raw CPS | LCPS | raw CPS |
| buffer | 0.0/0.0 | 39.4/26.6 | 0/0 | 25.4/19.2 | 0/0 | 32.8/24.4 |
| xa | | | 656.4 | 65947.8 | | |
| No ctrl | 0 | 35.6 | | | 0 | 30 |
| ctrl | 0 | 31 | | | | |
| ctrl + aza | | | 1.1 | 140.6 | 0.8 | 130 |
| xist | 0 | 29.8 | | | | |
| xist + aza | 67.4 | 7187.6 | 44.7 | 4518.4 | 26.1 | 2814.2 |
| smchd1 | 0 | 29.2 | | | | |
| smchd1 + aza | 2.2 | 273.4 | | | | |
| ctcf + aza | | | | | 0.3 | 78.4 |
| xist + ctcf + aza | | | 6.8 | 718 | | |
| eed + aza | | | 1.7 | 207 | 1.6 | 213.6 |
| eed + xist + aza | | | 28.9 | 2933.8 | | |
| dxz + aza | | | | | 0.7 | 122.8 |
| xist + dxz4 | 0 | 27 | | | | |
| xist + dxz4 + aza | 32.9 | 3536.6 | | | | |
| firre + aza | | | | | 0.5 | 98.6 |
| firre + xist | | | | | 0 | 24.2 |

Reactivation of Mecp2 was measured in the immortalized monoclonal MEFs with the reporter GFP (Bird) or LUC (Bedalov) fused to Mecp2 on the Xi; as shown in FIGS. 8A and 8B, significant levels of reactivation of Mecp2 expression were obtained in both LUC (8A) and GFP (8B) test models after treatment with Aza plus an XIST-targeted LNA.

REFERENCES

1. J. Starmer, T. Magnuson, Development 136, 1 (2009).
2. C. M. Disteche, Annual review of genetics 46, 537 (2012).
3. A. Wutz, R. Agrelo, Dev Cell 23, 680 (2012).
4. C. J. Brown et al., Cell 71, 527 (1992).
5. J. Wang et al., Nat Genet 28, 371 (2001).
6. A. Kohlmaier et al., PLoS Biol 2, E171 (2004).

7. K. Plath et al., J Cell Biol 167, 1025 (2004).
8. J. Zhao et al., Molecular cell 40, 939 (2010).
9. Y. Marahrens, et al., Genes Dev 11, 156 (1997).
10. E. Yildirim et al., Cell 152, 727 (2013).
11. C. J. Brown, H. F. Willard, Nature 368, 154 (1994).
12. G. Csankovszki, A. Nagy, R. Jaenisch, J Cell Biol 153, 773 (2001).
13. S. Bhatnagar et al., Proc Natl Acad Sci USA 111, 12591 (2014).
14. W. Mak et al., Science 303, 666 (2004).
15. M. Sugimoto, K. Abe, PLoS Genet 3, e116 (2007).
16. J. Zhao, B. K. Sun, J. A. Erwin, J. J. Song, J. T. Lee, Science 322, 750 (2008).
17. K. Sarma et al., Cell 159, 869 (2014).
18. Y. Jeon, J. T. Lee, Cell 146, 119 (2011).
19. Y. Hasegawa et al., Dev Cell 19, 469 (2010).
20. A. Wutz, Nat Rev Genet 12, 542 (2011).
21. D. H. Lundgren, et al., Expert Rev Proteomics 7, 39 (2010).
22. L. Ting, R. Rad, S. P. Gygi, W. Haas, Nat Methods 8, 937 (2011).
23. S. Schoeftner et al., The EMBO journal 25, 3110 (2006).
24. M. E. Blewitt et al., Nat Genet 40, 663 (2008).
25. J. T. Kung et al., Molecular cell 57, 361 (2015).
26. M. H. Kagey et al., Nature 467, 430 (2010).
27. J. R. Dixon et al., Nature 485, 376 (2012).
28. M. Merkenschlager, D. T. Odom, Cell 152, 1285 (2013).
29. L. L. Hall, M. Byron, G. Pageau, J. B. Lawrence, J Cell Biol 186, 491 (2009).
30. V. Singh, P. Sharma, N. Capalash, Current cancer drug targets 13, 379 (2013).
31. M. E. Ashour, et al, Nature reviews. Cancer 15, 137 (2015).
32. S. F. Pinter et al., Genome Res 22, 1864 (2012).
33. S. Lin, et al., Molecular and cellular biology 31, 3094 (2011).
34. W. Li et al., Nature 498, 516 (2013).
35. J. M. Dowen et al., Cell 159, 374 (2014).
36. J. M. Calabrese et al., Cell 151, 951 (2012).
37. L. F. Zhang, K. D. Huynh, J. T. Lee, Cell 129, 693 (2007).
38. L. Carrel, H. F. Willard, Nature 434, 400 (2005).
39. J. B. Berletch et al., Human genetics 130, 237 (2011).
40. C. Feig, D. T. Odom, The EMBO journal 32, 3114 (2013).
41. C. T. Ong, V. G. Corces, Nat Rev Genet 15, 234 (2014).
42. M. Vietri Rudan et al., Cell reports 10, 1297 (2015).
43. E. Splinter et al., Genes Dev 25, 1371 (2011).
44. E. P. Nora et al., Nature 485, 381 (2012).
45. T. Nagano et al., Nature 502, 59 (2013).
46. S. S. Rao et al., Cell 159, 1665 (2014).
47. S. Sun et al., Cell 153, 1537 (2013).
48. A. Castello et al., Cell 149, 1393 (2012).
49. S. C. Kwon et al., Nature structural & molecular biology 20, 1122 (2013).
50. A. Thompson et al., Anal Chem 75, 1895 (2003).
51. G. C. McAlister et al., Anal Chem 84, 7469 (2012).
52. A. C. Tolonen, W. Haas, J Vis Exp, (2014).
53. G. C. McAlister et al., Anal Chem 86, 7150 (2014).
54. M. P. Weekes et al., Cell 157, 1460 (2014).
55. J. K. Eng, et al., J Am Soc Mass Spectrom 5, 976 (1994).
56. J. E. Elias, S. P. Gygi, Nat Methods 4, 207 (2007).
57. E. L. Huttlin et al., Cell 143, 1174 (2010).
58. A. K. Hadjantonakis, L. L. Cox, P. P. Tam, A. Nagy, Genesis 29, 133 (2001).
59. S. Heinz et al., Molecular cell 38, 576 (2010).
60. M. D. Robinson, D. J. McCarthy, G. K. Smyth, Bioinformatics 26, 139 (2010).
61. E. Lieberman-Aiden et al., Science 326, 289 (2009).
62. E. Yildirim, et al., Nat Struct Mol Biol 19, 56 (2012).
63. Y. C. Lin et al., Nat Immunol 13, 1196 (2012).
64. S. Selvaraj, R. D. J, V. Bansal, B. Ren, Nat Biotechnol 31, 1111 (2013).
65. P. A. Knight, D. Ruiz, I M A Journal of Numerical Analysis 33, 1029 (2012).
66. M. Imakaev et al., Nat Methods 9, 999 (2012).

TABLE 5

| iDRiP proteomics results-Spectral counts of proteins pulled down by iDRiP and identified by mass spectrometry. | | | | | |
|---|---|---|---|---|---|
| UniProt Entry Name | Human Gene ID | Human Protein | Human Gene symbol | Gene Synonyms | Accession numbers |
| PLIN1_MOUSE | 5346 | PLIN1 | PLIN1 | PLIN; FPLD4; PERI; perilipin | NM_001145311; NM_002666; XM_005254934; |
| Q3UJB0_MOUSE | 10992 | SF3B2 | SF3B2 | SF3b1; Cus1; SF3b150; SAP145; SF3B145 | XM_005273726; XM_011544740; NM_006842 NM_003292; XM_011509955; |
| TPR_MOUSE | 7175 | TPR | TPR | GUITHDRAFT_135836 | NM_003292; XM_011509955; |
| PLIN4_MOUSE | 729359 | PLIN4 | PLIN4 | KIAA1881; S3-12; MDA_GLEAN10011097 | XM_011528237; XM_006722866; XM_011528235; XM_006722868; NM_001080400; XM_011528233; XM_011528236; XM_011528234 |
| NB5R3_MOUSE | 1727 | NBR5 | CYB5R3 | B5R; DIA1; CB5R | NM_007326; NM_000398; NM_001129819; NM_001171660; NM_001171661; |
| ATRX_MOUSE | 546 | ATRX | ATRX | ATR2; SFM1; ZNF-HX; SHS; XH2; RAD54; JMS; MRXHF1; RAD54L; XNP; ATIG8600; CHR20; F22O13.8; F22O13_8 | XM_005262155; XM_005262154; XM_006724667; XM_006724668; XM_000489; XM_005262156; XM_005261253; XR_938400; ; NM_138270; XM_005262157; NM_138271; XM_006724666 |
| MPP10_MOUSE | 10199 | MPP10 | MPHOSPH10 | CT90; PPP1R106; MPP10P; MPP10; PANDA_013440 | NM_005791 |
| RFA1_MOUSE | 6117 | RFA1 | RPA1 | P1CST_79093; LMJF_28_1820; LINJ_28_1940; GUITHDRAFT_166372; REPA1; RF-A; RP-A; MST075; HSSB; RPA70; PHATRDRAFT_14457; NGA_0366300; LPMP_28_1930; CHLREDRAFT_176094; LBRM_28_1990; THAPSDRAFT_40884; GUITHDRAFT_79993 | NM_002945 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| DDX50_MOUSE | 79009 | DDX50 | DDX50 | DDX21; PAL_GLEAN10020554; RH-1I/GuB; mcdrh; GU2; GUB | NM_024045; XM_005270148; XM_011540143; XM_011540144 |
| RFC1_MOUSE | 5981 | RFC1 | RFC1 | YOR217W; CDC44; CaO19.14180; GUITHDRAFT_100231; GUITHDRAFT_160531; RFC140; PO-GA; RECC1; A1; MHCBFB; RFC; CHLREDRAFT_150793; AtRFC1; replication factor C1; AT5G22010; replication factor C 1; EMIHUDRAFT_558179; CaO19.6891 | NM_001204747; XM_011513730; XM_002913; XM_011513731 |
| HP1B3_MOUSE | 50809 | HP1B3 | HP1BP3 | HP1BP74; HP1-BP74; Anapl_13059 | XM_005245875; XM_005245879; XM_005245876; XM_005245878; XM_005245877; NM_016287; XM_011541535; XM_011541532; XM_011541533; XM_011541534 |
| TOP2B_MOUSE | 7155 | TOP2B | TOP2B | top2bets; TOPIIB | XR_940497; NM_001068; XM_005265427; XM_011534057 |
| RIF1_MOUSE | 55183 | RIF1 | RIF1 | PICST_28386; YBR275C | XR_922954; NM_001177663; XM_005246665; XR_922957; XR_022055; XR_922956; XM_011511393; NM_001177664; NM_001177665; XM_011511394; NM_018151; XM_011511395 |
| EPIPL_MOUSE | 83481 | EPIPL | EPPK1 | EPIPL1; EPIPL | XM_011517325; NM_031308; |
| PSPC1_MOUSE | 55269 | PSPC1 | PSPC1 | PANDA_015253; MDA_GLEAN10004221; PSP1 | XM_006719844; XM_011535140; XR_941619; XM_011535142; XM_011535139; XM_011535137; XR_941616; ; NM_001042414; XR_941617; XM011535138; XM_011535141; XM_011535143; NR_003272; NR_044998 |
| HNRLL_MOUSE | 92906 | HNRLL | HNRNPLL | HNRPLL; SRRF | XM_005264640; XM_011533165; XM_005264639; XR_939744; NM_138934; XM_011533166; NM_001142650 |
| RRBP1_MOUSE | — | — | | | |
| RL14_MOUSE | 9045 | RL14 | RPL14 | OSTLU_9318; CAG-ISL-7; L14; CTG-B33; RL14; hRL14; CHLREDRAFT_145271 | NM_001034996; NM_003973 |
| SMC1A_MOUSE | 8243 | SMC1A | SMC1A | SMC1; PANDA_016538; SMC1L1; SMCB; SB1.8; SMC1alpha; DXS423E; CDLS2; SMC-1A | ; NM_006306; NM_001281463 |
| NOC2L_MOUSE | 26155 | NOC2L | NOC2L | NIR; PPP1R112; NET15; NET7 | NM_015658 |
| A2AJ72_MOUSE | 8939 | FUBP3 | FUBP3 | FBP3 | XM_011519172; XM_006717314; XM_005272232; XM_006717312; XM_011519173; XM_006717313; NM_003934; XM_011519174; XM_011519171; XR_929871 |
| DNJB6_MOUSE | 10049 | DNJ | DNAJB6 | DJ4; HHDJ1; LGMDIE; MRJ; MSJ-1; HSJ2; HSJ-2; DnaJ; LGMID1D | ; XM_005249515; XM_005249516; XM_058246; NM_005494; XM_006715823; XM_011515704 |
| KIF4_MOUSE | 24137 | KIF4A | KIF4A | PANDA_006442; MDA_GLEAN10002731; PAL_GLEAN10005701; KIF4; KIF4G1; MRX100 | XM_01130893; ; NM_012310 |
| 1433T_MOUSE | 10971 | 1433T | YWHAQ | IC5; 14-3-3; HSI;; TREES_T100010476 | NM_006826 |
| SURF6_MOUSE | 6838 | SURF6 | SURF6 | RRP14; EGK_07243 | NR_103874; NM_006753; NM_001278942 |
| KI20A_MOUSE | 10112 | KI20A | KIF20A | MDA_GLEAN10012479; Anap_l14151; PANDA_011785; PAL_GLEAN10016825; RAB6KIFL; MKLP2 | NM_005733; XR_948224 |
| PDS5B_MOUSE | 23047 | PDS5B | PDS5B | APRIN; AS3; CG008 | XM_011535002; XM_005266298; XM_011535001; NM_015032; NM_015928; XM_011534999; XM_011535000; |
| ZN638_MOUSE | 27332 | ZN638 | ZNF638 | ZFML; Zfp638; NP220 | XM_011532767; XR_939678; NM_001014972; NM_001252613; XM_006711989; XM_011532769; XM_011523768; NM_001252612; NM_014497; XM_005264263 |
| RAD21_MOUSE | 5885 | RAD21 | RAD21 | HRAD21; SCC1; MCD1; NXP1; CDLS4; HR21; hHR21; PANDA_018369; PAL_GLEAN10021417; MDA_GLEAN10024618 | NM_006265 |
| SMHD1_MOUSE | 23347 | SMHD1 | SMCHD1 | — | XM_011525645; NM_015295; XM_011525646; ; XM_011525643; XM_011525644; XR_935054; |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| DDX10_MOUSE | 1662 | DDX10 | DDX10 | HRH-J8 | XM_011525642; XM_011525647; XR_935055; XR_430039 XM_011542646; NM_004398 |
| PDIP3_MOUSE | 84271 | PDIP3 | POLDIP3 | SKAR; PDIP46 | XM_011530457; NM_032311; NM_178136; NM_001278657; XR_937942; NR_103820 |
| K0020_MOUSE | 9933 | K0020 | KIAA0020 | PUF6; HA-8; HLA-HA8; PEN; XTP5; PUF-A | NM_001031691; NM_014878 |
| CPSF7_MOUSE | 79869 | CPFS7 | CPSF7 | CFIm59; PAL_GLEAN10011510; UY3_12626 | XM_011545257; XM_011545263; XM_005274303; NM_001142565; XM_011545258; XM_011545262; XM_005274299; XM_011545260; NM_024811; XM_011545261; NM_001136040; XM_005274298; XM_011545259 |
| ELYS_MOUSE | 25909 | ELYS | AHCTF1 | MSTP108; MST108; ELYS; TMBS62 | XM_006711758; XR_949137; NM_015446; XM_011544156; XR_426916; XM_006711759; XM_011544157; XR_949136 |
| APE_HMOUSE | 327 | ACPH | APEH | AARE; D3S48E; D3F15S2; ACPH; DNF15S2; APH; OPH; CB1_000145050; PAL_GLEAN10009189; AAP | XM_005265097; XM_011533658; XM_005265098; XM_011533656; XM_011533660; XM_011533657; XM_011533659; XM_011533662; ; XM_011533661; XM_011533663; NM_001640 |
| TDIF2_MOUSE | 30836 | TDIF2 | DNTTIP2 | LPTS-RP2; ERBP; FCF; HSU15552; TdIF2; MDA_GLEAN10013834 | NM_014597 |
| NXF1_MOUSE | 10482 | NXF1 | NXF1 | TREES_T100020891; MEX67; TAP; PAL_GLEAN10011461 | NM_001081491; NM_006362 |
| PRP19_MOUSE | 27339 | PRP19 | PRPF19 | hPSO4; PSO4; UBOX1; PRP19; SNEV; NMP200; TREES_T100002308; EGK_06157; CB_1002300027; nmp-200 | NM_014502 |
| SF3A3_MOUSE | 10946 | SF3A3 | SF3A3 | TREES_T100000917; GB11549; PRP9; PRPF9; SAP61; SF3a60; NGZ_0471300 | NM_006802; XM_005270390 |
| PSA1_MOUSE | 5682 | B4E0X6 | PSMA1 | CC2; NU; HC2; HEL-S-275; PROS30 | NM_001143937; NM_002786; NM_148976 |
| WDR46_MOUSE | 9277 | WDR46 | WDR46 | PANDA002273; C6orf11; FP221; BING4; UTP7; PAL_GLEAN10007103 | XM_011547332; XM_011548316; XM_011548317; XM_011514993; XM_011547730; XM_011547729; NM_005452; XM_011547333; XM_011514992; XM_011548119; XM_0111548118; NM_001164267 |
| RED_MOUSE | 3550 | RED | IK | RED; CSA2 | NM_006083 |
| SNUT1_MOUSE | 9092 | SNUT1 | SART1 | Snu66; SART1259; SNRNP110; Ara1; HOMS1 | XM_011535345; XM_011535344; XR_950099; NM_005146 |
| Q0VBL3_MOUSE | 64783 | RBM15 | RBM15 | SPEN; OTT; OTT1 | XM_011541967; NM_001201545; XM_011541965; XM_011541966; XM_011541964; XM_011541969; NM_022768; XM_011541968 |
| Q8BK35_MOUSE | 29997 | GSCR2 | GLTSCR2 | P1CT1; P1CT-1 | NM_015710 |
| TPX2_MOUSE | 22974 | TPX2 | TPX2 | MDA_GLEAN10014018; AacL_AAEL004112; DIL-2; REPP86; C20orf1; p100; GD:C20orf1; C20orf2; DIL2; FLS353; HCA519; HCTP4; AT1G03780; targeting protein for XKLP2; F21M11_31; F21M11.31; PAL_GLEAN10024200; AgaP_AGAP011054; ENSANGG00000017293; AgaP_ENSANGG00000017293; F12P19_13; thioredocin-dependent peroxidase 2; AT1G65970; PROXIREDOXIN TPX2; F12P19.13; ARALYDRAFT475704 | XM_011528697; XM_011528698; NM_0121112; XM_011528700; XM_011528699 |
| LAS1L_MOUSE | 81887 | LAS1L | LAS1L | Las1-like; dJ475B7.2; LAS1-like | XM_005262304; XM_005262305; NM_001170649; NM_001170650; XM_005262306; XR_430522; XM_011531045; XM_05262301; XM_005262307; XM_011531046; NM_031206; XR_244504; ; XR_938411; XR_938412 |
| ZFR_MOUSE | 51663 | ZFR | ZFR | SPG71; ZFR1; PAL_GLEAN10014079 | XR_427659; NM_016107 |
| AMY1_MOUSE | | | | | |
| RL27A_MOUSE | 6157 | RL27A | RPL27A | L27A; RPL27; YHR010W | NM_032650; NM_000990 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| UBF1_MOUSE | 7343 | UBF1 | UBTF | NPOR-90; UBF-1; UBF2; UBF1; UNF | XM_006722061; NM_014233; XM_006722059; XM_006722060; XM_011525177; NM_001076683; NM_001076684; NR_045058 |
| VP26A_MOUSE | 9559 | VP26A | VPS26A | MDA_GLEAN10020826; GUITHDRAFT_135609; MNC6_7; AT5G53530; MNC6.7; vacuolar protein sorting 26A; Hbeta58; HB58; PEP8A; VPS26 | NM_001035260; NM_004896; XM_011540378 |
| ALDH2_MOUSE | 217 | ALDH2 | ALDH2 | LINJ_25_1160; LMJF_25_1120; PAL_GLEAN10008876; ALDH1; ALDH-E2; ALDM; EMIHUDRAFT_350230; LPMP_251150 | NM_001204889; NM_000690; |
| DHB4_MOUSE | 3295 | DHB4 | HSD17B4 | MFE-2; PRLTS1; SCR8C1; DBP; MPF-2 | NM_001292028; NM_001292027; NM_001199292; ; NM_001199291; NM_000414 |
| IMA1_MOUSE | 3838 | IMA1 | KPNA2 | UY3_02579; IPOA1; QIP2; SRP1alpha; RCH1; Anapl_03182; PANDA_014057; PAL_GLEAN10014864 | XM_011524783; NM_002266 |
| SPB5_MOUSE | 5268 | SPB5 | SERPINB5 | maspin; P15 | NM_002639; XM_006722483 |
| TIAR_MOUSE | 7073 | TIAR | TIAL1 | TIAR; TCBP | XM_005270108; XR_428715; XM_005270109; ; XM_005270110; XR_945808; NM_003252; NM_001033925 |
| SMRC1_MOUSE | 6599 | SMRC1 | SMARCC1 | BAF155; Rsc8; CRACC1; SW13; SRG3 | XM_011534034; XM_011534035; NM_003074 |
| LARP7_MOUSE | 51574 | LARP7 | LARP7 | UY3_01935; ALAZS; P1P7S; HDCMA18P | ; NM_015454; NM_016648; NR_049768; NM_001267039 |
| NSUN2_MOUSE | 54888 | NSUN2 | NSUN2 | TRM4; SALI; MRT5; M1SU | NM_017755; ; NM_001193455; NR_037947 |
| NOL8_MOUSE | 55035 | NOL8 | NOL8 | C9orf34; NOP132; bA62C3.4; bA62C3.3 | XM_006717169; XM_006717170; XM_011518824; XM_011518828; NR_046106; XM_006717173; XM_006717168; XM_011518825; XM_006717166; XM_011518826; XM_011518827; NM_017948; XM_006717172; XR_929816; XM_006717167; NM_001256394 |
| ERMP1_MOUSE | 79956 | ERMP1 | ERMP1 | FXNA; KIAA1815; bA207C16.3; PAL_GLEAN10021042 | XR_9293338; NM_024896; XM_011518034; XR_428431; XM_005251587; XR_929337; XR_929340 |
| NPA1P_MOUSE | 9875 | NPA1P | URB1 | C21orf108; NPA1; YKL014C | NM_014825 |
| UTP20_MOUSE | 27340 | UTP20 | UTP20 | P1CST_74252; CaO19.9301; CaO19.10668; DRIM; YBL004W; CaO19.1733; MICPUN_107415; CaO19.3159; PAL_GLEAN10015492 | NM_014503; XM_006719343 |
| LAP2A_MOUSE | 7112 | LAP2B | TMPO | LAP2beta; LAP2; CMD1T; LEMD4; TP; PRO0868 | ; NM_001032284; XM_005269132; XM_005269130; NM_001032283; NM_003276 |
| REQU_MOUSE | 5977 | REQU | DPF2 | REQ; MDA_GLEAN10017910; UB1D4; ubi-d4; PAL_GLEAN10011379 | XR_950008; XM_005274149; NM_006268 |
| PLSL_MOUSE | 3936 | PLSL | LCP1 | plastin-2; CP64; LC64P; L-PLASTIN; LPL; PLS2; HEL-S-37; LCP-1; EGK_09301; Plastibn-2 | XM_005266374; NM_002298 |
| SCAF8_MOUSE | 22828 | SCAF8 | SCAF8 | RBM16 | NM_014892; NM_001286194; NM_001286189; NM_001286199; NM_001286188 |
| ABCF1_MOUSE | 23 | ABCF1 | ABCF1 | D1CPUDRAFT_157052; PAL_GLEAN10001332; ABC27; ABC50; LMJF_03_0160; LINJ_03_0150 | NM_001025091; NM_001090 |
| DCA13_MOUSE | 25879 | DCA13 | DCAF13 | WDSOF1; HSPC064; GM83 | NM_015420 |
| SMRC2_MOUSE | 6601 | SMRC2 | SMARCC2 | CRACC2; BAF170; Rsc8 | NM_139067; NM_001130420; XM_005269101; XM_005269104; XM_005269102; XM_011538693; XM_005269103; XM_011538694; NM_003075 |
| TRA2A_MOUSE | 29896 | TRA2A | TRA2A | AWMS1; HSU53209 | NM_013293; NM_001282757; NM_001282759; XM_005249725; XM_011515331; XM_006715713; NM_001282758 |
| POGZ_MOUSE | 23126 | POGZ | POGZ | ZNF635; ZNF635m; ZNF280E; PANDA_007985 | XM_011509331; NM_015100; XM_005244999; XR_921760; NM_001194938; XM_005245006; XM_011509330; XM_145796; NM_207171; XM_005245000; XM_005245001; XM_005245005; XM_001194937 |
| CHERP_MOUSE | 10523 | CHERP | CHERP | MDA_GLEAN10007202; SCAF6; SRA1; DAN16 | NM_006387 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| RBM12_MOUSE | 10137 | RBM12 | RBM12 | CPNE1; Anapl_04462; AS27_09836; EGK_02457; SWAN; HR1HFB2091; PANDA_004540; TREES_T100008592 | NM_001198838; NM_001198840; NM_152838; NM_006047 |
| PHIP_MOUSE | 55023 | PHIP | PHIP | WDR11; DCAF14; BRWD2; ndrp | XM_011535919; NM_017934; XM_005248729; XM_011535917; XM_011535918; XR_942499 |
| ATPG_MOUSE | 509 | ATPG; Q8TAS0 | ATP5C1 | ATP5CL1; ATP5C | NM_005174; NM_001001973; XM_011519490 |
| LRC59_MOUSE | 55379 | LRC59 | LRRC59 | p34; PRO1855; PAL_GLEAN10019724; UY3_00259; TREES_T100015351 | NM_018509 |
| MFAP1_MOUSE | 4236 | MFAP1 | MFAP1 | AMF; PAL_GLEAN10023540; PANDA_001004; EGK_17436 | NM_005926 |
| SNW1_MOUSE | 22938 | SNW1 | SNW1 | SKIIP; SKIP; PRPF45; Prp45; Bx42; NCOA-62; NGA_0680000 | NM_012245; XM_005267414; XM_005267413 |
| RAVR1_MOUSE | 125950 | RAVR1 | RAVER1 | — | NM_133452; XM_011527671; XM_011527672 |
| EMC4_MOUSE | 51234 | EMC4 | EMC4 | PIG17; TMEM85; EGK_17318; PAL_GLEAN10023658; PANDA_014713; YGL231C | NM_001286420; NM_016454 |
| BRX1_MOUSE | 55299 | BRX1 | BRIX1 | BXDC2; BRIX; PANDA_008108; PAL_GLEAN10001729 | NM_018321 |
| DAZP1_MOUSE | 26528 | DAZP1 | DAZAP1 | — | XM_005259535; XM_005259536; NM_170711; XM_011527906; XM_011527904; XM_011527908; XM_005259534; XM_011527909; NM_018959; XM_005259531; ; XM_011527907; XM_011527910; XM_011527905 |
| WDR12_MOUSE | 55759 | Q53T99; WDR12 | WDR12 | PAL_GLEAN10026133; YTM1; MDA_GLEAN10017295 | XM_011511469; NM_018256 |
| CELF2_MOUSE | 10659 | CELF2 | CELF2 | CUGBP2; NAPOR; BRUNOL3; ETR-3; ETR3; PAL_GLEAN10015786 | NM_001083591; NM_006561; XM_006717373; XM_011519294; XM_011519295; XM_011519297; XM_011519298; XM_005252534; XM_006717371; NM_001025076; XM_006717374; XM_006717375; XM_011519299; NM_001025077; XM_005252357; XM_005252358; XM_006717369; XM_011519296; XM_006717370 |
| ADNP_MOUSE | 23394 | ADNP | ADNP | EGK_02296; MED28; ADNP1; PANDA_000791 | ; NM_181442; NM_001282531; NM_001282532; NM_015339; XM_011528747; XM_011528748 |
| B9EJ54_MOUSE | 23165 | NU205 | NUP205 | C7orf14 | XM_005250235; NM_015135 |
| E9PW12_MOUSE | — | | | | |
| Q3TA68_MOUSE | 134430 | WDR36 | WDR36 | TA-WDRP; GLC1G; UTP21; TAWDRP | NM_139281; XM_011543163; |
| DEGS1_MOUSE | 8560 | DEGS1 | DEGS1 | DES1; MLD; DEGS-1; Des-1; MIG15; DEGS; FADS7 | XM_011544317; NM_003676; XM_011544318; NM_144780 |
| RPA1_MOUSE | 25885 | RPA1 | POLR1A | A190; RPO14; RPA194; RPA1; RPO1-4 | XM_006711983; NM_015425 |
| PTRF_MOUSE | 284119 | PTRF | PTRF | PANDA_011158; cavin-1; CAVIN; CAVIN1; CGL4; FKSG13 | ; NM_012232; XM_005257242 |
| COPB2_MOUSE | 9276 | COPB2 | COPB2 | beta'-COP; CHLREDRAFT_154280; PAL_GLEAN10015932; Beta'-COP | NM_004766; XM_011513317; NR_023350 |
| SPT5H_MOUSE | 6829 | SPT5H | SUPT5H | Tat_CT1; SPT5H; SPT5; PAL_GLEAN10001502; CB1_000338026 | NM_003169; XM_005259183; NM_001111020; NM_001130824; NM_001130825; XM_006723337 |
| AURKB_MOUSE | 9212 | AURKB | AURKB | STK5; aurkb-sv2; AurB; ARK2; PPP1R48; aurkb-sv1; AIM-1; A1K2; IPL1; A1M1; STK12; STK-1; ARK-2 | XM_011524070; XR_934118; NM_001256834; XM_011524071; XR_934117; NM_001284526; NM_004217; XM_011524072 |
| PSA3_MOUSE | 5684 | PSA3 | PSMA3 | EGK_18227; PSC3; HC8; NGA_0516100 | NM_152132; NM_002788; NR_038123 |
| ACTN3_MOUSE | 49860 | CRNN | CRNN | DRC1; SEP53; C1orf10; PDRC1 | NM_016190 |
| AATM_MOUSE | 2806 | AATM | GOT2 | mitAAT; KAT1V; KAT4; FABPpm; mAspAT; FABP-1; PAL_GLEAN10016182 | NM_001286220; NM_002080 |
| CATL1_MOUSE | 1515 | CATL2 | CTSV | CTSL1; CTSL; CTSL2; PANDA_020645; CATL2; CTSU | NM_001333; NM_001201575 |
| TRFL_MOUSE | 4057 | TRFL | LTF | LF; PLF; Lf; HEL110; HLF2; GIG12 | ; NM_002343; NM_001199149 |
| SODC_MOUSE | 6647 | V9HWC9; SODC | SOD 1 | YJR104C; CRS4; SOD1L1; DKFZP469M1833; hSod1; HEL-S-44; ALS1; 1POA; ALS; SOD; homodimer; | ; NM_000454 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| HSPB1_MOUSE | 3315 | HSPB1 | HSPB1 | EMIHUDRAFT_96386; PHATRDRAFT_12583; SPAPADRAFT_146717; PICST_89018; CU/ZN-SOD Hsp25; HEL-S-102; SRP27; HS.76067; HSP27; CMT2F; HSP28; HMN28; PAL_GLEAN10012025; UY3_14010 | NM_001540; |
| SBP1_MOUSE | 8991 | SBP1 | SELENBP1 | SBP; SBP56; SP56; HEL-S-134P; hSBP; LPSB | XM_011510110; XM_011510111; NM_001258288; XR_921993; NM_001258289; NM_003944 |
| RL13A_MOUSE | 23521 | RL13A | RPL13A | YDL082W; TSTA1; L13A | NR_073024; NM_001270491; NM_012423 |
| HEXB_MOUSE | 3074 | HEXB; A0A024R AJ6 | HEXB | ENC-1AS; HEL-248; PAL_GLEAN10024890; EGK_16586 | ; NM_001292004; NM_000521 |
| PNPH_MOUSE | 4860 | PNPH; V9HWH6 | PNP | NP; PRO1837; PUNP; CB1_001481042 | NM_000270; |
| H2AX_MOUSE | 3014 | H2AX | H2AFX | H2A/X; H2A.X; H2AX; EGK_06977 | NM_002105 |
| ACADM_MOUSE | 34 | ACADM | ACADM | ACAD1; MCAD; MCADH | NM_001127328; NM_001286042; NM_001286043; ; NM_000016; NM_001286044; NR_022013 |
| EXOSX_MOUSE | 5394 | EXOSX | EXOSC10 | Rrp6p; p4; PMSCL2; PM-Scl; PMSCL; p2; PM/Scl-100l RRP6; p3 | XM_005263475; NM_002685; XM_005263476; NM_001001998; XM_011541595 |
| PAXB1_MOUSE | 94104 | PAXB1 | PAXBP1 | GCFC1; GCFC; FSAP105; C21orf66; BM020 | XM_006724066; XM_011529804; XM_011529805; NM_016631; NR_027873; NM_013329; NM_145328; XM_006724067; NM_058191 |
| CSRN3_MOUSE | 80034 | CSRN3 | CSRNP3 | FAM130A2; PA1P-2; TA1P2; PPP1R73 | NM_024969; XM_005246865; NM_001172173 |
| NUP43_MOUSE | 348995 | NUP43 | NUP43 | p42; bA350J20.1 | XM_011535799; XM_005266961; XM_011535798; NM_198887; XM_005266960; XM_005266962; XR_942420; NM_024647; NR_104456 |
| KDM2A_MOUSE | 22992 | KDM2A | KDM2A | CXXC8; FBL11; FBL7; JHDM1A; FBXL11; LILINA | NR_027473; NM_012308; XM_011544860; XM_006718479; XM_006718480; XM_011544861; XM_011544862; NM_001256405 |
| SUMO2_MOUSE | 6613 | SUMO2; A0A024R 8S3 | SUMO2 | Smt3A; HSMT3; SMT3H2; SMT3B; SUMO3 | NM_001005849; NM_006937 |
| RUXE_MOUSE | 6635 | RUXE | SNRPE | SME; Sm-E; B-raf; HYPT11 | NM_001304464; NR_130746; NM_003094 |
| RS30_MOUSE | 2197 | UB1M | FAU | FAU1; MNSFbeta; RPS30l Fub1; Fubi; S30; asr1 | NM_001997 |
| RL32_MOUSE | 6161 | RL32 | RPL32 | L32; PP9932 | NM_000994; NM_001007073; NM_001007074 |
| PP1G_MOUSE | 5501 | PP1G; A0A024R BP2 | PPP1CC | PP-1G; PPP1G; PP1C | ; XM_011538505; XM_011538504; NM_001244974; NM_002710 |
| CRNL1_MOUSE | 51340 | CRNL1 | CRNKL1 | HCRN; CLF; CRN; MSTP021; Clf1; SYF3 | NM_001278627; NM_001278626; NM_001278628; NM_001278625; NM_016652 |
| IMB1_MOUSE | 3837 | IMB1 | KPNB1 | NTF97; IMB1; IPO1; IPOB; Impnb | NM_002265; NM_001276453 |
| PEBP1_MOUSE | 5037 | PEBP1 | PEBP1 | HCNP; HEL-S-34; HCNPpp; PBP; PEBP-1; HEL-210; PEBP; RKIP | NM_002567 |
| TP53B_MOUSE | 7158 | TP53B | TP53BP1 | p202; 53BP1 | XM_011521986; XR_931898; XR_931899; NM_001141980; XM_011521985; NM_005657; XM_011521984; NM_001141979; XM_005254635 |
| RL19_MOUSE | 6143 | RL19; J3KTE4 | RPL19 | L19 | NM_000981; XM_005257564 |
| CO1A2_MOUSE | 1278 | CO1A2 | COL1A2 | OI4 | ; NM_000089 |
| SSRP1_MOUSE | 6749 | SSRP1 | SSRP1 | FACT80; FACT; T160 | NM_003146; XM_005274194; XM_011545218 |
| SMCA4_MOUSE | 6597 | SMCA4 | SMARCA4 | BAF190; RTPS2; SNF2; hSNF2b; SW12; BAF190A; MRD16; SNF2LB; BRG1; SNF2L4 | NM_001128844; ; XM_005260031; NM_005260033; XM_005260034; NM_001128846; XM_005260032; XM_005260035; XM_006722847; NM_001128845; NM_001128848; NM_003072; XM_006722845; XM_006722846; NM_001128849; XM_005260028; XM_005260030; XM_011528198; NM_001128847 |
| CAPR1_MOUSE | 4076 | CAPR1 | CAPRIN1 | RNG105; GPIP137; GRIP137; M11S1; GPIAP1; p137GPI | XR_0930869; NM_005898; NM_203364 |
| SYHC_MOUSE | 3035 | SYHC | HARS | USH3B; HRS | ; NM_001258042; NM_001289093; NM_001258040; NM_001289092; NM_001289094; NM_002109; NM_001258041 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
| --- | --- | --- | --- | --- | --- |
| CTCF_MOUSE | 10664 | CTCF | CTCF | MRD21 | NM_006565; XM_005255775; ; NM_001191022 |
| HCFC1_MOUSE | 3054 | HCFC1 | HCFC1 | HCF1; HCF1; PPP1R89; VCAF; MRX3; CFF; HCF; HCF-1 | XM_006724816; XM_011531147; ; XM_011531144; XM_011531146; XM_011531150; XM_011531148; NM_005334; XM_006724815; XM_011531149; XM_011531145 |
| BAP31_MOUSE | 10134 | BAP31 | BCAP31 | CDM; DXS1357E; 6C6-AG; BAP31; DDCH | NM_001139441; NM_001256447; NM_001129457; NM_005745 |
| CBX5_MOUSE | 23468 | CBX5 | CBX5 | HEL25; HP1; HP1A | NM_001127321; NM_001127322; NM_012117 |
| CLH1_MOUSE | 1213 | CLH1; A0A087WVQ6 | CLTC | CLTCL2; CHC17; CLH-17; Hc; CHC | XM_011524279; XM_011524280; XM_01152481; XM_005257012; NM_001288653; NM_004859 |
| PDS5A_MOUSE | 23244 | PDS5A | PDS5A | PIG54; SCC112; SCC-112 | NM_001100400; XM_011513673; XM_011513674; NM_015200; NM_001100399; XM_011513672 |
| TPM4_MOUSE | 9169 | SCAFB | SCAF11 | SRSF21P; SFRS21P; CASP11; SIP1; SRRP129 | XM_011538985; NM_004719; XM_011538986; XM_006719692; XM_011538984; XM_005269230; XM_011538983; XM_011538987 |
| REXO4_MOUSE | 57109 | REXO4 | REXO4 | XPMC2H; XPMC2; REX4q | NM_001279350; NR_103996; NM_020385; NM_001279351; NR_103995; NM_001279349 |
| CNFN_MOUSE | 84518 | CNFN | CNFN | PLAC8L2 | XM_005259332; XM_011527396; NM_032488; XM_011527397 |
| RS9_MOUSE | 6203 | RS9 | RPS9 | S9 | XM_011547987; XM_011548358; XM_011548624; XR_431025; XR_431068; XR_953069; NM_001013; XM_005278288; XM_006726201; XM_006726202; XM_011547988; XM_011548623; XR_254260; XR_254311; XR_431090; XR_952765; XR_952994; XM_011547789; XM_011547790; XR_431067; XR_952920; XR_952995; XR_953155; XR_254518; XR_953156; XM_005277274; XM_006725965; XR_431057; XR_431069; XR_952922; XR_952996; XR_953068; XM_005278287; XM_011548167; XR_254517; XR_952766; XR_953070; XR_953157; XM_005277315; XM_011548359; XR_431058; XR_952764; XR_952919; XM_005277084; XM_005277085; XM_011548166; XR_430207; XR_431099 |
| RPA34_MOUSE | 1-849 | RPA34 | CD3EAP | CAST; PAF49; ASE-1; ASE1 | NM_001297590; NM_012099 |
| LC7L2_MOUSE | 51631 | LC7L | LUC7L | CGI-74; LUC7B2; CGI-59 | ; NM_001244585; NM_016019; NM_001270643 |
| DHX33_MOUSE | 56919 | DHX33 | DHX33 | DDX33 | XR_934069; NM_001199699; NM_020162 |
| TNPO1_MOUSE | 3842 | TNPO1 | TNPO1 | MIP; IPO2; MIP1; TRN; KPNB2 | XM_005248500; NM_153188; XR_948249; NM_002270; XM_005248501 |
| MAK16_MOUSE | 84549 | MAK16 | MAK16 | MAK16L; RBM13 | NM_032509 |
| NU107_MOUSE | 57122 | NU107 | NUP107 | NUP84 | XM_005269037; NM_020401; XM_011538576 |
| WDR3_MOUSE | 10885 | WDR3 | WDR3 | UTP12; DIP2 | NM_006784 |
| BOREA_MOUSE | 55143 | BOREA | CDCA8 | DasraB; BOR; MESRGP; BOREALIN | NM_018101; NM_001256875 |
| MAL2_MOUSE | 114569 | MAL2 | MAL2 | — | NM_052886; XM_011516807 |
| CARF_MOUSE | 55602 | CARF | CDKN2AIP | CARF | XM_005263118; NM_017632 |
| NUP93_MOUSE | 9688 | NUP93 | NUP93 | NIC96 | NM_001242795; XM_005256263; NM_014669; NM_001242796 |
| NKRF_MOUSE | 55922 | NKRF | NKRF | NRF; ITBA4 | XM_011531365; NM_001173488; NM_001173487; NM_017544; |
| RBM34_MOUSE | 23029 | RBM34 | RBM34 | — | XM_011544134; NM_015014; NM_001161533; XM_011544133; NR_027762 |
| UTP15_MOUSE | 84135 | UTP15 | UTP15 | NET21 | NM_001284431; XM_011543680; NM_001284430; NM_032175 |
| EMC1_MOUSE | 23065 | EMC1 | EMC1 | KIAA0090 | XM_005245788; ; XM_005245787; NM_001271429; NM_001271427; NM_001271428; NM_015047 |
| ELOA1_MOUSE | 6924 | ELOA1 | TCEB3 | TCEB3A; SIII; EloA; SIII_p110 | NM_003198 |
| P66A_MOUSE | 54815 | P66A | GATAD2A | p66alpha | XM_005259956; XM_011528104; XM_005259962; XM_006722780; XM_011528106; XM_011528107; NM_017660; XM_005259957; XM_005259961; NM_001300094; XM_005259959; XM_005259960; XM_011528105; XM_011528108 |
| SPF45_MOUSE | 84991 | SPF45 | RBM17 | SPF45 | NM_032905; NM_001145547 |
| SF3A1_MOUSE | 10291 | SF3A1 | SF3A1 | PRPF21; PRP21; SF3A120; SAP114 | ; NM_005877; NM_001005409 |
| NU133_MOUSE | 55746 | NU133 | NUP133 | hNUP133 | ; NM_018230 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| THOC1_MOUSE | 9984 | THOC1 | THOC1 | HPR1; P84N5; P84 | XM_011525773; XM_011525774; NM_005131; XM_011525772 |
| NOL6_MOUSE | 65083 | NOL6 | NOL6 | NRAP; bA311H10.1; UTP22 | NM_022917; NM_139235; NM_130793 |
| NDC1_MOUSE | 55706 | NDC1 | NDC1 | NET3, TMEM48 | XM_011541766; NR_033142; XM_006710762; NM_018087; NM_001168551 |
| CCAR2_MOUSE | 57805 | CCAR2 | CCAR2 | p30 DBC; DBC1; KIAA1967; NET35; p30DBC; DBC-1 | XM_011544604; NM_199205; NR_033902; XM_011544603; NM_021174 |
| LEGL_MOUSE | 29094 | LEGL | LGALSL | GRP; HSPC159 | NM_014181 |
| P66B_MOUSE | 57459 | P66B | GATAD2B | MRD18; P66beta; p68 | XM_005245364; XM_011509808; NM_020699; XM_006711469 |
| FLNC_MOUSE | 2318 | FLNC | FLNC | ABP-280; ABPA; MPD4; ABPL; MFM5; ABP280A; FLN2 | ; NM_001127487; NM_001458 |
| DDX1_MOUSE | 1653 | DDX1 | DDX1 | DBP-RB; UKVH5d | NM_004939 |
| DNJC9_MOUSE | 23234 | DNJC9 | DNAJC9 | JDD1; HDJC9; SB73 | NM_015190 |
| PTBP2_MOUSE | 58155 | PTBP2 | PTBP2 | nPTB; PTBLP; brPTB | XR_946723; XT946722; NM001300987; NR_125357; XM_011541876; XM_011541875; XR_946720; NM_001300986; NM_001300988; NM_02190; NM_001300990; NR_125356; XM_011541874; XR_946721; NM_001300985; NM_001300989 |
| SMC6_MOUSE | 79677 | SMC6 | SMC6 | hSMC6; SMC-6; SMC6L1 | XR_939716; NM_001142286; XM_011533107; XM_011533108; NM_024624 |
| SFXN1_MOUSE | 94081 | SFXN1 | SFXN1 | — | XM_005266102; NM_022754 |
| RLP24_MOUSE | 51187 | RLP24 | RSL24D1 | HRP-L30-iso; TVAS3; RLP24; C15orf15; L30; RPL24; RPL24L | NM_016304 |
| RTCB_MOUSE | 51493 | RTCB | RTCB | HSPC117; C22orf28; DJ149A16.6; FAAP | NM_014306 |
| CPSF5_MOUSE | 11051 | CPSF5 | NUDT21 | CFIM25; CPSF5 | NM_007006 |
| LSM7_MOUSE | 51690 | LSM7 | LSM7 | YNL147W | XM_011528061; NM_016199 |
| RER1_MOUSE | 11079 | RER1 | RER1 | — | XM_005244713; XM_011540543; NM_007033; XM_011540542; XM_006710306; |
| NSA2_MOUSE | 10412 | NSA2 | NSA2 | CDK105, TINP1; HUSSY-29; HUSSY29; HCLG1; HCL-G1 | XM_011543098; NM_001271665; XR_948227; NM_014886; NR_073403 |
| RRP15_MOUSE | 51018 | RRP15 | RRP15 | CGI-115; KIAA0507 | XM_011509597; NM_016052 |
| CISY_MOUSE | 1431 | A0A024R B75; CISY | CS | — | NM_004077; NM_198324 |
| RFC5_MOUSE | 5985 | RFC5 | RFC5 | RFC36 | XM_011538645; NM_001130112; NM_001130113; NM_007370; NM_001206801; XM_011538643; XM_011538644; NM_181578 |
| SYRC_MOUSE | 5917 | SYRC | PARS | HLD9; DALRD1; ArgRS | NM_002887; |
| PHF6_MOUSE | 84295 | PHF6 | PHF6 | BFLS; BORJ; CENP-31 | NM_001015877; NM_032335; ; NM_032458 |
| SUN1_MOUSE | 23353 | SUN1 | SUN1 | UNC84A | NM_001171945; NM_001130965; NM_001171944; NM_025154; NM_001171946 |
| CALL3_MOUSE | 810 | CALL3 | CLAML3 | CLP | NM_005185 |
| TGM5_MOUSE | 9333 | TGM5 | TGM5 | TGASE5; TGM6; TGX; PSS2; TGMX; TGASEX | XM_0115222291 XR_931948; NM_201631; NM_004245; XM_011522230 |
| CPNS2_MOUSE | 84290 | CPNS2 | CAPNS2 | | NM_032330 |
| FIP1_MOUSE | 81608 | FIP1 | FIP1L1 | FIP1; Rhc; hFip1 | XM_005265770; NM_001134937; XM_005265768; XM_005265781; NM_030917; XM_005265769; XM_005265773; XM_005265774; XM_005265778; XM_005265779; ; XM_005265771; NM_001134938; XM_005265780; XM_005265782; XM_005265776; XM_005265777; XM_005265772; XM_005265775 |
| EVPL_MOUSE | 2125 | EVPL | EVPL | EVPK | XM_011524516; NM_001988 |
| SNAA_MOUSE | 8775 | SNAA | NAPA | SNAPA | XM_011537437; NR_038457; NM_003827; XM_011527436; NR_039456 |
| RRP8_MOUSE | 23378 | RRP8 | RRP8 | NML; KIAA0409 | XR_930858; XM_011519955; XR_930859; NM_015324; XR_930860 |
| XRN2_MOUSE | 22803 | XRN2 | XRN2 | — | XM_011529184; NM_012255 |
| NDUA9_MOUSE | 4704 | NDUA9 | NDUFA9 | CI-39k; CI39k; CC6; NDUFFS2L; SDR22E1 | ; NM_005002 |
| CPSF1_MOUSE | 29894 | CPSF1 | CPSF1 | CPFS160; P/c1.18; HSU37012 | XM_006716548; XM_011516999; NM_013291; XM_006716550; XM_011516998; XM_011516997; XM_006716549 |
| AR6P4_MOUSE | 51329 | AR6P4 | ARL6IP4 | SRrp37; SR-25; SFRS20; SRp25 | NR_103512; NM_001002252; NM_001278380; NM_018694; NM_001278378; NM_001278379; NM_001002251; NM_016638 |
| CAF1A_MOUSE | 10036 | CAF1A | CHAF1A | CAF-1; CAF1B; CAF1; CAF1P150; P150 | XR_936135; XM_011527607; XM_011527605; XM_011527606; NM_005483 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| INCE_MOUSE | 3619 | INCE | ICNENP | — | XM_011544998; XM_011544995; XM_011544997; XM_006718533; XM_011544996; NM_001040694; NM_020238 |
| RFC2_MOUSE | 5982 | RFC2 | RFC2 | RFC40 | XR_927506; NM_001278792; NM_001278793; NM_002914; NM_181471; ; NM_001278791; XM_006716080 |
| SNF5_MOUSE | 6598 | SNF5 | SMARCB1 | MRD15; Snr1; INI1; RDT; RTPS1; SWNTS1; PPP1R144; SNF5; Sth1p; SNF5L1; BAF47; hSNFS | ; XM_011546908; XM_011546909; NM_001007468; NM_003073; XM_011530346; XM_011530345 |
| HNRPC_MOUSE | 3183 | HNRPC | HNRNPC | HNRNP; SNRPC; C1; C2; HNRPC | NM_031314; XM_011536708; XM_006720125; XM_011536710; NM_001077442; XM_011536709; ; NM_004500; NM_001077443; XM_011536711; XM_011536712 |
| B0LM42_MOUSE | 29028 | ATAD2 | ATAD2 | PRO2000; CT137; ANCCA | XM_011516995; XM_011516996; XR_928326; XM_011516994; NM_014109 |
| D3YUU6_MOUSE | 64794 | DDX31 | DDX31 | PPP1R25 | XM_011518923; XM_005272206; XM_011518921; XM_011518924; NM_138620; XR_246600; XR_929836; XM_006717236; NM_022779; XM_005272207; XM_011518922 |
| E9PWW9_MOUSE | 57466 | SFR15 | SCAF4 | SRA4; SFRS15 | NM_001145445; XM_006724036; NM_001145444; XM_005261017; XM_006724035; NM_020706 |
| E9PZM8_MOUSE G3X963_MOUSE | — 5646 | TYR3 | PRSS3 | PRSS4; TRY4; TRY3; MTG; T9 | ; NM_001197098; NM_007343; NM_001197097; XM_011517965; NM_002771 |
| Q3TWW8_MOUSE Q6NZQ2_MOUSE | — 10180 | RBM6 | RBM6 | DEF-3; HLC-11; 3G2; g16; NY-LU-12; DEF3 | NM_005777; XM_005264787; XM_005264786; XM_005264785; XM_005264788; NM_001167582; XM_005264784; XM_006712916; XR_940359; XR_940360 |
| Q6PFF0_MOUSE | 4288 | K167 | MK167 | KIA; MIB-1; MIB-; PPP1R105 | NM_002417; NM_001145966; XM_006717864; XM_011539818 |
| Q9ZIR9_MOUSE | 56252 | YLPM1 | YLPM1 | PPP1R169; ZQP3; C14orf170; ZAP113 | XM_005267860; XM_011536966; XM_011536967; NM_019589; XR_943494 |
| S4R1W5_MOUSE | 142 | PARP1 | PARP1 | PARP; PARP-1; ADPRT1; PPOL; pADPRT-1; ADPRT; ADPRT 1; ARTD1 | NM_001618 |
| E9PVX6_MOUSE | 9790 | BMS1 | BMS1 | ACC; BMS1L | XR_428728; XM_005271846; XM_005271849; XM_006718081; XM_014753; XM_005271848; XR_246522; XM_005271847; XM_011540403; XM_011540402 |
| D3YWX2_MOUSE | 10940 | PQP1 | PQP1 | — | NM_001145860; NM_01145861; NM_015029; XM_011516800; XM_011516801 |
| Q921K2_MOUSE | 9416 | DDX23 | DDX23 | prp28; SNRNP100; PRPF28; U5-100K; U5-100KD | NM_004818 |
| SUN2_MOUSE | 25777 | SUN2 | SUN2 | UNC84B | NM_015374; XM_011530105; XM_011530104; NM_001199580; NM_01199579 |
| SAFB1_MOUSE | 6294 | SAFB1 | SAFB | HAP; HET; SAF-B1; SAFB1 | XM_006722839; NR_037699; NM_001201340; NM_001201339; NM_001201338; NM_002967 |
| HNRL2_MOUSE | 221092 | HNRL2 | HNRNPUL2 | HNRPUL2; SAF-A2 | NM_001079559 |
| CHD4_MOUSE | 1108 | CHD4 | CHD4 | Mi2-BETA; Mi-2b; CHD-4 | XM_006718958; NM_001273; XM_006718962; XM_006718960; XM_006718959; XM_005253668; XM_006718961; NM_001297553 |
| TCOF_MOUSE | 6949 | TCOF | TCOF1 | treacle; MFD1; TCS1; TCS | NM_001008656; XM_005268504; XM_005268505; NM_001135243; XM_005268509; NM_000356; NM_001008657; NM_001135245; XM_011537678; XR_427780; XM_005268502; XM_005268507; XR_427778; XM_005268506; XM_005268508; ; NM_001135244; XM_005268503; XR_427779; NM_001195141 |
| RRP1B_MOUSE | 23076 | RRP1B | RRP1B | PPP1R136; KIAA0179; NNP1L; Nnp1; RRP1 | NM_015056 |
| LA_MOUSE | 6741 | LA | SSB | La; La/SSB; LARP3 | NM_003142; NM_001294145; |
| Q6PGF5_MOUSE | 3187 | HNRH1 | HNRNPH1 | HNRPH1; hnRNPH; HNRPH | XM_006714862; XM_005265895; XM_006714863; XM_011534541; XM_005265901; XM_005265896; XM_011534542; XM_011534543; XM_011534544; NM_001257293; NM_005520; XM_011534547; XM_005265902; XM_011534545; XM_011534546 |
| Q8K205_MOUSE | 9221 | NOLC1 | NOLC1 | NOPP130; NOPP140; P130; NS5ATP13 | XM_005270273; NM_004741; NM_001284389; NM_001284388 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| HMGB2_MOUSE | 3148 | HMGB2 | HMGB2 | HMG2 | NM_002129; NM_001130688; NM_001130689 |
| HNRH2_MOUSE | 3188 | HNRH2 | HNRNPH2 | FTP3; HNRPH'; HNRPH2; hnRNPH' | ; NM_019597; NM_001032393 |
| TR150_MOUSE | 9967 | TR150 | THRAP3 | TRAP150 | XM_005271371; XR_246308; NM_005119 |
| SNR40_MOUSE | 9410 | SNR40 | SNRNP40 | PRPF8BP; 40K; SPF38; WDR57; HPRP8BP; PRP8BP | NM_004814 |
| MTA2_MOUSE | 9219 | MTA2 | MTA2 | MTA1L1; PID | NM_004739 |
| RRP5_MOUSE | 22984 | RRP5 | PDCD11 | NFBP; RRP5; ALG-4; ALG4 | NM_014976; XM_011539538; XM_011539540; XM_005269647; XM_011539539 |
| CO1A1_MOUSE | 1277 | CO1A1 | COL1A1 | O14 | NM_000088; ; XM_005257059; XM_005257058; XM_011524341 |
| CATA_MOUSE | 847 | CATA | CAT | — | ; NM_001752 |
| PSA2_MOUSE | 5683 | A0A024R A52; PSA2 | PSMA2 | OSMA2; HC3; MU; PSC2 | NM_002787 |
| PUF60_MOUSE | 22827 | PUF60 | PUF60 | SIAHBP1; RoBPI; FIR; VRJS | NM_001271096; NM_001271097; NM_001136033; NM_014281; ; NM_001271100; NM_078480; XM_011516929; NM_001271098; XM_011516930; NM_001271099 |
| SF01_MOUSE | 7536 | SF01 | SF1 | MBBP; D11S636; ZCCHC25; BBP; ZFM1; ZNF162 | NM_001178031; NR_033649; NR_033650; NM_001178030; XM_011545247; NM_201995; NM_201998; XM_011545245; ; NM_004630; XM_011545244; XM_011545248; NM_201997; XM_011545246 |
| IMMT_MOUSE | — | | | | |
| DDX54_MOUSE | 79039 | DDX54 | DDX54 | DP97 | NM_001111322; NM_024072 |
| RBM19_MOUSE | 9904 | RBM19 | RBM19 | — | XM_011539038; XR_944848; NM_016196; NM_001146698; NM_001146699 |
| SMCA5_MOUSE | 8467 | SMCA5 | SMARCA5 | ISWI; SNF2H; hISWI; WCRF135; hSNF2H | NM_003601; XM_011532361 |
| GLYR1_MOUSE | 84656 | GLYR1 | GLRY1 | BM045; N-PAC; NP60; HIBDL | XM_005255638; XM_011522717; XR_932954; XM_005255640; NM_032569; XM_005255639; XM_011522716; XM_011522718; XM_005255637; XR_243321 |
| PSIP1_MOUSE | 11168 | PSIP1 | PSIP1 | PSIP2; p52; DFS70; LEDGF; p75; PAIP | XM_005251358; XM_011517698; NM_001128217; NM_033222; XM_011517697; XM_011517700; NM_021144; XM_011517699 |
| NOG1_MOUSE | 23560 | NOG1; D2CFK9 | GTPBP4 | CRFG; NGB; NOG1 | NM_012341 |
| PSA6_MOUSE | 5687 | PSA6 | PSMA6 | IOTA; p27K; PROS27 | ; NM_001282234; NM_002791; NM_001282232; NM_001292233; NR_104110 |
| D3Z0M9_MOUSE | 9295 | SRS11 | SRSF11 | dJ677H15.2; p54; SFRS11; NET2 | XM_005271339; XM_011542429; NM_004768; XM_011542430; NM_001190987; XM_005271338; XM_006711037; XM_011542432; XM_006711038; XM_011542433; XR_426640; XM_011542428; XM_006711039 |
| DHX9_MOUSE | 1660 | DHX9 | DHX9 | DDX9; LKP; NHD2; NDHII; RHA | ; NM_001357; NM_030588; NR_033302 |
| DHX15_MOUSE | 1665 | DHX15 | DHX15 | PRPF43; HRH2; PRP43; DBP1; DDX15; PrPp43p | XR_925314; NM_001358 |
| ELAV1_MOUSE | 1994 | ELAV1 | ELAVL1 | ELAV1; MeIG; Hua; HUR | XM_011527777; NM_001419 |
| CDC5L_MOUSE | 988 | CDC5L | CDC5L | PCDC5RP; CDC50LIKE; dJ319D22.1; CEF1; CDC5 | XM_006715289; NM_001253; XR_926346 |
| NUP98_MOUSE | 10236 | HNPRP | HNRNPR | hnRNP-R; HNRPR | XM_011540473; XM_005245711; XM_011540472; NM_001102399; NM_001102397; XM_011540474; NM_001102476; NM_001297621; NM_001297622; XM_011540471; XM_011540475; XM_011540477; NM_001102398; NM_001297620; NM_005826 |
| RBM28_MOUSE | 55131 | RBM28 | RBM28 | ANES | XM_011516370; XM_011516371; NM_018077; NM_001166135; XR_927487; |
| Q8C2Q7_MOUSE | 79026 | AHNK | AHNAK | AHNAKRS | XM_005274240; XM_005274242; XM_005274243; XM_011545250; XM_005274241; XM_005274244; NM_024060; XM_005274245; XM_005274249; NM_001620 |
| PRP8_MOUSE | 10594 | PRP8 | PRPF8 | SNRNP220; HPRP8; PRPC8; PRP8; RP13 | NM_006445; |
| U520_MOUSE | 23020 | U520 | SNRNP200 | ASCC3L1; BRR2; RP33; U5-200KD; HELIC2 | ; NM_014014 |
| BAZIB_MOUSE | 9031 | BAZIB | BAZIB | WBSCR9; WBSR10; WSTF | NM_032408; NM_023005; XM_005250683; |
| UST48_MOUSE | 1650 | A0A024R AD5; OST48 | DDOST | OST; OST48; AGER1; OKSWc145; CDG1R; WBP1 | ; NM_005216 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| P53_MOUSE | 7157 | H2EHT1; K7PPA8; P53; A0A087 WXZ1; A0A087X 1Q1; Q53GA5; A0A087 WT22 | TP54 | TRP53; BCC7; P53; LFS1 | NM_001126112; NM_001276697; NM_01126115; ; NM_01126114; NM_001276698; NM_001276761; NM_001126118; NM_001126113; NM_001126117; NM_001276695; NM_001276699; NM_001276760; NM_000546; NM_001126116; NM_001276696 |
| LYZ1_MOUSE | 1E+08 | XP32 | C1orf68 | XP32; LEP7 | NM_001024679 |
| H2A1_MOUSE | 5725 | PTBP1 | PTBP1 | pPTB; PTB3; HNRNP-1; PTB; HNRNPI; PTB-T; PTB2; HNRP1; PTB-1; PTB4 | XR_244034; NM_002819; XR_244035; XM_005259597; NM_031991; NM_175847; XM_005259598; NM_031990 |
| RL27_MOUSE | 6155 | A0A024R 1V4; RL27 | RPL27 | L27 | NM_000988 |
| RS6_MOUSE | | | | | |
| RBBP6_MOUSE | 5930 | RBBP6 | RBBP6 | P2P-R; MY038; RBQ-1; SNAMA; PACT | XM_005255461; NM_018703; XM_005255462; NM_006910; NM_032626 |
| LYAR_MOUSE | 55646 | LYAR | LYAR | ZC2HC2; ZYLAR | XM_011513505; NM_001145725; NM_017816; XM_011513506 |
| PSA_MOUSE | 9520 | PSA | NPEPPS | PSA; AAP-S; MP100 | XM_011525496; NM_006310 |
| RRP12_MOUSE | 23223 | RRP12 | RRP12 | KIAA0690 | NM_015179; XM_011539556; XM_011539557; XM_011539555; NM_001145114; NM_001284337 |
| WDR43_MOUSE | 23160 | WDR43 | WDR43 | NET12; UTP5 | NM_015131 |
| RS27_MOUSE | 6232 | RS27 | RPS27 | MPS-1; S27; MPS1 | NM_001030 |
| RL24_MOUSE | 6152 | RL24 | RPL24 | HEL-S-310; L24 | NM_000986 |
| RFOX2_MOUSE | 23543 | RFOX2 | RBFOX2 | FOX2; Fox-2; HNRBP2; HRNBP2; RBM9; RTA; fxh; dJ106I20.3 | XM_006724190; XM_006724193; XM_006724185; XM_006724187; XM_011530036; NM_001031695; NM_001082577; XM_005261428; XM_005261430; XM_005261431; XM_005261432; XM_005261433; XM_005261437; NM_001082579; XM_005261429; XM_006724186; XM_006724194; XM_006724192; NM_001082578; NM_014309; NM_001082576; XM_005261435; XM_006724188; XM_006724189; XM_006724191 |
| MYEF2_MOUSE | 50804 | MYEF2 | MYEF2 | myEF-2; MSTP156; HsT18564; MEF-2; MST156 | XM_005254424; XM_006720553; XM_005254422; XM_005254425; NM_001301210; NM_016132; XM_005254427; XM_011521657; NR_125408 |
| MATR3_MOUSE | 9782 | MATR3 | MATR3 | MPD2; ALS21; VCPDM | NM_001282278; NM_018834; NM_001194956; NM_199189; ; NM_01194954; NM_001194955 |
| RBM39_MOUSE | 9584 | RBM39 | RBM39 | CAPERalpha; FSAP59; CAPER; HCC1; RNPC2 | XM_011529110; NM_184237; XM_006723891; XM_006723893; NM_001242599; NM_184234; ; NM_001242600; NR_040722; XM_006723890; XM_01152911; NM_004902; NR_040723; NM_184241; NR_040724; NM_184244 |
| PRP6_MOUSE | 24148 | PRP6 | PRPF6 | TOM; ANT-1; Prp6; hPrp6; C20orf14; RP60; ANT1; SNRNP102; U5-102K | XM_006723769; ; NM_012469 |
| SSF1_MOUSE | 56342 | SSF1 | PPAN | SSF-1; SSF1; BXDC3; SSF; SSF2 | NM_020230 |
| ILF2_MOUSE | 3608 | ILF2 | ILF2 | NF45; PRO3063 | NM_001267809; NM_004515 |
| TMM43_MOUSE | 79188 | TMM43 | TMEM43 | LUMA; ARVC5; ARVD5; ADMD7 | XM_011534109; ; NM_024334 |
| PK1IP_MOUSE | 55003 | PK1IP1 | PAK1IP1 | bA421M1.5; PIP1; hPIP1; MAK11; WDR84 | XM_005249204; XM_011514720; XM_006715129; XM_011514721; NM_017906 |
| GSDMA_MOUSE | 284110 | GSDMA | GSDMA | FKSG9; GSDM; GSDM1 | XM_006721832; XM_011524651; NM_178171 |
| SON_MOUSE | 6651 | SON | SON | NREBP; BASS1; DBP-5; C21orf50; SON3 | NR_103797; NM_138927; NM_001291412; NM_003103; NR_103798; NM_001291411; NM_032195; NM_138925; NR_103796 |
| E9Q5C9_MOUSE | — | | | | |
| E9Q6E5_MOUSE | — | | | | |
| Q8VHM5_MOUSE | — | | | | |
| TOP2A_MOUSE | 7153 | TOP2A | TOP2A | TOP2; TP2A | XM_005257632; XM_011525165; NM_001067 |
| FINC_MOUSE | 2335 | FINC | FN1 | FNZ; GFND; C1G; ED-B; GFND2; MSF; FINC; FN; LETS | XM_005246416; ; XM_005246413; NM_212476; XM_005246407; XM_005246410; XM_005246414; XM_212474; XM_005246402; XM_005246408; XM_005246409; XM_005246399; NM_054034; XM_005246400; XM_005246403; XM_005246405; |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| | | | | | XM_005246406; XM_005246415; NM_002026; XM_005246398; XM_005246401; XM_005246404; XM_005246412; XM_005246417; XM_005246397; XM_005246411; NM_212478; NM_212482; NM_212475 |
| RASK_MOUSE | 3845 | RASK | KRAS | KI-RAS; NS; K-RAS4B; K-RAS4A; RASK2; CFC2; K-RAS2B; KRAS2; KRAS1; C-K-RAS; K-RAS2A; NS3 | XM_011520653; NM_004985; ; XM_006719069; NM_033360 |
| HNRPQ_MOUSE | 10492 | HNRPQ | SYNCRIP | GRY-RBP; HNRPQ1; PP68; hnRNP-Q; GRYRBP; NSAP1; HNRNPQ | XM_005248636; XM_005248637; NM_001159676; ; NM_001159673; NM_001159674; NM_001159677; NM_001159675; NM_001253771; NM_006372; XM_005248635 |
| MYH10_MOUSE | 4628 | MYH10 | MYH10 | NMMHC-IIB; NMMHCB | NM_001256095; XM_011523875; XM_011523877; XM_011523879; XM_011523880; XM_011523876; XM_005256651; NM_005964; XM_011523878; NM_001256012 |
| DDX51_MOUSE | 317781 | DDX51 | DDX51 | — | XM_011538256; NM_175066 |
| DEK_MOUSE | 7913 | DEK | DEK | D6S231E | XM_011514889; NM_001134709; XR_926307; NM_003472 |
| NOP16_MOUSE | 51491 | NOP16 | NOP16 | HSPC185; HSPC111 | NM_001291306; NM_016391; NM_001256539; NM_001291540; NM_001291305; XM_011534567; NM_001291308; XM_011534566; NM_001291307 |
| RBM14_MOUSE | 10432 | RBM14 | RBM14 | COAA; TMEM137; SIP; SYTIP1; PSP2 | NM_001198837; ; NM_001198836; NM_006328; NM_032886 |
| RL4_MOUSE | 6124 | RL4 | RPL4 | L4 | NM_000968 |
| ADT1_MOUSE | 291 | SDT1 | SLC25A4 | AAC1; ANT; ANT1; PEO2; PEO3; 1; ANT 1; MTDPS12; T1 | NM_001151; |
| HNRPL_MOUSE | 3191 | HNRPL | HNRNPL | HNRPL; hnRNP-L; P/OKcl.14 | XM_011526887; XR_243927; XM_011526886; XM_011526889; NM_001533; NM_001005335; XM_011526888; XM_011526890 |
| NONO_MOUSE | 4841 | NONO | NONO | P54; PPP1R114; NMT55; NRB54; P54NRB | NM_001145410; NM_007363; NM_001145409; NM_001145408 |
| DNMT1_MOUSE | 1786 | I6L9H2; DNMT1 | DNMT1 | AIM; CXXC9; DNMT; MCMT; ADCADN; HSN1I | XM_011527773; ; NM_001130823; NM_001379; XM_011527772; XM_011527774 |
| E9Q616_MOUSE | — | | | | |
| HNRPM_MOUSE | 4670 | HNRPM | HNRNPM | HTGR1; NAGR1; hnRNP M; HNRPM; CEAR; HNRNPM4; HNRPM4 | NM_005968; XM_005272478; XM_005272480; XM_005272483; NM_005272479; XM_005272481; NM_001297418; NM_031203; |
| FBX50_MOUSE | 342897 | FBX50 | NCCRP1 | NCCRP-1; FBXO50 | NM_001001414; XM_011526906 |
| PSB1_MOUSE | 5689 | PSB1 | PSMB1 | PSC5; PMSB1; HC5 | NM_002793 |
| SRSF5_MOUSE | 6430 | SRSF5 | SRSF5 | HRS; SRP40; SFRS5 | XM_005267999; XR_943505; NM_006925; XM_005267998; XR_943506; NM_001039465; XM_005268000; XM_011537077 |
| CAN1_MOUSE | 823 | CAN1 | CAPN1 | muCL; CANPL1; muCANP; CANP; CANP1 | NM_001198868; NR_040008; XM_006718698; XM_011545292; NM_005186; NM_001198869 |
| ZN326_MOUSE | 284695 | ZN326 | ZNF36 | Zfp326; ZAN75; dJ871E2.1; ZIRD | NM_181781; XM_005270780; XM_005270779; XM_011541288; XM_011541289; XM_011541290; NM_182975; NM_182976 |
| CASPE_MOUSE | 23581 | CASPE | CAP14 | — | NM012114; XM011527861 |
| COX2_MOUSE | 4513 | COX2; U5Z487 | COX2 | COII; MTCO2 | |
| MAOX_MOUSE | 4199 | MAOX | MEI | HUMNDME; MES | XM_011535836; NM_002395 |
| RL7_MOUSE | 6129 | RL7 | RPL7 | L7; humL7-1 | XM_006716463; NM_000971 |
| NDKA_MOUSE | 4830 | NDKA | NME1 | GAAD; NB; AWD; NBS; NDPK-A; NDPKA; NDKA; NM23; NM23-H1 | ; NM_198175; NM_000269 |
| TPM3_MOUSE | 7170 | TPM3 | TPM3 | NEM1; HEL-189; OK/SW-cl.5; TM30nm; TM-5; TH5; CAPM1; TM3; TM30; CFTD; hscp30; TPMsk3; HEL-S-82p; TRK | XM_006711520; XM_006711521; XM006711523; NR_103461; XM_006711517; NM_001043353; XM_006711522; XM_006711519; XM_011509950; XM_011509953; NM_001278190; NM_152263; XM_011509952; NM_153649; XM_006711515; XM_011509954; NM_001278189; XM_011509951; NM_001278188; NM_001278191; XM_006711518; NM_001043351; NM_001043352; NR_103460 |
| RS2_MOUSE | 6187 | RS2 | RPS2 | LLREP3; S2 | NM_002952 |
| RL12_MOUSE | 6136 | RL12 | RPL12 | L12 | NM_000976 |
| H11_MOUSE | 3024 | H11 | HISTH1A | H1.1; HIST1; H1A; H1F12 | NM_005325 |
| CAPZB_MOUSE | 832 | CAPZB | CAPBZ | CAPB; CAPZ; CAPPB | XM_011542229; NM_001206541; NM_004930; XM_006710938; XM_011542230; |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| LIS1_MOUSE | 5048 | LIS1 | PAFAH1B1 | LIS1; LIS2; MDCR; PAFAH; MDS | NM_001206540; XM_011542228; NM_001282162 XM_011523902; XM_011523903; XM_011523904; NM_000430; XM_011523901; |
| HMGB1_MOUSE | 3146 | HNGB1 | HNGB1 | HNG3; SBP-1; HNG1 | XM_005266368; XM_011535056; XM_011535055; XR_941568; NM_002128; XM_005266363; XM_005266365 |
| RS10_MOUSE | 1.01E+08 | S4R435 | RPS10-NUDT3 | — | NM_001202470 |
| PHB_MOUSE | 5245 | PHB | PHB | HEL-S-54e; PHB1; HEL-215 | ; NM_002634; NM_001281715; NM_001281496; NM_001281497 |
| NACAM_MOUSE | — | | | | |
| PHF5A_MOUSE | 84844 | PHF5A | PHF5A | DAP14b; INI; Rds3; bK223H9.2; SF3B7; SF3b14b | NM_032758 |
| RS3A_MOUSE | 6189 | RS3A; B7Z3M5 | RPS3A | S3A; MFTL; FTE1 | NM_001267699; NM_001006 |
| ZCH18_MOUSE | 124245 | ZCH18 | ZC3H18 | NHN1 | XM_011522864; XM_011522863; XM_011522865; XM_011522862; NM_001294340; NM_144604 |
| FUBP2_MOUSE | 8570 | FUBP2 | KHSRP | FUBP2; FBP2; KSRP | XM_005259668; NM_003685; XM_011528395 |
| DDX17_MOUSE | 10521 | DDX17 | DDX17 | RH70; P72 | NM_001098505; NM_030881; NM_001098504; ; NM_006386 |
| LC7L3_MOUSE | 51747 | LC7L3 | LUC7L3 | hLuc7A; CRA; CREAP-1; CROP; LUC7A; OA48018 | XM_005257448; NM_006107; XM_005257449; XM_006721943; XM_005257455; NM_016424; XM_005257454; XM_005257452; XM_005257450 |
| EWS_MOUSE | 2130 | EWS | EWSR1 | EWS; bK984G1.4 | XM_005261389; XM_011529999; XM_011530001; NM_013986; XM_011529995; XM_011529997; XM_011529996; ; NM_001163285; NM_001163286; XM_005261390; XM_011529998; NM_001163287; NM_011530000; XM_011530200; NM_005243 |
| UT14A_MOUSE | 10813 | UT14A | UTP14A | NYCO16; dJ537K23.3; SDCCAG16 | XM_011531264; NM_001166221; NM_006649; XM_005262363 |
| PWP2_MOUSE | 5822 | PWP2 | PWP2 | EHOC-17; UTP1; PWP2H | XM_011529667; NM_005049 |
| CPNE1_MOUSE | 8904 | CPNE1 | CPNE1 | COPN1; CPN1 | NM_152931; NM_152927; NM_152930; NM_152925; NR_037188; NM_003915; NM_152926; NM_001198863; NM_152928 |
| H2AW_MOUSE | 55506 | A0A024QZP6; H2AW | H2AFY2 | macroH2A2 | NM_018649 |
| SLTM_MOUSE | 79811 | SLTM | SLTM | Met | XM_011522027; XM_011522030; XM_011522023; XM_011522032; XR_931906; NM_017968; XM_011522024; XM_011522026; NM_001013843; XM_011522022; XM_011522028; XM_006720690; XM_011522029; NM_024755; XM_006720686; XM_011522025; XM_011522031 |
| GNL3_MOUSE | 27354 | GNL3 | GNL3 | C77032; E21G3; NNP47; NS | NM_206826; NM_014366; NM_206825 |
| PYGB_MOUSE | 5834 | PYGB | PYGB | GPBB | NM_002862 |
| NAT10_MOUSE | 55226 | NAT10 | NAT10 | NET43; ALP | XM_011520197; NM_001144030; NM_024662 |
| DDX52_MOUSE | 11056 | DDX52 | DDX52 | HUSSY19; ROK1 | XM_011546776; NM_007010; XR_951954; NM_001291476; XM_011524232; XM_011546775; XM_011524233; NM_152300 |
| PRAF3_MOUSE | 10550 | PRAF3 | ARL6IP5 | jmw; HSPC127; DERP11; JWA; PRAF3; addicsin; GTRAP3-18; hp22 | NM_006407 |
| SRSF4_MOUSE | 6429 | SRSF4 | SRSF4 | SFRS4; SRP75 | XM_011541951; NM_005626 |
| SP16H_MOUSE | 11198 | SP16H | SUPT16H | FACTP140; SPT16; CDC68; SPT16/CDC68 | NM_007192; ; XM_011536381 |
| TADBP_MOUSE | 23435 | TADBP | TARDBP | ALS10; TDP-43 | NM_007375; XR_946596; ; XR_946597 |
| SF3B1_MOUSE | 34251 | SF3B1 | SF3B1 | PRPF10; SAP155; MDS; SF3b155; Hsh155; PRP10 | XR_241302; NM_001005526; XR_241300; NM_012433; XM_011510867; ; XM_011510868 |
| NU155_MOUSE | 9631 | NU155 | NUP155 | ATFB15; N155 | XM_011514166; XM_011514164; NM_00178312; XM_011514165; NM_004298; NM_153485 |
| SMC3_MOUSE | 9126 | SMC3 | SMC3 | BAM; HCAP; SMC3L1; CSPG6; CDLS3; BMH | ; NM_005445 |
| ROA0_MOUSE | 10949 | ROA0 | HNRNPA0 | HNRPA0 | NM_006805 |
| SSRA_MOUSE | 6745 | SSRA | SSR1 | TRAPA | NM_003144; NM_001292008; NR_120448 |
| NH2L1_MOUSE | 4809 | NH2L1 | NHP2L1 | NHPX; SSFA1; FA-1; FA1; SNU13; SNRNP15-5; 15.5K; SPAG12; OTK27 | XM_011530201; NM_005008; NM_001003796 |
| S10AE_MOUSE | 57402 | S10AE | S100A14 | BCMP84; S100A15 | XM_005245362; NM_020672 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| NOP56_MOUSE | 10528 | NOP56 | NOP56 | SCA36; NOL5A | NR_027700; ; NM_006392 |
| RPN2_MOUSE | 6185 | RPN2 | RPN2 | SWP1; RPNII; RPN-II; RIBIIR | XM_006723850; NM_002951; XM_006723851; XM_005260491; XM_006723849; NM_001135771; XM_00672852 |
| RBP2_MOUSE | 5903 | RBP2 | RANBP2 | ANE1; TRP1; TRP2; ADANE; NUP358; HAE3 | XM_011511576; NM_006267; XM_005264002; XM_005264004; XM_011511575; XM_005264003; XM_005264007; XM_011511577; XM_005264005; XM_011511578; |
| DKC1_MOUSE | 1736 | DKC1 | DKC1 | DKC; XAP10; NAP57; NOLA4; CBF5; DKCX | ; NR_110021; NM_001288747; NR_110023; NM_001363; NR_110022; NM_001142463 |
| IDE_MOUSE | 3416 | IDE | IDE | INSULYSIN | XM_005269769; ; XM_005269766; XR_945727; NM_004969; NM_001165946 |
| SAS10_MOUSE | 57050 | SAS10 | UTP3 | SAS10; CRL1; CRLZ1 | NM_020368 |
| AL9A1_MOUSE | 223 | AL9A1 | ALDH9A1 | E3; ALDH7; ALDH9; TMABADH; ALDH4 | NM_000696; ; XM_011509294 |
| PSA7_MOUSE | 5688 | PSA7 | PSMA7 | RC6-1; HSPC; XAPC7; C6 | NM_002792; NM_152255 |
| G5E8Z3_MOUSE | — | | | | |
| Q8BGJ5_MOUSE | — | | | | |
| Q9QUK9_MOUSE | — | | | | |
| FBRL_MOUSE | 2091 | FBRL | FBL | FIB; FLRN; RNU31P1 | XM_011548799; XM_011526623; XM_011548798; XM_005258651; NM_001436 |
| CEBPZ_MOUSE | 10153 | CEBPZ | CEBPZ | HSP-CBF; CBF2; BOC1; CBF | NM_005760 |
| ACTN4_MOUSE | 81 | ACTN4 | ACTN4 | FSGS; FSGS1; ACTININ-4 | XM_006723406; NM_004924; XM_005259282; ; XM_005259281 |
| DDX21_MOUSE | 9188 | DDX21 | DDX21 | GURDB; GUA; RH-II/GuAl RH-II/GU | NM_004728; NM_001256910; XM_011540336 |
| Q8BVY0_MOUSE | 26156 | RL1D1 | RSL1D1 | PBK1; L12; UTP30; CS1G | NM_015659 |
| PLEC_MOUSE | — | — | — | — | — |
| E9Q7G0_MOUSE | 4926 | NUMA1 | NUMA1 | NMP-22; NUMA | XM_011545059; XM_011545066; NM_001286561; XM_011545054; XM_011545060; XM_011545064; XM_011545062; XM_011545065; NR_104476; XM_011545063; XM_011545055; XM_011545061; NM_006185; XM_011545057; XM_011545058; XM_006718564; XM_011545056 |
| ADT2_MOUSE | 292 | ADT2 | SLC25A5 | ANT2; T2; AAC2; T3; 2F1 | ; NM_001152 |
| LAP2B_MOUSE | 7112 | LAP2B; LAP2A | TMPO | LAP2; CMD1T; LEMD4; TP; PRO0868 | ; NM_001032284; XM_005269132; XM_005269130; NM_001032283; NM_003276 |
| NOP58_MOUSE | 51602 | NOP58 | NOP58 | NOP5/NOP58; NOP5; HSPC120 | NM_015934 |
| SRSF1_MOUSE | — | | | | |
| TGM1_MOUSE | — | | | | |
| ILF3_MOUSE | — | | | | |
| H2B1F_MOUSE | 8340; 8341 | — | — | — | — |
| E1QN31_MOUSE | 4839 | NOP2 | NOP2 | NSUN1; p120; NOP120; NOL1 | XM_005253691; NM_006170; NM_001033714; NM_001258310; NM_001258308; NM_001258309; XM_011520962 |
| PRDX4_MOUSE | 10549 | PRDX4 | PRDX4 | AOE37-2; PRX-4; HEL-S-97n; AOE372 | NM_006406; XM_005274438; |
| PSB5_MOUSE | 5693 | PSB5 | PSMB5 | MB1; X; LMPX | XM_005267871; NM_002797; NM_001144932; NM_001130725 |
| PDIA1_MOUSE | 5034 | A0A024R8S5; PDIA1 | P4HB | PHDB; P4Hbeta; PO4DB; PROHB; ERBA2L; GIT; DSI; PDI; PDIA1; PO4HB | ; NM_000918 |
| NUCL_MOUSE | 4691 | NUCL | NCL | C23 | NM_005381 |
| THIO_MOUSE | 7295 | H9ZYJ2; THIO | TXN | TRDX; TRX1; TRX | NM_003329; NM_001244938 |
| DDX3L_MOUSE | 8653 | DDX3Y | DDX3Y | DBY | ; XM_006724878; NM_001122665; NM_001302552; NM_004600; XM_011531471 |
| TPIS_MOUSE | 7167 | V9HWK1; Q53HE2; TPIS | TPI1 | TPID; HEL-D-49; TPI; TIM | NM_001159287; NM_000365; NM_001258026; |
| RL18_MOUSE | — | | | | |
| RL6_MOUSE | 6128 | A0A024RBK3; Q8TBK5; RL6 | RPL6 | TXREB11 TAXREB107; SHUJUN-2; L6 | XM_006719548; XM_006719546; NM_000970; NM_001024662; XM_006719547; XM_006719549; XM_011538647; XM_011538646 |
| SAHH_MOUSE | 191 | SAHH | AHCY | SAHH; adoHcyase | XM_005260317; ; XM_005260316; XM_011528660; XM_011528657; XM_011528658; XM_011528659; NM_000687; NM_001161766; XM_011528656 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| KPYM_MOUSE | 5315 | A0A024R5Z9; V9HWB8; B4DNK4; KPYM | PKM | CTHBP; HEL-S-30; PK3; OIP3; TCB; THBP1; PKM2 | NM_001206796; NM_001206797; XM_011521673; XM_005254445; XM_011521670; XM_011521672; NM_002654; NM_001206798; XM_005254443; XM_006720570; XM_011521671; NM_001206799; NM_182470; NM_182471 |
| CALM_MOUSE | — | | | | |
| RUXF_MOUSE | 6636 | RUXF | SNRPF | Sm-F; snRNP-F; SMF | NM_003095 |
| SMD2_MOUSE | 6633 | SMD2 | SNRPD2 | SMD2; SNRPD1; Sm-D2 | NM_004597; NM_177542; XM_005259180 |
| TOP1_MOUSE | 7150 | TOP1 | TOP1 | TOP1 | XM_011529033; ; XM_011529032; NM_003286 |
| HNRPD_MOUSE | — | | | | |
| VDAC1_MOUSE | — | | | | |
| ARGI1_MOUSE | 383 | ARGI1 | ARG1 | — | NM_000045; NM_001244438; ; XM_011535801 |
| RALY_MOUSE | — | | | | |
| CPNE_MOUSE | 8895 | CPNE3 | CPNE3 | CPN3; PRO1071 | XM_005251093; NM_003909 |
| DDX18_MOUSE | 8886 | DDX18 | DDX18 | MrDb | NM_006773 |
| DDX27_MOUSE | 55661 | DDX27 | DDX27 | HSPC259; Drs1p; dJ686N3.1; PP3241; DRS1; RHLP | NM_017895; XM_011528888 |
| ROAA_MOUSE | 3182 | ROAA | HNRNPAB | HNRPAB; ABBP1 | NM_004499; NM_031266 |
| NOG2_MOUSE | 29889 | NOG2 | GNL2 | Hug2; Ngp-1; Nog2; NGP1; HUMAUANT1G | XM_011541300; NM_013285 |
| RL17_MOUSE | — | | | | |
| GGCT_MOUSE | 79017 | GGCT | GGCT | C7orf24; GGC; CRF21; GCTG | NM_001199817; NM_024051; NM_001199815; NM_001199816; NR_037669 |
| NVL_MOUSE | 4931 | NVL | NVL | — | XM_011544199; NM_001243146; XM_011544202; XM_011544198; XM_011544201; NM_206840; XM_011544196; XM_011544197; XM_011544200; ; NM_001243147; NM_002533 |
| PSB3_MOUSE | 5691 | PSB3 | PSMB3 | HC10-II | NR_104195; NM_002795; NR_104194 |
| LOXE3_MOUSE | 59344 | LOXE3 | ALOXE3 | ARCI3; eLOX3; E-LOX3; eLOX-3 | NM_001165960; ; NM_021628 |
| D3YWT1_MOUSE | 3189 | HNRH3 | HNRNPH3 | HNRPH3; 2H9 | XM_005269753; XM_005269748; XM_005269752; XM_006717816; XM_005269751; XM_011539743; XM_006717817; XM_005269749; XM_005269754; NM_012207; NM_021644; XM_011539742 |
| HNRPF_MOUSE | — | | | | |
| FILA2_MOUSE | — | | | | |
| DSG1A_MOUSE | 1828 | DSG1 | DSG1 | CDHF4; DSG; PPKS1; EPKHIA; SPPK1; DG1; EPKHE | ; NM_001942 |
| SRSF7_MOUSE | — | | | | |
| MYH9_MOUSE | 4627 | MYH9 | MYH9 | BDPLT6; DFNA17; FTNS; NMMHCA; EPSTS; NMHC-II-A; MHA; NMMHC-11A | XM_011530197; ; NM_002473 |
| SON_MOUSE | — | | | | |
| RBM25_MOUSE | 58517 | RBM25 | RBM25 | Snu71; NET52; RED120; RNPC7; S164; fSAP94 | XR_943501; NM_021239; XM_011537044; XM_011537045 |
| PCNA_MOUSE | 5111 | PCNA | PCNA | ATDL2 | NM_002592; NM_182649 |
| TRA2B_MOUSE | 6434 | TRA2B | TRA2B | PPP1R156; SFRS10; TRAN2B; SRFS10; TRA2-BETA; Htra2-beta | XM_011513072; XM_006713724; NM_004593; ; NM_001243879; XM_005247703 |
| DDX5_MOUSE | — | | | | |
| EFTU_MOUSE | 7284 | EFTU | TUFM | COXPD4; EFTU; P43; EF-TuMT | ; NM_003321; XM_011545928 |
| UHRF1_MOUSE | — | | | | |
| SFPQ_MOUSE | 6421 | SFPQ | SFPQ | PPP1R140; PSF; POMP100 | XM_005271113; XM_005271115; XM_011541950; XM_005271112; NM_005066 |
| DDX24_MOUSE | 57062 | DDX24 | DDX24 | — | NM_020414 |
| HNRDL_MOUSE | 9987 | HNRDL | HNRNPDL | LGMD1G; HNRNP; HNRPDL; JKTBP2; JKTBP; 1aAUF1 | NM_031372; ; NM_005463; NM_001207000; NR_003249 |
| HNRPC_MOUSE | — | | | | |
| U2AF2_MOUSE | 11338 | U2AF2 | U2AF2 | U2AF65 | XM_006722994; NM_001012478; ; NM_007279; XM_011526410 |
| H13_MOUSE | 3007 | H13 | HIST1H1D | H1.3; H1s-2; H1F3; H1D | NM_005320 |
| HNRPK_MOUSE | — | | | | |
| RS27A_MOUSE | 6233 | RS27A | RPS27A | UBC; UBCEP80; S27A; UBCEP1; CEP80; CEL112; UBA80 | NM_002954; NM_001177413; ; NM_001135592 |
| TBB5_MOUSE | 203068 | TBB5 | TUBB | M40; TUBB1; CDCBM6; OK/SW-cl.56; TUBB5 | ; NM_001293213; NM_001293214; NM_001293212; NR_120608; NM_001293215; NM_001293216; NM_178014 |
| FUBP1_MOUSE | — | | | | |
| G3X9B1_MOUSE | 55127 | HETA1 | HEATR1 | UTP10; BAP28 | NM_018072; NM_011544219 |
| HNRPU_MOUSE | 3192 | HNRPU | HNRNPU | HNRPU; SAF-A; U21.1; hmRNP U | NM_004501; NM_031844 |
| HSP7C_MOUSE | 3312 | HSP7C | HSPA8 | LAP1; LAP-1; HSC70; HSPA10; HEL-33; HDC54; HSC71; HSP71; HSP73; HEL-S-72p; NIP71 | ; XM_011542798; NM_153201; NM_006597 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| SRRM2_MOUSE | — | | | | |
| HS71B_MOUSE | 3304; 3303 | — | — | — | — |
| ROA1_MOUSE | 3178; 144983 | — | — | — | — |
| MBB1A_MOUSE | 10514 | MBB1A | MYBBP1A | PAP2; P160 | NM_001105538; NM_014520; XM_011523616 |
| NPM3_MOUSE | 10360 | NPM3 | NPM3 | TMEM123; PORMIN | NM_006993 |
| MDHM_MOUSE | 4191 | A0A024R4K3; MDHM; B3KTM1; G3XAL0 | MDH2 | MGC:3559; M-MDH; MOR1; MDH | NR_104165; NM_001282403; NM_001282404; NM_005918 |
| H14_MOUSE | 3008 | H14 | HIST1H1E | H1F4; dJ221C16.5; H1.4; H1E; H1s04 | NM_005321 |
| ATPB_MOUSE | 506 | V9HW31; ATPB | ATP5B | ATPMB; HEL-S-271; ATPSB | NM_001686 |
| H2AY_MOUSE | 9555 | H2AY | H2AFY | H2AFJ; H2a.y; H2AF12M; H2A/y; mH2A1; macroH2A1.2; MACROH2A1.1 | NM_138609; XM_011543731; XR_948308; NM_004893; XM_005272132; XM_005272134; XM_011543735; XR_948310; XM_011543728; XR_948306; XR_948307; XM_005272135; XM_011543730; XM_011543733; XR_948309; NM_138610; XM_011543729; XM_011543732; NM_001040158; XM_011543734; XR_948311; XM_011514323; NM_001008844; NM_004415 |
| DESP_MOUSE | 1832 | DESP | DSP | DCWHKTA; DP; DP1; DPI1 | |
| ANXA2_MOUSE | 302 | A0A024R5Z7; ANXA2 | ANXA2 | LPC2; ANX2L4; LIP2; LPC2D; PAP-IV; ANX2; P36; HEL-S-270; CAL1H | NM_004039; XM_011521475; XM_011521476; NM_001002858; NM_001002857; NM_001136015; XM_011521477 |
| VIME_MOUSE | 7431 | VIME | VIM | CTRCT30; HEL113 | XM_011519649; XM_006717500; NM_003380 |
| ROA2_MOUSE | 3181 | ROA2 | HNRNPA2B1 | HNRPA2; RNPA2; SNRPB1; HNRNPA2; HNRPB1; IBMPFD2; HNRPA2B1; HNRPB1 | XR_242076; XR_242077; NM_002137; XR_428077; XR_428078; XM_006715714; NM_031243; XM_005249729 |
| ATPA_MOUSE | 498 | ATPA; V9HW26 | ATP5A1 | hATP1; ATP5A; HEL-S-123m; MOM2; COXPD22; OMR; ATPM; MC5DN4; ORM; ATP5AL2 | NM_001257334; ; NM_001001937; XM_011526018; NM_001001935; XM_001257335; NM_004046 |
| NPM_MOUSE | 4869 | NPM | NPM1 | B23; NPM | XM_005265920; ; NM_001037738; NM_002520; NM_199185; XM_011534564 |
| LMNA_MOUSE | 4000 | LMNA | LMNA | LMN1; LMNL1; EMD2; FPL; IDC; CDCD1; LMNC; CDDC; CMD1A; FPLD; PRO1; LFP; LGMD1B; CMT2B1; FPLD2; HGPS; LDP1 | XR_921781; NM_005572; NM_170707; NM_170708; ; NM_001282624; NM_001282626; NM_001282625; XM_011509534; NM_001257374; XM_0115909533 |
| MUP17_MOUSE | — | | | | |
| THOC4_MOUSE | 10189 | THOC4 | ALYREF | ALY/REF; THOC4; BEF; ALY; REF | NM_005782; XR_933919 |
| U5S1_MOUSE | 9343 | U5S1 | EFTUD2 | MFDGA; Snrp116; Snu114; SNRNP116; U5-116KD; MFDM | NM_001258353; NM_001142605; XR_934602; NM_001258354; NM_004247; |
| HDAC1_MOUSE | 3065 | Q6IT96; HDAC1 | HDAC1 | RPD3; GON-10; HD1; RPD3L1 | XM_011541309; NM_004964 |
| NEP1_MOUSE | 10436 | NEP1 | EMG1 | C2F; Grcc2f; NEP1 | ; XM_011520907; NM_006331 |
| | 7528 | YY1 | YY1 | NF-EI; INO80S; UCRBP; DELTA; YIN-YANG-1 | NM_003403 |
| | 23429 | RYBP | RYBP | AAP1; DEDAF; YEAF1 | XM_011548867; XM_011548866; NM_012234 |
| | 2146 | EZH2 | EZH2 | KMT6; KMT6A; WVS; EZH2b; ENX-1; EZHI; ENX1; WVS2 | XM_011515896; XM_011515897; XM_011515901; NM_001203249; XM_005249964; XM_011515884; XM_011515890; XM_011515894; XM_011515899; NM_004456; XM_011515886; XM_011515892; XM_011515900; NM_152998; XM_011515888; XM_011515889; XM_011515902; ; NM_001203247; NM_001203248; XM_005249962; XM_011515895; XM_011515883; XM_005249963; XM_011515885; XM_011515887; XM_011515898; XM_011515891; XM_011515893 |
| | 8726 | EED | EED | HEED; WAIT1 | XM_011545330; XM_005274373; XM_011545331; XM_011535329; XR_247215; ; NM_003797l NM_152991 |
| | 3720 | JARID2 | JARID2 | JMJ | XM_011514578; NM_004973; XM_011514580; NM_001267040; NM_011514581; XM_011514579; XM_011514584; XM_011514583; XM_005249089; XM_011514582 |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| | 23512 | SUZ12 | SUZ12 | CHET9; JJAZ1 | XM_005257954; XM_011524578; NM_015355; XM_006721794; XM_011524576; XM_011524577; |
| | 84733 | CBX2 | CBX2 | CDCA6; SRXY5; M33 | XM_011525382; XM_011525383; NM_032647; NM_005189; |
| | 8535 | CBX4 | CBX4 | NBP16; PC2 | XM_011525399; NM_003655 |
| | 23468 | CBX5 | CBX5 | HEL25; HP1; HP1A | NM_001127321; NM_001127322; NM_012117 |
| | 23466 | CBX6 | CBX6 | — | NM_001127321; NM_001127322; NM_012117 |
| | 23492 | CBX7 | CBX7 | — | XM_006724178; XM_006724174; XM_006724176; NM_175709; XM_006724175; XM_011530025; XM_005261413; XM_006724177 |
| | 57332 | CBX8 | CBX8 | RC1; PC3 | NM_020649 |
| | 6015 | RING1 | RING1 | RING1A; RNF1; MDA_GLEAN10006855; AT5G10380; ATRING1; F12B17.270; F12B17_270; PAL_GLEAN10007107 | XM_008581826; XM_002914334; XM_011282270; XM_004711741; XM_010994566; NM_001114959; XM_008263251; XM_008160095; XM_006144236; XM_003789083; XM_003768961; XM_003421045; XM_003340366; XM_003882095; XM_004673367; XM_004043802; NM_001081482; XM_009450849; XM_007939317; XM_004817207; XM_004817208; XM_004770597; XM_004770598; XM_006105473; XM_007972961; XM_010848711; XM_005891414; XM_007460823; XM_003808593; NM_001048128; XM_006738062; XM_004479796; XM_001493382; XM_005603802; NM_001190235; XM_002746424; XM_007093228; XM_003897435; XM_008693443; XM_002809147; NM_002931; XM_010357860; XM_004617672; XM_005867940; XM_005867939; XM_005867938; XM_008060264; XM_010949097; XM_006769154; XM_006769153; XM_006769152; XM_004389800; XM_004389799; XM_006202134; XM_006860350; NM_121076; XM_009398851; XM_008501211; XM_008507909; XM_008507908; XM_007186905; XM_006180513; XM_005553330; XM_003923131; XM_011373441; XM_006050304; XM_004267748; XM_003271891; XM_007527425; XM_006907387; NM_001105051; XM_004018744; XM_005979771; XM_004407693; XM_004326287; XM_004424282; XM_005696449; XM_004590264 |
| | 6045 | RNF2 | RNF2 | UY3_04118; RING1B; Anapl_15990; PAL_GLEAN10017658; RING2; BAP-1; DING; HIPI3; BAP1; TREES_T100002675; AS27_08110 | XM_007056701; NM_001133961; XM_009240017; XM_010010379; XM_005030750; XM_005030748; XM_005030749; XM_005622432; XM_537164; XM_003785791; XM_005232734; XM_004313674; XM_011588767; XM_011588768; XM_011588769; XM_008066104; XM_007166956; XM_007166955; XM_008249917; XM_002722443; XM_010184804; XM_010131884; XM_009940829; XM_009582679; XM_009967773; XM_008588367; XM_006872706; XM_004808116; XM_004808117; XM_004767958; XM_004767956; XM_004767957; XM_009636901; XM_003264459; XM_004088945; XM_004613710; XM_005856664; XM_009902653; XM_006907738; XM_005667822; XM_005667824; XM_005667826; XM_005667821; XM_003130379; XM_005667823; XM_005667825; XM_006135799; XM_010853086; XM_009979151; |

TABLE 5-continued iDRiP proteomics results-Spectral counts of proteins pulled down by iDRiP and identified by mass spectrometry.

| UniProt Entry Name | Human Gene ID | Human Protein | Human Gene symbol | Gene Synonyms | Accession numbers |
|---|---|---|---|---|---|
| | | | | | XM_009191712; XM_002893395; XM_514507; XM_003308638; XM_009439610; XM_009439605; XM_007937694; XM_005531309; XM_006267565; XM_008945965; XM_009919202; XM_011227014; XM_002920849; XM_006089858; XM_005049912; XM_005049913; XM_001516642; XM_007668980; XM_006037004; XM_005146513; XM_005893101; XM_005893100; XM_004372913; XM_010406351; XM_010580692; XM_011509852; NM_007212; XM_005245413; XM_011509851; XM_010155175; XM_009074584; XM_007434510; XM_005963396; XM_005963397; XM_010213372; XM_004468429; XM_004468430; XM_004468431; XM_005487039; XM_009463539; XM_011364545; XM_004688568; XM_004688569; XM_009997849; XM_005506534; XM_004943287; XM_422295; XM_004943285; XM_004943286; XM_003208502; XM_010715546; XM_010715547; XM_009088429; XM_009481357; XM_001490007; XM_008534655; XM_006772947; XM_006772948; XM_006185546; XM_003925286; XM_004424928; XM_005690974; XM_008968563; XM_003815602; XM_008145953; XM_006143866; XM_005443319; XM_009865895; XM_010204370; XM_006060513; XM_006060510; XM_006060512; XM_006060511; XM_002190830; XM_009275831; XM_011291005; XM_004001340; XM_007989177; XM_007989176; XM_007989179; XM_010368958; XM_010368957; XM_004275227; XM_007523806; XM_005540227; XM_005540230; XM_005540228; XM_005540229; XM_005540231; NM_001101203; XM_004028047; XM_004028046; XM_004578826; XM_010084954; XM_009556366; XM_006198790; XM_009506697; XM_010313112; XM_009324640; XM_003767510; XM_010591103; XM_002760258; XM_008984832; XM_008984833; XM_007451138; XM_007451139; XM_010992086; XM_010992085; XM_007096230; XM_004013869; XM_009884364; XM_009672662; XM_008635395; XM_008635394; XM_005290711; XM_010116863; XM_009947654; XM_010165133; XM_004405742; XM_006732908; XM_006732907; XM_009808327; XM_010296946; XM_008494822; XM_005997271; XM_001366864; XM_004706673; XM_004706674; XM_010973308; XM_010973311; XM_008930821; XM_005423737; XM_008697076; XM_008697084; XM_008697091; XM_009695548 |

TABLE 6 iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
| --- | --- | --- | --- | --- | --- |
| MINT_MOUSE | 23013 | MINT | SPEN | HIAA0929; MINT; SHARP; RBM15C | NM_015001 |
| FIBB_MOUSE | 2244 | FIBB | FGB | HEL-S-78p | NM_005141; ; NM_001184741 |
| CO1A2_MOUSE | 1278 | CO1A2 | COL1A2 | OI4 | NM_000089 |
| IKIP_MOUSE | 121457 | IKIP | IKBIP | IKIP | NM_153687; NM_201613; NM_201612 |
| RGAP1_MOUSE | 29127 | RGAP1 | RACGAP1 | CYK4; MgcRacGAP; ID-GAP; HsCYK-4 | NM_001126104; XM_005268814; XM_011538235; XM_011538242; XM_005268813; XM_011538240; NM_013277; XM_006719359; XM_011538241; XM_011538243; NM_001126103; XM_005268815; XM_011538236; XM_005268812; XM_011538237; XM_011538238; XM_011538239 |
| RFC1_MOUSE | 5981 | RFC1 | RFC1 | RFC140; PO-GA; RECC1; A1; MHCBFB; RFC | NM_001204747; XM_011513730; NM_002913; XM_011513731 |
| COCA1_MOUSE | 1303 | COCA1 | COL12A1 | BA209D8.1; COL12A1L; DJ234P15.1 | XM_011535436; NM_004370; XM_011535435; NM_080645; XM_011535434 |
| NEP_MOUSE | 4311 | NEP | MME | CALLA; NEP; CD10; SFE | XM_006713647; NM_007289; XM_011512856; NM_007287; XM_006713646; NM_007288; XM_011512855; XM_011512858; XM_011512857; NM_000902 |
| NUP88_MOUSE | 4927 | NUP88 | NUP88 | — | XM_011523893; XM_005256659; NM_002532 |
| UHRF1_MOUSE | 29128 | UHRF1 | UHRF1 | RNF106; ICBP90; Np95; hNP95; hUHRF1; huNp95 | NM_001290052; XM_011527942; ; NM_001290051; NM_001048201; NM_001290050; NM_013282 |
| WAPL_MOUSE | 23063 | WAPL | WAPAL | KIAA0261; WAPL; FOE | XM_011539547; XM_011539548; XM_006717729; NM_015045 |
| ZFR_MOUSE | 51663 | ZFR | ZFR | SPG71; ZFR1 | XR_427659; NM_016107 |
| BAK_MOUSE | 578 | BAK | BAK1 | BAK; BAK-LIKE; CDN1; BCL2L7 | XM_011514779; XM_011514780; NM_001188 |
| NU133_MOUSE | 55746 | NU133 | NUP133 | hNUP133 | NM_018230 |
| Q8BVY0_MOUSE | — | — | — | — | — |
| CO1A1_MOUSE | 1277 | CO1A1 | COL1A1 | OI4 | NM_000088; ; XM_005257059; XM_005257058; XM_011524341 |
| NHP2_MOUSE | 55651 | NHP2 | NHP2 | DKCB2; NHP2P; NOLA2 | NM_001034833; NM_017838 |
| HELLS_MOUSE | 3070 | HELLS | HELLS | PASG; LSH; Nbla10143; SMARCA6 | NM_001289067; NM_001289071; NM_001289073; NM_001289074; NM_001289075; NM_001289068; NM_001289070; NM_001289069; NM_001289072; NM_018063 |
| HNRPU_MOUSE | 3192 | HNRPU | HNRNPU | HNRPU; SAF-A; U21.1; hnRNP U | NM_004501; NM_031844 |
| LRWD1_MOUSE | 222229 | LRWD1 | LRWD1 | CENP-33; ORCA | XM_005250204; NM_152892 |
| RCC1_MOUSE | 1104 | RCC1 | RCC1 | CHC1; SNHG3-RCC1; RCC1-I | NM_001048199; NM_001269; NM_001048195; NR_030725; NR_030726; NM_001048194 |
| MBB1A_MOUSE | 10514 | MBB1A | MYBBP1A | PAP; P160 | NM_001105538; NM_014520; XM_011523616 |
| MYEF2_MOUSE | 50804 | MYEF2 | MYEF2 | myEF-2; MSTP156; HsT18564; MEF-2; MST156 | XM_005254424; XM_006720553; XM_005254422; XM_005254425; NM_001301210; NM_016132; XM_005254427; XM_011521657; NR_125408 |
| LRP1_MOUSE | 4035 | LRP1 | LRP1 | CD91; IGFBP3R; A2MR; LRP1A; APOER; APR; LRP; TGFBR5 | NM_002332; |
| NXF1_MOUSE | 10482 | NXF1 | NXF1 | MEX67; TAP | NM_001081491; NM_006362 |
| RL7L_MOUSE | 285855 | RL7L | RPL7L1 | dJ475N16.4 | XM_005249026; NM_198486 |
| HXA5_MOUSE | 3202 | HXA5 | HOXA5 | HOX1.3; HOX1; HOX1C | NM_019102 |
| SMHD1_MOUSE | 23347 | SMHD1 | SMCHD1 | — | XM_011525645; NM_015295; XM_011525646; ; XM_011525643; XM_011525644; XR_935054; XM_011525642; XM_011525647; XR_935055; XR_430039 |
| NFIC_MOUSE | 4782 | NFIC | NFIC | NFI; NF-I; CTF; CTF5 | NM_001245005; NM_005597; XM_005259563; XM_006722759; NM_205843; NM_001245002; NM_001245004; XM_005259564 |
| P53_MOUSE | 7157 | H2EHT1 | TP53 | TRP53; BCC7; P53; LFS1 | NM_001126112; NM_001276697; NM_001126115; ; NM_001126114; NM_001276698; NM_001276761; NM_001126118; NM_001126113; NM_001126117; |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| CELF2_MOUSE | 10659 | CELF2 | CELF2 | CUGBP2; NAPOR; BRUNOL3; ETR-3; ETR3 | NM_001276695; NM_001276699; NM_001276760; NM_000546; NM_001126116; NM_001276696 NM_001083591; NM_006561; XM_006717373; XM_011519294; XM_011519295; XM_011519297; XM_011519298; XM_005252354; XM_006717371; NM_001025076; XM_006717374; XM_006717375; XM_011519299; NM_001025077; XM_005252357; XM_005252358; XM_006717369; XM_011519296; XM_006717370 |
| XPO5_MOUSE | 57510 | XPO5 | XPO5 | exp5 | NM_020750 |
| GAPR1_MOUSE | 152007 | GAPR1 | GLIPR2 | C9orf19; GAPR-1; GAPR1 | NM_001287012; NM_001287014; NR_104638; NM_001287011; NR_104640; NR_104641; NR_104637; NR_104639; XM_011517714; NM_001287013; NM_022343; NM_001287010 |
| MSH2_MOUSE | 4436 | MSH2 | MSH2 | HNPCC; HNPCC1; FCC1; COCA1; LCFS2 | NM_000251; XM_005264332; NM_001258281; XR_939685; ; XM_011532867 |
| PNO1_MOUSE | 56902 | PNO1 | PNO1 | KHRBP1; RRP20 | NM_020143 |
| TSP1_MOUSE | 7057 | TSP1 | THBS1 | TSP; TSP1; THBS; THBS-1; TSP-1 | XM_011521970; XR_931897; XM_011521971; NM_003246 |
| LBR_MOUSE | 3930 | LBR | LBR | PHA; DHCR14B; TDRD18; LMN2R | XM_011544187; NM_002296; XM_011544185; XM_011544186; NM_194442; XM_005273125 |
| PGS1_MOUSE | 633 | PGS1 | BGN | PG-S1; DSPG1; SLRR1A; PGI | NM_001711 |
| PCOC1_MOUSE | 5118 | PCOC1 | PCOLCE | PCPE-1; PCPE1; PCPE | NM_002593 |
| RING1_MOUSE | 6015 | RING1 | RING1 | RING1A; RNF1 | NM_002931 |
| ROA0_MOUSE | 10949 | ROA0 | HNRNPA0 | HNRPA0 | NM_006805 |
| RB15B_MOUSE | 29890 | RB15B | RBM15B | HUMAGCGB; OTT3 | NM_013286 |
| FBLN4_MOUSE | 30008 | FBLN4 | EFEMP2 | UPH1; FBLN4; ARCL1B; MBP1 | NM_016938; ; NR_037718 |
| HNRL2_MOUSE | 221092 | HNRL2 | HNRNPUL2 | HNRPUL2; SAF-A2 | NM_001079559 |
| NIP7_MOUSE | 51388 | NIP7 | NIP7 | HSPC031; CGI-37; KD93 | NM_001199434; NM_016101 |
| J3QQ16_MOUSE | — | — | — | — | — |
| RRP1B_MOUSE | 23076 | RRP1B | RRP1B | PPP1R136; KIAA0179; NNP1L; Nnp1; RRP1 | NM_015056 |
| DCLK1_MOUSE | 9201 | DCLK1 | DCLK1 | CL1; CLICK1; DCDC3A; DCAMKL1; DCLK | XM_006719893; XM_005266592; NM_001195430; NM_001195416; NM_001195415; NM_004734 |
| ACADS_MOUSE | 35 | ACADS | ACADS | ACAD3; SCAD | NM_000017; NM_001302554 |
| MD1L1_MOUSE | 8379 | MD1L1 | MAD1L1 | TXBP181; TP53I9; MAD1; PIG9 | XM_011515570; XM_005249877; XM_011515567; XM_011515571; NM_001013837; NM_001304525; XM_011515568; ; NM_001013836; NM_001304523; NM_003550; XM_011515569; NM_001304524 |
| XRN2_MOUSE | 22803 | XRN2 | XRN2 | — | XM_011529184; NM_012255 |
| CO6A2_MOUSE | 1292 | CO6A2 | COL6A2 | PP3610 | XR_937439; NM_058175; NM_058174; XR_937438; NM_001849; ; XM_011529452; XM_011529451 |
| TADBP_MOUSE | 23435 | TADBP | TARDBP | ALS10; TDP-43 | NM_007375; XR_946596; ; XR_946597 |
| MYOF_MOUSE | 26509 | MYOF | MYOF | FER1L3 | XM_006717760; NM_133337; XM_005269693; XM_011539632; XM_011539633; NM_013451; XM_005269694 |
| NID2_MOUSE | 22795 | NID2 | NID2 | NID-2 | XM_005267405; XM_005267406; XM_005267407; NM_007361 |
| MGN2_MOUSE | 55110 | MGN2 | MAGOHB | mago; MGN2; magoh | NM_018048; XM_005253402; NM_001300739; XM_011520718 |
| SNTB2_MOUSE | 6645 | SNTB2 | SNTB2 | SNT2B2; SNT3; SNTL; D16S2531E; EST25263 | NM_006750; NM_130845 |
| H3BJG4_MOUSE | — | — | — | — | — |
| KDM2A_MOUSE | 22992 | KDM2A | KDM2A | CXXC8; FBL11; FBL7; JHDM1A; FBXL11; LILINA | NR_027473; NM_012308; XM_011544860; XM_006718479; XM_006718480; XM_011544861; XM_011544862; NM_001256405 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| DJC10_MOUSE | 54431 | DJC10 | DNAJC10 | ERdj5; MTHr; JPDI; PDIA19 | NM_001271581; NM_018981; NR_073367; NR_073366; NR_073365 |
| MAOM_MOUSE | 4200 | MAOM | ME2 | ODS1 | NM_002396; XR_935223; ; NM_001168335 |
| SUN2_MOUSE | 25777 | SUN2 | SUN2 | UNC84B | NM_015374; XM_011530105; XM_011530104; NM_001199580; NM_001199579 |
| Q921K2_MOUSE | — | — | — | — | — |
| GPX1_MOUSE | 2876 | GPX1 | GPX1 | GSHPX1; GPXD | NM_000581; NM_201397; |
| DYR_MOUSE | 1719 | DYR | DHFR | DHFRP1; DYR | NM_000791; NM_001290357; ; NM_001290354; NR_110936 |
| G5E924_MOUSE | — | — | — | — | — |
| LEG8_MOUSE | 3964 | LEG8 | LGALS8 | Po66-CBP; PCTA-1; Gal-8; PCTA1 | NM_201544; XM_011544188; NM_201543; NM_006499; NM_201545 |
| LYOX_MOUSE | 4015 | LYOX | LOX | — | NM_001178102; ; NM_002317 |
| EIF2A_MOUSE | 83939 | EIF2A | EIF2A | EIF-2A; MST089; CDA02; MSTP004; MSTP089 | XM_011513224; XM_011513223; NM_032025 |
| PTBP2_MOUSE | 58155 | PTBP2 | PTBP2 | nPTB; PTBLP; brPTB | XR_946723; XR_946722; NM_001300987; NR_125357; XM_011541876; XM_011541875; XR_946720; NM_001300986; NM_001300988; NM_021190; NM_001300990; NR_125356; XM_011541874; XR_946721; NM_001300985; NM_001300989 |
| STT3B_MOUSE | 201595 | STT3B | STT3B | SIMP; CDG1X; STT3-B | XM_011533465; NM_178862 |
| HNRPM_MOUSE | 4670 | HNRPM | HNRNPM | HTGR1; NAGR1; hnRNPM; HNRPM; CEAR; HNRNPM4; HNRPM4 | NM_005968; XM_005272478; XM_005272480; XM_005272483; XM_005272479; XM_005272481; NM_001297418; NM_031203; |
| FARP1_MOUSE | 10160 | FARP1 | FARP1 | CDEP; FARP1-IT1; PPP1R75; PLEKHC2 | NM_001001715; NM_001286839; XM_011521046; NM_005766 |
| ERH_MOUSE | 2079 | A0A024R6D4 | ERH | DROER | NM_004450 |
| SMD2_MOUSE | 6633 | SMD2 | SNRPD2 | SMD2; SNRPD1; Sm-D2 | NM_004597; NM_177542; XM_005259180 |
| PTPRS_MOUSE | 5802 | PTPRS | PTPRS | PTPSIGMA | XM_006722809; XM_006722810; XM_006722820; NM_002850; XM_005259606; XM_005259607; XM_006722808; XM_006722815; NM_130854; XM_011528157; NM_130855; XM_005259610; XM_006722812; XM_006722819; NM_130853; XM_005259600; XM_006722817; XM_006722818; XM_011528158; ; XM_006722814; XM_005259601; XM_005259609; XM_006722811 |
| MYO1D_MOUSE | 4642 | MYO1D | MYO1D | myr4; PPP1R108 | XR_934470; NM_001303280; NM_001303279; NM_015194 |
| NB5R3_MOUSE | 1727 | NB5R3 | CYB5R3 | B5R; DIA1 | NM_007326; NM_000398; NM_001129819; NM_001171660; NM_001171661; |
| RM46_MOUSE | 26589 | RM46 | MRPL46 | P2ECSL; LIECG2; C15orf4 | NM_022163 |
| NEDD4_MOUSE | 4734 | NEDD4 | NEDD4 | RPF1; NEDD4-1 | NM_001284339; XM_011521626; XM_011521624; NM_006154; NR_104302; XM_011521627; NM_001284338; NM_198400; XM_011521625; NM_001284340 |
| FBRL_MOUSE | 2091 | FBRL | FBL | FIB; FLRN; RNU3IP1 | XM_011548799; XM_011526623; XM_011548798; XM_005258651; NM_001436 |
| LXN_MOUSE | 56925 | LXN | LXN | TCI; ECI | NM_020169 |
| RAB9A_MOUSE | 9367 | RAB9A | RAB9A | RAB9 | NM_004251; NM_001195328 |
| HMGCL_MOUSE | 3155 | HMGCL | HMGCL | HL | NM_000191; NM_001166059 |
| Q8VHM5_MOUSE | — | — | — | — | — |
| ITPR3_MOUSE | 3710 | ITPR3 | ITPR3 | IP3R; IP3R3 | XM_011514577; ; NM_002224; XM_011514576 |
| DHB12_MOUSE | 51144 | DHB12 | HSD17B12 | SDR12C1; KAR | XM_011520156; NM_016142 |
| PHIP_MOUSE | 55023 | PHIP | PHIP | DCAF14; WDR11; BRWD2; ndrp | XM_011535919; NM_017934; XM_005248729; XM_011535917; XM_011535918; XR_942499 |
| PTBP3_MOUSE | 9991 | PTBP3 | PTBP3 | ROD1 | XM_006717346; XM_005252324; XM_011519267; NM_001244897; NM_005156; XM_006717343; XM_011519266; NM_001163788; NM_001244898; NM_001163790; XM_011519265; NM_001244896 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| NUP43_MOUSE | 348995 | NUP43 | NUP43 | p42; bA350J20.1 | XM_011535799; XM_005266961; XM_011535798; NM_198887; XM_005266960; XM_005266962; XR_942420; NM_024647; NR_104456 |
| ROAA_MOUSE | 3182 | ROAA | HNRNPAB | HNRPAB; ABBP1 | NM_004499; NM_031266 |
| KAD3_MOUSE | 50808 | Q7Z4Y4; KAD3 | AK3 | AK3L1; AKL3L1; AK6; AKL3L; FIX | NM_001199855; NM_001199853; NM_016282; NM_001199854; NM_001199852; NM_001199856 |
| RBM14_MOUSE | 10432 | RBM14 | RBM14 | COAA; TMEM137; SIP; SYTIP1; PSP2 | NM_001198837; ; NM_001198836; NM_006328; NM_032886 |
| MYH1_MOUSE | 4619 | MYH1 | MYH1 | HEL71; MyHC-2x; MYHSA1; MYHa; MyHC-2X/D | NM_005963 |
| RBBP6_MOUSE | 5930 | RBBP6 | RBBP6 | P2P-R; MY038; RBQ-1; SNAMA; PACT | XM_005255461; NM_018703; XM_005255462; NM_006910; NM_032626 |
| RFC2_MOUSE | 5982 | RFC2 | RFC2 | RFC40 | XR_927506; NM_001278792; NM_001278793; NM_002914; NM_181471; ; NM_001278791; XM_006716080 |
| Q0VBL3_MOUSE | — | — | — | — | — |
| E9Q5G3_MOUSE | — | — | — | — | — |
| RALY_MOUSE | 22913 | RALY | RALY | P542; HNRPCL2 | XM_005260336; XM_011528694; NM_007367; NM_016732; XM_011528695; XM_005260334 |
| STA5A_MOUSE | 6776 | STA5A; Q59GY7; A8K6I5; K7EK35 | STAT5A | MGF; STAT5 | NM_001288720; NM_001288719; XM_005257624; NM_001288718; NM_003152 |
| PHF5A_MOUSE | 84844 | PHF5A | PHF5A | SAP14b; INI; Rds3; bK223H9.2; SF3B7; SF3b14b | NM_032758 |
| ADRO_MOUSE | 2232 | ADRO | FDXR | ADXR | XM_006721772; XM_011524532; NM_001258015; XM_011524528; XM_011524531; NM_001258016; XM_011524527; XM_011524530; XM_011524533; NM_004110; NR_047576; NM_001258013; NM_001258014; XM_011524529; NM_001258012; NM_024417 |
| RT11_MOUSE | 64963 | RT11 | MRPS11 | HCC-2 | NM_176805; XM_011521946; XM_005254978; XM_011521947; NM_022839; XM_005254977 |
| BAZ1B_MOUSE | 9031 | BAZ1B | BAZ1B | WBSCR9; WBSCR10; WSTF | NM_032408; NM_023005; XM_005250683; |
| RAVR1_MOUSE | 125950 | RAVR1 | RAVER1 | — | NM_133452; XM_011527671; XM_011527672 |
| E41L2_MOUSE | 2037 | E41L2 | EPB41L2 | 4.1G; 4.1-G | XM_006715362; XM_011535523; NM_001431; XM_011535527; XR_942326; XR_942328; NM_001135554; XM_006715356; XM_011535531; XM_011535535; NM_001252660; XM_005266840; XM_011535522; XM_11535526; XM_011535530; XM_011535534; XM_011535521; XM_011535525; XM_011535528; XM_011535529; XM_011535532; NM_001199389; NM_001135555; NM_001199388; XM_005266841; XM_011535524; XM_011535533; XM_011535536 |
| DCA13_MOUSE | 25879 | DCA13 | DCAF13 | HSPC064; WDSOF1; GM83 | NM_015420 |
| Q3TIX6_MOUSE | — | — | — | — | — |
| CLK3_MOUSE | 1198 | CLK3 | CLK3 | PHCLK3/152; PHCLK3 | XM_005254153; XM_011521210; XM_011521206; XM_011521209; XM_011521208; NM_003992; XM_005254151; XM_006720384; XM_011521205; XR_931746; NM_001292; XM_011521207; NM_001130028 |
| LAP2_MOUSE | 55914 | LAP2 | ERBB2IP | HEL-S-78; LAP2; ERBIN | XM_011543514; NM_001253698; NM_018695; ; XM_005248554; XM_005248555; NM_001006600; NM_001253699; XM_006714660; NM_001253697; NM_001253701 |
| WDR33_MOUSE | 55339 | WDR33 | WDR33 | WDC146; NET14 | XM_005263697; NM_001006623; NM_018383; XM_011511436; NM_001006622 |
| SMC3_MOUSE | 9126 | SMC3 | SMC3 | BAM; HCAP; SMC3L1; CSPG6; CDLS3; BMH | NM_005445 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| GULP1_MOUSE | 51454 | GULP1 | GULP1 | CED6; CED-6; GULP | XM_006712583; XM_006712585; XM_006712589; XM_011511327; XM_011511332; NM_001252668; NM_001252669; XM_011511328; XM_011511329; XM_006712590; XM_011511331; XM_011511334; NM_016315; NR_045563; XM_006712581; XM_011511333; XM_011511335; XM_006712580; XM_006712582; XM_006712584; NR_045562; XM_011511330 |
| LS14A_MOUSE | 26065 | LS14A | LSM14A | C19orf13; RAP55A; RAP55; FAM61A | XM_011547018; NM_015578; XM_011526708; XM_005276949; XM_005258719; XM_005258720; XM_005258721; XM_005276948; NM_001114093; XM_005276950 |
| MCU_MOUSE | 90550 | MCU | MCU | C10orf42; CCDC109A | NR_073062; NM_138357; NM_001270679; NM_001270680 |
| KANK2_MOUSE | 25959 | KANK2 | KANK2 | PPKWH; SIP; ANKRD25; MXRA3 | NM_001136191; NM_015493 |
| ALDH2_MOUSE | 217 | ALDH2 | ALDH2 | ALDHI; ALDH-E2; ALDM | NM_001204889; NM_000690; |
| CBR2_MOUSE | — | — | — | — | — |
| MAAI_MOUSE | 2954 | MAAI | GSTZ1 | GSTZ1-1; MAAI; MAI | XM_011536671; NM_001513; XM_005267559; NM_145871; NM_145870; XM_011536670 |
| TRA2A_MOUSE | 29896 | TRA2A | TRA2A | AWMS1; HSU53209 | NM_013293; NM_001282757; NM_001282759; XM_005249725; XM_011515331; XM_006715713; NM_001282758 |
| TENC1_MOUSE | 23371 | TENC1 | TNS2 | C1TEN; TENC1; C1-TEN | XM_006719303; NM_015319; XM_006719304; XM_011538079; NM_170754; XM_006719302; NM_198316 |
| ACSF2_MOUSE | 80221 | ACSF2 | ACSF2 | AVYV493; ACSMW | XR_934566; XR_934563; XR_934564; NM_025149; XR_429924; NM_001288970; XM_006722110; XM_011525294; XR_934567; NM_001288968; NM_001288969; NM_001288971; NM_001288972; XR_934565; NR_110232 |
| PRP19_MOUSE | 27339 | PRP19 | PRPF19 | hPSO4; PSO4; UBOX4; PRP19; SNEV; NMP200 | NM_014502 |
| ENV1_MOUSE | — | — | — | — | — |
| PR38A_MOUSE | 84950 | PR38A | PRPF38A | Prp38 | NM_032864; XM_011542315; NM_032284 |
| RRP5_MOUSE | 22984 | RRP5 | PDCD11 | NFBP; RRP5; ALG-4; ALG4 | NM_014976; XM_011539538; XM_011539540; XM_005269647; XM_011539539 |
| SQRD_MOUSE | 58472 | SQRD | SQRDL | CGI-44; PRO1975; SQOR | NM_001271213; NM_021199 |
| THOC3_MOUSE | 84321 | THOC3 | THOC3 | hTREX45; THO3 | XM_011534668; XM_011534666; NM_032361; XM_011534667 |
| THIKA_MOUSE | 30 | THIK | ACAA1 | ACAA; THIO; PTHIO | NM_001130410; XM_006713122; NR_024024; NM_001607; XM_011533650; ; XM_006713123 |
| P5CR2_MOUSE | 29920 | P5CR2 | PYCR2 | P5CR2 | NM_001271681; NM_013328 |
| PDK3_MOUSE | 5165 | PDK3 | PDK3 | CMTX6; GS1-358P8.4 | ; NM_001142386; NM_005391 |
| Q8BGJ5_MOUSE | — | — | — | — | — |
| S12A2_MOUSE | 6558 | S12A2 | SLC12A2 | BSC2; NKCC1; BSC; PPP1R141 | NM_001256461; NM_001046; XM_011543588; NR_046207 |
| RRMS2_MOUSE | 5939 | RBMS2 | RBMS2 | SCR3 | XM_005269059; XM_002898; XM_006719543; XM_011538639; XM_005269060; XM_011538640; XM_006719541; XM_006719542; XM_006719544; XM_011538637; XM_005269061; XM_011538642; XM_005269066; XM_011538638; XM_011538641 |
| PLRG1_MOUSE | 5356 | PLRG1 | PLRG1 | PRPF46; PRL1; PRP46; Cwc1; TANGO4 | NM_002669; NM_001201564 |
| RINI_MOUSE | 6050 | RINI | RNH1 | RAI; RNH | XM_011520263; XM_011546605; XM_011520257; XM_011546606; NM_203383; XM_011546603; NM_203389; XM_011520261; XM_011546604; XM_011546609; XM_011546607; XM_011546608; NM_203386; NM_203388; XM_011520259; XM_011520262; XM_011546602; XM_011520260; XM_011546610; XM_011520256; NM_002939; NM_203385; NM_203387; XM_011520255; XM_011520258; NM_203384 |
| CDK4_MOUSE | 1019 | CDK4 | CDK4 | PSK-J3; CMM3 | NM_052984; NM_000075 |
| ACADM_MOUSE | 34 | ACADM | ACADM | ACAD1; MCAD; MCADH | NM_001127328; NM_001286042; NM_001286043; ; NM_000016; NM_001286044; NR_022013 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| HNRPK_MOUSE | 3190 | HNRPK | HNRNPK | TUNP; CSBP; HNRPK | XM_011518616; NM_002140; NM_031262; XM_005251965; ; XM_005251960; XM_005251961; NM_031263; XM_005251964; XM_005251966; XM_005251963 |
| GPX41_MOUSE | 2879 | Q6PI42 | GPX4 | GPx-4; MCSP; snPHGPx; PHGPx; GSHPx-4; snGPx | NM_002085; NM_001039847; NM_001039848 |
| RBM3_MOUSE | 5935 | RBM3 | RBM3 | IS1-RNPL; RNPL | NM_001017430; XM_011543939; NM_001017431; NM_006743; XM_011543938 |
| SNR40_MOUSE | 9410 | SNR40 | SNRNP40 | PRPF8BP; 40K; SPF38; WDR57; HPRP8BP; PRP8BP | NM_004814 |
| KHDR1_MOUSE | 10657 | KHDR1 | KHDRBS1 | Sam68; p62; p68 | NR_073498; NR_073499; NM_001271878; NM_006559 |
| ILK_MOUSE | 3611 | ILK | ILK | HEL-S-28; p59ILK; ILK-1; ILK-2; P59 | XM_005252904; NM_001278441; ; XM_011520065; XM_005252905; NM_001014795; NM_001278442; NM_001014794; NM_004517 |
| GAR1_MOUSE | 54433 | GAR1 | GAR1 | NOLA1 | NM_032993; NM_018983 |
| CSTF1_MOUSE | 1477 | CSTF1 | CSTF1 | CstFp50; CstF-50 | NM_001033522; NM_001033521; NM_001324; XM_011528600 |
| UGGG1_MOUSE | 56886 | UGGG1 | UGGT1 | UGCGL1; HUGT1; UGT1 | XM_006712635; XR_922969; NM_020120; NM_001025777; NR_027671; XM_006712634; XM_006712636 |
| CPSF4_MOUSE | 10898 | CPSF4 | CPSF4 | CPSF30; NAR; NEB1 | XM_011515755; XM_011515756; NM_006693; XM_011515757; NM_001081559; XM_011515758; XM_011515759 |
| IF4A3_MOUSE | 9775 | IF4A3 | EIF4A3 | MUK34; NMP265; NUK34; eIF4AIII; RCPS; DDX48 | XM_011525522; NM_014740 |
| PCBP2_MOUSE | 5094 | PCBP2 | PCBP2 | HNRNPE2; HNRPE2; hnRNP-E2 | NM_001128912; NM_001128911; NM_001128914; NM_001098620; NM_031989; NM_001128913; NM_005016 |
| QKI_MOUSE | 9444 | QKI | QKI | Hqk; QK; QK3; hqkI; QK1 | XM_011536259; XM_011536260; XR_942633; ; XM_011536258; NM_206853; NM_001301085; NM_006775; XM_011536261; NM_206854; XR_245557; NM_206855 |
| ACADV_MOUSE | 37 | ACADV | ACADVL | ACAD6; LCACD; VLCAD | XM_011523829; XR_934023; NM_001270447; XR_934021; NM_001270448; NM_000018; XM_006721516; ; XM_011523830; XR_934022; NM_001033859 |
| ELAV1_MOUSE | 1994 | ELAV1 | ELAVL1 | ELAV1; MelG; Hua; HUR | XM_011527777; NM_001419 |
| FINC_MOUSE | 2335 | FINC | FN1 | FNZ; GFND; CIG; ED-B; GFND2; MSF; FINC; FN; LETS | XM_005246416; ; XM_005246413; NM_212476; XM_005246407; XM_005246410; XM_005246414; NM_212474; XM_005246402; XM_005246408; XM_005246409; XM_005246399; NM_054034; XM_005246400; XM_005246403; XM_005246405; XM_005246406; XM_005246415; NM_002026; XM_005246398; XM_005246401; XM_005246404; XM_005246412; XM_005246417; XM_005246397; XM_005246411; NM_212478; NM_212482; NM_212475 |
| WDR3_MOUSE | 10885 | WDR3 | WDR3 | UTP12; DIP2 | NM_006784 |
| SRSF9_MOUSE | 8683 | SRSF9 | SRSF9 | SFRS9; SRp30c | NM_003769 |
| NPM_MOUSE | 4869 | NPM | NPM1 | B23; NPM | XM_005265920; ; NM_001037738; NM_002520; NM_199185; XM_011534564 |
| FUBP2_MOUSE | 8570 | FUBP2 | KHSRP | FUBP2; FBP2; KSRP | XM_005259668; NM_003685; XM_011528395 |
| HNRPD_MOUSE | 3184 | HNRPD | HNRNPD | P37; AUF1; AUF1A; HNRPD; hnRNPD0 | ; NM_002138; NM_001003810; NM_031370; NM_031369 |
| UTP15_MOUSE | 84135 | UTP15 | UTP15 | NET21 | NM_001284431; XM_011543680; NM_001284430; NM_032175 |
| IMMT_MOUSE | — | — | — | — | — |
| CD2A1_MOUSE | 1029 | CD2A2 | CDKN2A | P16INK4A; CMM2; P14; P16INK4; P19; P19ARF; CDKN2; INK4; TP16; MTS1; INK4A; | XM_011517676; XR_929166; ; NM_058197; NM_058196; XR_929165; NM_001195132; XR_929162; NM_058195; XM_011517675; XM_011517678; XM_011517679; XR_929159; NM_000077; XM_011517677; XR_929161; XR_929163; XM_005251343; XR_929164 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| RSMB_MOUSE | 6628 | Q66K91 | SNRPB | P14ARF; ARF; MTS-1; P16-INK4A; CDK4I; MLM; P16 CCMS; COD; Sm-B/B'; SmB/SmB'; snRNP-B; SNRPB1; SmB/B' | NM_198216; NM_003091; |
| IMA1_MOUSE | 3838 | IMA1 | KPNA2 | IPOA1; QIP2; SRP1alpha; RCH1 | XM_011524783; NM_002266 |
| THIL_MOUSE | 38 | THIL | ACAT1 | ACAT; MAT; T2; THIL | XM_006718834; XM_006718835; NM_000019; |
| RT07_MOUSE | 51081 | RT07 | MRPS7 | S7mt; bMRP27a; MRP-S7; RPMS7; RP-S7; MRP-S | NM_015971 |
| MEN1_MOUSE | 4221 | MEN1 | MEN1 | MEAI; SCG2 | NM_130800; NM_130802; NM_130799; XM_011545041; NM_130804; NM_000244; XM_005274001; NM_130801; NM_130803; XM_011545040; ; XM_011545042 |
| HNRPF_MOUSE | 3185 | HNRPF | HNRNPF | HNRPF; OK/SW-cl.23; mcs94-1 | NM_001098207; NM_001098208; NM_001098204; NM_001098205; NM_001098206; NM_004966 |
| ROA3_MOUSE | 220988 | ROA3 | HNRNPA3 | 2610510D13Rik; D10S102; HNRPA3; FBRNP | NM_194247; XM_005246380; XM_006712365; XM_005246381 |
| NCOA5_MOUSE | 57727 | NCOA5 | NCOA5 | bA465L10.6; CIA | NM_020967; XM_011528951; XM_005260474 |
| KIF4_MOUSE | 24137 | KIF4A | KIF4A | KIF4; KIF4G1; MRX100 | XM_011530893; ; NM_012310 |
| FBLN1_MOUSE | 2192 | Q8NBH6 | FBLN1 | FBLN; FIBL1 | NM_006486; NM_001996; ; NM_006485; NM_006487 |
| SYWM_MOUSE | 10352 | SYWM | WARS2 | TrpRS | XM_006710283; NM_015836; NM_201263; XM_011540493; XM_005270350; XM_011540495; XM_011540494 |
| GELS_MOUSE | 2934 | GELS | GSN | AGEL; ADF | XM_006717075; XM_011518587; NM_198252; XM_005251940; XM_005251945; XM_011518584; XM_011518594; XM_005251943; XM_011518594; XM_011518586; XM_011518592; NM_001127666; XM_006717079; XM_0115118589; NM_001127664; XM_011518585; XM_011518588; XM_011518590; XM_011518593; ; NM_000177; NM_001127662; NM_001127663; NM_001127667; XM_011518591; NM_001258029; NM_001127665; NM_001258030 |
| UTP20_MOUSE | 27340 | UTP20 | UTP20 | DRIM | NM_014503; XM_006719343 |
| TENA_MOUSE | 3371 | TENA | TNC | 150-225; GMEM; JI; GP; TN; TN-C; DFNA56; HXB | XM_011518624; XM_011518627; ; XM_005251974; XM_011518629; XM_006717100; XM_011518622; XM_011518623; XM_011518626; XM_005251972; XM_006717097; XM_005251975; XM_011518625; XM_006717096; XM_011518628; XM_011518630; NM_002160; XM_005251973; XM_006717098; XM_006717101 |
| SENP3_MOUSE | 26168 | SENP3 | SENP3 | Ulp1; SMT3IP1; SSP3 | NM_015670 |
| CPT2_MOUSE | 1376 | CPT2 | CPT2 | CPTASE; CPT1; IIAE4 | ; XM_005270484; NM_000098 |
| RBBP7_MOUSE | 5931 | RBBP7 | RBBP7 | RbAp46 | XM_011545553; NM_001198719; XM_011545554; NM_002893 |
| AOFA_MOUSE | 4128 | AOFA | MAOA | MAO-A | NM_000240; NM_001270458; |
| ECHB_MOUSE | 3032 | ECHB | HADHB | ECHB; MSTP029; MTPB; TP-BETA | NM_001281513; NM_000183; XM_011532803; ; NM_001281512; XM_011532804 |
| E9QNN1_MOUSE | — | — | — | — | — |
| Q91VA7_MOUSE | 3420 | A0A087WZN1 | IDH3B | RP46; H-IDHB | XM_005260716; XR_937066; ; NM_174856; NM_174855; NM_001258384; NM_006899 |
| PYC_MOUSE | 5091 | A0A024R5C5 | PC | PCB | XM_006718577; ; NM_001040716; XM_011545086; XM_005274031; XM_005274032; XM_006718578; XM_006718579; NM_000920; XM_011545087; NM_022172; XM_011545085; XM_011545088 |
| DNMT1_MOUSE | 1786 | I6L9H2 | DNMT1 | AIM; CXXC9; DNMT; MCMT; | XM_011527773; ; NM_001130823; NM_001379; XM_011527772; XM_011527774 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| ROA2_MOUSE | 3181 | ROA2 | HNRNPA2B1 | ADCADN; HSN1E HNRPA2; RNPA2; SNRPB1; HNRNPA2; HNRNPB1; IBMPFD2; HNRPA2B1; HNRPB1 | XR_242076; XR_242077; NM_002137; ; XR_428077; XR_428078; XM_006715714; NM_031243; XM_005249729 |
| LARP7_MOUSE | 51574 | LARP7 | LARP7 | ALAZS; PIP7S; HDCMA18P | NM_015454; NM_016648; NR_049768; NM_001267039 |
| PREP_MOUSE | 10531 | PREP | PITRM1 | PreP; MP1 | XM_005252345; XM_011519292; NM_014968; NM_001242307; NM_001242309; XM_006717362; NM_014889 |
| EDC4_MOUSE | 23644 | EDC4 | EDC4 | RCD-8; HEDLS; Ge-1; RCD8; GE1; HEDL5 | NM_014329 |
| RFOX2_MOUSE | 23543 | RFOX2 | RBFOX2 | FOX2; Fox-2; HNRBP2; HRNBP2; RBM9; RTA; fxh; dJ106I20.3 | XM_006724190; XM_006724193; ; XM_006724185; XM_006724187; XM_011530036; NM_001031695; NM_001082577; XM_005261428; XM_005261430; XM_005261431; XM_005261432; XM_005261433; XM_005261437; NM_001082579; XM_005261429; XM_006724186; XM_006724194; XM_006724192; NM_001082578; NM_014309; NM_001082576; XM_005261435; XM_006724188; XM_006724189; XM_006724191 |
| SMD3_MOUSE | 6634 | SMD3 | SNRPD3 | SMD3; Sm-D3 | NM_001278656; NR_103819; NM_004175 |
| ODBA_MOUSE | 593 | ODBA | BCKDHA | MSU; MSUD1; BCKDE1A; OVD1A | ; NM_000709; NM_001164783 |
| RT23_MOUSE | 51649 | RT23 | MRPS23 | CGI-138; HSPC329; MRP-S23 | NM_016070 |
| RBP2_MOUSE | 5903 | RBP2 | RANBP2 | ANE1; TRP1; TRP2; ADANE; NUP358; IIAE3 | XM_011511576; NM_006267; XM_005264002; XM_005264004; XM_011511575; XM_005264003; XM_005264007; XM_011511577; XM_005264005; XM_011511578; |
| NIPA_MOUSE | 51530 | NIPA | ZC3HC1 | HSPC216; NIPA | NM_001282190; XM_005250403; NM_001282191; XM_011516288; XM_011516289; XM_011516290; NM_016478 |
| KAD1_MOUSE | 203 | Q6FGX9 | AK1 | HTL-S-58j | XM_005251786; ; XM_011518348; XM_011518349; NM_000476 |
| SUCB2_MOUSE | 8801 | SUCB2 | SUCLG2 | GBETA | XR_940506; XR_245062; NM_001177599; NM_003848 |
| PRP8_MOUSE | 10594 | PRP8 | PRPF8 | SNRNP220; HPRP8; PRPC8; PRP8; RP13 | NM_006445; |
| NCPR_MOUSE | 5447 | NCPR | POR | P450R; CPR; CYPOR | ; NM_000941 |
| LMNB1_MOUSE | 4001 | LMNB1 | LMNB1 | LMN2; LMNB; LMN; ADLD | NM_001198557; XR_948250; ; NM_005573 |
| SF3B4_MOUSE | 10262 | SF3B4 | SF3B4 | SF3b49; Hsh49; AFD1; SAP49 | ; NM_005850 |
| A2ANY6_MOUSE | 23195 | MDN1 | MDN1 | — | XM_011535635; XR_942362; XM_005248700; XM_006715405; XM_011535636; ; NM_014611 |
| LAP2B_MOUSE | 7112 | LAP2B; LAP2A | TMPO | LAP2; CMD1T; LEMD4; TP; PRO0868 | ; NM_001032284; XM_005269132; XM_005269130; NM_001032283; NM_603276 |
| GNL3_MOUSE | 26354 | GNL3 | GNL3 | C77032; E21G3; NNP47; NS | NM_206826; ; NM_014366; NM_206825 |
| RL6_MOUSE | 6128 | A0A024RBK3; Q8TBK5; RL6 | RPL6 | TXREB1; TAXREB107; SHUJUN-2; L6 | XM_006719548; XM_006719546; NM_000970; NM_001024662; XM_006719547; XM_006719549; XM_011538647; XM_011538646 |
| RBM22_MOUSE | 55696 | RBM22 | RBM22 | Cwc2; ZC3H16; fSAP47 | NM_018047 |
| MYO5A_MOUSE | 4644 | MYO5A | MYO5A | GS1; MYO5; MYH12; MYR12 | XM_011521610; XM_011521611; NM_001142495; XM_011521607; ; NM_000259; XM_005254398; XM_011521606; XM_005254397; XM_011521609; XM_011521612; XM_011521608 |
| HYOU1_MOUSE | 10525 | HYOU1 | HYOU1 | HSP12A; ORP-150; Grp170; ORP150; GRP-170 | XM_005271392; XM_011548779; NM_001130991; XM_011548780; XM_011548781; XM_011548782; NM_006389; XM_011542557; XM_005271394; XR_947790; XR_953214; XM_005271393; XM_011542558; XM_011548778 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| ACDSB_MOUSE | 36 | ACDSB | ACADSB | 2-MEBCAD; ACAD7; SBCAD | ; NM_001609 |
| NOL11_MOUSE | 25926 | NOL11 | NOL11 | — | NM_015462; NM_001303272 |
| HEMH_MOUSE | 2235 | HEMH; Q7KZA3 | FECH | FCE; EPP | NM_000140; XM_011525882; NM_001012515; ; XM_011525881 |
| SNUT2_MOUSE | 10713 | SNUT2 | USP39 | SNRNP65; HSPC332; 65K; SAD1; CGI-21 | NM_006590; NM_001256726; NM_001256728; NR_046347; XM_011532488; XR_939653; NM_001256725; NM_001256727; XM_006711922; XR_939652; XM_006711923; XM_011532487 |
| NOG1_MOUSE | 23560 | NOG1; D2CFK9 | GTPBP4 | CRFG; NGB; NOG1 | NM_012341 |
| NEP1_MOUSE | 10436 | NEP1 | EMG1 | C2F; Grcc2f; NEP1 | ; XM_011520907; NM_006331 |
| WDR61_MOUSE | 80349 | WDR61 | WDR61 | REC14; SKI8 | NM_001303248; NM_001303247; XM_011522094; XR_931918; NM_025234 |
| RFC3_MOUSE | 5983 | RFC3 | RFC3 | RFC38 | XM_011535174; NM_002915; NM_181558; XM_011535173; XM_011535175; XM_011535172; XM_011535176 |
| Q3TWW8_MOUSE | 6431 | SRSF6 | SRSF6 | SRP55; B52; HEL-S-91; SFRS6 | ; NR_034009; XR_936608; NM_006275 |
| PPIL2_MOUSE | 23759 | PPIL2 | PPIL2 | CYP60; Cyp-60; CYC4; UBOX7; hCyP-60 | XM_011530047; XM_011530051; XM_011530041; XM_011530045; NM_148175; XM_011530046; XM_011530048; XM_011530050; XM_005261447; XM_011530043; NM_014337; XM_005261448; XM_011530042; XM_011530044; XM_011530049; NM_148176 |
| HDAC1_MOUSE | 3065 | Q6IT96; HDAC1 | HDAC1 | RPD3; GON-10; HD1; RPD3L1 | XM_011541309; NM_004964 |
| PAPD1_MOUSE | 55149 | PAPD1 | MTPAP | PAPD1; SPAX4 | ; NM_018109 |
| MCM3_MOUSE | 4172 | MCM3 | MCM3 | P1-MCM3; P1.h; HCC5; RLFB | NM_002388; NM_001270472 |
| SRSF7_MOUSE | 6432 | SRSF7 | SRSF7 | SFRS7; 9G8; AAG3 | XM_011533032; XR_939708; XR_426994; NM_001195446; XR_939711; NM_001031684; XM_005264484; XM_005264485; XR_939709; XR_939710; NM_006276 |
| THIM_MOUSE | 10449 | THIM | ACAA2 | DSAEC | NM_006111 |
| PKIIP_MOUSE | 55003 | PKIIP | PAKIIP1 | bA421M1.5; PIP1; hPIP1; MAK11; WDR84 | XM_005249204; XM_011514720; XM_006715129; XM_011514721; NM_017906 |
| ATAD1_MOUSE | 84896 | ATAD1 | ATAD1 | THORASE; FNP001; AFDC1 | XM_005270251; XM_011540302; XM_005270253; XR_945847; NM_032810; XM_005276252; XM_011540303; XM_011540304 |
| Q3U821_MOUSE | — | — | — | — | — |
| SYYM_MOUSE | 51067 | SYYM | YARS2 | MT-TYRRS; TYRRS; MLASA2; CGI-04 | XR_931297; XR_931299; ; XR_242892; XR_429036; XR_931298; XR_242891; NM_001040436; XR_931296; NM_015936 |
| RU17_MOUSE | 6625 | RU17 | SNRNP70 | U1-70K; Snp1; U170K; SNRP70; U1AP; U1RNP; RPU1; RNPU1Z | XM_011527241; NM_001009820; NM_001301069; NM_003089; XM_005259178; XM_011527240 |
| NUP85_MOUSE | 79902 | NUP85 | NUP85 | FROUNT; Nup75 | XR_429921; NM_024844; XR_243683; XM_005257690; XM_011525267; NM_001303276; XM_005257693; XM_005257692; XM_006722094; XM_011525268; XR_934552 |
| E9Q5F4_MOUSE | — | | | | |
| POGZ_MOUSE | 23126 | POGZ | POGZ | ZNF635; ZNF635m; ZNF280E | XM_011509331; NM_015100; XM_005244999; XR_921760; NM_001194938; XM_005245006; XM_011509330; NM_145796; NM_207171; XM_005245000; XM_005245001; XM_005245005; NM_001194937 |
| WDR12_MOUSE | 55759 | Q53T99; WDR12 | WDR12 | YTM1 | XM_011511469; NM_018256 |
| RL12_MOUSE | 6136 | RL12 | RPL12 | L12 | NM_000976 |
| ARL2_MOUSE | 402 | ARL2 | ARL2 | ARFL2 | NM_001667; NM_001199745 |
| RPAB3_MOUSE | 5437 | RPAB3 | POLR2H | RPABC3; RPB8; RPB17 | XM_011534667; XM_006713666; XM_006713670; NM_001278700; NM_001278714; XM_005247541; NM_001278698; XM_006713668; NM_001278699; NM_001278715; NM_006232 |
| CALX_MOUSE | 821 | CALX | CANX | P90; IP90; CNX | XM_011534664; XM_011534665; NM_001024649; NM_001746 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| AP2A2_MOUSE | 161 | AP2A2 | AP2A2 | HIP9; HYPJ; ADTAB; CLAPA2; HIP-9 | XM_011519928; NM_012305; NM_001242837; XM_011519930; XR_930847; XM_011519929 |
| EFGM_MOUSE | 85476 | E5KND5; EFGM | GFM1 | EGF1; COXPD1; GFM; EFG; hEFG1; EFG1; EFGM | ; NM_024996; XM_006713795; XM_011513247 |
| CELF1_MOUSE | 10658 | CELF1 | CELF1 | CUGBP1; NAB50; hNab50; CUG-BP; CUGBP; BRUNOL2; NAPOR; EDEN-BP | XM_011519847; XM_011519853; XM_011519856; XM_011519855; XM_011519859; NM_001172640; NM_006560; XM_011519849; XM_011519854; XM_011519851; XM_011519852; NM_001172639; XM_011519850; XM_011519857; NM_198700; XM_011519848; XM_011519858; NM_001025596 |
| ARAF_MOUSE | 369 | ARAF | ARAF | A-RAF; ARAF1; PKS2; RAFA1 | XM_011543909; XM_011543907; XM_011543906; ; XM_006724529; NM_001256196; XM_011543908; NM_001256197; NM_001654 |
| HNRPC_MOUSE | — | | | | |
| SMCA5_MOUSE | 8467 | SMCA5 | SMARCA5 | ISWI; SNF2H; hISWI; WCRF135; hSNF2H | NM_003601; XM_011532361 |
| HNRH1_MOUSE | 3187 | HNRH1 | HNRNPH1 | HNRPH1; hnRNPH; HNRPH | XM_006714862; XM_005265895; XM_006714863; XM_011534541; XM_005265901; XM_005265896; XM_011534542; XM_011534543; XM_011534544; NM_001257293; NM_005520; XM_011534547; XM_005265902; XM_011534545; XM_011534546 |
| RBM4B_MOUSE | 83759 | RBM4B | RBM4B | ZCCHC21B; ZCRB3B; RBM4L; ZCCHC15; RBM30 | XR_247214; NM_001286135; XR_247213; XM_011545297; NM_031492 |
| MTMR5_MOUSE | 6305 | MTMR5 | SBF1 | CMT4B3; MTMR5; DENND7A | XM_005261931; XM_005261935; XM_011530709; XM_011530710; XM_011530707; NM_002972; XR_938344; ; XM_011530708; XM_011530711 |
| RL23_MOUSE | 9349 | RL23 | RPL23 | rpL17; L23 | NM_000978 |
| DDX3X_MOUSE | 1654 | DDX3X | DDX3X | DBX; DDX14; DDX3; CAP-Rf; HLP2 | ; NM_024005; NM_001356; NR_126093; XM_011543892; NM_001193417; NM_001193416; NR_126094 |
| NMRL1_MOUSE | 57407 | NMRL1 | NMRAL1 | HSCARG; SDR48A1 | XM_006720905; NM_020677; XM_006720906; XM_006725239; XM_011522566; XM_005255447; XM_006725238; NM_001305141; XM_005255446; XM_006725236; XM_011546747; XM_006725237; XM_011522567; XM_011546748; NM_001305142 |
| TR150_MOUSE | 9967 | TR150 | THRAP3 | TRAP150 | XM_005271371; XR_246308; NM_005119 |
| NAT10_MOUSE | 55226 | NAT10 | NAT10 | NET43; ALP | XM_011520197; NM_001144030; NM_024662 |
| ODPB_MOUSE | 5162 | ODPB | PDHB | PHE1B; PDHE1-B; PDHBD | XM_011533828; NM_000925; NR_033384; NM_001173468; |
| DDX1_MOUSE | 1653 | DDX1 | DDX1 | DBP-RB; UKVH5d | NM_004939 |
| ECHA_MOUSE | 3030 | ECHA | HADHA | MTPA; LCHAD; ECHA; GBP; TP-ALPHA; HADH; LCEH | NM_000182; |
| PREB_MOUSE | 10113 | PREB | PREB | SEC12 | XM_011532471; XM_011532472; XR_939649; XM_006711914; XR_939648; NM_013388 |
| LA_MOUSE | 6741 | LA | SSB | La; La/SSB; LARP3 | NM_003142; NM_001294145; |
| PDIP2_MOUSE | 26073 | PDIP2 | POLDIP2 | POLD4; p38; PDIP38 | NM_001290145; NM_015584 |
| AGAP3_MOUSE | 116988 | AGAP3 | AGAP3 | CRAG; cnt-g3; AGAP-3; CENTG3; MRIP-1 | NM_001281300; XM_005249942; XM_005249943; XM_011515780; NM_001042535; NM_031946 |
| CO6A1_MOUSE | 1291 | CO6A1 | COL6A1 | OPLL | NM_001848; |
| CRNL1_MOUSE | 51340 | CRNL1 | CRNKL1 | HCRN; CLF; CRN; MSTP021; Clf1; SYF3 | NM_001278627; NM_001278626; NM_001278628; NM_001278625; NM_016652 |
| MATR3_MOUSE | 9782 | MATR3 | MATR3 | MPD; ALS21; VCPDM | NM_001282278; NM_018834; NM_001194956; NM_199189; ; NM_001194954; NM_001194955 |
| PRP17_MOUSE | 51362 | PRP17 | CDC40 | PRP17; PRPF17; EHB3 | NM_015891; XM_011535880 |
| RL7_MOUSE | 6129 | RL7 | RPL7 | L7; humL7-1 | XM_006716463; NM_000971 |
| NUCL_MOUSE | 4691 | NUCL | NCL | C23 | NM_005381 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
| --- | --- | --- | --- | --- | --- |
| RS9_MOUSE | 6203 | RS9 | RPS9 | S9 | XM_011547987; XM_011548358; XM_011548624; XR_431025; XR_431068; XR_953069; NM_001013; XM_005278288; XM_006726201; XM_006726202; XM_011547988; XM_011548623; XR_254260; XR_254311; XR_431090; XR_952765; XR_952994; XM_011547789; XM_011547790; XR_431067; XR_952920; XR_952995; XR_953155; XR_254518; XR_953156; XM_005277274; XM_006725965; XR_431057; XR_431069; XR_952922; XR_952996; XR_953068; XM_005278287; XM_011548167; XR_254517; XR_952766; XR_953070; XR_953157; XM_005277315; XM_011548359; XR_431058; XR_952764; XR_952919; XM_005277084; XM_005277085; XM_011548166; XR_430207; XR_431099 |
| HTRA2_MOUSE | 27429 | HTRA2 | HTRA2 | PARK13; OMI; PRSS25 | ; NM_145074; XM_005264266; NM_013247 |
| E9Q7G0_MOUSE LRC59_MOUSE | — 55379 | LRC59 | LRRC59 | p34; PRO1855 | NM_018509 |
| THOC2_MOUSE | 57187 | THOC2 | THOC2 | THO2; CXorf3; hTREX120; dJ506G2.1 | XM_005262447; XM_011531369; XM_011531372; ; XM_011531368; XM_011531374; XR_938550; XR_938552; NM_001081550; XM_011531373; XR_938551; XM_005262450; XR_938553; NM_020449; XM_011531367; XM_011531370; XM_011531371 |
| ERLN2_MOUSE | 11160 | ERLN2 | ERLIN2 | NET32; SPFH2; Erlin-2; SPG18; C8orf2 | XM_005273392; XM_006716280; NM_001003790; NM_007175; ; NM_001003791 |
| GALK1_MOUSE | 2584 | GALK1 | GALK1 | GALK; HEL-S-19; GK1 | ; NM_000154 |
| SAFB1_MOUSE | 6294 | SAFB1 | SAFB | HAP; HET; SAF-B1; SAFB1 | XM_006722839; NR_037699; NM_001201340; NM_001201339; NM_001201338; NM_002967 |
| RL28_MOUSE | 6158 | RL28 | RPL28 | L28 | NM_001136135; NM_001136137; NM_001136136; NM_001136134; XM_005259132; NM_000991 |
| MYO1C_MOUSE | 4641 | MYO1C | MYO1C | myr2; MMI-beta; MMIb; NMI | NM_033375; NM_001080950; NM_001080779 |
| SRS10_MOUSE | 10772 | SRS10 | SRSF10 | PPP1R149; SFRS13A; TASR2; SFRS13; TASR; TASR1; FUSIP1; FUSIP2; NSSR; SRp38; SRrp40 | NM_001191009; NM_001191006; NM_001191007; NM_001300937; NM_054016; NR_034035; NM_001191005; NM_006625; NM_001300936 |
| E9PYF4_MOUSE ACAD9_MOUSE | — 28976 | ACAD9 | ACAD9 | NPD002 | NR_033426; XR_427367; XM_011512742; ; NM_014049 |
| KIF2A_MOUSE | 3796 | B0AZS5; KIF2A | KIF2A | KIF2; CDCBM3; HK2 | NM_004520; NM_001243952; NM_001098511; NM_001243953 |
| IDH3A_MOUSE | 3419 | B4DJB4; IDH3A | IDH3A | — | XM_005254334; NM_005530; XM_005254337; XM_005254336 |
| PWP2_MOUSE | 5822 | PWP2 | PWP2 | EHOC-17; UTP1; PWP2H | XM_011529667; NM_005049 |
| CPSF7_MOUSE | 79869 | CPSF7 | CPSF7 | CFIm59 | XM_011545257; XM_011545263; XM_005274303; NM_001142565; XM_011545258; XM_011545262; XM_005274299; XM_011545260; NM_024811; XM_011545261; NM_001136040; XM_005274298; XM_011545259 |
| Q6PGF5_MOUSE NUP93_MOUSE | — 9688 | NUP93 | NUP93 | NIC96 | NM_001242795; XM_005256263; NM_014669; NM_001242796 |
| H14_MOUSE | 3008 | H14 | HIST1H1E | H1F4; dJ221C16.5; H1.4; H1E; H1s-4 | NM_005321 |
| FUND2_MOUSE | 65991 | FUND2 | FUNDC2 | HCBP6; DC44; PD03104; HCC3 | NM_023934 |
| APT_MOUSE | 353 | APT | APRT | APRTD; AMP | NM_000485; ; NM_001030018 |
| MCM5_MOUSE | 4174 | B1AHB0; MCM5 | MCM5 | CDC46; P1-CDC46 | XM_006724242; NM_006739 |
| CLPX_MOUSE | 10845 | CLPX | CLPX | — | XR_931743; XM_011521164; NM_006660 |
| RBM8A_MOUSE | 9939 | RBM8A; A0A023T787 | RBM8A | BOV-1C; BOV-1B; DEL1q21.1; ZRNP1; TAR; BOV-1A; C1DELq21.1; RBM8B; MDS014; | ; NM_005105 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| L2GL1_MOUSE | 3996 | L2GL1 | LLGL1 | RBM8; Y14; ZNRP HUGL-1; HUGL1; HUGL; DLG4; LLGL | XM_011523851; XM_011523853; XM_011523854; XM_011523856; XM_011523850; XM_011523855; NM_004140; XM_011523852; XM_011523849 |
| SMC5_MOUSE | 23137 | SMC5 | SMC5 | SMC5L1 | NM_015110; XM_005251837; XM_005251839; XM_005251838 |
| NAA15_MOUSE | 80155 | NAA15 | NAA15 | TBDN100; NATH; NAT1P; Ga19; NARG1; TBDN | XM_005263236; NM_057175 |
| RS11_MOUSE | 6205 | RS11 | RPS11 | S11 | NM_001015 |
| ATAD3_MOUSE | 83858; 55210 | — | — | — | — |
| TIAR_MOUSE | 7073 | TIAR | TIAL1 | TIAR; TCBP | XM_005270108; XR_428715; XM_005270109; ; XM_005270110; XR_945808; NM_003252; NM_001033925 |
| RL9_MOUSE | 6133 | RL9 | RPL9 | L9; NPC-A-16 | NM_000661; NM_001024921; XM_005262661 |
| ACO13_MOUSE | 55856 | ACO13 | ACOT13 | HT012; PNAS-27; THEM2 | NM_001160094; NM_018473 |
| WDR82_MOUSE | 80335 | WDR82 | WDR82 | PRO2730; WDR82A; MSTP107; SWD2; MST107; PRO34047; TMEM113 | XM_011534136; XM_011534137; NM_025222 |
| PTRF_MOUSE | 284119 | PTRF | PTRF | cavin-1; CAVIN; CAVIN1; CGL4; FKSG13 | ; NM_012232; XM_005257242 |
| DDX5_MOUSE | 1655 | DDX5 | DDX5 | p68; HUMP68; HLR1; G17P1 | XM_006721738; XM_011524456; XM_011524457; NM_004396; XM_005257111 |
| WDR5_MOUSE | 11091 | WDR5 | WDR5 | CFAP89; SWD3; BIG-3 | NM_017588; NM_052821; XM_005272163 |
| CDC73_MOUSE | 79577 | CDC73 | CDC73 | HRPT2; HYX; C1orf28; FIHP; HRPT1; HPTJT | XM_006711537; ; NM_024529 |
| RM03_MOUSE | 11222 | RM03 | MRPL3 | RPML3; MRL3; COXPD9 | ; NM_007208 |
| THOC6_MOUSE | 79228 | THOC6 | THOC6 | BBIS; fSAP35; WDR58 | NM_024339; NM_001142350 |
| RL13A_MOUSE | 23521 | RL13A | RPL13A | TSTA1; L13A | NR_073024; NM_001270491; NM_012423 |
| RL22_MOUSE | 6146 | RL22 | RPL22 | EAP; HBP15; L22; HBP15/L22 | NM_000983 |
| DAZP1_MOUSE | 26528 | DAZP1 | DAZAP1 | — | XM_005259535; XM_005259536; NM_170711; XM_011527906; XM_011527904; XM_011527908; XM_005259534; XM_011527909; NM_018959; XM_005259531; ; XM_011527907; XM_011527910; XM_011527905 |
| E41L3_MOUSE | 23136 | E41L3 | EPB41L3 | 4.1B; DAL-1; DAL1 | XM_011525619; XM_011525620; XM_011525611; XM_011525625; XM_011525626; XM_011525635; XM_011525609; XM_011525612; XM_011525613; XM_011525614; XM_011525615; XM_011525628; XM_011525631; NM_001281535; XM_011525607; XM_011525616; XM_011525621; XM_011525624; XM_011525630; NM_001281533; XM_011525610; XM_011525623; XM_011525627; NM_001281534; XM_011525606; XM_011525617; XM_011525618; XM_011525622; XM_011525629; XM_011525632; XM_011525637; XM_011525633; XM_011525636; NM_012307; XM_011525608; XM_011525634 |
| RBMX_MOUSE | 27316 | RBMX | RBMX | RBMXP1; HNRNPG; hnRNP-G; RBMXRT; HNRPG; RNMX | NR_028477; NR_028476; NM_001164803; ; NM_002139 |
| IDHP_MOUSE | 3418 | IDHP | IDH2 | IDP; IDPM; mNADP-IDH; IDH; IDHM; D2HGA2; ICD-M | ; NM_001289910; NM_002168; NM_001290114 |
| DDX27_MOUSE | 55661 | DDX27 | DDX27 | HSPC259; Drs1p; dJ686N3.1; PP3241; DRS1; RHLP | NM_017895; XM_011528888 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| NTKL_MOUSE | 57410 | NTKL | SCYL1 | GKLP; TAPK; TRAP; HT019; NKTL; NTKL; P105; TEIF | NM_020680; XM_005274120; XM_005274118; NM_001048218; XM_005274121 |
| RL22L_MOUSE | 200916 | RL22L | RPL22L1 | — | NM_001099645; XM_005247205 |
| RBM10_MOUSE | 8241 | RBM10 | RBM10 | GPATC9; GPATCH9; DXS8237E; TARPS; ZRANB5; S1-1 | ; NM_152856; XM_005272678; XM_005272679; NM_001204467; NM_005676; NM_001204466; XM_011543989; NM_001204468; XM_006724563; XM_005272677 |
| TBL3_MOUSE | 10607 | TBL3 | TBL3 | UTP13; SAZD | NM_006453 |
| Q99N15_MOUSE | — | | | | |
| RL3_MOUSE | 6122 | RL3 | RPL3 | ASC-1; TARBP-B; L3 | NM_000967; NM_001033853 |
| HNRDL_MOUSE | 9987 | HNRDL | HNRNPDL | LGMD1G; HNRNP; HNRPDL; JKTBP2; JKTBP; laAUF1 | NM_031372; ; NM_005463; NM_001207000; NR_003249 |
| B1B0C7_MOUSE | — | | | | |
| TIM44_MOUSE | 10469 | TIM44 | TIMM44 | TIM44 | NM_006351 |
| TOP2A_MOUSE | 7153 | TOP2A | TOP2A | TOP2; TP2A | XM_005257632; XM_011525165; NM_001067; |
| FBLN2_MOUSE | 2199 | FBLN2 | FBLN2 | — | XM_006713026; NM_001004019; NM_001165035; NM_001998 |
| ILF2_MOUSE | 3608 | ILF2 | ILF2 | NF45; PRO3063 | NM_001267809; NM_004515 |
| U2AF2_MOUSE | 11338 | U2AF2 | U2AF2 | U2AF65 | XM_006722994; NM_001012478; ; NM_007279; XM_011526410 |
| CDC5L_MOUSE | 988 | CDC5L | CDC5L | PCDC5RP; CDC5-LIKE; dJ319D22.1; CEF1; CDC5 | XM_006715289; NM_001253; XR_926346 |
| SND1_MOUSE | 27044 | SND1 | SND1 | TDRD11; p100 | NM_014390; XM_011516051 |
| ETFB_MOUSE | 2109 | ETFB | ETFB | FP585; MADD | NM_001014763; ; NM_001985 |
| SMC2_MOUSE | 10592 | B7ZLZ7; A8K984; B3KMB1; SMC2; A0A024R158 | SMC2 | SMC-2; CAP-E; SMC2L1; CAPE | XM_011518150; XM_011518149; XM_011518151; XM_011518153; NM_006444; XM_011518148; NM_001042550; XM_006716933; XM_011518152; NM_001265602; XM_011518154; NM_001042551 |
| DDX54_MOUSE | 79039 | DDX54 | DDX54 | DP97 | NM_001111322; NM_024072 |
| RAI14_MOUSE | 26064 | RAI14 | RAI14 | NORPEG; RAI13 | XM_011514022; XM_011514024; XM_011514016; XM_011514019; XM_011514520; XM_011514025; NM_001145521; NM_001145525; NM_001145522; XM_006714469; XM_011514018; XM_011514021; XM_011514017; NM_001145523; NM_015577; XM_011514020; XM_011514023 |
| PCNA_MOUSE | 5111 | PCNA | PCNA | ATLD2 | NM_002592; NM_182649 |
| CNOT1_MOUSE | 23019 | CNOT1 | CNOT1 | NOT1; AD-005; CDC39; NOT1H | NM_206999; NM_001265612; NR_049763; NM_016284 |
| CPSF3_MOUSE | 51692 | CPSF3 | CPSF3 | CPSF-73; CPSF73 | XM_005246167; XM_011510362; NM_016207; XM_005246168 |
| RS2_MOUSE | 6187 | RS2 | RPS2 | LLREP3; S2 | NM_002952 |
| PPIL4_MOUSE | 85313 | PPIL4 | PPIL4 | HDCME13P | NM_139126 |
| FXR1_MOUSE | 8087 | FXR1 | FXR1 | FXR1P | XM_005247816; NM_001013438; XM_005247814; XM_011513216; XM_005247815; XM_006713775; XM_011513215; XM_011513217; NM_005087; NM_001013439; XM_005247813 |
| COR1C_MOUSE | 23603 | A0A024RBI5; COR1C | CORO1C | HCRNN4 | XM_011538124; NM_014325; XM_011538125; NM_001105237; XR_944514; NM_001276471 |
| DNLI1_MOUSE | 3978 | DNLI1; B4DM52; F5GZ28 | LIG1 | — | NR_110296; NM_001289064; XM_006723215; XR_430200; NM_000234; NM_001289063; XR_243932; ; XM_005258934; XM_006723216 |
| RM22_MOUSE | 29093 | RM22 | MRPL22 | MRP-L25; RPML25; HSPC158; L22mt; MRP-L22 | NM_014180; NM_001014990 |
| RBM5_MOUSE | 10181 | RBM5 | RBM5 | RMB5; G15; H37; LUCA15 | XM_006712917; ; XM_011533261; XM_011533262; NM_005778; NR_03627; XM_006712919; XR_427245 |
| U520_MOUSE | 23020 | U520 | SNRNP200 | ASCC3L1; BRR2; RP33; U5-200KD; HELIC2 | ; NM_014014 |
| MCM6_MOUSE | 4175 | MCM6 | MCM6 | MCG40308; Mis5; P105MCM | ; NM_005915 |
| CPSF2_MOUSE | 53981 | CPSF2 | CPSF2 | CPSF100 | XM_005267767; NM_017437 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| FXR2_MOUSE | 9513 | FXR2 | FXR2 | FMR1L2; FXR2P | XR_243572; ; NM_004860 |
| CPSF5_MOUSE | 11051 | CPSF5 | NUDT21 | CFIM25; CPSF5 | NM_007006 |
| RL14_MOUSE | 9045 | RL14 | RPL14 | CAG-ISL-7; L14; CTG-B33; RL14; hRL14 | NM_001034996; NM_003973 |
| TRA2B_MOUSE | 6434 | TRA2B | TRA2B | PPP1R156; SFRS10; TRAN2B; SRFS10; TRA2-BETA; Htra2-beta | XM_011513072; XM_006713724; NM_004593; ; NM_001243879; XM_005247703 |
| VWA8_MOUSE | 23078 | VWA8 | VWA8 | KIAA0564 | NM_001009814; XM_011535006; NM_015058; XM_006719791; XM_011535007 |
| NAA38_MOUSE | 51691 | LSM8 | LSM8 | NAA38 | NM_016200 |
| HNRPQ_MOUSE | — | | | | |
| TRAP1_MOUSE | 10131 | TRAP1 | TRAP1 | TRAP-1; HSP90L; HSP 75; HSP75 | NM_001272049; ; XM_011522345; NM_016292 |
| STAG1_MOUSE | 10274 | STAG1 | STAG1 | SCC3A; SA1 | XM_011512332; XM_011512331; NM_005862; XM_011512333; XM_011512329; XM_011512330 |
| DDX17_MOUSE | 10521 | DDX17 | DDX17 | RH70; P72 | NM_001098505; NM_030881; NM_001098504; ; NM_006386 |
| ERD21_MOUSE | 10945 | ERD21 | KDELR1 | HDEL; PM23; ERD2; ERD2.1 | XM_011526358; NM_006801 |
| RL18A_MOUSE | 6142 | RL18A | RPL18A | L18A | NM_000980 |
| UBXN1_MOUSE | 51035 | UBXN1 | UBXN1 | SAKS1; UBXD10; 2B28 | XM_011545090; NM_001286077; XM_005274033; NM_015853; NM_001286078 |
| EPDR1_MOUSE | 54749 | EPDR1 | EPDR1 | MERP-1; MERP1; EPDR; UCC1 | NM_001242946; NM_001242948; NM_017549 |
| KAP0_MOUSE | 5573 | KAP0 | PRKAR1A | ACRDYS1; CAR; CNC; PPNAD1; ADOHR; CNC1; PRKAR1; TSE1; PKR1 | XM_011524985; ; NM_212471; NM_001278433; NM_001276290; XM_011524984; NM_001276289; NM_212472; XM_011524983; NM_002734 |
| CBR4_MOUSE | 84869 | CBR4 | CBR4 | SDR45C1 | XR_938789; XM_005263315; XM_006714392; XM_011532386; XM_006714391; NM_032783; XM_011532385; XM_005263316 |
| RL13_MOUSE | 6137 | RL13; A8K4C8 | RPL13 | D16S444E; L13; D16S44E; BBC1 | NM_001243130; NM_033251; NM_000977; NM_001243131 |
| SFPQ_MOUSE | 6421 | SFPQ | SFPQ | PPP1R140; PSF; POMP100 | XM_005271113; XM_005271115; XM_011541950; XM_005271112; NM_005066 |
| PDS5B_MOUSE | 23047 | PDS5B | PDS5B | AS3; CG008; APRIN | XM_011535002; XM_005266298; XM_011535001; NM_015032; NM_015928; XM_011534999; XM_011535000; |
| KPCI_MOUSE | 5584 | KPCI | PRKCI | PKCI; DXS1179E; nPKC-iota | NM_002740 |
| THOC4_MOUSE | 10189 | THOC4 | ALYREF | ALY/REF; THOC4; BEF; ALY; REF | NM_005782; XR_933919 |
| SF3B3_MOUSE | 23450 | SF3B3 | SF3B3 | SAP130; RSE1; STAF130; SF3b130 | NM_012426 |
| E9QN31_MOUSE | — | | | | |
| AKT1_MOUSE | 207 | AKT1 | AKT1 | AKT; PKB-ALPHA; RAC; PRKBA; RAC-ALPHA; CWS6; PKB | NM_005163; XM_011536544; NM_001014431; XM_005267401; XM_011536543; NM_001014432; |
| NOP56_MOUSE | 10528 | NOP56 | NOP56 | SCA36; NOL5A | NR_027700; ; NM_006392 |
| SMU1_MOUSE | 55234 | SMU1 | SMU1 | SMU-1; BWD; fSAP57 | XM_005251503; NM_018225 |
| MTA1_MOUSE | 9112 | MTA1 | MTA1 | — | XM_011537305; XM_011537309; XM_011537301; XM_011537304; XM_011537311; XM_011537315; ; XM_011537306; XM_011537308; XM_011537314; XM_011537310; XM_011537302; XM_011537303; XM_011537307; NM_004689; NM_001203258; XM_011537312; XM_011537313 |
| BUB3_MOUSE | 9184 | BUB3 | BUB3 | BUB3L; hBUB3 | NM_004725; ; NM_001007793 |
| RPF2_MOUSE | 84154 | RPF2 | RPF2 | bA397G5.4; BXDC1 | NM_001289111; NM_032194 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| ATLA3_MOUSE | 25923 | ATLA3 | ATL3 | HSN1F | ; NM_015459; XM_006718493; XM_006718494; XM_011544902; NM_001290048 |
| NSA2_MOUSE | 10412 | NSA2 | NSA2 | CDK105; TINP1; HUSSY-29; HUSSY29; HCLG1; HCL-G1 | XM_011543098; NM_001271665; XR_948227; NM_014886; NR_073403 |
| ACON_MOUSE | 50 | ACON | ACO2 | ACONM; ICRD | ; NM_001098 |
| DNJC3_MOUSE | 5611 | DNJC3 | DNAJC3 | PRKRI; HP58; P58; ERdj6; P58IPK; ACPHD | XM_011521105; NM_006260; XM_011521104; |
| RPB2_MOUSE | 5431 | RPB2; B4DH29; C9J4M6; B4DHJ3; C9J2Y9 | POLR2B | POL2RB; hRPB140; RPB2 | NM_001303269; NM_000938; NM_001303268 |
| RL11_MOUSE | 6135 | RL11 | RPL11 | L11; DBA7; GIG34 | NM_000975; NM_001199802; |
| PRP6_MOUSE | 24148 | PRP6 | PRPF6 | TOM; ANT-1; Prp6; hPrp6; C20orf14; RP60; ANT1; SNRNP102; U5-102K | XM_006723769; ; NM_012469 |
| LSM2_MOUSE | 57819 | LSM2 | LSM2 | YBL026W; C6orf28; G7B; snRNP | NM_021177 |
| RS28_MOUSE | — | | | | |
| K6PF_MOUSE | 5213 | A0A024R0Y5; PFKAM | PFKM | PFKA; PFK1; PFK-1; PFKX; PPP1R122; ATP-PFK; GSD7 | NM_001166688; NM_001166687; NM_001166686; XM_005268976; XM_005268978; ; XM_005268977; XM_011538487; XM_005268974; XM_005268975; XM_005268979; XM_011538488; NM_000289 |
| NU155_MOUSE | 9631 | NU155 | NUP155 | ATFB15; N155 | XM_011514166; XM_011514164; NM_001278312; XM_011514165; NM_004298; NM_153485 |
| PTH2_MOUSE | 51651 | PTH2 | PTRH2 | 2; CFAP37; PTH; CGI-147; IMNEPD; PTH; BIT1; PTH 2 | XM_011524886; NM_001015509; XM_005257447; XM_011524887; NM_016077 |
| FLOT1_MOUSE | 10211 | FLOT1 | FLOT1 | — | XM_005275502; XM_005275503; XM_005272759; XM_005272760; XM_006725672; XM_006726072; XM_005248780; XM_005274909; XM_005275335; XM_005248781; XM_005274910; XM_006714947; XM_006725971; XM_005275336; XM_006725465; NM_005803 |
| NIPS2_MOUSE | 2631 | NIPS2 | GBAS | NIPSNAP2 | NM_001483; NM_001202469 |
| PUF60_MOUSE | 22827 | PUF60 | PUF60 | SIAHBP1; RoBPI; FIR; VRJS | NM_001271096; NM_001271097; NM_001136033; NM_014281; ; NM_001271100; NM_078480; XM_011516929; NM_001271098; XM_011516930; NM_001271099 |
| SMAL1_MOUSE | 50485 | SMAL1 | SMARCAL1 | HHARP; HARP | ; XM_006712557; NM_014140; NM_001127207; XM_005246632; XM_005246631 |
| MPPB_MOUSE | 9512 | MPPB | PMPCB | P-52; MPPB; Beta-MPP; MPP11; MPPP52 | XM_005250717; XM_006716181; XR_242267; NM_004279 |
| RBM39_MOUSE | 9584 | RBM39 | RBM39 | CAPERalpha; FSAP59; CAPER; HCC1; RNPC2 | XM_011529110; NM_184237; XM_006723891; XM_006723893; NM_001242599; NM_184234; ; NM_001242600; NR_040722; XM_006723890; XM_011529111; NM_004902; NR_040723; NM_184241; NR_040724; NM_184244 |
| SNX3_MOUSE | 8724 | SNX3 | SNX3 | Grd19; MCOPS8; SDP3 | NM_001300929; NM_001300928; ; NM_003795; NM_152828; NM_152827 |
| RBBP4_MOUSE | 5928 | RBBP4 | RBBP4 | lin-53; RBAP48; NURF55 | NM_005610; NM_001135255; NM_001135256 |
| AL4A1_MOUSE | 8659 | AL4A1 | ALDH4A1 | P5CD; P5CDh; ALDH4 | XR_946786; XM_011542353; NM_003748; NM_170726; XM_011542352; NM_001161504; |
| SMC1A_MOUSE | 8243 | G8JLG1; SMC1A | SMC1A | SMCB; SB1.8; SMC1alpha; DXS423E; CDLS2; SMC1; SMC1L1 | ; NM_006306; NM_001281463 |
| ILF3_MOUSE | 3609 | ILF3 | ILF3 | MMP4; DRBP76; MPP4; NFAR2; NF-AT-90; NF110b; MPHOSPH4; | ; XM_005259895; XM_011527984; XM_006722742; XM_011527987; XM_011527986; NM_004516; NM_012218; NM_017620; XM_011527985; NM_001137673; NM_153464 |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| SERPH_MOUSE | 871 | SERPH | SERPINH1 | DRBF; NF90a; NF90b; NFAR; NFAR-1; TCP110; NF90; CBTF; NF110; TCP80 PPROM; RA-A47; CBP2; PIG14; CBP1; gp46; AsTP3; HSP47; OI10; SERPINH2 | ; NM_001235; XM_006718729; XM_011545327; NM_001207014; XM_011545326 |
| AP2A1_MOUSE | 160 | AP2A1 | AP2A1 | ADTAA; AP2-ALPHA; CLAPA1 | NM_014203; XM_011526556; XM_011526557; NM_130787 |
| CCAR2_MOUSE | 57805 | CCAR2 | CCAR2 | p30 DBC; DBC1; KIAA1967; NET35; p30DBC; DBC-1 | XM_011544604; NM_199205; NR_033902; XM_011544603; NM_021174 |
| SUCB1_MOUSE | 8803 | SUCB1; E5KS60 | SUCLA2 | SCS-betaA; MTDPS5; A-BETA | XM_011535293; NM_003850; ; XM_011535292; XR_941688 |
| RM14_MOUSE | 64928 | RM14 | MRPL14 | L32mt; MRPL32; MRP-L32; L14mt; MRP-L14; RMPL32; RPML32 | XM_005249301; NM_032111; XM_011514814; XM_005249300; XM_005249299 |
| RPB1_MOUSE | 5430 | RPB1 | POLR2A | RPB1; RPO2; RpIILS; POLR2; RPBh1; POLRA; hRPB220; hsRPB1; RPOL2 | ; NM_000937 |
| AGK_MOUSE | 55750 | AGK | AGK | MULK; MTDPS10; CATC5; CTRCT38 | XM_011516397; XM_005250023; NM_018238; |
| CSDE1_MOUSE | 7812 | CSDE1 | CSDE1 | UNR; D1S155E | NM_001007553; NM_001242892; NM_007158; NM_001242893; NM_001130523; NM_001242891 |
| PDLI7_MOUSE | 9260 | PDLI7 | PDLIM7 | LMP3; LMP1 | XM_011534699; NR_103804; XM_011534697; XM_011534700; XM_011534698; XM_011534696; NM_213636; NM_005451; NM_203352; NM_203353 |
| RB6I2_MOUSE | 23085 | RB6I2 | ERC1 | ELKS; ERC-1; RAB6IP2; Cast2 | XM_011520940; NM_178039; NR_027948; NM_001301248; XM_011520938; XM_011520942; XR_931510; XM_011520943; XR_931509; XM_011520936; NR_027949; XM_011520937; NM_178040; XM_011520939; XM_011520941; XM_011520944; XR_931508; NR_027946 |
| CHD4_MOUSE | 1108 | CHD4 | CHD4 | Mi2-BETA; Mi-2b; CHD-4 | XM_006718958; NM_001273; XM_006718962; XM_006718960; XM_006718959; XM_005253668; XM_006718961; NM_001297553 |
| PRDX3_MOUSE | 10935 | PRDX3 | PRDX3 | AOP-1; SP-22; AOP1; MER5; prx-III; HBC189; PRO1748 | NR_126105; NM_014098; NM_006793; NR_126103; NM_001302272; NR_126102; NR_126106 |
| AP2M1_MOUSE | 1173 | AP2M1 | AP2M1 | AP50; mu2; CLAPM1 | NM_004068; NM_001025205 |
| LIMA1_MOUSE | 51474 | LIMA1 | LIMA1 | SREBP3; EPLIN | NM_001243775; XM_011538455; NM_001113547; ; NM_001113546; NM_016357 |
| GOLI4_MOUSE | 27333 | GOLI4 | GOLIM4 | GPP130; GIMPC; P138; GOLPH4 | XM_005247365; XM_005247364; NM_014498; XM_005247366 |
| HCFC1_MOUSE | 3054 | HCFC1 | HCFC1 | HCF1; HFC1; PPP1R89; VCAF; MRX3; CFF; HCF; HCF-1 | XM_006724816; XM_011531147; ; XM_011531144; XM_11011531146; XM_011531150; XM_011531148; NM_005334; XM_006724815; XM_011531149; XM_011531145 |
| E41L1_MOUSE | 2036 | E41L1 | EPB41L1 | MRD11; 4.1N | XM_011528669; XM_011528677; XM_011528681; XM_011528684; XM_011528670; XM_011528674; XM_011528686; XM_011528666; XM_011528685; XM_011528675; XM_011528676; XM_011528679; XM_011528680; NM_001258329; NM_012156; XM_011528667; XM_011528668; XM_011528671; XM_011528672; XM_011528685; NM_001258330; XM_011528664; XM_011528665; XM_011528682; |

TABLE 6-continued iDRiP proteomics results - Multiplexed quantitation of proteins pulled down by iDRiP and identified by mass spectrometry.

| UniProt Entry Name | Human Gene ID | Human Protein | Human Gene Symbol | Gene Synonyms | Accession numbers |
|---|---|---|---|---|---|
| TMM65_MOUSE | 157378 | TMM65 | TMEM65 | — | XM_011528683; NM_177996; XM_011528673; XM_011528678 |
| SMD1_MOUSE | 6632 | SMD1 | SNRPD1 | HsT2456; SMD1; SNRPD; Sm-D1 | XM_011516847; NM_194291 NM_006938; NM_001291916 |
| RT05_MOUSE | 64969 | RT05 | MRPS5 | MRP-S5; S5mt | XM_006712694; XR_922989; NM_031902 |
| DHX15_MOUSE | 1665 | DHX15 | DHX15 | PRPF43; HRH2; PRP43; DBP1; DDX15; PrPp43p | XR_925314; NM_001358 |
| MK03_MOUSE | 5595 | MK03; L7RXH5 | MAPK3 | P44ERK1; P44MAPK; ERK-1; PRKM3; ERT2; HUMKER1A; p44-ERK1; p44-MAPK; ERK1; HS44KDAP | NM_001040056; XR_243293; NM_001109891; NM_002746; |
| CPSF1_MOUSE | 29894 | CPSF1 | CPSF1 | CPSF160; P/cl.18; HSU37012 | XM_006716548; XM_011516999; NM_013291; XM_006716550; XM_011516998; XM_011516997; XM_006716549 |
| SYMC_MOUSE | 4141 | SYMC | MARS | MRS; SPG70; MTRNS; METRS | XM_006719398; NM_004990; XM_011538353; |
| LPPRC_MOUSE | 10128 | LPPRC | LRPPRC | CLONE-23970; LRP130; LSFC; GP130 | XM_011532474; ; XM_006711915; XM_006711916; XM_011532473; NM_133259 |
| RL27A_MOUSE | 6157 | RL27A | RPL27A | L27A | NM_032650; NM_000990 |
| SRSF1_MOUSE | 6426 | SRSF1 | SRSF1 | SFRS1; SRp30a; ASF; SF2; SF2p33 | NR_034041; XM_006722012; XR_429911; XR_429912; NM_001078166; NM_006924 |
| BOP1_MOUSE | 23246 | BOP1 | BOP1 | — | ; NM_015201 |
| IMDH2_MOUSE | 3615 | IMDH2 | IMPDH2 | IMPD2; IMPDH-II | XM_006713128; ; NM_000884 |
| H31_MOUSE | 8353; 8358; 8357; 8968; 8350; 8351; 8355; 8354; 8356; 8352 | — | — | — | — |
| AACS_MOUSE | 65985 | AACS | AACS | ACSF1; SUR-5 | XM_005253611; XR_242960; NM_023928; XM_005253609; XM_005253610; XM_011538692 |
| PDS5A_MOUSE | 23244 | PDS5A | PDS5A | PIG54; SCC112; SCC-112 | NM_001100400; XM_011513673; XM_011513674; NM_015200; ; NM_001100399; XM_011513672 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of activating an inactive X-linked allele in a cell of a female heterozygous mammalian subject, the method comprising administering to the cell
(i) a DNA methyltransferase (DNMT) Inhibitor; and
(ii) an inhibitory nucleic acid targeting Xist RNA, wherein the inhibitory nucleic acid is complementary to at least 8 consecutive nucleotides of XIST RNA.

2. The method of claim 1, wherein the X-linked allele is an epigenetically silenced or hypomorphic allele on the active X-chromosome.

3. The method of claim 1, wherein the subject has an X-linked disorder selected from the group consisting of Rett Syndrome, CDKL5 Syndrome, and Fragile X Syndrome, and the DNMT Inhibitor and the inhibitory nucleic acid targeting Xist RNA are administered in an amount sufficient to alleviate or partially arrest at least one clinical manifestation of the X-linked disorder or its complications.

4. The method of claim 1, wherein the inactive X-linked allele is associated with an X-linked disorder selected from the group consisting of Rett Syndrome, CDKL5 Syndrome, and Fragile X Syndrome, and the DNMT Inhibitor and the inhibitory nucleic acid targeting Xist RNA are administered in an amount sufficient to alleviate or partially arrest at least one clinical manifestation of the X-linked disorder or its complications.

5. The method of claim 1, wherein the cell is in a living subject.

6. The method of claim 1, wherein the inhibitory nucleic acid comprises at least one ribonucleotide, at least one deoxyribonucleotide; or at least one bridged nucleotide.

7. The method of claim 6, wherein the bridged nucleotide is a LNA nucleotide, a cEt nucleotide or a ENA modified nucleotide.

8. The method of claim 1, wherein the inhibitory nucleic acid does not comprise three or more consecutive guanosine nucleotides or does not comprise four or more consecutive guanosine nucleotides.

9. The method of claim 1, wherein the inhibitory nucleic acid is 8 to 30 nucleotides in length.

10. The method of claim 1, wherein at least one nucleotide of the inhibitory nucleic acid is a nucleotide analogue.

11. The method of claim 1, wherein at least one nucleotide of the inhibitory nucleic acid comprises a 2' O-methyl.

12. The method of claim 1, wherein one or more of the nucleotides of the inhibitory nucleic acid comprise 2'-fluoro-deoxyribonucleotides and/or 2'-O-methyl nucleotides.

13. The method of claim 1, wherein the nucleotides of the inhibitory nucleic acid comprise a phosphorothioate internucleotide linkage between at least two nucleotides, or between all nucleotides.

14. The method of claim 1, wherein the subject is a human.

15. The method of claim 1, wherein the inactive X-linked allele was inactivated by Xist RNA.

16. The method of claim 1, wherein the inhibitory nucleic acid is complementary to at least 10 consecutive nucleotides of XIST RNA.

17. The method of claim 1, wherein the inhibitory nucleic acid is complementary to at least 12 consecutive nucleotides of XIST RNA.

18. The method of claim 1, wherein the inhibitory nucleic acid is complementary to at least 15 consecutive nucleotides of XIST RNA.

* * * * *